US010775385B2

(12) United States Patent
O'Connell et al.

(10) Patent No.: US 10,775,385 B2
(45) Date of Patent: Sep. 15, 2020

(54) TREATMENT OF AUTOIMMUNE AND INFLAMMATORY DISORDERS WITH ASYMMETRIC TNF ALPHA TRIMERS

(71) Applicant: UCB Biopharma SPRL, Brussels (BE)

(72) Inventors: James Philip O'Connell, Slough Berkshire (GB); John Robert Porter, Slough Berkshire (GB); Alastair Lawson, Slough Berkshire (GB); Boris Kroeplien, Slough Berkshire (GB); Stephen Edward Rapecki, Slough Berkshire (GB); Timothy John Norman, Slough Berkshire (GB); Graham John Warrellow, Slough Berkshire (GB); Tracy Lynn Arakaki, Slough Berkshire (GB); Alex Buntin Burgin, Slough Berkshire (GB); William Ross Pitt, Slough Berkshire (GB); Mark Daniel Calmiano, Slough Berkshire (GB); David Andreas Schubert, Slough Berkshire (GB); Daniel John Lightwood, Slough Berkshire (GB); Rebecca Jayne Wootton, Slough Berkshire (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

(21) Appl. No.: 15/736,614

(22) PCT Filed: Oct. 22, 2015

(86) PCT No.: PCT/EP2015/074491
§ 371 (c)(1),
(2) Date: Dec. 14, 2017

(87) PCT Pub. No.: WO2016/202412
PCT Pub. Date: Dec. 22, 2016

(65) Prior Publication Data
US 2018/0231562 A1   Aug. 16, 2018

(30) Foreign Application Priority Data

Jun. 18, 2015 (GB) .................................. 1510758.4

(51) Int. Cl.
| | | |
|---|---|---|
| *G01N 33/68* | (2006.01) | |
| *C07K 14/525* | (2006.01) | |
| *C07K 14/705* | (2006.01) | |
| *C07K 16/24* | (2006.01) | |
| *A61P 37/00* | (2006.01) | |
| *C07D 401/14* | (2006.01) | |
| *C07D 471/00* | (2006.01) | |
| *C07D 213/72* | (2006.01) | |
| *C07D 235/04* | (2006.01) | |
| *C07D 239/26* | (2006.01) | |
| *C07D 471/04* | (2006.01) | |
| *A61K 47/64* | (2017.01) | |
| *A61P 35/00* | (2006.01) | |

(52) U.S. Cl.
CPC ..... *G01N 33/6845* (2013.01); *A61K 47/6425* (2017.08); *A61P 35/00* (2018.01); *A61P 37/00* (2018.01); *C07D 213/72* (2013.01); *C07D 235/04* (2013.01); *C07D 239/26* (2013.01); *C07D 401/14* (2013.01); *C07D 471/00* (2013.01); *C07D 471/04* (2013.01); *C07K 14/525* (2013.01); *C07K 14/70575* (2013.01); *C07K 16/241* (2013.01); *G01N 33/6854* (2013.01); *G01N 33/6863* (2013.01); *C07K 2317/55* (2013.01); *C07K 2317/92* (2013.01); *G01N 2333/525* (2013.01); *G01N 2500/02* (2013.01)

(58) Field of Classification Search
None
See application file for complete search history.

(56) References Cited

U.S. PATENT DOCUMENTS

| | | |
|---|---|---|
| 4,908,372 A | 3/1990 | Carr et al. |
| 7,691,815 B2 | 4/2010 | Liang |
| 7,993,636 B2 | 8/2011 | Mayumi et al. |
| 8,377,441 B2 | 2/2013 | Chang |
| 9,908,944 B2 | 3/2018 | Padkjaer et al. |
| 10,428,148 B2 | 10/2019 | Katagiri et al. |
| 10,705,094 B2 | 7/2020 | O'Connell et al. |
| 2001/0018507 A1 | 8/2001 | Rathjen et al. |

(Continued)

FOREIGN PATENT DOCUMENTS

| | | |
|---|---|---|
| CA | 2005053 A1 | 6/1990 |
| CN | 1204320 A | 1/1999 |

(Continued)

OTHER PUBLICATIONS

Alzani et al., Biochemistry 34:6344-6350 (1995).

(Continued)

*Primary Examiner* — Elly-Gerald Stoica
(74) *Attorney, Agent, or Firm* — Medler Ferro Woodhouse & Mills PLLC

(57) ABSTRACT

A new, stable trimeric TNFα structure is disclosed with distorted symmetry which can bind to the TNFR1 receptor to attenuate signalling therefrom, which can be used in the treatment and/or prevention of diseases associated with the soluble TNFα/TNFR1 interaction. Membrane-bound TNFα is not affected in its ability to signal through TNFR2, and thus the new structure of TNFα may be used in therapies which do not significantly raise the risk of infection or malignancy.

4 Claims, 36 Drawing Sheets
Specification includes a Sequence Listing.

(56) References Cited

U.S. PATENT DOCUMENTS

| | | |
|---|---|---|
| 2002/0110868 A1 | 8/2002 | Dahiyat et al. |
| 2003/0060461 A1 | 3/2003 | Kodama et al. |
| 2004/0067982 A1 | 4/2004 | Zheng et al. |
| 2006/0222624 A1 | 10/2006 | Bratt et al. |
| 2007/0117755 A1 | 5/2007 | Liang |
| 2009/0022659 A1 | 1/2009 | Olson et al. |
| 2009/0269357 A1 | 10/2009 | Ke et al. |
| 2010/0266613 A1 | 10/2010 | Harding et al. |
| 2010/0297111 A1 | 11/2010 | Beirnaert |
| 2011/0250130 A1 | 10/2011 | Benatuil et al. |
| 2013/0018105 A1 | 1/2013 | Carroll et al. |
| 2014/0112929 A1 | 4/2014 | Batuwangala et al. |
| 2014/0165223 A1 | 6/2014 | Carroll et al. |

FOREIGN PATENT DOCUMENTS

| | | |
|---|---|---|
| CN | 1700930 A | 11/2005 |
| CN | 104428293 A | 5/2015 |
| CN | 104619709 A | 5/2015 |
| EP | 0288088 A2 | 10/1988 |
| EP | 0492448 A1 | 1/1992 |
| JP | H0596 A | 1/1993 |
| JP | 2003-040888 A | 2/2003 |
| JP | 2008-539772 A | 11/2008 |
| JP | 2010-172307 A | 8/2010 |
| JP | 2011519836 A | 7/2011 |
| JP | 2012-509312 A | 4/2012 |
| WO | WO 93/06489 A1 | 4/1993 |
| WO | WO 93/14083 A1 | 7/1993 |
| WO | 1994/18325 A1 | 8/1994 |
| WO | 1997/22587 A1 | 6/1997 |
| WO | WO 02/098869 A2 | 12/2002 |
| WO | 2004/012673 A2 | 2/2004 |
| WO | 2006/122786 A2 | 11/2006 |
| WO | 2007/060411 A1 | 5/2007 |
| WO | 2009/020848 A2 | 8/2008 |
| WO | 2008/144757 A1 | 11/2008 |
| WO | WO 2008/144753 A2 | 11/2008 |
| WO | 2009/132037 A1 | 10/2009 |
| WO | WO 2009/155723 A2 | 12/2009 |
| WO | 2010/058419 A1 | 5/2010 |
| WO | WO 2010/118404 A2 | 10/2010 |
| WO | WO 2013/024040 A2 | 2/2013 |
| WO | WO 2013/186229 A1 | 12/2013 |
| WO | WO 2014/001557 A1 | 1/2014 |
| WO | WO 2014/009295 A1 | 1/2014 |
| WO | WO 2014/009296 A1 | 1/2014 |
| WO | WO 2014/040076 A1 | 3/2014 |
| WO | WO 2014/123696 A1 | 8/2014 |
| WO | WO 2014/165223 A1 | 10/2014 |
| WO | WO 2015/086496 A1 | 6/2015 |
| WO | WO 2015/086498 A1 | 6/2015 |
| WO | WO 2015/086499 A1 | 6/2015 |
| WO | WO 2015/086500 A1 | 6/2015 |
| WO | WO 2015/086501 A1 | 6/2015 |
| WO | WO 2015/086502 A1 | 6/2015 |
| WO | WO 2015/086503 A1 | 6/2015 |
| WO | WO 2015/086504 A1 | 6/2015 |
| WO | WO 2015/086505 A1 | 6/2015 |
| WO | WO 2015/086506 A1 | 6/2015 |
| WO | WO 2015/086507 A1 | 6/2015 |
| WO | WO 2015/086508 A1 | 6/2015 |
| WO | WO 2015/086509 A1 | 6/2015 |
| WO | WO 2015/086511 A1 | 6/2015 |
| WO | WO 2015/086512 A1 | 6/2015 |
| WO | WO 2015/086513 A1 | 6/2015 |
| WO | WO 2015/086519 A1 | 6/2015 |
| WO | WO 2015/086520 A1 | 6/2015 |
| WO | WO 2015/086521 A1 | 6/2015 |
| WO | WO 2015/086523 A1 | 6/2015 |
| WO | WO 2015/086525 A1 | 6/2015 |
| WO | WO 2015/086526 A1 | 6/2015 |
| WO | WO 2015/086527 A1 | 6/2015 |
| WO | WO 2016/050975 A1 | 4/2016 |
| WO | WO 2016/149436 A1 | 9/2016 |
| WO | WO 2016/149437 A1 | 9/2016 |
| WO | WO 2016/149439 A1 | 9/2016 |
| WO | WO 2016/168633 A1 | 10/2016 |
| WO | WO 2016/168638 A1 | 10/2016 |
| WO | WO 2016/168641 A1 | 10/2016 |
| WO | WO 2016/198398 A1 | 12/2016 |
| WO | WO 2016/198400 A1 | 12/2016 |
| WO | WO 2016/198401 A1 | 12/2016 |
| WO | WO 2016/202411 A1 | 12/2016 |
| WO | WO 2016/202413 A1 | 12/2016 |
| WO | WO 2016/202414 A1 | 12/2016 |
| WO | WO 2016/202415 A1 | 12/2016 |
| WO | WO 2017/023902 A1 | 2/2017 |
| WO | WO 2017/023905 A1 | 2/2017 |
| WO | WO 2017/167993 A1 | 10/2017 |
| WO | WO 2017/167994 A1 | 10/2017 |
| WO | WO 2017/167995 A1 | 10/2017 |
| WO | WO 2017/167996 A1 | 10/2017 |

OTHER PUBLICATIONS

Andersen et al., Protein Science 15:2558-2567 (2006).
Baldwin et al., PNAS 93:1021-1026 (1996).
Eck et al., Journal of Biological Chemistry 264:17595-17605 (1989).
Ganesan et al., Pharmazie 67:374-379 (2012).
Garcia et al. in: D. Wallach et al. (eds), Advances in TNF Family Research, Advances in Experimental Medicine and Biology 691:187-201 (2011), DOI 10.1007/978-1-4419-6612-4_20.
Grell et al., Cell 83:793-802 (1995).
He et al., Science 310:1022-1025 (2005).
Hoffmann et al., PLOS One 7:e31298 (2012).
Hu et al., Journal of Biological Chemistry 288:27059-27067 (2013).
Jones et al., Journal of Cell Science S13:11-18 (1990).
Kim et al., Journal of Molecular Biology 374:1374-1388 (2007).
Liang et al., Journal of Biological Chemistry 288:13799-13807 (2013).
Loetscher et al., Journal of Biological Chemistry 266:18324-18329 (1991).
Ma et al., Journal of Biological Chemistry 289:12457-12466 (2014).
Mascarenhas et al., BMC Structural Biology 12:8 (2012).
Nesbitt et al., Inflammatory Bowel Diseases 13:1323-1332 (2007).
Silvian et al., ACS Chemical Biology 6:636-647 (2011).
Simon et al., Nature Chemical Biology 9:200-205 (2013).
Sudhamsu et al., PNAS 110:19896-19901 (2013).
Tracey et al., Pharmacology & Therapeutics 117:244-279 (2007).
Zalevsky et al., Journal of Immunology 179:1872-1883 (2007).
Zhu et al., Immunology Letters 102:177-183 (2006).
Cha et al., "High Resolution Crystal Structure of a Human Tumor Necrosis Factor-α Mutant with Low Systemic Toxicity," The Journal of Biological Chemistry 273(4):2153-2160 (1998).
Mukai et al., "Solution of the Structure of the TNF-TNFR2 Complex," Biochemistry 3(148):1-11 (2010).
Non-Final Office Action issued in U.S. Appl. No. 15/736,520, dated Feb. 28, 2019.
Non-Final Office Action issued in U.S. Appl. No. 15/736,336, dated Apr. 24, 2019.
Non-Final Office Action issued in U.S. Appl. No. 15/736,535, dated Apr. 25, 2019.
Non-Final Office Action issued in U.S. Appl. No. 15/736,558, dated Apr. 26, 2019.
Lloyd et al., "Modelling the human immune response: performance of a 10" human antibody repertoire against a broad panel of therapeutically relevant antigens," Protein Engineering, Design & Selection 22(3):159-168 (2009).
Fang et al., "TNF: a structure and function relationship," Foreign Medical Immunology, vol. 26, No. 2. (2003). [Machine translation].
Sedger et al., "TNF and TNF-receptors: From Mediators of Cell Death and Inflammation to Therapeutic Giants—Past, Present, and Future," Cytokine & Growth Factor Reviews, 25:453-473 (2014).
Shibata et al., "Creation and X-ray Structure Analysis of the Tumor Necrosis Factor Receptor-1-selective Mutant of a Tumor Necrosis Factor-alpha Antagonist," J. Biol. Chem, 283(2): 998-1007 (2008).
Office Action in U.S. Appl. No. 15/736,336 dated Oct. 3, 2019.
Office Action in U.S. Appl. No. 15/736,520 dated Oct. 7, 2019.

(56) References Cited

OTHER PUBLICATIONS

Office Action in U.S. Appl. No. 15/736,535 dated Nov. 8, 2019.
Office Action in U.S. Appl. No. 15/736,558 dated Nov. 8, 2019.
Japanese Patent Office Search Report dated Oct. 25, 2019.
Office Action in EP 15784370.7 dated Jan. 30, 2020.
Notice of Allowance in U.S. Appl. No. 15/736,520 dated Feb. 26, 2020.
Non-final Office Action in U.S. Appl. No. 15/736,558 dated Apr. 21, 2020.
Notice of Allowance in U.S. Appl. No. 15/736,336 dated Jun. 4, 2020.
Non-final Office Action in U.S. Appl. No. 15/736,535 dated May 4, 2020.

| Compound | STRUCTURE |
|---|---|
| 1 | 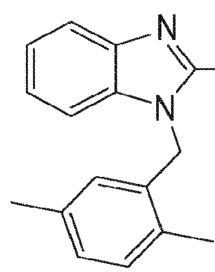 |
| 2 | 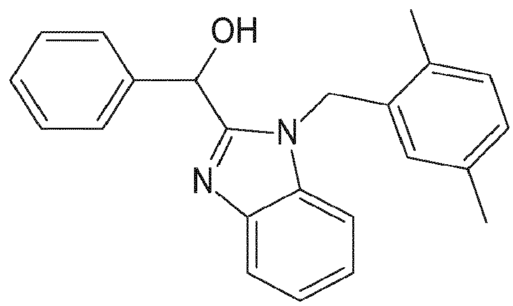 |
| 3 | 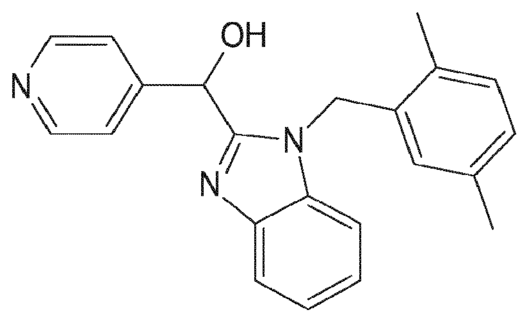 |
| 4 | 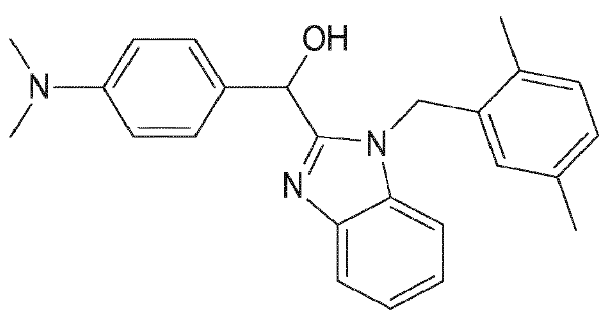 |
| 5 | 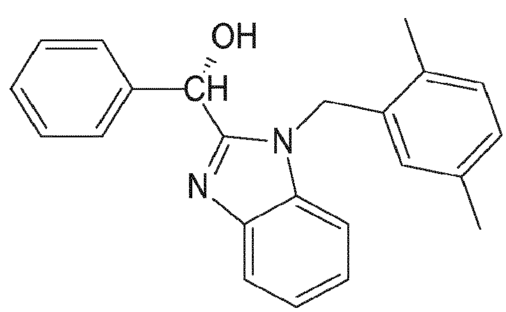 |

| 11 |  |
| --- | --- |
| 12 |  |
| 13 |  |
| 14 |  |
| 15 |  |

| 21 |  |
| 22 |  |
| 23 |  |
| 24 |  |
| 25 |  |

| 26 |  |
| 27 |  |
| 28 |  |
| 29 |  |
| 30 |  |

| 31 |  |
| 32 |  |
| 33 |  |
| 34 |  |
| 35 |  |

FIG. 1H

| 36 | |
| 37 | |
| 38 | |
| 39 | |
| 40 | |

| 46 |  |
| 47 |  |
| 48 |  |
| 49 |  |
| 50 |  |

(TNFα / Compound 3) + TNFR (TNFa / TNFR) + Compound 3

Compound 3 Binding Kinetics (Biacore)

Compound 15 Binding Kinetics (Biacore)

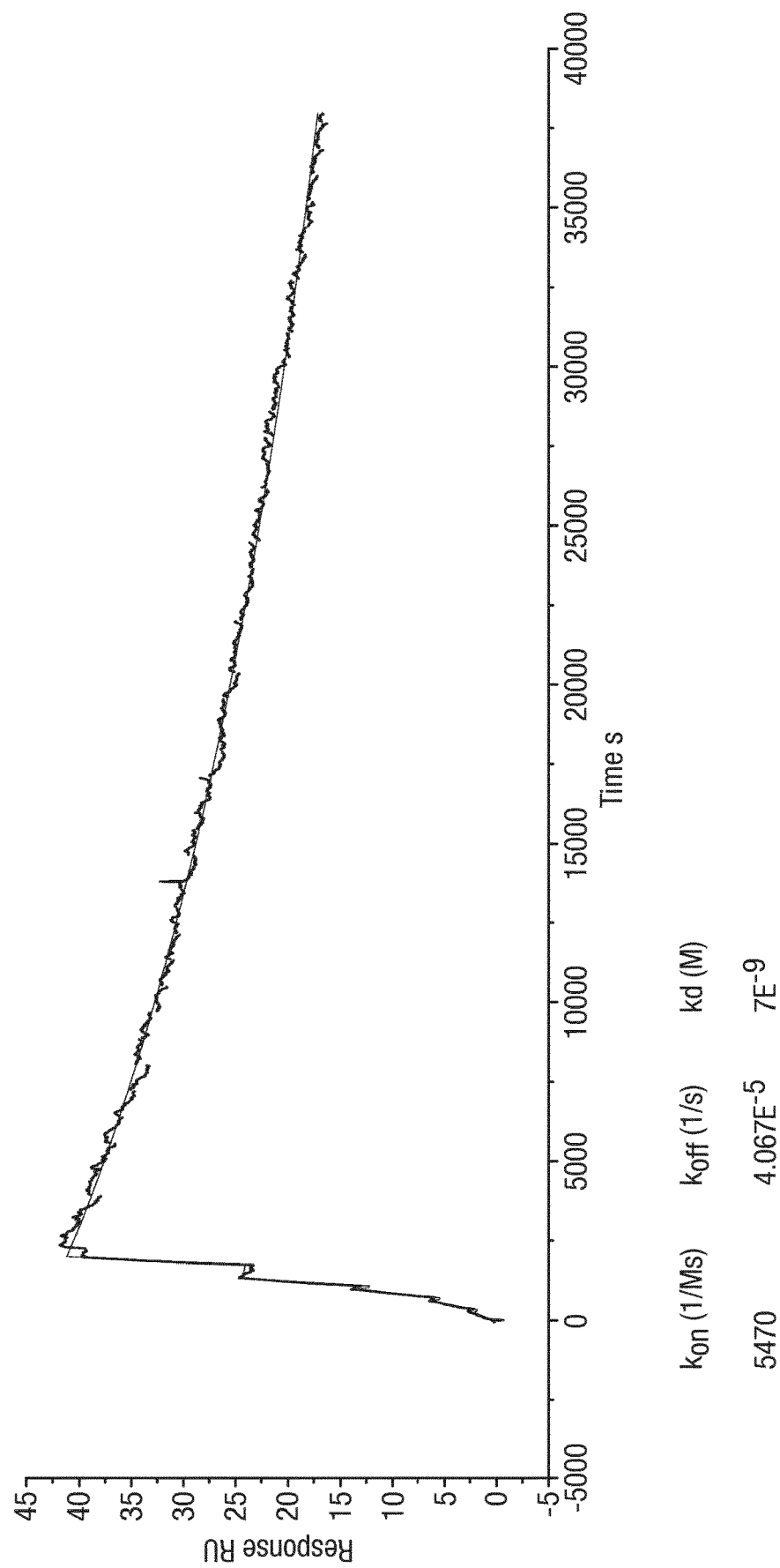

TREATMENT OF AUTOIMMUNE AND INFLAMMATORY DISORDERS WITH ASYMMETRIC TNF ALPHA TRIMERS

REFERENCE TO AN ELECTRONIC SEQUENCE LISTING

The contents of the electronic sequence listing (00890007US1seqlist.txt; Size: 41,863 bytes; and Date of Creation Dec. 13, 2017) is herein incorporated by reference in its entirety.

FIELD OF THE INVENTION

This invention relates to novel stable, asymmetric, trimeric TNFα structures, and their use in therapy. The invention further relates to complexes of trimeric TNFα structures with small molecules which can bind to the TNFR1 receptor, but attenuate signalling therefrom, which can be used in the treatment and/or prevention of disease. The invention further relates to crystals of the asymmetric trimeric TNFα structures and complexes, and the use of 3-D structure models obtained from such crystals in methods for the determination of novel trimeric TNFα inhibitors.

BACKGROUND OF THE INVENTION

The Tumour Necrosis Factor (TNF) superfamily is a family of proteins that share a primary function of regulating cell survival and cell death. Members of the TNF superfamily share a common core motif, which consists of two antiparallel β-pleated sheets with antiparallel β-strands, forming a "jelly roll" β-structure. Another common feature shared by members of the TNF superfamily is the formation of homo- or heterotrimeric complexes. It is these trimeric forms of the TNF superfamily members that bind to, and activate, specific TNF superfamily receptors.

TNFα is the archetypal member of the TNF superfamily—forming a symmetrical homotrimer. Dysregulation of TNFα production has been implicated in a number of pathological conditions of significant medical importance. For example, TNFα has been implicated in rheumatoid arthritis, inflammatory bowel diseases (including Crohn's disease), psoriasis, Alzheimer's disease (AD), Parkinson's disease (PD), pain, epilepsy, osteoporosis, asthma, systemic lupus erythematosus (SLE) and multiple sclerosis (MS). Other members of the TNF superfamily have also been implicated in pathological conditions, including autoimmune disease.

Conventional antagonists of TNF superfamily members are macromolecular and act by inhibiting the binding of the TNF superfamily member to its receptor. Examples of conventional antagonists include anti-TNFα antibodies, particularly monoclonal antibodies, such as infliximab (Remicade®), adalimumab (Humira®) and certolizumab pegol (Cimzia®), or soluble TNFα receptor fusion proteins, such as etanercept (Enbrel®). These both inhibit soluble TNFα and its interaction with the receptor TNFR1 (responsible for inflammation) and membrane-bound TNFα and its interaction with the receptor TNFR2 (involved in the immune response).

SUMMARY OF THE INVENTION

The present inventors have obtained extensive structural understanding of a new, stable, asymmetric trimeric structure of TNFα. This TNFα trimer acts by binding to TNFR1, but is less able, or unable, to initiate signalling downstream of TNFR1. This TNFα trimer may adopt this structure through forming a complex with a class of small molecular entities (SME) at the centre of the trimer. The present inventors have also obtained an extensive structural understanding of such compounds, the pharmacophore which can induce the asymmetric TNFα trimeric structure, and the key interactions of residues within the TNFα trimer which contact the pharmacophore to induce the asymmetric TNFα trimer. These asymmetric TNFα trimers and complexes can be used in the treatment of conditions mediated by TNFα. The present inventors have also found that membrane-bound TNFα trimers and complexes do not disrupt the signalling downstream of TNFR2. Last, the present inventors have identified novel asymmetric TNFα trimer crystal forms which may be used in structural-based methods of rational drug design to determine novel compounds which may induce the asymmetric TNFα trimer.

Accordingly, the present invention provides an asymmetrical TNFα trimer of a protein subunit comprising the amino-acid sequence of SEQ ID NO: 36, or corresponding sequence, wherein said TNFα trimer adopts a conformation, when determined by x-ray crystallography, with the Cα atoms of residues 12-18, 47-50, 54-64, 76-82, 91-97, 117-125, 129-137, and 150-156 of SEQ ID NO: 36, or corresponding sequence, for all subunits within 0.9 Å RMSD [root mean square deviation] of the same atoms of the Reference Structure Compound34.pdb, said TNF-α trimer being able to bind TNFR1, but wherein signalling from said bound TNFR1 is attenuated or antagonised, optionally for use in a method of therapy practised on the human or animal body.

Herein the terms "asymmetrical TNFα trimer", "asymmetric TNFα trimer" or "TNFα trimer of the invention" are used interchangeably to mean the same. Herein, the TNFα trimer of the invention is non-naturally occurring (given the nature of its asymmetric conformation). "Antagonists" or "antagonism" of the TNFR1 receptor can be understood from the use of the terms herein, and, for example, are broadly intended to represent the means that result in a functional prevention or reduction of TNFR1 signalling regardless of the mechanism of action (unless stated otherwise). Herein "and/or" means "and or or".

The invention also provides a complex comprising a TNFα trimer of a protein subunit comprising the amino-acid sequence of SEQ ID NO: 36, or corresponding sequence, and a compound that is capable of binding to the TNFα trimer, whereby the compound-trimer complex binds to TNFR1 and attenuates the signalling induced by the trimer through TNFR1, wherein the compound, as determined by x-ray crystallography, comprises a pharmacophore which is bound within the TNFα trimer such that it is within 4 Å of all of the following residues: Leu57 of subunit A; Tyr119 of subunit B; Gly121 of subunit B; Gly122 of subunit B; Tyr59 of subunit C; Leu120 of subunit C; and Tyr151 of subunit C, and wherein the pharmacophore consists of 2 fused 5- or 6-member rings (with centres at "R3" and "R2"), one ring (with centre at R2) with an H bond acceptor ("A1") and which is also substituted through a linking non-hydrogen atom to a further 5- or 6-member ring (with centre at "R4").

Further provided is a TNFα trimer crystal with Space Group P 21 21 21, P 21 21 2, or P 1 21 1. Such crystals may be used for the structural elucidation and comparison of TNFα trimers of the invention, or may be used in methods for determining compounds which form complexes with TNFα trimer to yield asymmetric TNFα trimer structures of the invention.

BRIEF DESCRIPTION OF THE FIGURES

Figure 1H:
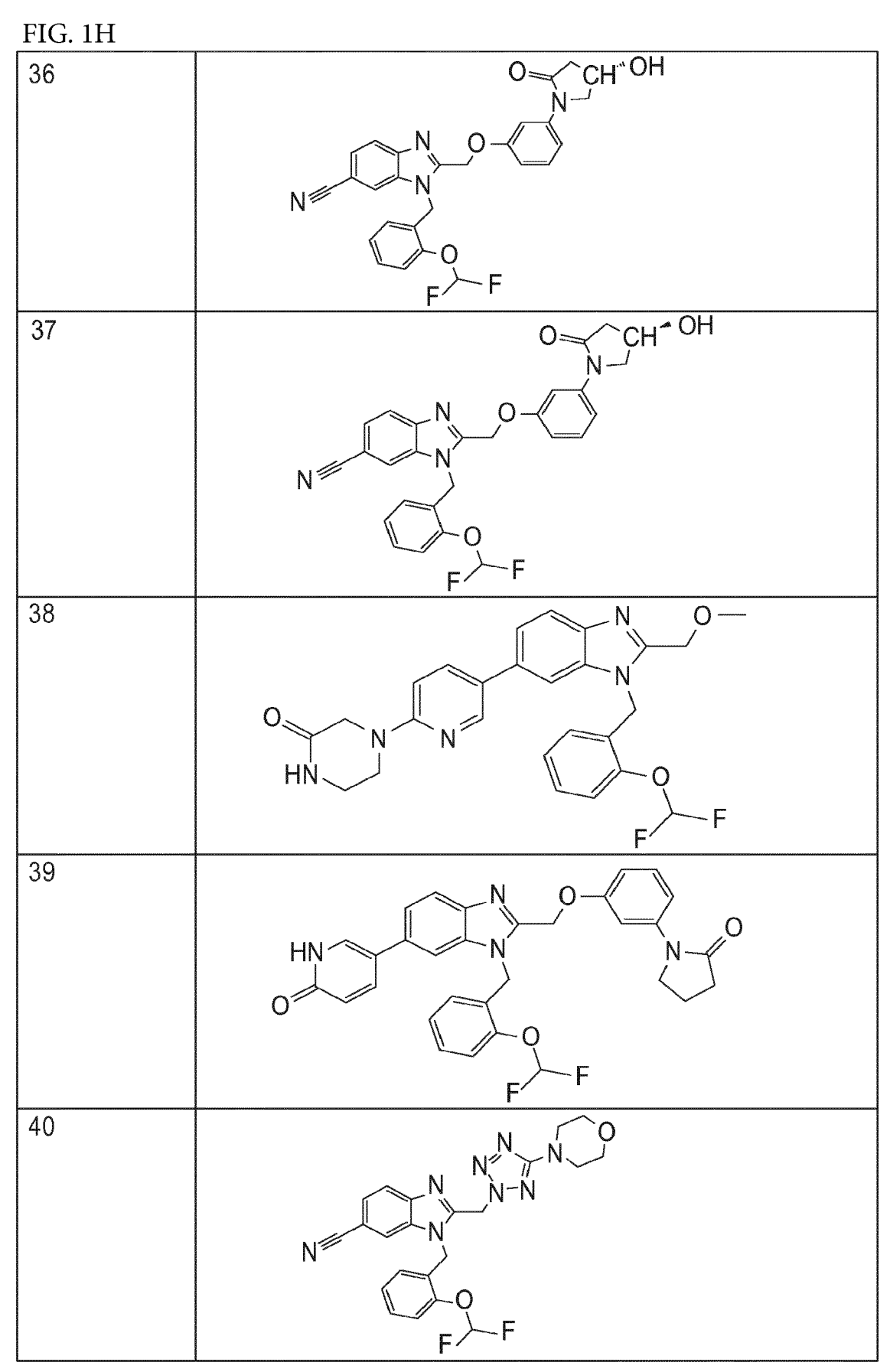

FIGS. 1A-1M show the structures of the Compounds of formulae (1)-(64) & (65).

FIG. 4 (top trace) shows the deconvoluted mass spectrogram of TNFα in a solution containing 10% v/v DMSO. FIG. 4 (middle trace) shows the deconvoluted mass spectrogram of TNFα in a solution containing 10% v/v DMSO and compound of formula (3).

FIG. 12C shows the binding kinetics for the compound of formula (39) with TNFα.

BRIEF DESCRIPTION OF THE SEQUENCE LISTING

Figure 1A:
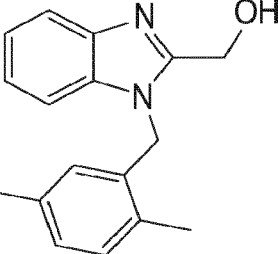
Figure 1A:
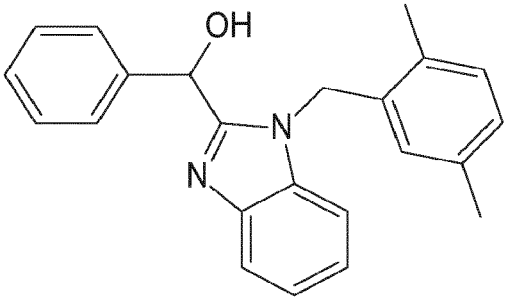
Figure 1A:
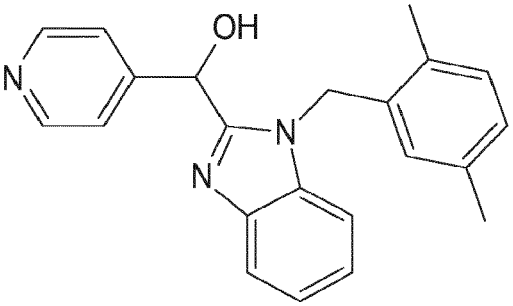
Figure 1A:
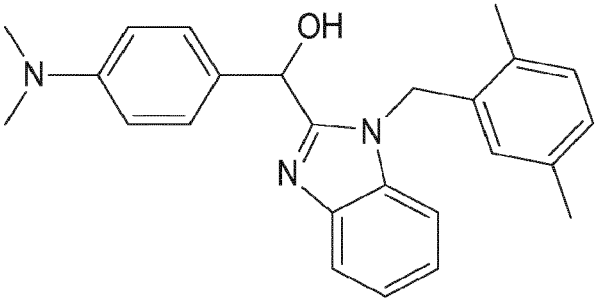
Figure 1A:
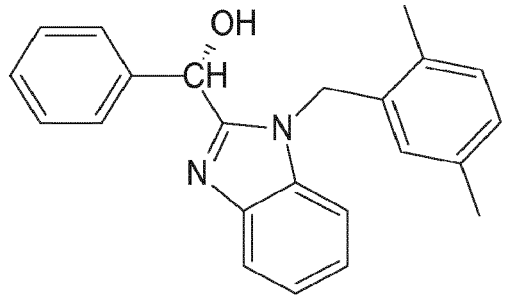
Figure 1B:
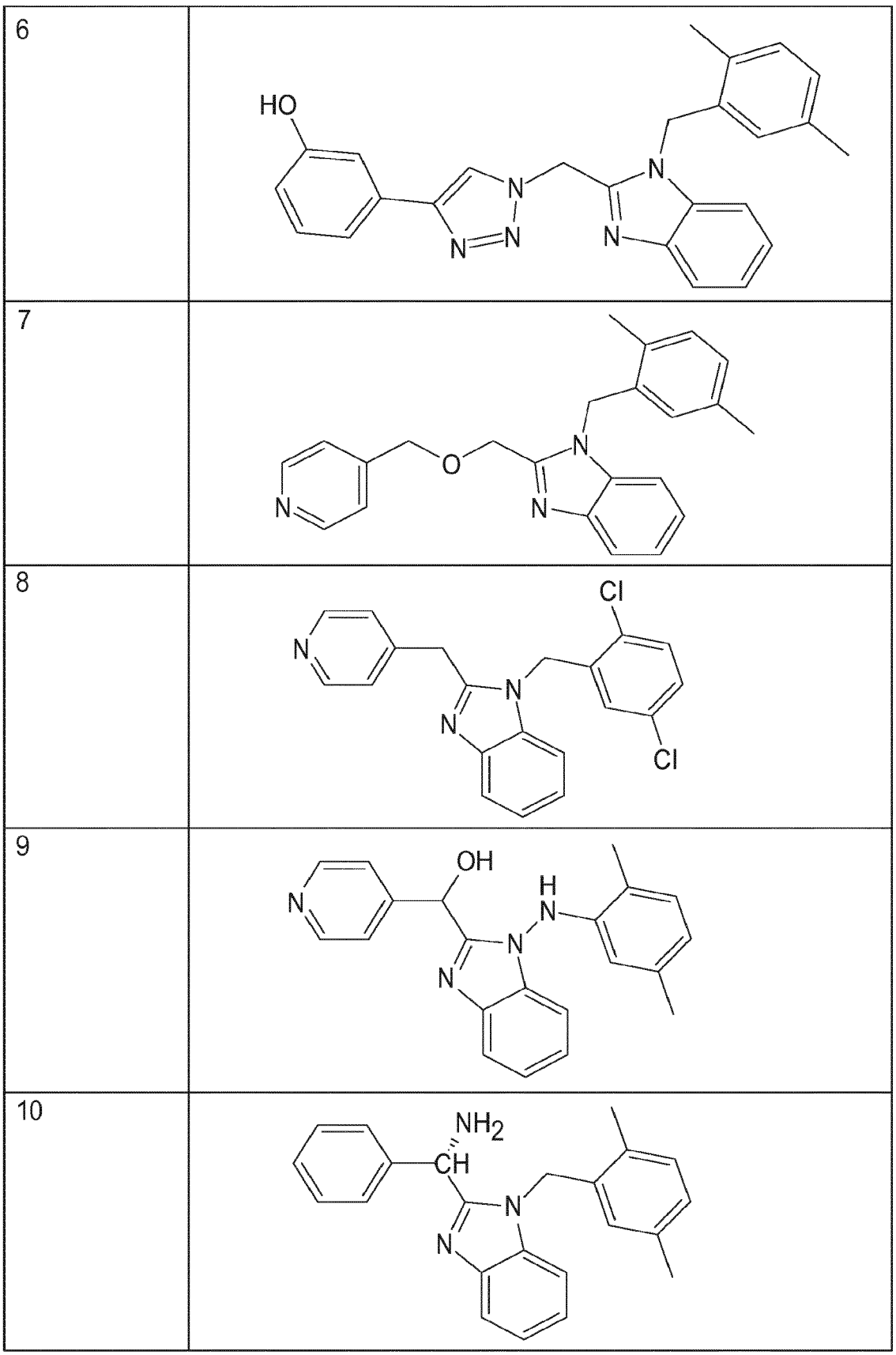
Figure 1C:
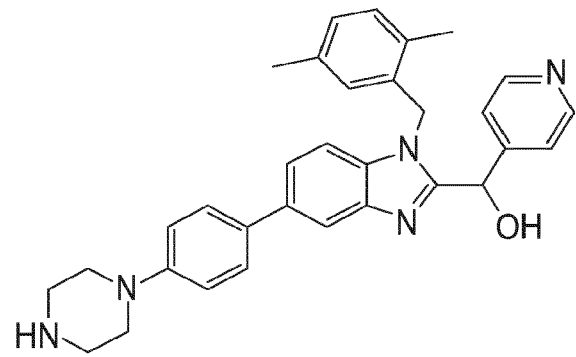
Figure 1C:
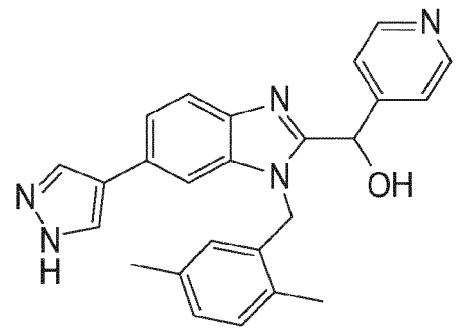
Figure 1C:
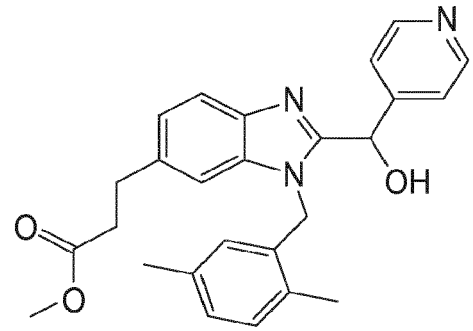
Figure 1C:
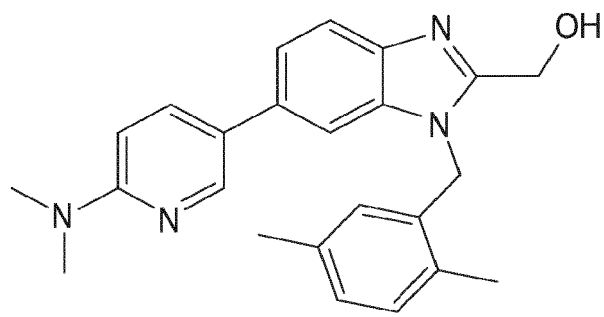
Figure 1C:
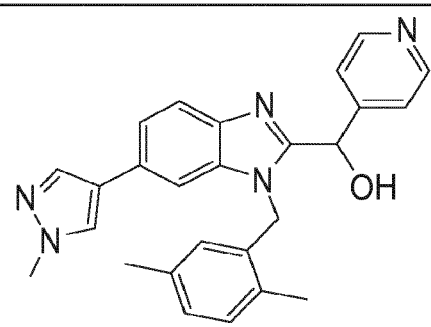
Figure 1D:
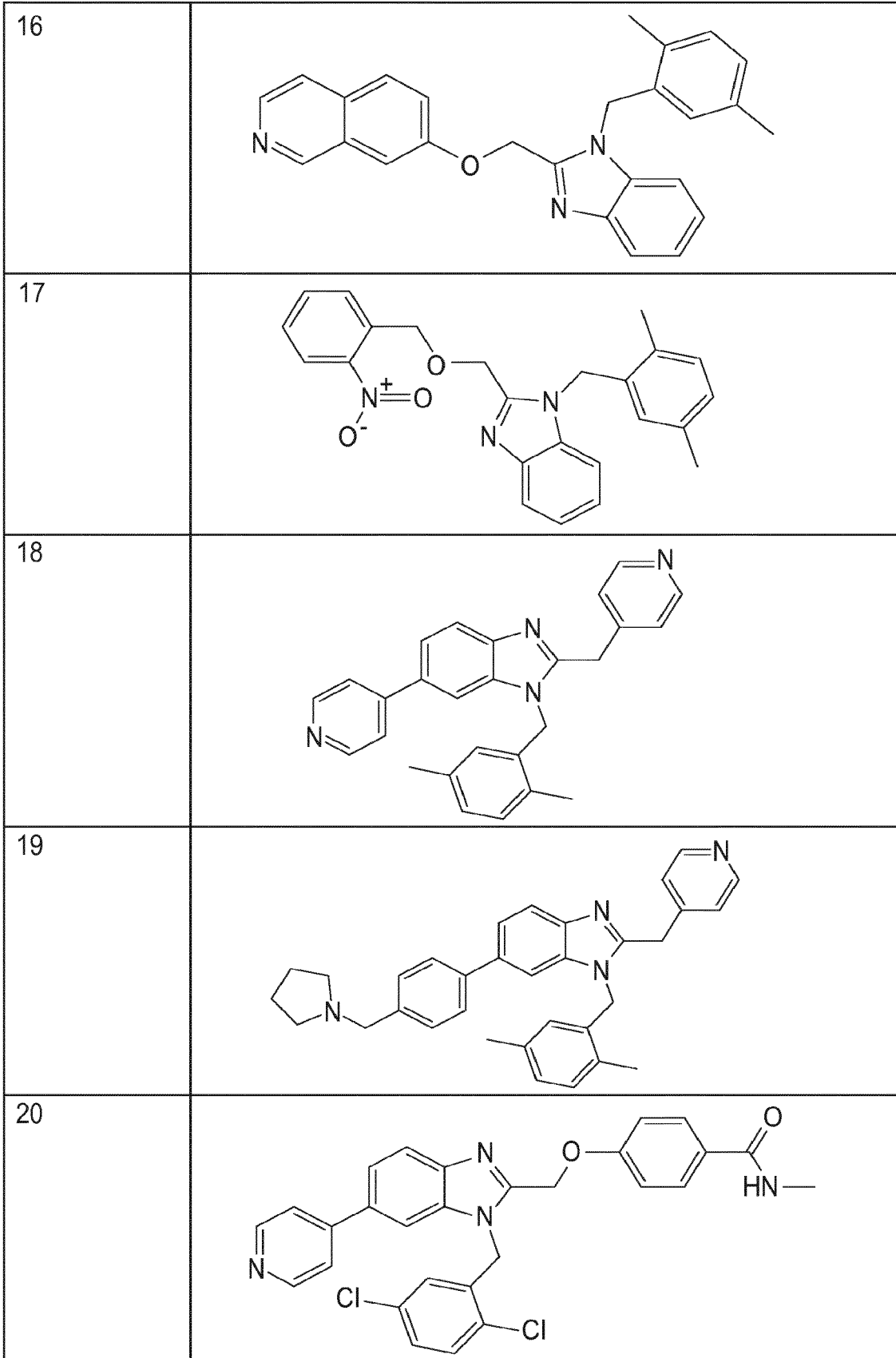
Figure 1E:
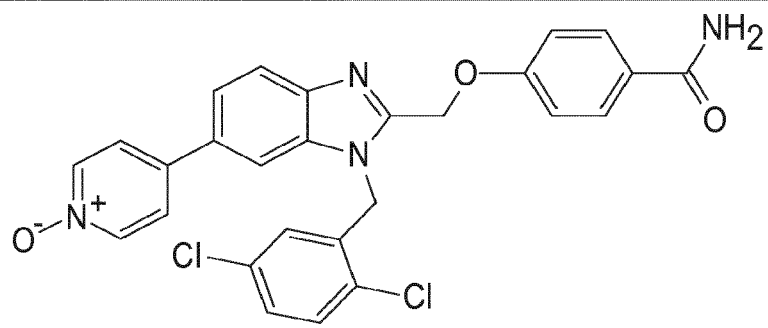
Figure 1E:
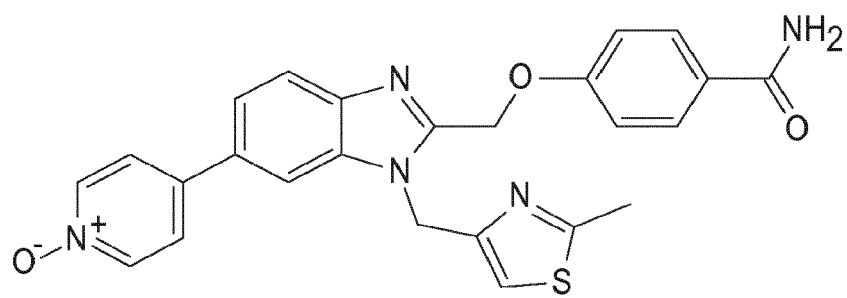
Figure 1E:
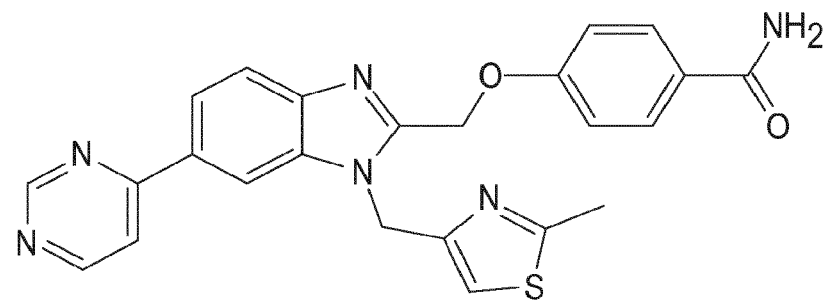
Figure 1E:
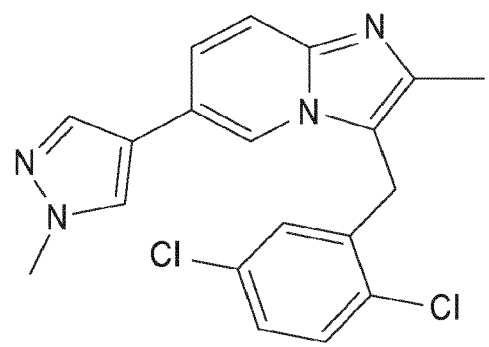
Figure 1E:
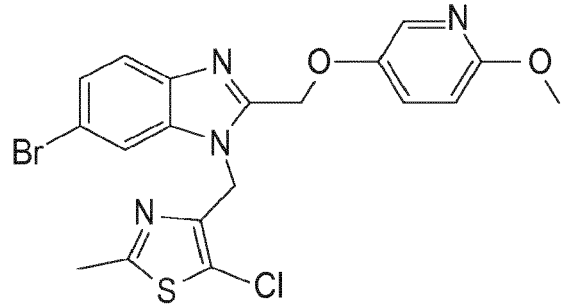
Figure 1F:
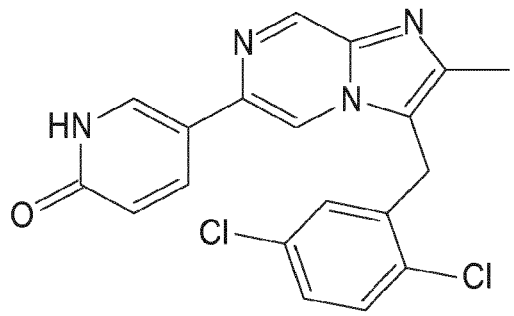
Figure 1F:
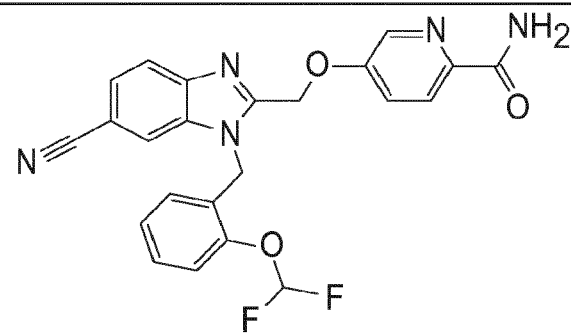
Figure 1F:
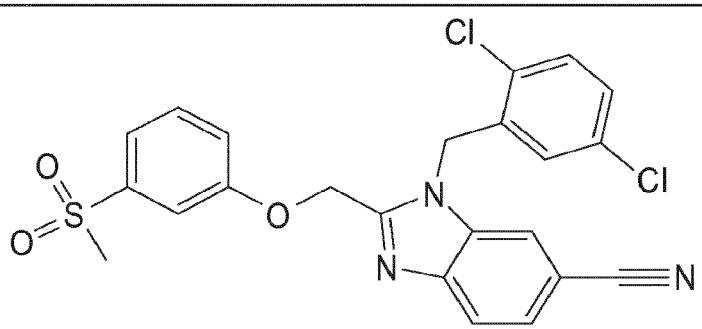
Figure 1F:
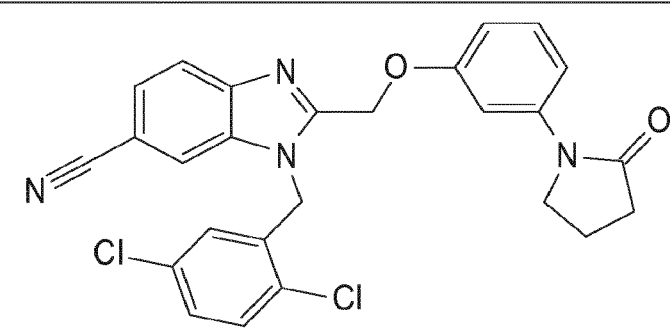
Figure 1F:
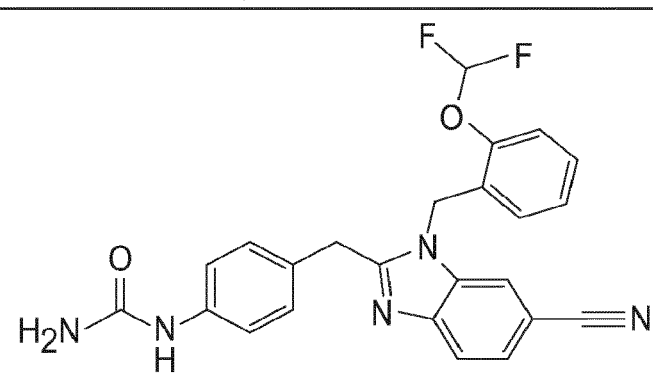
Figure 1G:
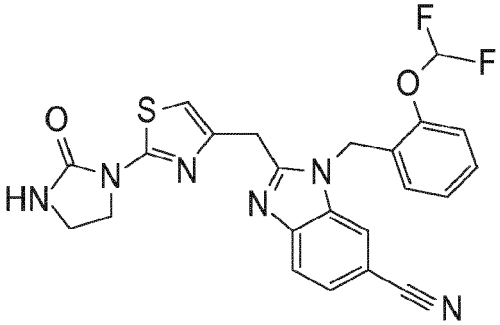
Figure 1G:
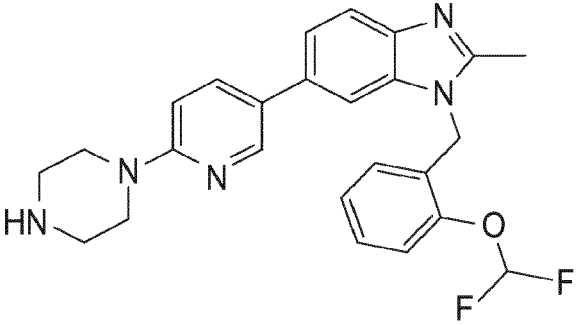
Figure 1G:
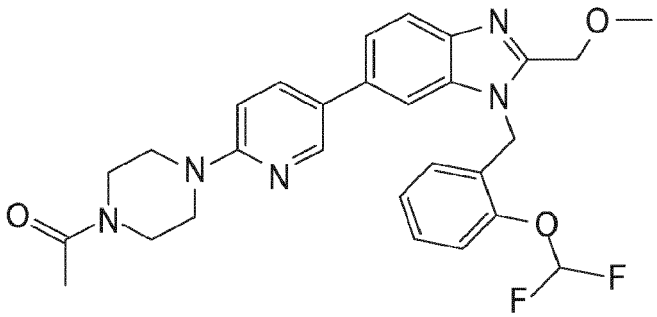
Figure 1G:
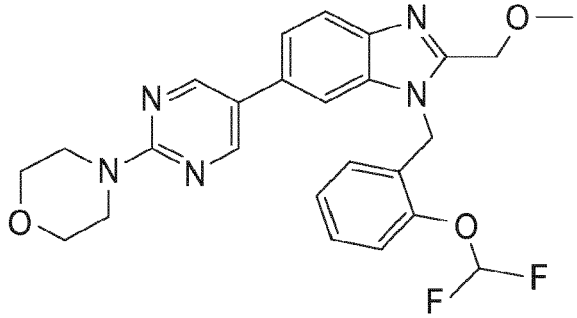
Figure 1G:
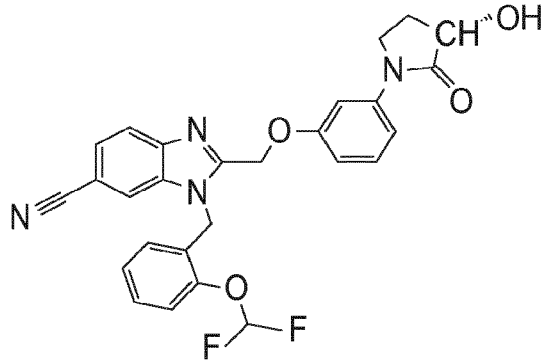
Figure 1I:
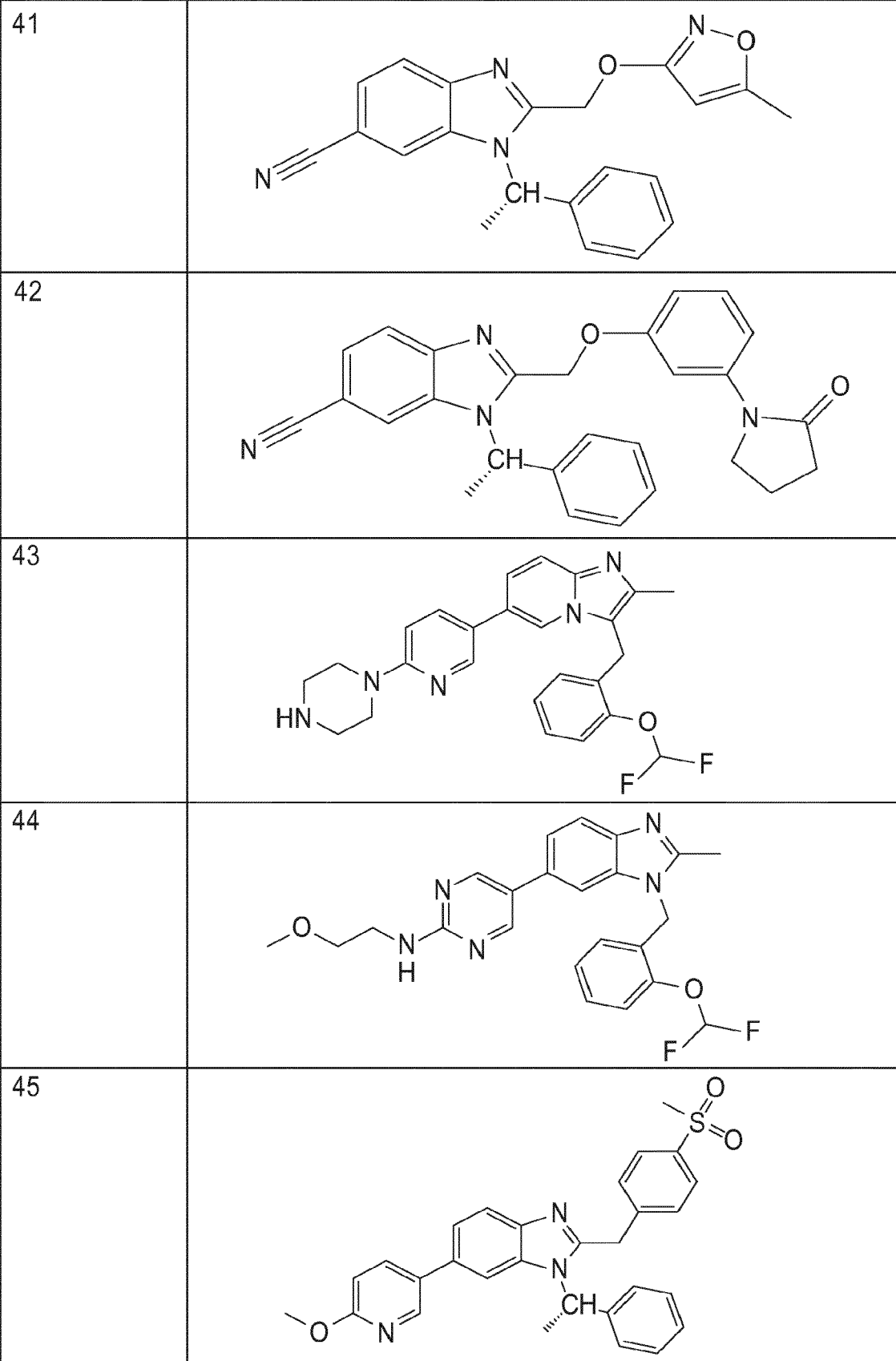
Figure 1J:
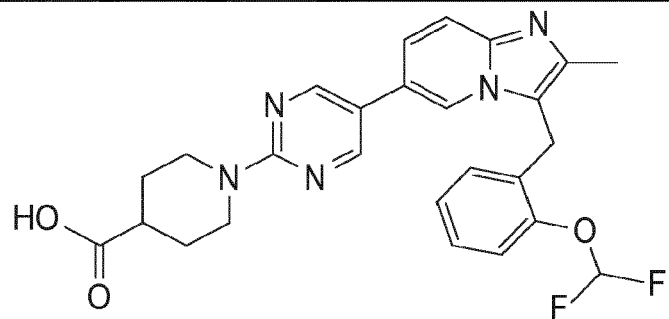
Figure 1J:
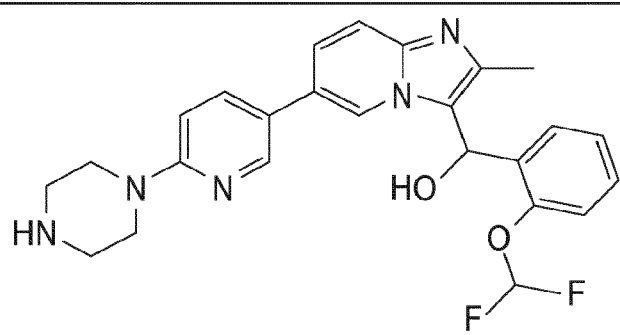
Figure 1J:
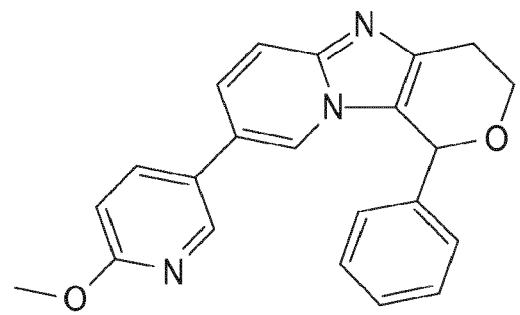
Figure 1J:
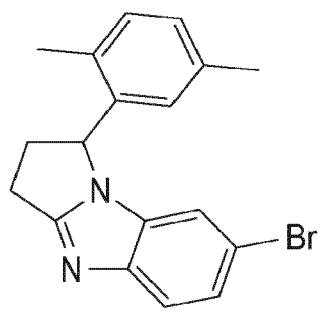
Figure 1J:
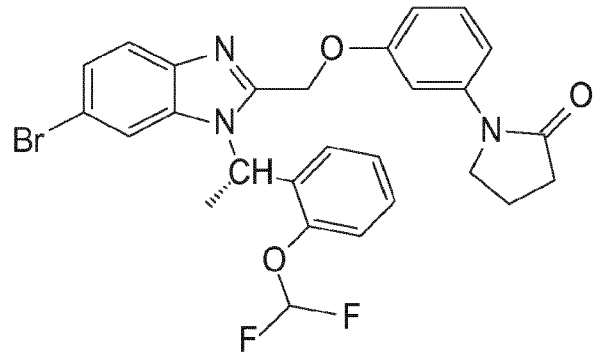
Figure 1K:
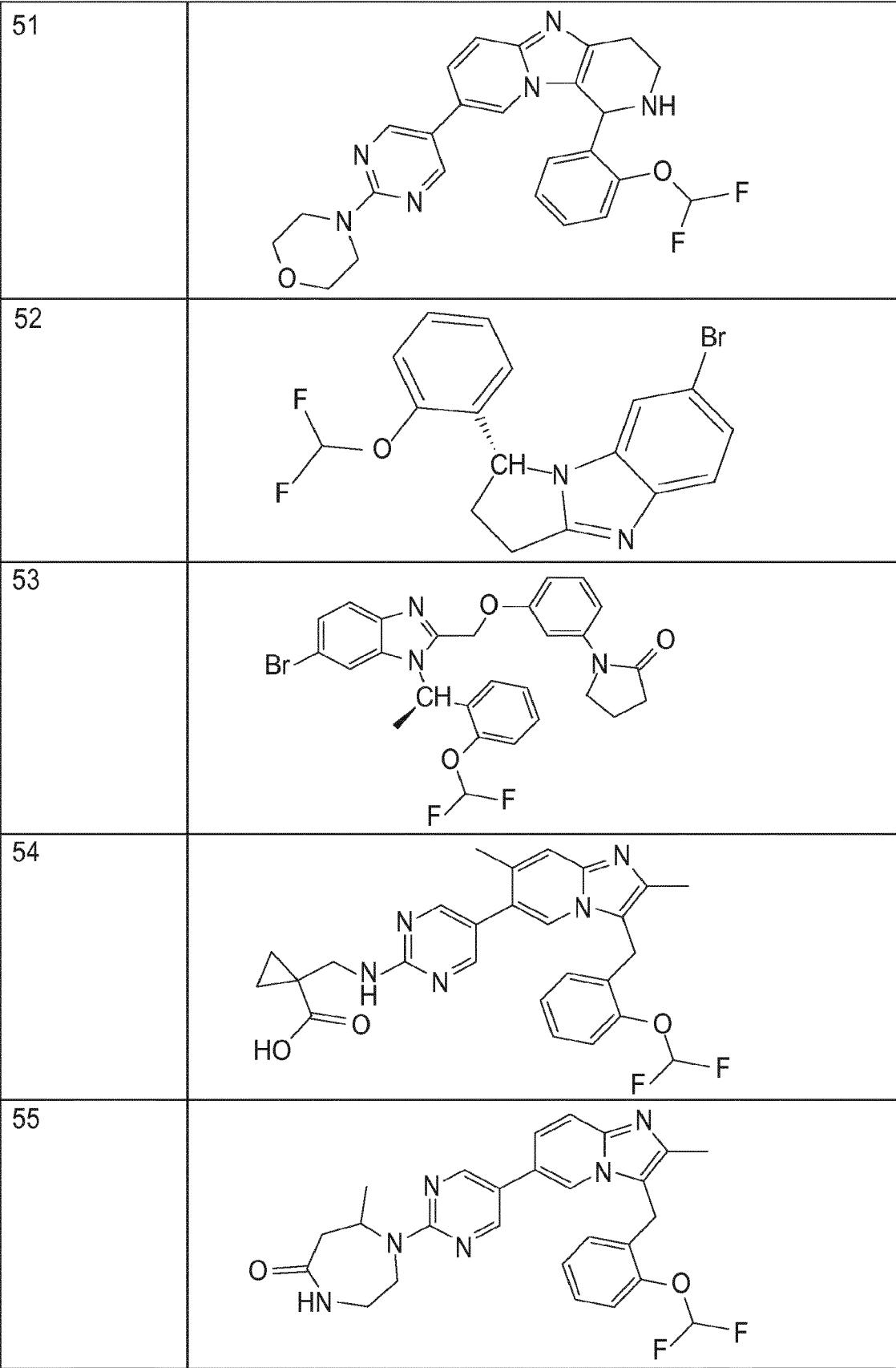
Figure 1L:
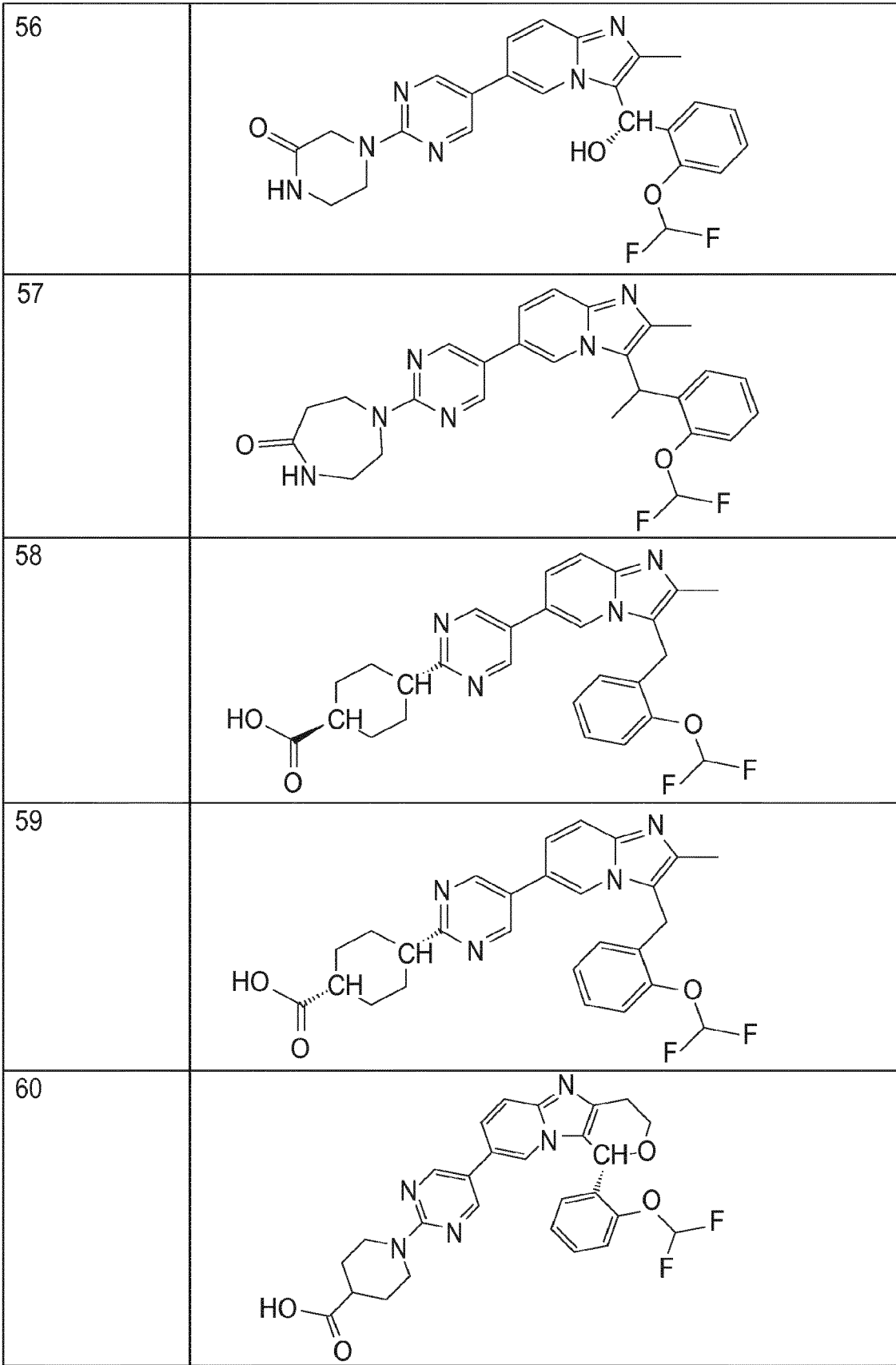
Figure 1M:
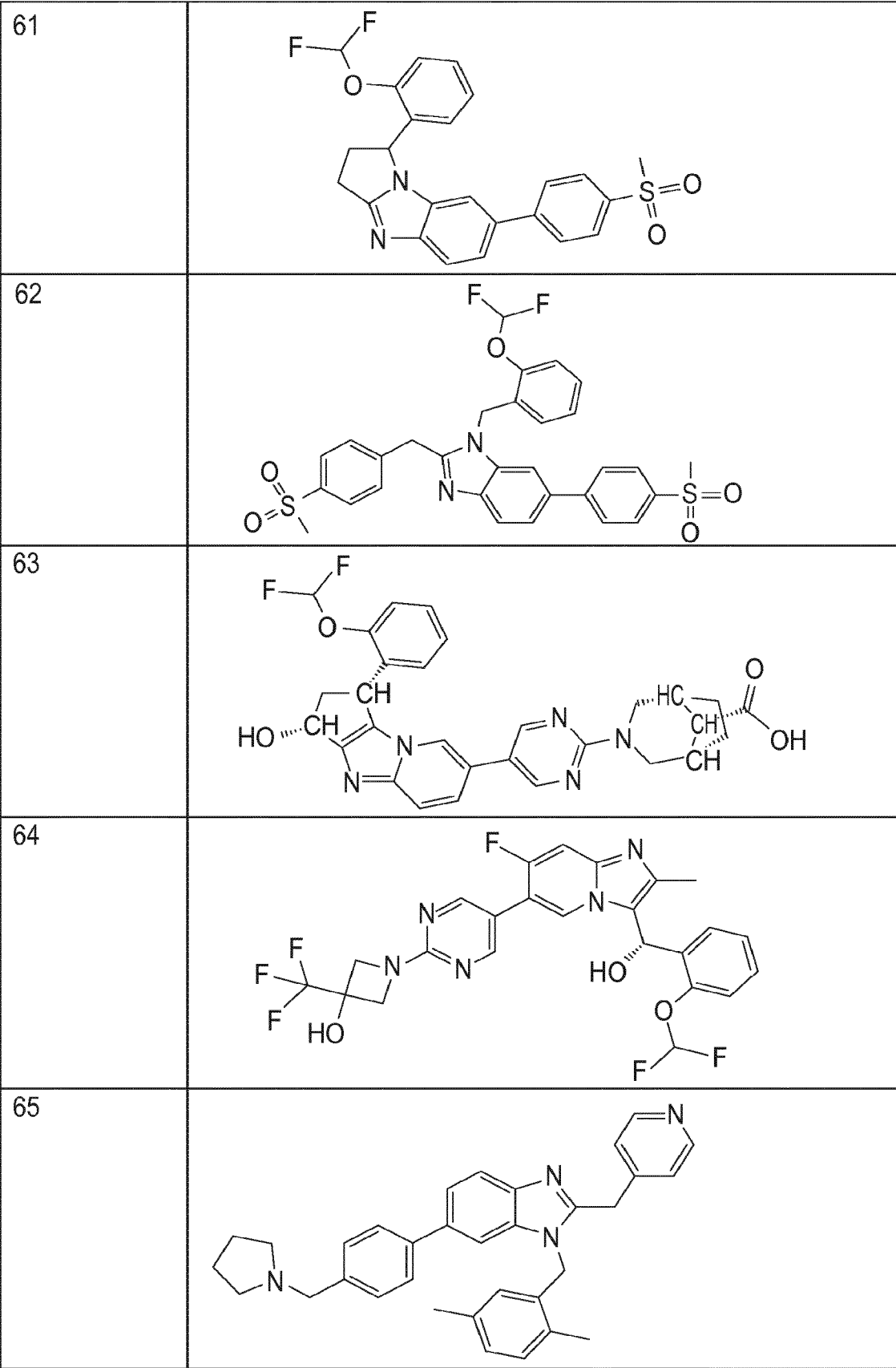

SEQ ID NO: 1 shows the LCDR1 of CA185_01974.0.
SEQ ID NO: 2 shows the LCDR2 of CA185_01974.0.
SEQ ID NO: 3 shows the LCDR3 of CA185_01974.0.
SEQ ID NO: 4 shows the HCDR1 of CA185_01974.0.
SEQ ID NO: 5 shows the HCDR2 of CA185_01974.0.
SEQ ID NO: 6 shows the HCDR3 of CA185_01974.0.
SEQ ID NO: 7 shows the amino acid sequence of the LCVR of CA185_01974.0.
SEQ ID NO: 8 shows the amino acid sequence of the HCVR of CA185_01974.0.
SEQ ID NO: 9 shows the DNA sequence of the LCVR of CA185_01974.0.
SEQ ID NO: 10 shows the DNA sequence of the HCVR of CA185_01974.0.
SEQ ID NO: 11 shows the amino acid sequence of the kappa light chain of CA185_01974.0.
SEQ ID NO: 12 shows the amino acid sequence of the mIgG1 heavy chain of CA185_01974.0.
SEQ ID NO: 13 shows the amino acid sequence of the mFab (no hinge) heavy chain of CA185_01974.0.
SEQ ID NO: 14 shows the DNA sequence of the kappa light chain of CA185_01974.0.
SEQ ID NO: 15 shows the DNA sequence of the mIgG1 heavy chain of CA185_01974.0.
SEQ ID NO: 16 shows the DNA sequence of the mFab (no hinge) heavy chain of CA185_01974.0.
SEQ ID NO: 17 shows the LCDR2 of CA185_01979.0.

SEQ ID NO: 18 shows the LCDR3 of CA185_01979.0.
SEQ ID NO: 19 shows the HCDR1 of CA185_01979.0.
SEQ ID NO: 20 shows the HCDR2 of CA185_01979.0.
SEQ ID NO: 21 shows the HCDR3 of CA185_01979.0.
SEQ ID NO: 22 shows the amino acid sequence of the LCVR of CA185_01979.0.
SEQ ID NO: 23 shows the amino acid sequence of the HCVR of CA185_01979.0.
SEQ ID NO: 24 shows the DNA sequence of the LCVR of CA185_01979.0.
SEQ ID NO: 25 shows the DNA sequence of the HCVR of CA185_01979.0.
SEQ ID NO: 26 shows the amino acid sequence of the kappa light chain of CA185_01979.0.
SEQ ID NO: 27 shows the amino acid sequence of the mIgG1 heavy chain of CA185_01979.0.
SEQ ID NO: 28 shows the amino acid sequence of the mFab (no hinge) heavy chain of CA185_01979.0.
SEQ ID NO: 29 shows the DNA sequence of the kappa light chain of CA185_01979.0.
SEQ ID NO: 30 shows the DNA sequence of the mIgG1 heavy chain of CA185_01979.0.
SEQ ID NO: 31 shows the DNA sequence of the mFab (no hinge) heavy chain of CA185_01979.0.
SEQ ID NO: 32 shows the amino acid sequence of rat TNFα.
SEQ ID NO: 33 shows the amino acid sequence of mouse TNFα.
SEQ ID NO: 34 shows the amino acid sequence of human TNFα.
SEQ ID NO: 35 shows the amino acid sequence of the soluble form of human TNFα.
SEQ ID NO: 36 shows the amino acid sequence of the soluble form of human TNFα, but without the initial "S" (which is a cloning artefact in SEQ ID NO: 35)

DETAILED DESCRIPTION OF THE INVENTION

In one embodiment there is provided an asymmetrical TNFα trimer of a protein subunit comprising (or consisting of) the amino-acid sequence of SEQ ID NO: 36, or corresponding sequence, wherein said TNFα trimer adopts a conformation, when determined by x-ray crystallography, with the Cα atoms of residues 12-18, 47-50, 54-64, 76-82, 91-97, 117-125, 129-137, and 150-156 of SEQ ID NO: 36, or corresponding sequence, for all subunits within 0.9 Å RMSD [root mean square deviation] of the same atoms of the Reference Structure Compound34.pdb, said TNF-α trimer being able to bind TNFR1, but wherein signalling from said bound TNFR1 is attenuated or antagonised, optionally for use in a method of therapy practised on the human or animal body.

The asymmetrical TNFα trimer or distorted TNFα trimer or TNFα trimer of the invention herein are novel structures of TNFα where the normal 3-fold axis of symmetry between the subunits in symmetrical or apo TNFα trimer (Eck and Sprang 1989 JBC 264:17595-605) is disrupted such that the trimer still binds TNFR1, but wherein signalling from said bound TNFR1 is attenuated or antagonised or completely inhibited. Structures of apo TNFα trimer are well known in the art such as 1A8M from the Protein Data Bank (PDB).

The term "corresponding sequence" indicates that the TNFα trimer of the invention may have the wild-type amino sequence of any known animal or human TNFα, in particular human TNFα, for instance SEQ ID NO:36. It may be soluble TNFα (sTNFα) or membrane-bound TNFα, or both.

Soluble homotrimeric TNFα (sTNF) is released from membrane-bound homotrimeric TNFα (mTNF) via proteolytic cleavage by the metalloprotease TNF alpha converting enzyme (TACE/ADAM17; though other proteinases can also release sTNF such as ADAM10, ADAM19, matrix metalloproteinase 7 and proteinase 3 which may yield corresponding soluble TNFα sequences that may be extended or truncated by 1, 2, 3, 4, or 5 amino acids relative to a TACE cleaved sTNFα such as SEQ ID NO: 36). The soluble 52 kDa trimeric sTNF takes on a triangular pyramid shape. A human sequence encompassed by the term mTNF is shown in SEQ ID NO: 34, and a human sequence encompassed by the term sTNF (the product of the action of TACE on SEQ ID NO: 34) is shown in SEQ ID NO: 36. Corresponding sequences of rat and mouse mTNFα are presented in SEQ ID NO:32 and 33, respectively. Corresponding sequences of TNFα from other animals (or known variants of the human sequence) may be readily overlaid with the SEQ ID NO:36 sequence and given the same amino acid numbering as for SEQ ID NO:36 (used in the numbering of TNFα amino acids herein). For instance, the sequence from various animals may be found within the Uniprot database (www.uniprot.org) including human sequences P01375 and Q5STB3. The corresponding sTNFα sequences may be the 157 amino acid C-terminal end of the mTNFα sequence (as SEQ ID NO:36) or may be longer or shorter by one, two or three amino acids (the rat and mouse sequences being 156 amino acids). The corresponding sTNFα sequence may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid substitutions relative to SEQ ID NO:36. The corresponding sTNFα sequence may have 80, 90, 95, 96, 97, 98, or 99% amino acid sequence identity to SEQ ID NO:36 over the length of SEQ ID NO:36.

TNFα trimers of the invention have a common asymmetric structure, as determined by x-ray crystallography (for instance by the methods detailed in Examples 18 and 19). TNFα trimers of the invention may be confirmed by overlaying the atomic coordinates of the Cα atoms of residues 12-18, 47-50, 54-64, 76-82, 91-97, 117-125, 129-137, and 150-156 (the β-sheet residues) of SEQ ID NO: 36, or corresponding sequence, for all subunits and establishing that they are within 0.9 Å RMSD [root mean square deviation] of the same atoms of the Reference Structure Compound34.pdb (for instance as described in Example 19).

The corresponding sequences of the β-sheet residues from any TNFα sequence may be readily determined. For instance the rat and mouse sTNFα sequences are the C-terminal 156 amino acids of mTNFα rather than the 157 of SEQ ID NO:36. It may readily be determined that the corresponding β-sheet residues for overlay in, for instance, the rat sTNFα sequence (of mTNFα sequence SEQ ID NO:32) are residues 12-18, 47-50, 54-64, 75-81, 90-96, 116-124, 128-136, and 149-155.

Atomic coordinates for 64 structures are given in the Supplementary Data of the present invention, each structure given the name "Compound X" which is equivalent to the term "CompoundX.pdb" with X being the formula number (X) of the Compound of FIG. 1 sitting at the centre of each trimer. The atomic coordinates for Reference Structure Compound34.pdb (the structure that is most average of the 64) may thus readily be loaded into appropriate software for the overlay to take place.

In carrying out the overlay the trimer subunit chains will need to be assigned with subunit labels A, B, and C. Which chain is A, B or C may be ascertained by measuring three distances in the x-ray crystallography determined structure between three C-alpha atoms of three identical residues— e.g. P117 in each chain (P116 in the mouse sTNFα sequence); (G121 is also appropriate).

The three distances form a triangle which is equilateral in apo TNFα but distorted in the asymmetric TNFα structures of the invention. The shortest distance is between BC and the longest between AC (for instance AC=13.8 Å, AB=12.3 Å, BC=10.2 Å); thus looking down through the axis of the molecule with N/C termini pointing towards you the longest distance defines C then A chains going anti-clockwise, then B and C again continuing anti-clockwise.

The determination that TNF-α trimers of the invention are able to bind TNFR1, but signalling from said bound TNFR1 is attenuated or antagonised, may be carried out by any of the appropriate methods discussed herein (for instance in Examples 6, 7, 8, 9, 10 [the Reporter Gene Assay], 12).

Given the advantageous properties of the TNF-α trimers of the invention, they are for use in a method of therapy practised on the human or animal body.

The TNF-α trimers of the invention may be administered to the human or animal body either directly or indirectly. By "indirectly" it is meant that symmetrical TNF-α trimer already within the animal or human may be rendered asymmetrical TNF-α trimers of the invention which may be used for therapy. In one embodiment TNF-α trimers of the invention may be administered to the human or animal body indirectly by administering to the animal or human a compound described herein [for instance Compounds (1)-(65)], which may, for instance, cause the formation of a complex of the invention as described herein which may be used in therapy.

The TNFα trimer of the invention may be for use in the treatment and/or prevention of one or more of autoimmune disorders, inflammatory disorders, neurological disorders, neurodegenerative disorders, pain disorders, nociceptive disorders or cardiovascular disorders. For instance, for use in the treatment and/or prevention of one or more of rheumatoid arthritis, Crohn's disease, psoriasis, systemic lupus erythematosus, Alzheimer's disease, Parkinson's disease and epilepsy.

In one aspect herein, the RMSD is within 0.85, 0.8, 0.7, 0.65, 0.6, 0.5, or 0.47 Å.

In a further embodiment there is, similarly, provided a method of treating and/or preventing one or more of autoimmune disorders, inflammatory disorders, neurological disorders, neurodegenerative disorders, pain disorders, nociceptive disorders or cardiovascular disorders, by directly or indirectly administering to a patient in need thereof an asymmetric TNFα trimer of a protein subunit comprising or consisting of the amino-acid sequence of SEQ ID NO: 36, or corresponding sequence, wherein said TNFα trimer adopts a conformation, when determined by x-ray crystallography, with the Cα atoms of residues 12-18, 47-50, 54-64, 76-82, 91-97, 117-125, 129-137, and 150-156 of SEQ ID NO: 36, or corresponding sequence, for all subunits within 0.9 Å RMSD of the same atoms of the Reference Structure Compound34.pdb, said TNF-α trimer being able to bind TNFR1, but wherein signalling from said bound TNFR1 is attenuated or antagonised.

In an aspect of the above embodiments, the conformation of the TNFα trimer of the invention is obtainable or obtained through the TNFα trimer forming a complex with any one of Compounds (1)-(65).

In particular embodiments of the invention: the TNFα trimer antagonises the signalling of the TNFR1 receptor (measured, for instance, by methods disclosed herein); the TNFα trimer has increased stability compared to the stability of a symmetrical TNFα trimer (measured, for instance, by methods disclosed herein), for instance the increase in stability results in an increase in the thermal transition midpoint ($T_m$) of the TNFα trimer of at least 1° C., of at least 10° C., or is between 10° C. and 20° C. (measured, for instance, by methods disclosed herein; the TNFα trimer has an increased binding affinity to the TNFR1 receptor compared to the binding affinity of a symmetrical TNFα trimer to the TNFR1 receptor (measured, for instance, by methods disclosed herein); the TNFα trimer has an increased binding affinity to the TNFR1 receptor by increasing the on rate ($k_{on-r}$) and/or decreasing the off rate ($k_{off-r}$) compared to the $k_{on-r}$ and $k_{off-r}$ values for binding of the symmetrical TNFα trimer to the TNFR1 receptor (measured, for instance, by methods disclosed herein); the TNFα trimer has an increased binding affinity to the TNFR1 receptor by increasing the on rate ($k_{on-r}$) compared to the $k_{on-r}$ value for binding of the symmetrical TNFα trimer to the TNFR1 receptor (measured, for instance, by methods disclosed herein).

In a further embodiment, and as described further herein, the $K_{D-r}$ of the TNFα trimer to the TNFR1 receptor is decreased compared to the $K_{D-r}$ of the symmetrical TNFα trimer to the TNFR1 receptor, wherein:

a) the $K_{D-r}$ of the TNFα trimer to the TNFR1 receptor is decreased by at least 10 times compared to the $K_{D-r}$ of the symmetrical TNFα trimer to the TNFR1 receptor;
b) the $K_{D-r}$ value of the TNFα trimer to the TNFR1 receptor is less than 10 nM.

In a further embodiment, and as described further herein the $K_{D-r}$ of the TNFα trimer to the TNFR1 receptor is decreased compared to the $K_{D-r}$ of the symmetrical TNFα trimer to the TNFR1 receptor, wherein:

a) the $K_{D-r}$ of the TNFα trimer to the TNFR1 receptor is decreased by at least 4 times compared to the $K_{D-r}$ of the symmetrical TNFα trimer to the TNFR1 receptor;
b) the $K_{D-r}$ value of the TNFα trimer to the TNFR1 receptor is less than 600 pM, for instance less than 200 pM.

In a further embodiment, the TNFα trimer of the invention binds to either of the following antibodies with a $K_{D-ab}$ of 1 nM or less: CA185_1979 with a light chain of sequence SEQ ID NO: 26 and heavy chain of sequence SEQ ID NO:27; or CA185_1974 with a light chain of sequence SEQ ID NO: 11 and heavy chain of sequence SEQ ID NO:12 (see herein, for methods of measurement and further information on these antibodies which are specific for the TNFα trimer of the invention). By such binding the TNFα trimer of the invention may be said to have adopted a "stable" asymmetric conformation.

The large number of crystal structures disclosed herein has resulted in the structural understanding of the TNFα trimer of the invention—in particular a clear understanding of the nature of the cleft or cavity or binding site at the centre of the TNFα trimer of the invention (see Example 20 and 21). In particular, the shape of the cavity may be occupied with a compound which forms a complex with the TNFα trimer of the invention to stabilise its advantageous asymmetric conformation. Example 20 describe the residues of TNFα trimer that are always involved in making <4 Å contacts with such compounds (for instance Compounds (1)-(64)), and Example 21 describes a pharmacophore that may be comprised within a compound that is understood to be needed for making these contacts. This understanding readily allows the skilled person to use the pharmacophore as a basis to design many different compounds which can stabilise the complexes of the present invention.

In a further embodiment there is thus provided a complex comprising a TNFα trimer of a protein subunit comprising or consisting of the amino-acid sequence of SEQ ID NO: 36, or corresponding sequence, and a compound that is capable of binding to the TNFα trimer, whereby the compound-trimer complex binds to TNFR1 and attenuates or antagonises the signalling induced by the trimer through TNFR1, wherein the compound, as determined by x-ray crystallography, comprises a pharmacophore which is bound within the TNFα trimer such that it is within 4 Å of all of the following residues: Leu57 of subunit A; Tyr119 of subunit B; Gly121 of subunit B; Gly122 of subunit B; Tyr59 of subunit C; Leu120 of subunit C; and Tyr151 of subunit C, and wherein the pharmacophore consists of 2 fused 5- or 6-member rings (with centres at "R3" and "R2"), one ring (with centre at R2) with an H bond acceptor ("A1") and which is also substituted through a linking non-hydrogen atom to a further 5- or 6-member ring (with centre at "R4").

The pharmacophore may have one or more of: the R2 ring being 5- or 6-membered; the R3 ring being 5- or 6-membered; the R4 ring being 5- or 6-membered; the R2 ring being aromatic; the R3 ring being aromatic; the R4 ring being aromatic; the R2 ring being heteroaromatic; the R3 ring being heteroaromatic; the R4 ring being heteroaromatic; the fused rings sharing 2 atoms; the linking non-hydrogen atom being Carbon, Nitrogen, or Oxygen (which may itself be part of a further ring of the compound that links the R2 ring with the R4 ring to form for instance a tricyclic compound comprising three fused rings—see Compounds 48, 49, 51, 52, 60, 61 or 63 for example); the A1 feature being through a nitrogen or oxygen atom in the R2 ring (which may hydrogen-bond to the sidechain of Tyr151 on subunit C of the TNFα trimer).

Generally R2 is a 5- or 6-membered ring.

In one embodiment R2 is a 5-membered ring. In one aspect of that embodiment, R2 is a 5-membered aromatic ring. In another aspect of that embodiment R2 is a 5-membered heteroaromatic ring.

In another embodiment R2 is a 6-membered ring. In one aspect of that embodiment, R2 is a 6-membered aromatic ring. In another aspect of that embodiment R2 is a 6-membered heteroaromatic ring.

Suitably the pi system of the aromatic/heteroaromatic R2 ring forms a CH-pi interaction with (suitably the C-Beta CH2 group of) the sidechain of Tyr59 on subunit C of the TNFα trimer.

Generally R3 is 5- or 6-membered ring.

In one embodiment R3 is a 5-membered ring. In one aspect of that embodiment, R3 is a 5-membered aromatic ring. In another aspect of that embodiment R3 is a 5-membered heteroaromatic ring.

In another embodiment R3 is a 6-membered ring. In one aspect of that embodiment, R3 is a 6-membered aromatic ring. In another aspect of that embodiment R3 is a 6-membered heteroaromatic ring.

Suitably the pi system of the aromatic/heteroaromatic R3 ring forms a pi stacking interaction with the aromatic ring of the sidechain of Tyr59 on subunit C of the TNFα trimer.

Suitably the pi system of the aromatic/heteroaromatic R3 ring forms a CH-pi interaction with (suitably the C-Delta CH2 group of) the sidechain of Leu57 on subunit A of the TNFα trimer.

Generally, R4 is a 5- or 6-membered ring.

In one embodiment, R4 is a 5-membered ring. In one aspect of that embodiment, R4 is a 5-membered aromatic ring. In another aspect of that embodiment R4 is a 5-membered heteroaromatic ring.

In another embodiment R4 is a 6-membered ring. In one aspect of that embodiment, R4 is a 6-membered aromatic ring. In another aspect of that embodiment R4 is a 6-membered heteroaromatic ring.

Suitably the pi system of the aromatic/heteroaromatic R4 ring forms a CH-pi interaction with (suitably the C-Delta CH2 group of) the sidechain of Leu57 on subunit A of the TNFα trimer.

Generally the fused R3 and R2 rings share 2 atoms.

Generally the linking non-hydrogen atom (the single atom linking [and thus not part of] R2 and R4 rings) is Carbon, Nitrogen, or Oxygen. In a first embodiment the linking non-hydrogen atom is Carbon. In a second embodiment, the linking non-hydrogen atom is Nitrogen. In a third embodiment, the linking non-hydrogen atom is Oxygen.

Generally, A1 is a nitrogen or oxygen atom in (i.e. part of) the R2 ring. Suitably A1 hydrogen-bonds to the sidechain of Tyr151 on subunit C of the TNFα trimer.

It will be apparent to the skilled person of the art that the pharmacophore represents the minimum structural and/or chemical features of the compound-trimer complex and therefore that the compound may include additional structural features.

For example, the compound of the compound-trimer complex may comprise the pharmacophore as defined above wherein the linking non-hydrogen atom is incorporated into an additional ring that links the R2 ring with the R4 ring, thereby forming a fused tricyclic compound (see Compounds 48, 49, 51, 52, 60, 61 or 63 for example).

The pharmacophore may have the R2, R3 and R4 ring, and A1 features arranged within the TNFα trimer structure according to the following Table:

| TNFα trimer amino acid | Pharmacophore Feature within 4 Å of the TNFα trimer amino acid |
| --- | --- |
| Tyr151 subunit C | A1 Hydrogen-bond acceptor |
| Tyr59 subunit C | R2, R3 rings |
| Leu120 subunit C | R2, R3 rings |
| Leu57 subunit A | R3, R4 rings |
| Tyr119 subunit B | R4 ring |
| Gly121 subunit B | R4 ring |
| Gly122 subunit B | R4 ring |

In a further aspect, the pharmacophore may have one or more of the distances between the R1, R2, R3 and A1 features about, exactly or within 10% of the value according to the following Table:

| Site 1 feature | Site 2 feature | Distance (Å) |
| --- | --- | --- |
| A1 | R2 | 1.187 |
| A1 | R3 | 2.737 |
| A1 | R4 | 5.661 |
| R2 | R3 | 2.107 |
| R2 | R4 | 4.650 |
| R3 | R4 | 5.088 |

In a yet further aspect, the pharmacophore may have one or more of the angles between the R1, R2, R3 and A1 features about, exactly or within 10% of the value according to the following Table:

| Site 1 feature | Site 2 feature | Site 3 feature | Angle (degrees) |
| --- | --- | --- | --- |
| R2 | A1 | R3 | 46.6 |
| R2 | A1 | R4 | 28.2 |
| R3 | A1 | R4 | 63.9 |
| A1 | R2 | R3 | 109.2 |
| A1 | R2 | R4 | 144.9 |
| R3 | R2 | R4 | 89.5 |
| A1 | R3 | R2 | 24.2 |
| A1 | R3 | R4 | 87.3 |
| R2 | R3 | R4 | 66.0 |
| A1 | R4 | R2 | 6.9 |
| A1 | R4 | R3 | 28.9 |
| R2 | R4 | R3 | 24.5 |

Advantageously, the R3-R2-R4 angle of the pharmacophore defines a banana shape which may be involved in the desymmetrisation of the TNFα trimer of the invention.

The compound comprising the pharmacophore may have 20-41 non-hydrogen atoms, and for instance may be any one of Compounds (1)-(65).

As described herein, the complex of the invention may similarly be for use in a method of therapy practised on the human or animal body (through direct [administration of the complex] or indirect [administration of the compound] administration), or may be directly or indirectly administered to a patient in need thereof in a method of treating and/or preventing one or more of autoimmune disorders, inflammatory disorders, neurological disorders, neurodegenerative disorders, pain disorders, nociceptive disorders, and/or cardiovascular disorders; for instance in the treatment and/or prevention of one or more of rheumatoid arthritis, Crohn's disease, psoriasis, systemic lupus erythematosus, Alzheimer's disease, Parkinson's disease and/or epilepsy.

As described herein, the complex of the invention may similarly comprise protein subunits comprising or consisting of the amino-acid sequence of SEQ ID NO: 36, or corresponding sequence.

In one embodiment the complex of the invention comprises the TNFα trimer of the invention.

In particular embodiments of the invention: the compound within the complex antagonises the signalling induced by the TNFα trimer through the TNFR1 receptor (measured, for instance, by methods disclosed herein); the compound increases the stability of the TNFα trimer compared to the stability of the TNFα trimer in the absence of the compound (measured, for instance, by methods disclosed herein), for instance the increase in stability results in an increase in the thermal transition midpoint ($T_m$) of the TNFα trimer of at least 1° C., of at least 10° C., or is between 10° C. and 20° C.; the compound increases the binding affinity of the TNFα trimer to the TNFR1 receptor compared to the binding affinity of the TNFα trimer to the TNFR1 receptor in the absence of the compound (measured, for instance, by methods disclosed herein), for instance the compound increases the binding affinity of the TNFα trimer to the TNFR1 receptor by increasing the on rate ($k_{on-r}$) and/or decreasing the off rate ($k_{off-r}$) compared to the $k_{on-r}$ and $k_{off-r}$ values for binding of the TNFα trimer to the TNFR1 receptor in the absence of the compound (as described herein); the compound increases the binding affinity of the TNFα trimer to the TNFR1 receptor by increasing the on rate ($k_{on-r}$) compared to the $k_{on-r}$ value for binding of the TNFα trimer to the TNFR1 receptor in the absence of the compound (measured, for instance, by methods disclosed herein).

In a further embodiment, and as described further herein, the compound decreases the $K_{D-r}$ of the TNFα trimer to the TNFR1 receptor compared to the $K_{D-r}$ of the TNFα trimer to the TNFR1 receptor in the absence of the compound, wherein:

a) the compound decreases the $K_{D-r}$ of the TNFα trimer to the TNFR1 receptor by at least 10 times compared to the $K_{D-r}$ of the TNFα trimer to the TNFR1 receptor in the absence of the compound;

b) the $K_{D-r}$ value of the TNFα trimer to the TNFR1 receptor in the presence of the compound is less than 10 nM.

In a further embodiment, and as described further herein, the compound decreases the $K_{D-r}$ of the TNFα trimer to the TNFR1 receptor compared to the $K_{D-r}$ of the TNFα trimer to the TNFR1 receptor in the absence of the compound, wherein:

a) the compound decreases the $K_{D-r}$ of the TNFα trimer to the TNFR1 receptor by at least 4 times compared to the $K_{D-r}$ of the TNFα trimer to the TNFR1 receptor in the absence of the compound;

b) the $K_{D-r}$ value of the TNFα trimer to the TNFR1 receptor in the presence of the compound is less than 600 pM, for instance less than 200 pM.

In a further embodiment, the compound has an $IC_{50}$ value of 500 nM or less (measured, for instance, by methods disclosed herein).

In a further embodiment of the invention, the complex binds to either of the following antibodies with a $K_{D-ab}$ of 1 nM or less: CA185_1979 with a light chain of sequence SEQ ID NO: 26 and heavy chain of sequence SEQ ID NO:27; or CA185_1974 with a light chain of sequence SEQ ID NO: 11 and heavy chain of sequence SEQ ID NO:12 (see herein, for methods of measurement and further information on these antibodies which are specific for the complexes and TNFα trimer of the invention). By such binding the complex of the invention may be said to adopt a "stable" asymmetric conformation.

In a further embodiment, a pharmaceutical composition is provided comprising the complex of the invention and a pharmaceutically acceptable carrier.

In a further aspect of the invention, the inventors present data supporting the TNFα trimer of the invention, the complex of the invention, and the methods of the invention may be used in therapy without a significant side effect of existing TNFα therapeutics.

Existing inhibitors of TNFα bind and neutralise both soluble and membrane-bound TNFα (sTNFα and mTNFα, respectively) (Nesbitt et al. Inflamm Bowel Dis 2007 13:1323-1332).

It is known that sTNFα has specificity for the TNFR1 receptor, and mTNFα for the TNFR2 receptor (Grell et al. Cell 1995 83:793-802).

Existing inhibitors have black box warnings on their labels describing potential serious consequences of their use in the context of serious infection (particularly TB [tuberculosis], bacterial sepsis, and fungal infections) and malignancy (including lymphoma).

The immune response to TB (as well as *Listeria*) is known to be driven by mTNFα (Garcia et al. Chapter 20 p 187-201 "Roles of Soluble and Membrane TNF and Related Ligands in Mycobacterial Infections: Effects of Selective and Non-selective TNF Inhibitors During Infection" in D. Wallach et al. (eds.), *Advances in TNF Family Research*, Advances in Experimental Medicine and Biology 691, DOI 10.1007/978-1-4419-6612-4_20).

A TNFα inhibitor in development that selectively inhibits sTNFα but not mTNFα has the characteristics of attenuating experimental arthritis without suppressing innate immunity to infection (Zalevsky et al. J of Immunology 2007 179: 1872-1883).

Example 22 investigates how the mTNFα conformation upon binding Compounds described herein does not affect TNFR2 function; TNFR2 proximal and downstream signalling is not impaired.

Accordingly, the TNFα trimer of the invention or the complex of the invention, may be for use in a method of therapy practised on the human or animal body, wherein the use does not induce or cause to worsen an infection and/or malignancy. For example the infection is TB and/or bacterial sepsis and/or fungal infection and/or the malignancy is lymphoma.

Similarly, the inventors provide in the methods of the invention that the administration to the patient in need thereof does not induce or cause to worsen an infection and/or malignancy in said patient. For example the infection is TB and/or bacterial sepsis and/or fungal infection and/or the malignancy is lymphoma.

Assays for Identifying Antagonists: TNFα of the Invention & Complex of the Invention The present inventors have developed assays for identifying antagonists of TNFα. Specifically, the present inventors have developed assays that can be used to identify compounds that bind to trimeric apo forms of TNFα, and that stabilise these trimers in a conformation that is capable of binding to the requisite TNF receptor (TNFR1), and so antagonise signalling through said receptor. Accordingly, the invention discloses assays that are useful for identifying antagonists of TNFα.

In particular, the assays described herein may be used to identify compounds that bind to trimeric apo forms of TNFα, and which form a compound-trimer complex which binds to the TNFR1.

In a preferred embodiment, the assays of the invention identify compounds that bind to the trimeric form of TNFα, but not to the monomeric form. In a particularly preferred embodiment, the compounds bind to and stabilise the trimeric form of TNFα, do not bind to the monomeric form and do not stabilise the dimeric form of TNFα. The stabilisation of TNFα trimers by test compounds may occur by the test compound inhibiting the exchange of monomer units between trimers.

Assays of the invention may comprise determining whether a test compound enhances the binding of the TNFα (TNFα trimers and complexes of the invention) to its receptor, and hence identify TNFα antagonists. In a preferred embodiment, assays of the invention may comprise determining whether a test compound enhances the binding of the TNFα to TNFR1, and hence identify TNFα antagonists which act by increasing the binding of reduced signalling, or non-signalling, forms of TNFα (TNFα trimers and complexes of the invention) to TNFR1.

Assays for identifying TNFα antagonists according to the invention may comprise incubating a sample of TNFα under conditions that destabilise the formation of trimers of TNFα, for example in the presence of DMSO, and measuring the extent to which a test compound stabilises the formation of TNFα trimers. Alternatively, assays for identifying TNFα antagonists according to the invention may involve binding of TNFα to a test compound, and measuring the extent of binding of the TNFα trimer of the invention or compound-trimer complex to the TNFR1.

TNFα and TNFR1 may be purified or present in mixtures, such as in cultured cells, tissue samples, body fluids or culture medium. Assays may be developed that are qualitative or quantitative, with the latter being useful for determining the binding parameters (affinity constants and kinetics) of the test compound to trimeric forms of TNFα, and also of the binding parameters of the TNFα trimer of the invention or compound-trimer complex to the requisite TNF receptor.

The amount of the monomeric, dimeric and trimeric forms of TNFα may be determined by measuring the mass of the monomeric, dimeric and trimeric forms, the molar amount of the monomeric, dimeric and trimeric forms, the concentration of the monomeric, dimeric and trimeric forms, and the molarity of the monomeric, dimeric and trimeric forms. This amount may be given in any appropriate units. For example, the concentration of the monomeric, dimeric and trimeric forms may be given in μg/ml, ng/ml or μg/ml. The mass of the monomeric, dimeric and trimeric forms may be given in pg, ng or μg.

The amount of the monomeric, dimeric or trimeric forms of TNFα in a sample of interest may be compared with the level of the monomeric, dimeric or trimeric forms of TNFα in another sample, such as a control sample, as described herein. In such a method, the actual amount of the monomeric, dimeric or trimeric forms of TNFα, such as the mass, molar amount, concentration or molarity of the monomeric, dimeric or trimeric forms of TNFα in the samples may be assessed. The amount of the monomeric, dimeric or trimeric forms of TNFα may be compared with that in another sample without quantifying the mass, molar amount, concentration or molarity of the monomeric, dimeric or trimeric forms of TNFα. Thus, the amount of the monomeric, dimeric or trimeric forms of TNFα in a sample according to the invention may be assessed as a relative amount, such as a relative mass, relative molar amount, relative concentration or relative molarity of the monomeric, dimeric or trimeric forms of TNFα based on a comparison between two or more samples.

In the present invention, libraries of compounds may be screened in order to identify antagonists of TNFα (i.e. using the assays disclosed herein). Such libraries typically comprise at least 260 compounds. Preferably, such libraries comprise at least 300, at least 500 or even at least 1000 compounds.

Mass Spectrometry Based Assays

The present inventors have found that mass spectrometry may be used to identify compounds that bind to trimeric forms of TNFα and that stabilise these trimers in a conformation (TNFα trimer or complex of the invention) that is capable of binding to TNFR1.

In particular, mass spectrometry may be used to assess whether a compound stabilises the trimeric form of TNFα.

Accordingly, the invention provides an assay for identifying a compound that is capable of binding to a trimeric TNFα protein, whereby the compound-trimer complex (or TNFα trimer of the invention) binds to TNFR1 and antagonises the signalling of the receptor comprising the steps of identifying the binding of a test compound to the trimeric form of TNFα in a sample and comparing the binding of the compound to the trimeric form of TNFα to corresponding values from control samples, which comprises conducting a mass spectrometric analysis on a sample containing the TNFα and the compound to detect the amount of the TNFα trimer and comparing the amount of TNFα trimer in the sample with a control sample and selecting a compound that is capable of binding to the trimeric form of TNFα, whereby the compound-trimer complex (or TNFα trimer of the invention) binds to TNFR1 antagonises the signalling of the receptor. The control sample may be identical to the sample being assayed, except that it lacks the test compound. The sample comprising the TNFα and the compound may further comprise a destabilising agent.

In the present invention, a test compound may be added to a solution of TNFα in the presence of a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent is preferably DMSO, typically at a concentration of 5%, 10% or higher. The resulting solution may be analysed using mass spectrometry.

Non-covalent complexes formed between TNFα and test compounds with binding affinities as weak as 1 mM can be detected. Binding stoichiometry may be obtained directly from presence or absence of complexes in which multiple molecules of the test compound are bound. Binding affinities ($K_D$ values) can be determined by measuring the TNFα–test compound complex (compound-trimer complex)/TNFα concentration ratio at known test compound concentrations.

The test compound stabilises the trimeric form of TNFα if it increases the proportion of trimer compared to the amount of trimer observed for a sample containing the TNFα and the destabilising agent in the absence of the test compound. The test compound may increase the amount of trimer by 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of trimer present in a sample containing the TNFα and the destabilising agent in the absence of the test compound.

The test compound may also increase the amount of trimer compared to that observed for a sample of the TNFα in the absence of both the destabilising agent and the test compound. The test compound may increase the amount of trimer by 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of trimer present in a sample containing TNFα in the absence of both the destabilising agent and the test compound.

Trimer stabilisation is evidenced in two ways in the mass spectrometric study.

First there is the physical dissociation of the TNFα trimer complex (or TNFα trimer of the invention) which can be measured by the ratio of monomer and trimer observed in the mass spectrum. The dimeric species is not observed in our studies. This dissociation may be an artefact of the high energy process used to introduce molecules into the mass spectrometer. None-the-less it can be used to assess the ability of the test compounds to stabilise the trimeric complex during the nebulisation and ionisation processes and thereby reduce the amount of monomer observed in the mass spectrum, the monomer/trimer ratio being used to determine the degree of stabilisation.

Second, under soft ionisation conditions less energy is imparted to the trimeric complex (or TNFα trimer of the invention) resulting in its intact transmission into the spectrometer thereby more closely reflecting the true solution composition. The electrospray ionisation process results in multiple charging of proteins because, in positive ionisation mode, basic functional groups within certain amino acids acquire a positive charge. Mass spectrometers measure the mass/charge ratio. Therefore, for example a nominally 52,000 Da TNFα trimer will appear at an m/z ratio of 5,200 if it is carrying 10 charges. It is this multiple charging effect that permits spectrometers with a limited mass range to be used in the study of multimeric protein complexes (or TNFα trimers of the invention). Software supplied with the spectrometer allow the user to deconvolute the data to give the mass of the protein as it would appear if it was to carry just a single charge (i.e. its true molecular weight based on its atomic composition).

In folded proteins where many amino acids are buried in the core with only a percentage exposed on the surface typically 6 to 8 positive charges are acquired. No one single charged species predominates, often several species (ions) are observed within a small range, these comprise what is known as the charge state envelope. At the other extreme, where a protein is totally denatured (i.e. unfolded) then many more amino acids are exposed and the typical number of charges acquired may be as high as 20, the charge state envelope also comprises a larger number of charged species as statistically there are now more available sites to accept a charge. Thus the number of charges and the number of charged species comprising the charge state envelope are sensitive readouts on the degree of protein folding. Further, if a folded protein can exist in multiple conformations which differ in the relative number of surface exposed amino acids then shifts in the charge state envelope will reflect these differences.

Under soft nano-electrospray ionisation conditions, mass spectrometric studies of intact, folded TNFα protein show that almost 100% of the TNFα trimer is detected, very little of the TNFα monomer is detected whilst the dimeric species is completely absent.

Under harsher ionization conditions, or when a destabilising agent is added to the TNFα sample, increased levels of the monomeric TNFα are observed with a concomitant reduction in the levels of the trimer. Only a very small quantity of dimer is observed.

Mass spectrometry may also be used to determine whether the test compound binds to the monomeric, dimeric and trimeric forms of TNFα.

Mass spectrometry may also be used to determine the stoichiometry of the test compounds with TNFα, i.e. how many molecules of the test compound bind to TNFα.

Mass spectrometry may also be used to determine whether the compound—TNFα trimer complex (or TNFα trimer of the invention) binds to TNFR1.

Mass spectrometry may also be used to measure the rates at which a test compound binds to TNFα (the "on" rate" $k_{on-c}$) and rate at which the test compound dissociates from the TNFα (the "off" rate or $k_{off-c}$). As used herein, the symbol "$K_{D-c}$" denotes the binding affinity (dissociation constant) of a test compound for TNFα. $K_{D-c}$ is defined as $k_{off-c}/k_{on-c}$. Test compounds may have slow "on" rates, which can be measured in minutes by mass spectral analysis of the TNFα and compound-trimer complex (or TNFα trimer of the invention) peak intensities. $K_{D-c}$ values for a test compound can be estimated by repeating this measurement at different TNFα: compound-trimer complex ratios. In a preferred embodiment, binding of compounds of the invention to TNFα trimers is characterized by fast "on" rates, ideally about $10^7\ M^{-1}s^{-1}$, with slow "off" rate, for example values typically of $10^{-3}\ s^{-1}$, $10^{-4}\ s^{-1}$, or no measurable "off" rate.

Mass spectrometry may also be used to determine whether the test compound binds to the TNFα in the presence of TNFR1. This may involve incubating the test compound with TNFα that has been pre-incubated with its receptor. The sample containing the test compound, and pre-incubated TNFα and receptor can then be fractionated to separate molecules according to their molecular size, for example by analytical gel filtration. The resulting fractions may be analysed using mass spectrometry to determine whether the test compound binds to TNFα in the presence of the requisite receptor. The compound will elute in the same fraction as the TNFα if it is bound to the TNFα. The compound will elute in a different fraction than the TNFα if it is not bound to the TNFα. In this case the compound will typically elute in a later gel filtration fraction than the TNFα.

Mass spectrometric methods may include, for example, matrix-assisted laser desorption/ionization mass spectrometry (MALDI MS), surface-enhanced laser desorption/ionization mass spectrometry (SELDI MS), time of flight mass spectrometry (TOF MS) and liquid chromatography mass spectrometry (LC MS).

Receptor-Ligand Binding Assays

Conventional antagonists act by inhibiting the binding of the TNFα to its receptor. The present inventors have used receptor-ligand binding assays to determine whether a test compound enhances the binding of TNFα trimer of the invention or complex of the invention to its receptor. Such receptor-ligand binding assays may be used to hence identify TNFα antagonists which act by increasing the binding of reduced-signalling, or non-signalling, forms of TNFα to TNFR1.

Accordingly, the invention provides an assay for identifying a compound that is capable of binding to a trimeric protein that is TNFα, whereby the compound-trimer complex binds to the TNFR1 and antagonises the signalling of the receptor comprising the step of measuring the level of trimeric TNFα bound to the requisite receptor in a sample comprising a test compound and comparing the level of trimeric TNFα bound to the requisite receptor to corresponding values from control samples, which comprises performing a receptor-ligand binding assay in which a sample of TNFα and the compound, is applied to TNFR1 that has been bound to a surface and comparing the amount of TNFα trimer bound to TNFR1 with a control sample and selecting a compound that is capable of binding to the trimeric form of TNFα, whereby the compound-trimer complex binds to the TNFR1 and antagonises the signalling of the receptor. The control sample may be identical to the sample being assayed, except that it lacks the test compound and/or it contains a known compound. The sample comprising the TNFα and the compound may further comprise a destabilising agent.

A test compound may be added to a solution comprising TNFα and destabilising agent. The level of binding of TNFR1 in the presence of the destabilising agent alone (in a control sample) can be compared with the level of binding of TNFα to its receptor in the presence of the destabilising agent and the test compound. The test compound enhances the binding of TNFα to its receptor if it increases the proportion of TNFα bound to its receptor compared to the level of binding of TNFα to its receptor observed for a sample containing TNFα and the destabilising agent in the absence of the test compound.

The test compound may increase the amount of TNFα bound to its receptor by 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of TNFα bound to its receptor in a sample containing TNFα in the absence of the test compound.

The receptor-ligand binding assay of the invention typically requires TNFα receptor bound to a support. The TNFα receptor may be bound directly to the support, or indirectly, using a linker molecule, such as avidin or streptavidin. The level of binding of TNFα to its receptor can then be assayed by adding a solution of TNFα with a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent is preferably DMSO, typically at a concentration of 5%, 10% or higher.

Binding of TNFα to its receptor is typically determined using an antibody that is specific to TNFα and which is bound to a marker. The marker can be any molecule that can be detected. For example, the marker can be a radioactive isotope (for example $^{125}I$, $^{32}P$, $^{35}S$ and $^{3}H$), fluorescent dye (for example fluorescein, rhodamine), enzyme-conjugate and the like. A substrate for the enzyme is used to quantify the amount of TNFα bound to the surface-bound receptor. Other markers include molecular labels that can be activated to produce light on exposure to certain stimuli, such as electricity. The choice of a marker will depend upon the detection system used.

Receptor-ligand binding assays may be carried out in several formats, including cell-based binding assays, solution-phase assays and immunoassays. The solid supports for receptor-ligand binding reactions preferably contain wells. In general, test compound-trimer complexes (or TNFα trimers of the invention) are incubated with the TNFα receptor for a specified period of time followed by measurement of the amount of the compound-trimer complex that is bound to the receptor. The level of bound compound-trimer complex (or TNFα trimer of the invention) may be calculated by measuring the marker using microscopy, fluorimetry, a scintillation counter, or any available immunoassay.

As used herein, the symbol "$k_{on-r}$" denotes the rate (the "on" rate) at which a compound-trimer complex (or TNFα trimer of the invention) binds to a TNFα receptor. As used herein, the symbol "$k_{off-r}$" denotes the rate (the "off" rate) at which a compound-trimer complex (or TNFα trimer of the invention) dissociates from a TNFα receptor. As used herein, the symbol "$K_{D-r}$" denotes the binding affinity (dissociation constant) of a compound-trimer complex (or TNFα of the invention) for its receptor. $K_{D-r}$ is defined as $k_{off-r}/k_{on-r}$.

Receptor-ligand binding assays may be used to measure the binding affinity of the compound-trimer complexes of the invention (or TNFα trimers of the invention) to TNFR1. In particular, competition assays may be used to compare the $k_{on-r}$ and $k_{off-r}$ values for compound-trimer complexes of the invention (or TNFα trimers of the invention) to TNFR1 and the $k_{on-r}$ and $k_{off-r}$ values of the TNFα binding to its receptor in the absence of the test compound (or apo TNFα), and to determine $K_{D-r}$ values for binding of compound-trimer complexes of the invention (or TNFα trimer of the invention) to the receptor.

Stability Assays

The present inventors have developed methods for determining the effect of test compounds on the stability of TNFα (or the stability of TNFα trimers of the invention relative to apo TNFα trimer). Accordingly, the invention provides an assay for identifying a compound that is capable of binding to a trimeric TNFα protein, whereby the compound-trimer complex binds to the requisite TNFα receptor and modulates the signalling of the receptor comprising the step of measuring the stability of the trimeric TNFα in a sample comprising the compound and comparing the stability of the trimeric TNFα to corresponding values from control samples, which comprises performing an assay to determine the $T_m$ of the trimeric form of TNFα in a sample of the TNFα and the compound, comparing the $T_m$ of the trimeric form of TNFα with a control sample and selecting a compound that is capable of binding to the trimeric form of TNFα, whereby the compound-trimer complex binds to the TNFα receptor and antagonises the signalling of the receptor. The control sample may be identical to the sample being assayed, except that it lacks the test compound and/or it contains a known compound. The sample comprising the TNFα and the compound may further comprise a destabilising agent.

A test compound may be added to a solution comprising TNFα and destabilising agent. The stability of the trimeric form of TNFα in the presence of the destabilising agent alone (in a control sample) can be compared with the stability of the trimeric form of TNFα in the presence of the destabilising agent and the test compound. The test compound enhances the stability of the trimeric form of TNFα if it increases the thermal transition midpoint ($T_m$) of the trimeric form of TNFα compared to the $T_m$ of the trimeric form of TNFα observed for a sample containing the TNFα and the destabilising agent in the absence of the test compound (or asymmetric TNFα trimer of the invention vs. symmetric TNFα). The $T_m$ of the trimeric form of TNFα is the temperature at which 50% of the biomolecules are unfolded. The $T_m$ of the trimeric form of TNFα in the presence and/or absence of the test compound may be measured using any appropriate technique known in the art, for example using differential scanning calorimetry (DSC) or fluorescence probed thermal denaturation assays.

The test compound may increase the $T_m$ of the trimeric form of TNFα by at least 1° C., at least 2° C., at least 5° C., at least 10° C., at least 15° C., at least 20° C. or more compared to the $T_m$ of the trimeric form of TNFα in a sample containing TNFα in the absence of the test compound (or asymmetric TNFα trimer of the invention vs. symmetric TNFα). Preferably the test compound increases the $T_m$ of the trimeric form of TNFα by at least 1° C., more preferably by at least 10° C. and even more preferably by between 10° C. and 20° C.

Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent is preferably DMSO, typically at a concentration of 5%, 10% or higher.

Isothermal Calorimetry Assays

The present inventors have developed isothermal calorimetry methods for determining the effect of test compounds on the binding affinity of TNFα for their receptors (or the effect of asymmetric TNFα trimers of the invention vs symmetric TNFα trimers on receptor binding).

Accordingly, the invention provides an assay for identifying a compound capable of binding to a trimeric TNFα, whereby the compound-trimer complex binds to TNFR1 and antagonises the signalling of the receptor comprising the step of measuring the level of trimeric TNFα bound to the receptor in a sample comprising the compound and comparing the level of trimeric TNFα bound to the receptor to corresponding values from control samples (or comparing the binding of asymmetric TNFα trimer of the invention with symmetric TNFα), which comprises performing an isothermal calorimetric analysis to measure the binding affinity of TNFα for the receptor in the presence of the compound; and comparing the binding affinity of TNFα for the receptor with a control sample and selecting a compound capable of binding to a trimeric TNFα, whereby the compound-trimer complex binds to the receptor and antagonises the signalling of the receptor. The control sample may be identical to the sample being assayed, except that it lacks the test compound and/or it contains a known compound.

Aliquots of TNFα may be added sequentially to a reservoir of the receptor. The volume of the aliquots may be in any appropriate range. The aliquots may be of any appropriate volume, such as from 0.1 μl to 10 μl. In a preferred embodiment the aliquots may be 0.5 μl, 1.0 μl, or 3.0 μl in volume. It may be possible to use larger volumes depending on the syringe volume.

Each addition of TNFα will result in the release or absorption of a small amount of heat as the TNFα trimers bind to the receptor. Typically, each addition of TNFα will result in the release of a small amount of heat as the TNFα trimers bind to the receptor. The amount of heat release can be measured using isothermal calorimetry, and this information used to obtain the binding affinity of TNFα with its receptor.

This process can be repeated using sequential additions of a solution comprising TNFα and a test compound to a reservoir of the receptor. Preferably the TNFα and test compound will be in the form of a compound-trimer complex (or an asymmetric TNFα trimer of the invention). Again, the amount of heat release can be measured using isothermal calorimetry, and this information used to obtain the binding affinity of the TNFα with its receptor.

The binding affinities of TNFα and compound-trimer complex (or symmetric vs. asymmetric TNFα trimer of the invention) may be compared to determine whether the compound increases the binding affinity of TNFα to its receptor.

The test compound may increase the binding affinity of TNFα to its receptor by 2 times, 3 times, 4 times, 5 times, 10 times, 20 times, 30 times, 40 times, 50 times, 60 times, 70 times, 80 times, 90 times, 100 times or more compared to the binding affinity of TNFα to its receptor in the absence of the test compound (or asymmetric TNFα trimer of the invention vs. symmetric TNFα trimer).

The binding affinity may be given in terms of binding affinities ($K_{D-r}$) and may be given in any appropriate units, such as μM, nM or pM. The smaller the $K_{D-r}$ value, the larger the binding affinity of TNFα to its receptor.

The $K_{D-r}$ value of TNFα for binding to its receptor in the presence of the test compound may be at least 1.5 times, 2 times, 3 times, 4 times, 5 times, 10 times, 20 times, 30 times, 40 times, 50 times, 60 times, 70 times, 80 times, 90 times, 100 times lower than the $K_{D-r}$ value of the TNFα for binding to its receptor in the absence of the test compound (or asymmetric TNFα trimer of the invention vs. symmetric TNFα trimer).

The $K_{D-r}$ value of TNFα for binding to its receptor in the presence of the test compound may be 1 μM, 100 nM, 10 nM, 5 nM, 1 nM, 100 pM, 10 pM or less. In a preferred embodiment the $K_{D-r}$ value of TNFα for binding to its receptor in the presence of the test compound is 1 nM or less (or asymmetric TNFα trimer of the invention vs. symmetric TNFα trimer).

Competition Assays

The present inventors have developed methods for identifying compounds that are capable of binding to a trimeric TNFα, whereby the compound-trimer complex binds to TNFR1 and antagonises the signalling of the receptor by investigating the ability of a test compound to compete with a probe compound for binding to a trimeric TNFα.

Accordingly, the invention provides an assay which comprises measuring the competition of a test compound with a probe compound for binding to the trimeric form of TNFα and comparing the level of competition thereby observed to corresponding values from control samples and selecting a compound that is capable of binding to a trimeric TNFα protein, whereby the compound-trimer complex binds to TNFR1 receptor and antagonises the signalling of the receptor.

The probe compound may comprise a compound in accordance with the invention that is radiolabelled. Radionuclei that may be used in the probes of the present invention include tritium ($^{3}$H), $^{14}$C, $^{18}$F, $^{22}$Na, $^{32}$F, $^{33}$F, $^{35}$S, $^{36}$Cl, $^{125}$I, $^{131}$I, and $^{99m}$Tc.

In particular, the competition assay may be a fluorescence polarization (FP) assay, where the degree of fluorescence polarization is related to the rotational relaxation time of a fluorescent molecule, and hence, molecular size. Large molecules exhibit a greater degree of polarization than small molecules. Thus, FP assays may be used to measure the interaction of a small fluorescent ligand or probe, with a larger protein, such as TNFα. The degree of polarization provides a direct measure of the bound/free ratio of the fluorescent ligand.

The invention therefore provides a method for identifying a compound that is capable of binding to a trimeric TNFα protein, whereby the compound-trimer complex binds to the TNFR1 receptor and antagonises the signalling of the receptor comprising the steps of measuring the competition of the compound with a probe compound for binding to the trimeric form of TNFα, comparing the level of competition observed to corresponding values from a control sample and selecting a compound that is capable of binding to a trimeric TNFα protein, whereby the compound-trimer complex binds to TNFR1 and antagonises the signalling of the receptor, wherein said method comprises performing a fluorescence polarization assay using the compound and a probe compound, comparing the degree of polarization of the probe compound in the presence of the compound with the degree of polarization in a control sample.

The ability of a test compound to compete with a probe or ligand may be quantified using standard terminology, such as half maximal inhibitory concentration ($IC_{50}$). In this context, $IC_{50}$ values represent the concentration of a compound that is required to result in a 50% inhibition of binding of the probe to the trimeric TNFα. The test compounds may have $IC_{50}$ values of 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 100 pM or less. Preferably, the test compounds have an $IC_{50}$ value of 200 nM or less. More preferably, the test compounds have an $IC_{50}$ value of 150 nM or less or an $IC_{50}$ value of 100 nM or less.

As mentioned above, in the present invention a library of compounds is typically subjected to one or more of the assays described herein in order to identify antagonists of TNFα. Such libraries, which may comprise at least 260 compounds, at least 300, at least 500 or even at least 1000 compounds, may be screened using fluorescence polarization.

When a library of compounds is screened using fluorescence polarization, the method may comprise selecting a compound as an antagonist of the TNFα if the compound results in a particular $IC_{50}$ value. For example, a compound may be identified as a antagonist of TNFα if the compound results in an $IC_{50}$ value of less than 50 μM. In some aspects, compounds are identified where they result in an $IC_{50}$ value of less than 500 nM, less than 200 nM or even less than 100 nM.

A compound from a library may also be identified as an antagonist of TNFα if it has the lowest $IC_{50}$ value out of all the compounds of the library that are tested. Likewise, a compound may be identified as an antagonist of TNFα where it has a low $IC_{50}$ value (i.e. a better $IC_{50}$ value) compared with other compounds of the library. For example, the 50% of compounds of the library which result in the lowest $IC_{50}$ values may be identified as antagonists. In some aspects, the 25% or even 10% of compounds of the library which result in the lowest $IC_{50}$ values may be identified as antagonists.

In one embodiment, the probe compound comprises a compound in accordance with the invention conjugated to a fluorescent ligand. Suitably, the fluorescent ligand is a fluorescent dye having a fluorescence lifetime of 10 ns or less. Typical examples of suitable fluorescent dyes include fluorescein, rhodamine, a Cy dye (for example Cy2, Cy3, Cy3B, Cy3.5, Cy5, Cy5.5 or Cy7), an Alexa Fluor® dye (for example Alexa Fluor® 350, 405, 430, 488, 532, 546, 555, 568, 594, 610, 633, 635, 647, 660, 680, 700, 750 or 790) or a BODIPY® dye (for example BODIPY FL, BODIPY R6G, BODIPY TMR or BODIPY TR). A specific example of a probe compound is described in Example 14.

The control sample may be identical to the sample being assayed, except that it lacks the test compound and/or it contains a known compound.

The sample comprising TNFα and the compound may further comprise a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent is preferably DMSO, typically at a concentration of 5%, 10% or higher.

Although fluorescence polarization may be used to identify antagonists of TNFα, in some aspects of the invention such antagonists may be identified by any assay described herein excluding fluorescence polarization (i.e. by a method that is not fluorescence polarization). In particular, binding of a compound to a trimeric TNFα, and competition of a compound with a probe compound for binding to the trimeric form of TNFα, may be determined by any method other than by fluorescence polarization.

Signalling Through TNFα Receptor TNFR1

The invention may involve a method for identifying a compound that can antagonise (i.e. prevent or reduce) signalling by TNFα-bound TNFR1.

In one embodiment, the invention may involve a method for identifying a compound that can prevent or reduce signalling by TNFα-bound TNFR1. Such a method may comprise contacting TNFR1 with both TNFα and a compound-trimer complex and detecting whether the test compound prevents or reduces the TNFα trimer signalling through the TNFR1. The amount of signalling from TNFR1 treated with the compound-trimer complex can be compared to the amount of signalling from TNFR1 treated with TNFα only (or asymmetric TNFα trimer of the invention vs. symmetric TNFα trimer).

To detect the level of signalling, assays that measure the downstream effects of TNFR1 signalling can be performed. For example, a L929 murine fibrosarcoma cell-killing assay can be used to assess the stimulation of cell death by TNFα. Inhibition of TNFα-induced IL-8 production by human monocytes may also be used to assess whether a test compound inhibits TNFα signalling via its receptor.

Antagonists of TNFα

Using the assays described herein, the present inventors have identified test compounds that bind to trimeric forms of TNFα. These compounds are small molecular entities (SMEs) that have a molecular weight of 1000 Da or less, 750 Da or less, or 600 Da or less. These compounds stabilise a conformation of the trimeric TNFα that binds to TNFR1 and antagonises the signalling of the receptor.

The stabilising effect of compounds of the invention on trimeric forms of TNFα may be quantified by measuring the thermal transition midpoint (Tm) of the trimers in the presence and absence of the compound (or similarly the asymmetric TNFα trimer of the invention vs. a symmetric TNFα trimer). Tm signifies the temperature at which 50% of the biomolecules are unfolded. Compounds which stabilise TNFα trimers will increase the Tm of the trimers. Tm may be determined using any appropriate technique known in the art, for example using differential scanning calorimetry (DSC) or fluorescence probed thermal denaturation assays.

The compounds may bind inside the central space present within the TNFα trimer (i.e. the core of the trimer).

These compounds may turn the TNFα into a TNFR1 antagonist. These compounds are therefore capable of blocking the TNFα signalling without having to compete with the high affinity interaction between the TNFα and its receptor.

The compounds identified by the methods of the invention are allosteric antagonists that bind to the natural agonists of the TNFR1 receptor, i.e. to trimeric forms of TNFα and drive these trimers to adopt a conformation that still binds to the TNFR1 and antagonises signalling by the receptor.

The compounds identified by the methods of the invention can convert the natural TNFα agonists into antagonists. In contrast, conventional TNFα antagonists bind to the TNFα or the TNF receptor and prevent the binding of the TNFα to the receptor.

The compounds identified by the methods of the invention are not limited in terms of their chemical formula or structure (except as provided herein), provided that they bind to TNFα and stabilise a conformation of the trimeric TNFα (e.g. a TNFα trimer of the invention) that binds to TNFR1 and antagonises the signalling of the receptor. The compounds identified by the methods of the invention can therefore be identified using the assays and methods described herein. The compounds identified by the methods of the invention may comprise a benzimidazole moiety or an isostere thereof, for example the compounds of formulae (1)-(65).

The compounds identified by the methods of the invention may increase the binding affinity of TNFα (in the form of a compound-trimer complex) to TNFR1 compared to the binding affinity of the TNFα to the receptor in the absence of the compounds.

The compounds identified by the methods of the invention bind to the trimeric forms of TNFα. Such compounds may bind specifically to the trimeric forms of one or more TNFα. A compound identified by the methods of the invention may bind specifically to only one of the TNF superfamily members (e.g. TNFα), but not to any other TNF superfamily members. A compound identified by the methods of the invention may also bind specifically to two, three, four or up to all of the TNF superfamily members. By specific, it will be understood that the compounds bind to the molecule or molecules of interest, in this case the trimeric form of TNFα, with no significant cross-reactivity to any other molecule, which may include other members of the TNF superfamily. Cross-reactivity may be assessed by any suitable method, for example surface plasmon resonance. Cross-reactivity of a compound for the trimeric form of TNFα with a molecule other than the trimeric form of that particular TNF superfamily member may be considered significant if the compound binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to the trimeric form of TNFα. A compound that is specific for the trimeric form of TNFα may bind to another molecule at less than 90%, 85%, 80%, 75%, 70%, 65%, 60%, 55%, 50%, 45%, 40%, 35%, 30%, 25% or 20% the strength that it binds to the trimeric form of TNFα. Preferably, the compound binds to the other molecule at less than 20%, less than 15%, less than 10% or less than 5%, less than 2% or less than 1% the strength that it binds to the trimeric form of TNFα.

The $K_{D-r}$ value of TNFα for binding to its receptor in the presence of the test compound (i.e. in the form of a compound-trimer complex) may be at least 1.5 times, 2 times, 3 times, 4 times, 5 times, 10 times, 20 times, 30 times, 40 times, 50 times, 60 times, 70 times, 80 times, 90 times, 100 times lower than the $K_{D-r}$ value of TNFα for binding to its receptor in the absence of the test compound. In a preferred embodiment, the $K_{D-r}$ value of the compound-trimer complex for binding to TNFα is decreased at least 1.5 times, preferably at least 3 times, more preferably at least 4 times the $K_{D-r}$ value of the TNFα trimer binding to the TNFR1 in the absence of the test compound, i.e. the binding affinity of the compound-trimer complex for the TNFR1 is preferably increased at least 1.5-fold, preferably at least three-fold, more preferably at least four-fold compared to the binding affinity of TNFα trimer to TNFR1 in the absence of test compound.

The decrease in the $K_{D-r}$ value of the compound-trimer complex for binding to TNFR1 compared to the $K_{D-r}$ value of the TNFα trimer alone binding to the receptor may result from an increase in the on rate ($k_{on-r}$) of the compound-trimer complex binding to the receptor compared to TNFα trimer alone, and/or a decrease in the off rate ($k_{off-r}$) compared to the TNFα trimer alone. In a preferred embodiment, the on rate ($k_{on-r}$) of the compound-trimer complex binding to the receptor is increased compared to the TNFα trimer alone. In another embodiment, the off rate ($k_{off-r}$) of the compound-trimer complex binding to the receptor is decreased compared to the TNFα trimer alone. In a further embodiment, the on rate ($k_{on-r}$) of the compound-trimer complex binding to the receptor is increased, and the off-rate ($k_{off-r}$) of the compound-trimer complex binding to the receptor is decreased, compared to the TNFα trimer alone. The $k_{on-r}$ value of the compound-trimer complex to TNFR1 may be increased by at least 1.5-fold or at least two-fold and preferably at least three fold compared to the $k_{on-r}$ value of the TNFα trimer binding to its receptor in the absence of the compound and/or the $k_{off-r}$ value of the compound-trimer complex to TNFR1 may be decreased by at least 1.2-fold, at least 1.6-fold, at least two-fold, more preferably at least 2.4-fold compared to the $k_{off-r}$ value of the TNFα trimer binding to its receptor in the absence of the compound. Similarly asymmetric TNFα trimers of the invention may be compared with symmetric TNFα trimers.

In one embodiment, the on-rate for compound binding to TNFα trimer ($k_{on-c}$) is faster than the on-rate for compound-trimer complex binding to TNFR1 ($k_{on-r}$). In another embodiment, the off-rate for compound-trimer complex binding to TNFR1 ($k_{off-r}$) is faster than the off-rate for compound binding to TNFα trimer ($k_{off-c}$). In a further embodiment, the on-rate for compound binding to TNFα trimer ($k_{on-c}$) is faster than the on-rate for compound-trimer complex binding to TNFR1 ($k_{on-r}$), and the off-rate for compound-trimer complex binding to TNFR1 ($k_{off-r}$) is faster than the off-rate for compound binding to TNFα trimer ($k_{off-c}$). In a preferred embodiment, the $K_{D-c}$ value of the compound for binding to TNFα trimer is lower than the $K_{D-r}$ value of the compound-trimer complex for binding to TNFR1, i.e. the compound has a higher affinity for the trimer than the compound-trimer complex has for the receptor.

The $k_{on-r}$, $k_{off-r}$, and $K_{D-r}$ values for both the compound-trimer complex and the TNFα trimer to TNFR1 may be determined using any appropriate technique, for example surface plasmon resonance, mass spectrometry and isothermal calorimetry, as described in the Examples herein. The $K_{D-r}$ value of TNFα for binding to its receptor in the presence of the test compound may be 1 μM, 100 nM, 10 nM, 5 nM, 1 nM, 100 pM, 10 pM or less. In a preferred embodiment the $K_{D-r}$ value of TNFα for binding to its receptor in the presence of the test compound (i.e. in a compound-trimer complex) is 1 nM or less. In a more preferred embodiment, the $K_{D-r}$ value of a compound-trimer complex for binding to TNFR1 is less than 600 pM, more preferably less than 500 pM, less than 400 pM, less than 300 pM, less than 200 pM, less than 100 pM or less than 50 pM. In a most preferred embodiment the $K_{D-r}$ value of a compound-trimer complex for binding to TNFR1 is less than 200 pM. This may similarly be done for asymmetric TNFα trimers of the invention vs. symmetric TNFα trimers.

Compounds identified by the methods of the invention may be identified by an assay which comprises determining the $K_{D-r}$ of the trimeric form of TNFα in a sample of TNFα and the compound; comparing the $K_{D-r}$ of the trimeric form of TNFα in the sample with a control sample; and selecting a compound of the invention.

The compounds identified by the methods of the invention may completely or partially inhibit signalling through TNFR1 when TNFα in the form of a compound-trimer complex binds to the receptor. The compound may act to reduce signalling through TNFR1 by at least 10%, 20%, 30%, 40%, 50%, 60%, 70%, 80%, 90% or 100%. Any change in the level of signalling may be measured by any appropriate technique, including measuring reporter gene activity by alkaline phosphatase or luciferase, NF-κB translocation using machines such as the Cellomics Arrayscan, phosphorylation of downstream effectors, recruitment of signalling molecules, or cell death.

The compounds identified by the methods of the invention may antagonise at least one of the downstream effects of signalling through TNFR1 when TNFα in the form of a compound-trimer complex binds to the receptor. Such effects are discussed herein and include TNFα-induced IL-8, IL17A/F, IL2 and VCAM production, TNFα-induced NF-κB activation and neutrophil recruitment. Standard techniques are known in the art for measuring the downstream effects of TNFα. The compounds identified by the methods of the invention may antagonise at least 1, 2, 3, 4, 5, 10 or up to all of the downstream effects of signalling through TNFR1.

The activity of the compounds identified by the methods of the invention may be quantified using standard terminology, such as $IC_{50}$ or half maximal effective concentration ($EC_{50}$) values. $IC_{50}$ values represent the concentration of a compound that is required for 50% inhibition of a specified biological or biochemical function. $EC_{50}$ values represent the concentration of a compound that is required for 50% of its maximal effect. The compounds identified by the methods of the invention may have $IC_{50}$ or $EC_{50}$ values of 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 100 pM or less. $IC_{50}$ and $EC_{50}$ values may be measured using any appropriate technique, for example cytokine production can be quantified using ELISA. $IC_{50}$ and $EC_{50}$ values can then be generated using a standard 4-parameter logistic model also known as the sigmoidal dose response model.

Antibody Assays

Antibodies for use in assays of the present invention are:
CA185_1979 with a light chain of sequence SEQ ID NO: 26 and heavy chain of sequence SEQ ID NO:27; or
CA185_1974 with a light chain of sequence SEQ ID NO: 11 and heavy chain of sequence SEQ ID NO:12.

Antibodies of the invention can be tested for binding to a compound-trimer complex by, for example, standard ELISA or Western blotting. An ELISA assay can also be used to screen for hybridomas that show positive reactivity with the target protein. The binding selectivity of an antibody may also be determined by monitoring binding of the antibody to cells expressing the target protein, for example by flow cytometry.

Antibodies of the invention selectively (or specifically) recognise at least one compound-trimer complex, i.e. epitopes within a compound-trimer complex (or epitopes within the asymmetric TNFα trimers of the invention). An antibody, or other compound, "selectively binds" or "selectively recognises" a protein when it binds with preferential or high affinity to the protein for which it is selective but does not substantially bind, or binds with low affinity, to other proteins. The selectivity of an antibody of the invention for a target a compound-trimer complex may be further studied by determining whether or not the antibody binds to other related compound-trimer complexes or whether it discriminates between them.

An antibody of the invention may bind specifically (or selectively) to compound-trimer complexes comprising the trimeric form of TNFα (or the asymmetric TNFα trimer of the invention).

By specific (or selective), it will be understood that the antibody binds to the compound-trimer complexes (or asymmetric TNFα trimer of the invention) of interest with no significant cross-reactivity to any other molecule, which may include test compounds in the absence of TNFα trimer or TNFα trimers in the absence of a test compound (symmetric TNFα). Cross-reactivity may be assessed by any suitable method described herein. Cross-reactivity of an antibody for a compound-trimer complex with a molecule other than the compound-trimer complex may be considered significant if the antibody binds to the other molecule at least about 5%, 10%, 15%, 20%, 25%, 30%, 35%, 40%, 45%, 50%, 55%, 60%, 65%, 70%, 75%, 80%, 85%, 90% or 100% as strongly as it binds to the compound-trimer complex of interest. An antibody that is specific (or selective) for the compound-trimer complex may bind to another molecule at less than about 90%, 85%, 80%, 75%, 70%, 65%, 60%, 55%, 50%, 45%, 40%, 35%, 30%, 25% or 20% the strength that it binds to the compound-trimer complex. The antibody may bind to the other molecule at less than about 20%, less than about 15%, less than about 10% or less than about 5%, less than about 2% or less than about 1% the strength that it binds to the compound-trimer complex. The antibody specifically (or selectively) binds to a compound-trimer complex compared with (i) the trimeric form of TNFα in the absence of the compound and/or (ii) the compound in the absence of TNFα trimer (or to asymmetric TNFα trimer of the invention vs. symmetric TNFα trimer).

The rates at which an antibody binds to a compound-trimer complex (or asymmetric TNFα trimer of the invention) is referred to herein as the "on" rate $k_{on-ab}$ and the rate at which the antibody dissociates from the compound-trimer complex (or asymmetric TNFα trimer of the invention) is referred to herein as the "off" rate or $k_{off-ab}$. As used herein, the symbol "$K_{D-ab}$" denotes the binding affinity (dissociation constant) of an antibody for a compound-trimer complex (or asymmetric TNFα trimer of the invention). $K_{D-ab}$ is defined as $k_{off-ab}/k_{on-ab}$. Antibodies may have slow "on" rates, which can be measured in minutes by mass spectral analysis of the compound-trimer complex and antibody peak intensities. $K_{D-ab}$ values for an antibody can be estimated by repeating this measurement at different antibody: compound-trimer complex ratios.

The $K_{D-ab}$ value of the antibody for binding to a compound-trimer complex (or asymmetric TNFα trimer of the invention) may be at least about 1.5 times, 2 times, 3 times, 4 times, 5 times, 10 times, 20 times, 30 times, 40 times, 50 times, 60 times, 70 times, 80 times, 90 times, 100 times, 200 times, 300 times or 400 times lower, or lower, than the $K_{D-ab}$ value of the antibody for binding to the trimeric TNFα in the absence of the compound (symmetric TNFα) and/or the $K_{D-ab}$ value of the antibody for binding to the compound in the absence of the trimeric TNFα. The $K_{D-ab}$ value of the antibody for binding to a compound-trimer complex (or asymmetric TNFα trimer of the invention) may be decreased at least about 10 times, at least about 100 times, at least about 200 times, at least about 300 times the $K_{D-ab}$ value of the TNFα trimer binding to the TNFR1 receptor in the absence of the test compound, i.e. the binding affinity of the antibody for the compound-trimer complex (or asymmetric TNFα trimer of the invention) is typically increased at least about 10-fold, suitably at least about 100-fold, more suitably at least about 200-fold, most suitably at least about 300-fold compared to the binding affinity of the antibody to the trimeric TNFα in the absence of the compound (or symmetric TNFα) and/or the binding affinity of the antibody to the compound in the absence of the trimeric TNFα.

The binding affinity may be given in terms of binding affinities ($K_{D-ab}$) and may be given in any appropriate units, such as μM, nM or pM. The smaller the $K_{D-ab}$ value, the larger the binding affinity of the antibody to the compound-trimer complex (or asymmetric TNFα trimer of the invention).

The $K_{D-ab}$ value of the antibody for binding to the compound-trimer complex (or asymmetric TNFα trimer of the invention) may be at least about 1.5 times, 2 times, 3 times, 4 times, 5 times, 10 times, 20 times, 30 times, 40 times, 50 times, 60 times, 70 times, 80 times, 90 times, 100 times lower, or even lower than the $K_{D-ab}$ value of the antibody for binding to the trimeric TNFα in the absence of the compound (or symmetric TNFα) and/or the $K_{D-ab}$ value of the antibody for binding to the compound in the absence of the trimeric TNFα.

The decrease in the $K_{D-ab}$ value of the antibody for binding to the compound-trimer complex (or asymmetric TNFα trimer of the invention) compared to the $K_{D-ab}$ value of the antibody binding to the trimeric TNFα in the absence of the compound (or symmetric TNFα) and/or the $K_{D-ab}$ value of the antibody for binding to the compound in the absence of the trimeric TNFα may result from an increase in the on rate ($k_{on-ab}$) of the antibody binding to the compound-trimer complex (or asymmetric TNFα trimer of the invention) compared to the antibody binding to the trimeric TNFα in the absence of the compound (symmetric TNFα) and/or the antibody binding to the compound in the absence of the trimeric TNFα; and/or a decrease in the off rate ($k_{off-at}$) compared to the antibody binding to the trimeric TNFα in the absence of the compound (or symmetric TNFα trimer) and/or the antibody binding to the compound in the absence of the trimeric TNFα.

The on rate ($k_{on-ab}$) of the antibody binding to the compound-trimer complex (or asymmetric TNFα trimer of the invention) is generally increased compared to the on rate of the antibody binding to the trimeric TNFα in the absence of the compound (symmetric TNFα) and/or the antibody binding to the compound in the absence of the trimeric TNFα. The off rate ($k_{off-ab}$) of the antibody binding to the compound-trimer complex (or asymmetric TNFα trimer of the invention) is generally decreased compared to the off rate of the antibody binding to the trimeric TNFα in the absence of the compound (symmetric TNFα) and/or the antibody binding to the compound in the absence of the trimeric TNFα. Most typically, the on rate ($k_{on-ab}$) of the antibody binding to the compound-trimer complex (or asymmetric TNFα trimer of the invention) is increased, and the off-rate ($k_{off-ab}$) of the antibody binding to the compound-trimer complex (or asymmetric TNFα trimer of the invention) is decreased, compared to the antibody binding to the trimeric TNFα in the absence of the compound (or symmetric TNFα) and/or the antibody binding to the compound in the absence of the trimeric TNFα.

The $k_{on-ab}$ value of the antibody binding to the compound-trimer complex (or asymmetric TNFα trimer of the invention) may be increased by at least about 1.5-fold or at least two-fold and typically at least about three fold compared to the $k_{on-ab}$ value of the antibody binding to the trimeric TNFα in the absence of the compound (symmetric TNFα) and/or the antibody binding to the compound in the absence of the trimeric TNFα and/or the $k_{off-ab}$ value of the antibody binding to the compound-trimer complex (or asymmetric TNFα trimer of the invention) may be decreased by at least about two-fold, at least about 10-fold, at least about 20-fold, at least about 30-fold, at least about 40-fold, at least about 50-fold, at least about 60-fold, at least about 70-fold, at least about 80-fold more suitably at least about 90-fold compared to the $k_{off-ab}$ value of the antibody binding to the trimeric TNFα in the absence of the compound (symmetric TNFα) and/or the antibody binding to the compound in the absence of the trimeric TNFα.

The $k_{on-ab}$, $k_{off-ab}$, and $K_{D-ab}$ values may be determined using any appropriate technique, for example surface plasmon resonance, mass spectrometry and isothermal calorimetry.

The $K_{D-ab}$ value of the antibody binding to a compound-trimer complex (or asymmetric TNFα trimer of the invention) may be 1 nM, 900 pM, 700 pM, 500 pM, 100 pM, 10 pM or less (typically down to about 1 pM). Antibodies of the invention will desirably bind to the compound-trimer complexes of the invention (or asymmetric TNFα trimers of the invention) with high affinity, for example in the picomolar range. The $K_{D-ab}$ value of the antibody binding to a compound-trimer complex (or asymmetric TNFα trimer of the invention) may be 1 nM or less, 900 pM or less, 700 pM or less, 500 pM or less, 400 pM or less, 300 pM or less, 200 pM or less, 100 pM or less, 90 pM or less, 80 pM or less, 70 pM or less, 60 pM or less, 50 pM or less, 40 pM or less, 30 pM or less, 20 pM or less, 10 pM or less (again, down to about 1 pM).

The antibody may be recombinantly produced by routine methods.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

One can easily determine whether an antibody binds to the same epitope as, or competes for binding with, a reference antibody by using routine methods known in the art. For example, to determine if a test antibody binds to the same epitope as a reference antibody of the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention.

To determine if an antibody competes for binding with a reference antibody, the above-described binding methodology is performed in two orientations. In a first orientation, the reference antibody is allowed to bind to a protein/peptide under saturating conditions followed by assessment of binding of the test antibody to the protein/peptide molecule. In a second orientation, the test antibody is allowed to bind to the protein/peptide under saturating conditions followed by assessment of binding of the reference antibody to the protein/peptide. If, in both orientations, only the first (saturating) antibody is capable of binding to the protein/peptide, then it is concluded that the test antibody and the reference antibody compete for binding to the protein/peptide. As will be appreciated by the skilled person, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50%, 75%, 90% or even 99% as measured in a competitive binding assay (see, e.g., Junghans et al., Cancer Res, 1990: 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

The antibodies of the invention may be used to identify compounds of the invention (or complexes of the invention or TNFα trimers of the invention) as described herein. The antibodies of the invention may also be used as target engagement biomarkers. A target engagement biomarker can be used to detect the engagement, i.e. the binding of a ligand to a target of interest. In the present case, the antibodies of the invention only bind to the complexes of compounds of the invention with trimeric forms of TNFα. Therefore, if an antibody of the invention is able to bind to a compound-trimer complex, this is evidence that the ligand (compound) has bound to the target of interest (TNFα trimer). Antibodies of the invention can be modified to add a detectable marker as described herein. Therefore, engagement of a compound of the invention with a target TNFα may be detected using such an antibody.

The use of antibodies of the invention as target engagement biomarkers is potentially useful in a clinical or preclinical environment, where a sample may be taken from a subject being treated according to the present invention. The sample obtained from the subject may be treated with an antibody of the invention in order to determine whether the compound used to treat the subject has bound to the target TNFα (or that asymmetric TNFα trimer of the invention has been formed in the subject). The sample obtained from the subject may be any appropriate tissue or fluid, such as blood, plasma or urine. The subject may be mammalian, typically human.

Accordingly, the invention provides the use of an antibody of the invention as a target engagement biomarker for the detection of a compound-trimer complex (or that an asymmetric TNFα trimer of the invention has been formed) comprising a trimeric TNFα protein and a compound that is capable of binding to the trimeric TNFα protein, whereby the compound-trimer complex (or asymmetric TNFα trimer of the invention) binds to TNFR1 and antagonises the signalling induced by the trimer through the receptor in a sample obtained from a subject.

Similarly, the present invention provides a method of detecting target engagement of a compound to a trimeric TNFα, whereby the compound-trimer complex binds to TNFR1 and antagonises the signalling induced by the trimer through the receptor, said method comprising:

(a) obtaining a sample from a subject administered said compound;

(b) contacting an antibody of the invention to said sample and a control sample, wherein said antibody is detectable;

(c) determining the amount of binding of said detectable antibody to said sample and said control sample, wherein binding of said detectable antibody to said sample greater than binding of said detectable antibody to said control sample indicates target engagement of said compound to said trimeric TNFα.

Methods of detecting antibodies, and measuring the amount of binding of an antibody to a target, are well known in the art. Typically, antibodies can be labelled. Such labels include enzymes, biotin/streptavidin, fluorescent proteins and fluorescent dyes.

Binding of an antibody to a target may be measured, for example, by an immunoassay method. Immunoassays include Western Blotting, ELISA, immunofluorescence, immunohistochemistry and flow cytometry. Any appropriate technique may be used to measure binding of the antibody to the TNFα.

In the method described above, binding of the detectable antibody to the sample from a subject who has been administered the compound is compared with binding of the antibody to a control sample. The control sample may be any appropriate sample. The control sample is typically a "negative control" which is representative of binding of the antibody to the TNFα in the absence of the compound. For example, the sample may be obtained from the patient prior to administration of the compound. The control may also be based on previously determined measurements e.g. from a number of samples from different subjects in the absence of compound. Measurements from about 5, 10, 20, 50 or 100 subjects may be used in determining the control value. The control may be an average value, or a range of all the values obtained.

The experimental conditions e.g. methods of detection are the same for the sample from a subject administered the compound, and for the control sample. The antibody is also the same in both cases.

Greater binding (increased binding) of the detectable antibody to the sample from the patient administered the compound compared with binding of the antibody to the control sample is indicative of target engagement of the compound to the trimeric TNFα. In other words, equivalent or lower binding (decreased binding) for the sample from the patient administered the compound relative to the control indicates that there is no target engagement of said compound. In other words, no significant difference in the two amounts indicates that there is no target engagement.

The skilled person can readily determine when there is increased binding relative to the control. For example when the control is a range of data, target engagement may be determined based on the spread of the data, the difference between the control data and the detected binding of the antibody in the sample in question, and calculated confidence levels. It is also possible to identify target engagement when the detected binding for the sample in question is higher than the maximum amount of binding detected in any negative control.

Target engagement may be detected if binding of the antibody is increased by about 30% or more relative to the highest amount in the control range. Target engagement may also be detected if binding of the antibody is increased by about 40% or more, or about 50% or more relative to the control range. The same applies when the control is an average value, or a single value based on a sample from the patient prior to administration of the compound. There is of course no upper limit to the percentage increase relative to the control.

An antibody of the invention may be used to screen for a compound that elicits a conformational change in a trimeric TNFα (generating an asymmetric TNFα trimer of the invention), wherein said conformational change antagonises the signalling of TNFR1 on binding of the trimeric TNFα.

Further Antibody Assays

As described herein, the present invention provides antibodies that selectively bind to at least one compound-trimer complex (or asymmetric TNFα trimer of the invention) described herein relative to their binding to the compound alone or to TNFα in the absence of the compound (or symmetric TNFα). These antibodies may be used to identify further compounds or classes of compounds having the same properties.

Accordingly, the invention provides an assay for identifying a compound of the invention comprising the steps of:

a) performing a binding assay to measure the binding affinity of a test compound-trimer complex to an antibody of the invention;

b) comparing the binding affinity as measured in step (a) with the binding affinity of a different compound-trimer complex known to bind with high affinity to the antibody referred to in step (a); and c) selecting the compound present in the compound-trimer complex of step (a) if its measured binding affinity is acceptable when considered in the light of the comparison referred to in step (b).

As will be appreciated, the "different" compound-trimer complex referred to in step (b) above will generally be a complex containing the same trimer as the compound-trimer complex of step (a), but a different compound. The compound may be any of compounds (1)-(65).

By "acceptable" in step (c) is meant that the binding affinity of the compound-trimer complex referred to in step (a) and the binding affinity of the different compound-trimer complex referred to in step (b) are approximately comparable. Selective binding of said antibody to said complex is typically measured relative to the binding of said antibody to TNFα in the absence of the compound or to the compound in the absence of TNFα.

The binding affinity of the compound-trimer complex referred to in step (a) will generally be superior to the binding affinity of the different compound-trimer complex referred to in step (b). Suitably, the difference in the binding affinity of the compound-trimer complex referred to in step (a) relative to the binding affinity of the different compound-trimer complex referred to in step (b) will be within limits of 10-fold, 20-fold, 50-fold, 100-fold, 200-fold or 500-fold.

Libraries of compounds can be assayed using the antibodies of the invention. The library compounds can be incubated with said antibody in the presence and absence of TNFα. A compound that forms part of a compound-trimer complex that binds to an antibody of the invention only in the presence of both the TNFα and the compound is a likely candidate to have the same activity as the compounds described herein. The assays disclosed herein may then be used to verify whether the test compound is a compound as described herein.

One or more of the antibodies of the invention may be used in the assay. A generic antibody that is capable of binding to complexes of any compound of the invention with TNFα may be used in the antibody assay of the invention.

The antibody assay of the present invention may be a high throughput assay that is capable of screening a large number of test compounds over a short space of time to identify compounds of the present invention.

The TNFα and its receptors may be purified or present in mixtures, such as in cultured cells, tissue samples, body fluids or culture medium. Assays may be developed that are qualitative or quantitative, with the latter being useful for determining the binding parameters (affinity constants and kinetics) of the test compound to trimeric forms of TNFα, and also of the binding parameters of the compound-trimer complex to TNFR1.

The sample comprising the TNFα and the compound may further comprise a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent may be DMSO, typically at a concentration of 5%, 10% or higher.

The test compounds may have any/all of the properties discussed above.

Therapeutic Indications

TNFα is the archetypal member of the TNF superfamily. TNFα is a pleiotropic cytokine that mediates immune regulation and inflammatory responses. In vivo, TNFα is also known to be involved in responses to bacterial, parasitic and viral infections. In particular, TNFα is known to have a role in rheumatoid arthritis (RA), inflammatory bowel diseases (including Crohn's disease), psoriasis, Alzheimer's disease (AD), Parkinson's disease (PD), pain, epilepsy, osteoporosis, asthma, sepsis, fever, Systemic lupus erythematosus (SLE) and Multiple Sclerosis (MS) and cancer. TNFα is also known to have a role in Amyotrophic Lateral Sclerosis (ALS), ischemic stroke, immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AM), obstructive uropathy, kidney allograft rejection, cisplatin-induced AM and obstructive uropathy.

A compound identified by the methods of the invention or a complex of the invention or a TNFα trimer of the invention may be used (directly or indirectly) to treat, prevent or ameliorate any condition that that can be treated, prevented or ameliorated by a conventional TNFα antagonist. The compound identified by the methods of the invention or the complex of the invention or the TNFα trimer of the invention may be used alone or in combination with a conventional TNFα antagonist. Any condition that results, partially or wholly, from pathogenic signalling through a TNF receptor by TNFα may in principle be treated, prevented or ameliorated according to the present invention. Pathogenic signalling through a TNF receptor by TNFα includes increased signalling through a TNF receptor over and above the normal physiological level of signalling, signalling through a TNF receptor which is initiated normally, but which fails to stop in response to normal physiological signals and signalling through a TNF receptor that is within the normal physiological range of magnitude, but which is initiated by non-physiological means.

The compounds identified by the methods of the present invention that interact with TNFα (and complexes of the invention and TNFα trimers of the invention) are accordingly beneficial in the treatment and/or prevention of various human ailments. These include autoimmune and inflammatory disorders; neurological and neurodegenerative disorders; pain and nociceptive disorders; and cardiovascular disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis, spontaneous infertility, osteoporosis, asthma and muscular dystrophy (including Duchenne muscular dystrophy).

Neurological and neurodegenerative disorders include Alzheimer's disease, Parkinson's disease, Huntington's disease, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction).

In particular, a compound identified by the methods of the invention or a complex of the invention (or TNFα trimer of the invention) may be used to treat or prevent inflammatory disorders, CNS disorders, immune disorders and autoimmune diseases, pain, osteoporosis, fever and organ transplant rejection. In a preferred embodiment, a compound identified by the methods of the invention or a complex of the invention (or TNFα trimer of the invention) may be used to treat or prevent rheumatoid arthritis, inflammatory bowel diseases (including Crohn's disease), psoriasis, Alzheimer's disease, Parkinson's disease, epilepsy, asthma, sepsis, systemic lupus erythematosus, multiple sclerosis, asthma, rhinitis, cancer and osteoporosis. In another preferred embodiment, a compound identified by the methods of the invention or a complex of the invention (or TNFα trimer of the invention) may be used to treat or prevent rheumatoid arthritis (RA), non specific inflammatory arthritis, erosive bone disease, chondritis, cartilage degeneration and/or destruction, juvenile inflammatory arthritis, Still's Disease (juvenile and/or adult onset), juvenile idiopathic arthritis, juvenile idiopathic arthritis (both oligoarticular and polyarticular forms), inflammatory bowel diseases (including Crohn's disease, ulcerative colitis, indeterminate colitis, pouchitis), psoriasis, psoriatic arthopathy, ankylosing spondylitis, Sjogren's Disease, Alzheimer's disease (AD), Behcet's Disease, Parkinson's disease (PD), amyotrophic lateral sclerosis (ALS), ischemic stroke, pain, epilepsy, osteoporosis, osteopenia, anaemia of chronic disease, cachexia, diabetes, dyslipidemia, metabolic syndrome, asthma, chronic obstructive airways (or pulmonary) disease, sepsis, fever, respiratory distress syndrome, systemic lupus erythematosus (SLE), multiple sclerosis (MS) immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AM), obstructive uropathy, kidney allograft rejection, cisplatin-induced AM and obstructive uropathy, eye diseases (including diabetic retinopathy, diabetic macular oedema, retinopathy of prematurity, age related macular degeneration, macular oedema, proliferative and/or non proliferative retinopathy, corneal vascularisation including neovascularization, retinal vein occlusion, various forms of uveitis and keratitis), thryoiditis, fibrosing disorders including various forms of hepatic fibrosis, various forms of pulmonary fibrosis, systemic sclerosis, scleroderma, cancer and cancer associated complications (including skeletal complications, cachexia and anaemia).

Pharmaceutical Compositions, Dosages and Dosage Regimes

Compounds identified by the methods of the invention and a compound-trimer complexes of the invention and TNFα trimers of the invention will typically be formulated into pharmaceutical compositions, together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. In a preferred embodiment the carrier is suitable for oral administration. Depending on the route of administration, the antagonist may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be preferable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present invention are kits comprising compounds identified by the methods of the invention and complexes of the invention (or TNFα trimers of the invention) and instructions for use. The kit may further contain one or more additional reagents, such as an additional therapeutic or prophylactic agent as discussed above.

The compounds identified by the methods of the invention and the compound-trimer complexes of the present invention (or TNFα trimers of the invention) or formulations or compositions thereof may be administered for prophylactic and/or therapeutic treatments.

In therapeutic applications, compounds and compound-trimer complexes (or TNFα trimers of the invention) are administered (directly or indirectly) to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is preferred.

A compound identified by the methods of the invention or a compound-trimer complex of the present invention (or TNFα trimer of the invention) may be administered via one or more routes of administration using one or more of a variety of methods known in the art. As will be appreciated by the skilled artisan, the route and/or mode of administration will vary depending upon the desired results. Examples of routes of administration for compounds or compound-trimer complexes of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, a compound identified by the methods of the invention or a compound-trimer complex of the present invention (or TNFα trimer of the invention) can be administered via a non-parenteral route, such as a topical, epidermal or mucosal route of administration. In an embodiment the compound identified by the methods of the invention or a compound-trimer complex of the invention (or TNFα trimer of the invention) is for oral administration. Indirect administration may also take place as described herein.

A suitable dosage of a compound identified by the methods of the invention or a compound-trimer complex of the invention (or TNFα trimer of the invention) may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, compounds identified by the methods of the invention or compound-trimer complexes of the invention (or TNFα trimers of the invention) may be co-administered with one or other more other therapeutic agents. For example, the other agent may be an analgesic, anaesthetic, immunosuppressant or anti-inflammatory agent.

Combined administration of two or more agents may be achieved in a number of different ways. Both may be administered together in a single composition, or they may be administered in separate compositions as part of a combined therapy. For example, the one may be administered before, after or concurrently with the other.

Crystals, Structural Determination Using Same, and Methods Using 3D Models

The present inventors have discovered that the TNFα trimer of the invention (or complexes of the invention) may be crystallised with novel crystals suitable for x-ray diffraction and for structural determination of the trimers. With quantity of structural information available, for the first time the present invention permits the use of molecular techniques to identify, select and design chemical entities (including inhibitors including those that comprise pharmacophores of the invention) which are capable of binding to the cavity at the centre of the TNFα trimer of the invention.

Accordingly a TNFα trimer crystal is provided with Space Group P 21 21 21 (most common), P 21 21 2, or P 1 21 1. The crystals may be made according to any of the methods known in the art, for instance described in Example 18 (or minor variations therefrom).

In one embodiment the crystals comprise sTNFα, in particular human sTNFα, for instance a polypeptide comprising or consisting of amino acid residues according to SEQ ID NO: 35 or 36.

In embodiments of the invention, the crystal may have unit cell dimensions a=54 Å±1-2 Å, b=81 Å±1-2 Å, c=93 Å±1-2 Å, alpha=90 degree, beta=90 degree, and gamma=90 degree (most common) or a=47.7 Å±1-2 Å, b=95.8 Å±1-2 Å, c=100.7 Å±1-2 Å, alpha=90 degree, beta=99.1 degree, and gamma=90 degree.

In one aspect the crystal comprises any of Compounds (1)-(64).

The crystals may be used to determine the structure of the complex or TNFα trimer of the invention therein, and the resulting 3D model may be stored on a computer, and may be used in methods for determining similar-functioning compounds within the complexes of the invention.

Thus, further provided is a computer comprising executable code for:

a) using the structural coordinates of a TNFα trimer according to any of Compound1.pdb to Compound64.pdb as a 3-dimensional model of an asymmetric TNFα trimer;
b) analysing a binding pocket in the centre of the trimer in the 3-dimensional model; and
c) screening in silico library for small molecules that fit into said binding site.

In a further embodiment there is provided a method of identifying a potential inhibitor of an apo TNFα trimer, comprising the steps of:

a) using the structural coordinates of a TNFα trimer according to any of Compound1.pdb to Compound64.pdb to generate a 3-dimensional model of an asymmetric TNFα trimer;
b) identifying residues of a binding pocket in the centre of the trimer in the 3-dimensional model;
c) generating a specific 3-D target using the binding site residues;
d) employing the specific 3-D target to design or select a potential inhibitor of TNFα trimer;
e) obtaining the potential inhibitor; and
f) contacting the potential inhibitor with an apo TNFα trimer in vitro to determine the ability of said potential inhibitor to interact with said apo TNFα trimer, whereby the ability to interact is an indication that said potential inhibitor of the apo TNFα trimer is determined.

Also provided is a method of designing a compound which binds to an apo TNFα trimer comprising the steps of:

a) using the atomic coordinates of a TNFα trimer according to any of Compound1.pdb to Compound64.pdb to build a 3-dimensional computer model of a binding pocket at the centre of the TNFα trimer;
b) assessing the stereochemical complementarity between a compound and the binding pocket;
c) optimizing stereochemical complementarity in an iterative approach by observing changes in the protein or compound that affect the protein/compound associations; and
d) designing a compound which optimize said protein/compound stereochemical complementarity.

Further provided is a method for identifying a candidate inhibitor that interacts with a binding pocket at the centre of an apo TNFα trimer, comprising the steps of:

a) obtaining a crystal of the invention;
b) obtaining the structural coordinates of amino acids of the crystal of step a);
c) generating a 3-D model of a TNFα trimer using the structural coordinates of the amino acids generated in step b),
d) determining a binding pocket at the centre of the TNFα trimer from the 3-D model;
e) performing computer fitting analysis to design or identify the candidate inhibitor which interacts with the binding pocket; and
f) contacting the designed or identified candidate inhibitor with an apo TNFα trimer in vitro to determine the effect of the inhibitor on TNFα activity.

Also provided is a method of identifying compounds that bind apo TNFα trimer, comprising the steps of:

a) obtaining a 3-D molecular model of a TNFα trimer using the crystals of the invention;
b) using the model of a) in a method of rational drug design to identify candidate compounds that can bind at the centre of the TNFα trimer; and
c) assaying for TNFα activity in the presence of the binding candidate compounds identified in step b) to thereby identify compounds that bind apo TNFα trimer.

Generally there is provided a use of the crystals of the invention (or of the structural co-ordinates of any of Compound1.pdb to Compound64.pdb) in the identification of an inhibitor of an apo TNFα trimer.

Assays to determine if a compound binds to a complex or TNFα of the invention are described herein.

The design of chemical entities that bind to or inhibit the TNFα binding pocket according to this invention generally involves consideration of two factors. First, the entity must be capable of physically and structurally associating with parts or all of the binding pocket. Non-covalent molecular interactions important in this association include hydrogen bonding, van der Waals interactions, hydrophobic interactions and electrostatic interactions.

Second, the entity must be able to assume a conformation that allows it to associate with the TNFα binding pocket directly. Although certain portions of the entity will not directly participate in these associations, those portions of the entity may still influence the overall conformation of the molecule. This, in turn, may have an impact on potency. Such conformational requirements include the overall three-dimensional structure and orientation of the chemical entity in relation to all or a portion of the binding pocket, or the spacing between functional groups of an entity comprising several chemical entities that directly interact with the TNFα binding pocket.

The potential inhibitory or binding effect of a chemical entity on the TNFα binding pocket may be analyzed prior to its actual synthesis and tested by the use of computer modeling techniques. If the theoretical structure of the given entity suggests insufficient interaction and association between it and the binding pocket, testing of the entity is obviated. However, if computer modeling indicates a strong interaction, the compound may then be synthesized and tested for its ability to bind to the binding pocket. This may be achieved by testing the ability of the molecule to inhibit TNFα protein using the assays described herein. In this manner, synthesis of inoperative compounds may be avoided.

A potential inhibitor of the TNFα binding pocket may be computationally evaluated by means of a series of steps in which chemical entities or fragments are screened and selected for their ability to associate with the TNFα binding pocket.

One skilled in the art may use one of several methods to screen chemical entities or fragments for their ability to associate with the TNFα binding pocket. This process may begin by visual inspection of, for example, a TNFα binding pocket on the computer screen based on the TNFα structure coordinates in Compound1.pdb to Compound64.pdb, or other coordinates which define a similar shape generated from a machine-readable storage medium. Selected fragments or chemical entities may then be positioned in a variety of orientations, or docked, within that binding pocket. Docking may be accomplished using software such as QUANTA® [Molecular Simulations, Inc., San Diego, Calif.; now part of Accelrys, San Diego, Calif.] and SYBYL® [Tripos Associates, St. Louis, Mo.], followed by energy minimization and molecular dynamics with standard molecular mechanics force fields, such as CHARMm® [Accelrys, San Diego, Calif.] and AMBER.

Specialized computer programs may also assist in the process of selecting fragments or chemical entities. These include:

1. GRID [P. J. Goodford, "A Computational Procedure for Determining Energetically Favorable Binding Sites on Biologically Important Macromolecules", J. Med. Chem., 28, pp. 849-857 (1985)]. GRID is available from Oxford University, Oxford, UK.
2. MCSS [A. Miranker et al, "Functionality Maps of Binding Sites: A Multiple Copy Simultaneous Search Method." Proteins: Structure, Function and Genetics, 11, pp. 29-34 (1991)]. MCSS is available from Molecular Simulations, San Diego, Calif. 3. AUTODOCK [D. S. Goodsell et al, "Automated Docking of Substrates to Proteins by Simulated Annealing", Proteins: Structure, Function, and Genetics, 8, pp. 195-202 (1990)]. AUTODOCK is available from Scripps Research Institute, La Jolla, Calif.
4. DOCK [I. D. Kuntz et al, "A Geometric Approach to Macromolecule-Ligand Interactions", J. Mol. Biol, 161, pp. 269-288 (1982)]. DOCK is available from University of California, San Francisco, Calif.
5. GLIDE [Schrodinger, Portland, Oreg. 97204, USA; Thomas A. Halgren, Robert B. Murphy, Richard A. Friesner, Hege S. Beard, Leah L. Frye, W. Thomas Pollard, and Jay L. Banks "Glide: A New Approach for Rapid, Accurate Docking and Scoring. 2. Enrichment Factors in Database Screening", J. Med. Chem., 47 (7), pp. 1750-1759 (2004)]

Once suitable chemical entities or fragments have been selected, they can be assembled into a single compound or complex of compounds. Assembly may be preceded by visual inspection of the relationship of the fragments to each other on the three-dimensional image displayed on a computer screen in relation to the structure coordinates of TNFα protein. This would be followed by manual model building using software such as QUANTA® and DISCOVERY STUDIO® [Molecular Simulations, Inc., San Diego, Calif.; now part of Accelrys, San Diego, Calif.], SYBYL® [Tripos Associates, St. Louis, Mo.] or MAESTRO [Schrodinger, Portland, Oreg. 97204, USA], or OPENEYE [Copyright © 1997-2006, OpenEye Scientific Software, SanteFe, N. Mex. 87508, USA].

Useful programs to aid one of skill in the art in building an inhibitor of a TNFα binding pocket in a step-wise fashion, including one fragment or chemical entity at a time, include:

1. CAVEAT [P. A. Bartlett et al, "CAVEAT: A Program to Facilitate the Structure-Derived Design of Biologically Active Molecules", in Molecular Recognition in Chemical and Biological Problems", Special Pub., Royal Chem. Soc, 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)]. CAVEAT is available from the University of California, Berkeley, Calif.
2. 3D Database systems such as ISIS (MDL Information Systems, San Leandro, Calif.). This area is reviewed in Y. C. Martin, "3D Database Searching in Drug Design", J. Med. Chem., 35, pp. 2145-2154 (1992).
3. HOOK [M. B. Eisen et al., "HOOK: A Program for Finding Novel Molecular Architectures that Satisfy the Chemical and Steric Requirements of a Macromolecule Binding Site", Proteins: Struct., Fund, Genet., 19, pp. 199-221 (1994)]. HOOK is available from Molecular Simulations, San Diego, Calif.

Instead of proceeding to build an inhibitor of a TNFα binding pocket in a step-wise fashion one fragment or chemical entity at a time as described above, inhibitory or other TNFα binding compounds may be designed as a whole or "de novo" using either an empty binding pocket or optionally including some portion(s) of a known inhibitor(s) or comprising the pharmacophore described herein. There are many de novo ligand design methods including:

1. LUDI [H.-J. Bohm, "The Computer Program LUDI: A New Method for the De Novo Design of Enzyme Inhibitors", J. Comp. Aid. Molec. Design, 6, pp. 61-78 (1992)]. LUDI is available from Molecular Simulations Incorporated, San Diego, Calif.; now Accelrys, San Diego, Calif.
2. LEGEND [Y. Nishibata et al, Tetrahedron, 47, p. 8985 (1991)]. LEGEND is available from Molecular Simulations Incorporated, San Diego, Calif.; now Acclerys, San Diego, Calif.

3. LEAPFROG® [available from Tripos Associates, St. Louis, Mo.].
4. SPROUT [V. Gillet et al, "SPROUT: A Program for Structure Generation", J. Comput. Aided Mol Design, 7, pp. 127-153 (1993)]. SPROUT is available from the University of Leeds, UK.
5. NEWLEAD (V. Tschinke and N. C. Cohen, "The NEW-LEAD Program: A New Method for the Design of Candidate Structures from Pharmacophoric Hypotheses", J. Med. Chem., 36, 3863-3870 (1993)).

Other molecular modeling techniques may also be employed in accordance with this invention [see, e.g., N. C. Cohen et al, "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)].

Once a chemical entity has been designed or selected by the above methods, the efficiency with which that chemical entity may bind to a TNFα binding pocket may be tested and optimized by computational evaluation. For example, an effective TNFα binding pocket inhibitor must preferably demonstrate a relatively small difference in energy between its bound and free states (i.e., a small deformation energy of binding). Thus, the most efficient TNFα binding pocket inhibitors should preferably be designed with a deformation energy of binding of not greater than about 10 kcal/mole, more preferably, not greater than 7 kcal/mole. TNFα binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to a TNFα binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C [M. J. Frisch, Gaussian, Inc., Pittsburgh, Pa. ©1995]; AMBER, version 4.1 [P. A. Kollman, University of California at San Francisco, ©1995]; QUANTA®/CHARMm® [Accelrys, San Diego, Calif.]; Insight II®/Discovery Studio® [Accelrys, San Diego, Calif. ©2001, 2002]; DelPhi [Accelrys, San Diego, Calif. ©2001, 2002]; and AMSOL [Quantum Chemistry Program Exchange, Indiana University]. These programs may be implemented, for instance, using a Silicon Graphics® workstation such as an INDIG02 with "IMPACT™" graphics. Other hardware systems and software packages will be known to those skilled in the art.

Another approach enabled by this invention, is the computational screening of small molecule databases for chemical entities or compounds that can bind in whole, or in part, to a TNFα binding pocket. In this screening, the quality of fit of such entities to the binding pocket may be judged either by shape complementarity or by estimated interaction energy [E. C. Meng et al., J. Comp. Chem., 13, pp. 505-524 (1992)].

According to another embodiment, the invention provides compounds which associate with a TNFα binding pocket produced or identified by the method set forth above.

Another particularly useful drug design technique enabled by this invention is iterative drug design. Iterative drug design is a method for optimizing associations between a protein and a compound by determining and evaluating the three-dimensional structures of successive sets of protein/compound complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized. The structures Compound1.pdb-Compound64.pdb are provided for this purpose.

In some cases, iterative drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex.

The following Examples illustrate the invention.

EXAMPLES

Example 1—Synthesis of the Compounds of Formulae (1)-(64) & (65)

Example 1(A)—Synthesis of the Compounds of Formulae (1)-(63) & (65)

| Compound No. | Disclosure of synthesis (PCT publication or application No.) |
|---|---|
| 1 | WO2013/186229 Example 1 |
| 2 | WO2013/186229 Example 3 |
| 3 | WO2013/186229 Example 2 |
| 4 | WO2013/186229 Example 6 |
| 5 | WO2013/186229 Example 3 |
| 6 | WO2013/186229 Example 11 |
| 7 | WO2013/186229 Example 12 |
| 8 | WO2013/186229 Example 14 |
| 9 | WO2013/186229 Example 40 |
| 10 | WO2013/186229 Example 21 |
| 11 | WO2013/186229 Example 55 |
| 12 | WO2013/186229 Example 53 |
| 13 | WO2013/186229 Example 51 |
| 14 | WO2013/186229 Example 27 |
| 15 | WO2013/186229 Example 44 |
| 16 | WO2013/186229 Example 29 |
| 17 | WO2013/186229 Example 17 |
| 18 | WO2013/186229 Example 34 |
| 19 | WO2013/186229 Example 330 |
| 20 | WO2013/186229 Example 260 |
| 21 | WO2013/186229 Example 400 |
| 22 | WO2013/186229 Example 704 |
| 23 | WO2013/186229 Example 705 |

-continued

| Compound No. | Disclosure of synthesis (PCT publication or application No.) |
|---|---|
| 24 | WO2014/009295 Example 9 |
| 25 | WO2013/186229 Example 384 |
| 26 | WO2014/009296 Example 1 |
| 27 | WO2013/186229 Example 216 |
| 28 | WO2013/186229 Example 205 |
| 29 | WO2013/186229 Example 206 |
| 30 | WO2013/186229 Example 177 |
| 31 | WO2013/186229 Example 178 |
| 32 | WO2013/186229 Example 490 |
| 33 | WO2013/186229 Example 457 |
| 34 | WO2013/186229 Example 445 |
| 35 | WO2013/186229 Example 211 |
| 36 | WO2013/186229 Example 219 |
| 37 | WO2013/186229 Example 221 |
| 38 | WO2013/186229 Example 493 |
| 39 | WO2013/186229 Example 89 |
| 40 | WO2013/186229 Example 140 |
| 41 | WO2013/186229 Example 148 |
| 42 | WO2013/186229 Example 156 |
| 43 | WO2014/009295 Example 4 |
| 44 | WO2013/186229 Example 513 |
| 45 | WO2013/186229 Example 727 |
| 46 | WO2014/009295 Example 23 |
| 47 | WO2014/009295 Example 314 |
| 48 | WO2015/086527 Example 42 |
| 49 | WO2015/086525 Example 1 |
| 50 | WO2013/186229 Example 1057 |
| 51 | WO2015/086527 Example 15 |
| 52 | WO2015/086525 Example 5 |
| 53 | WO2013/186229 Example 1055 |
| 54 | WO2014/009295 Example 69 |
| 55 | WO2014/009295 Example 274 |
| 56 | WO2014/009295 Example 221 |
| 57 | WO2014/009295 Example 307 |
| 58 | WO2014/009295 Example 41 |
| 59 | WO2014/009295 Example 42 |
| 60 | WO2015/086527 Example 64 |
| 61 | WO2015/086525 Example 96 |
| 62 | WO2013/186229 Example 583 |
| 63 | WO2015/086526 Example 94 |
| 65 | WO2013/186229 Example 330 |

Example 1(B)—Synthesis of the Compound of Formula (64)

Nomenclature

Compounds were named with the aid of ACD/Name Batch (Network) ver. 12.0 or Accelyrs Draw 4.0

Abbreviations

| DCM: | Dichloromethane | EtOAc: | Ethyl acetate |
|---|---|---|---|
| DMF: | N,N-Dimethylformamide | MeOH: | Methanol |
| DMSO: | Dimethylsulfoxide | SiO$_2$: | Silica |
| Et2O: | Diethyl ether | h: | Hour |
| THF: | Tetrahydrofuran | RT: | retention time |
| r.t.: | Room temperature | MeCN: | Acetonitrile |
| br.: | Broad | M: | Mass |
| Brine: | Saturated aqueous sodium chloride solution | | |
| HPLC: | High Performance Liquid Chromatography | | |
| LCMS: | Liquid Chromatography Mass Spectrometry | | |
| ES+: | Electrospray Positive Ionisation | | |
| TEA: | Triethylamine | | |
| TLC: | thin layer chromatography | | |

Analytical Conditions

All NMRs were obtained either at 300 MHz or 400 MHz.

All reactions involving air or moisture-sensitive reagents were performed under a nitrogen atmosphere using dried solvents and glassware.

All compound LCMS data were determined by using the method below.

Method 1:

Waters Acquity-SQD, Waters Acquity UPLC BEH C18, 2.1×50 mm, 1.7 μm column

Mobile phase A: 10 mM Ammonium Formate+0.1% Ammonia

Mobile phase B: 95 MeCN+5% H$_2$O+0.1% Ammonia

Gradient program (Flow Rate 1.0 mL/min, Column Temperature 40° C.):

| Time | A % | B % |
|---|---|---|
| 0.00 | 95 | 5 |
| 0.50 | 95 | 5 |
| 1.75 | 5 | 95 |
| 2.00 | 5 | 95 |
| 2.25 | 95 | 5 |

It will be apparent to the one skilled in the art that different retention times (RT) may be obtained for LCMS data if different analytical conditions are used.

Optical rotations were measured using an Optical Activity PolAAR 2001 polarimeter.

Intermediate 1

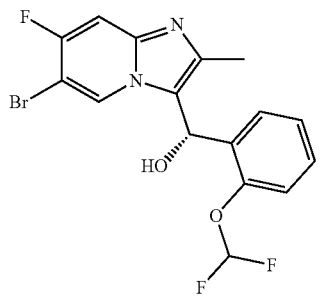 [SMILES: Cc1nc2cc(F)c(Br)cn2c1[C@@H](O)c1ccccc1OC(F)F]

(6-Bromo-7-fluoro-2-methylimidazo[1,2-a]pyridin-3-yl)[2-(difluoromethoxy)phenyl]-methanol—Enantiomer A The racemic title compound was prepared following the procedure described in patent application WO 2014/009295. The racemic mixture thus prepared was separated into the constituent enantiomers by chiral chromatography as detailed below:

The title compound was isolated by purification of racemic (6-Bromo-7-fluoro-2-methylimidazo[1,2-a]pyridin-3-yl)[2-(difluoromethoxy)phenyl]-methanol under LC conditions on Chiralpak AD (100*500 mm*mm, flow 300 mL/min, 30° C., 2-PrOH/heptane 1/9, injection of 230 mL solution at a concentration of 7.5 g/L). The first eluting enantiomer (RT 27 min) was collected and the fractions were evaporated to yield enantiomer A. [α]−12.8°. The second eluting enantiomer (RT 50 min) was collected and the fractions were evaporated to yield enantiomer B. [α]+12.7°

Intermediate 2

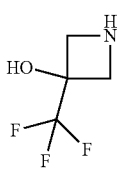

3-(trifluoromethyl)azetidin-3-ol

To a solution of 1-boc-3-azetidinone (11.3 g, 58.4 mmol,) and (trifluoromethyl)trimethylsilane (9.22 g, 64.3 mmol) in THF (100 mL) cooled to ~−5° C. on an ice/brine bath was added portion wise caesium fluoride (9.77 g, 64.3 mmol). The resultant mixture was allowed to stir at r.t, TLC analysis after 4 hours at indicated complete consumption of starting material and a less polar component. The reaction was quenched by the addition of saturated aqueous ammonium chloride solution (100 mL) and the aqueous phase extracted with EtOAc (3×100 mL). The organic phase was separated, dried over sodium sulphate, filtered and the volatiles were removed in vacuo to give a crude oil. The oil thus obtained was dissolved in DCM (100 mL) and trifluoroacetic acid (40 mL) added. The mixture was stirred at ambient temperature for 4 hr. The volatiles were removed in vacuo and the residue azeotroped with toluene (3×150 mL) to give the title compound trifluoroacetate salt as a brown solid (15 g). $^1$H NMR (400 MHz, d$_6$ DMSO): δ/ppm 9.48 (s, 2H), 7.95 (d, J 0.3 Hz, 1H), 4.28 (d, J 13.1 Hz, 2H), 4.06 (m, 2H).

The compound thus obtained was used in the subsequent reaction without further purification.

Intermediate 3

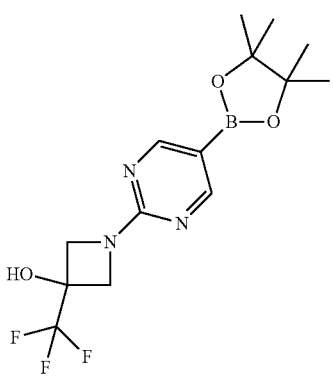 [SMILES: CC1(C)OB(c2cnc(N3CC(O)(C(F)(F)F)C3)nc2)OC1(C)C]

1-[5-(4,4,5,5-tetramethyl-1,3,2-dioxaborolan-2-yl)pyrimidin-2-yl]-3-(trifluoromethyl)azetidin-3-ol To a solution of Intermediate 2 (12 g) in acetonitrile (150 mL) was added TEA (30 mL) and 2-chloro-5-(4,4,5,5-tetramethyl-1,3,2-dioxaborolan-2-yl)pyrimidine (16 g) and the reaction stirred at 65° C. for 18 hours. The solvents were removed in vacuo and the solid residue triturated and washed with distilled water to give a beige solid and dried under high vacuum to give the title compound as a beige solid (18.5 g). $^1$H NMR (300 MHz, d$_6$ DMSO): δ/ppm 8.53 (2H, s), 7.46 (1H, s), 4.33-4.31 (2H, m), 4.10-4.08 (2H, m), 1.29 (12H, s). LCMS (ES$^+$) RT 1.14 min, 346.0 (M+H)$^+$.

Compound (64)

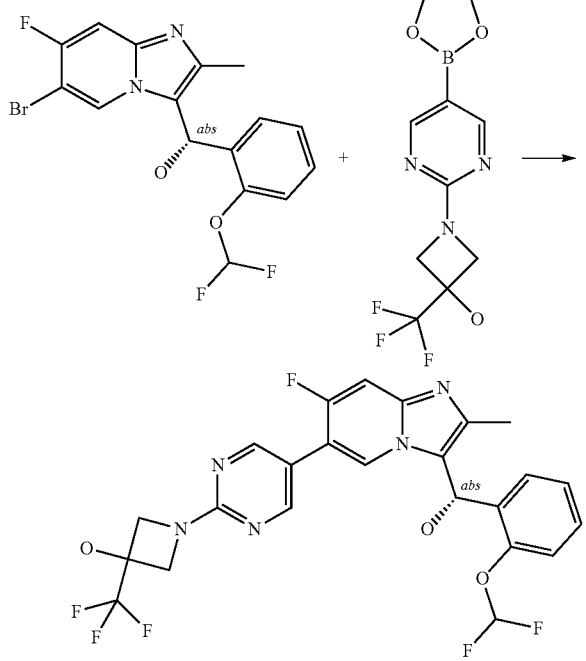

1-[5-[3-[(S)-[2-(difluoromethoxy)phenyl]-hydroxymethyl]-7-fluoro-2-methylimidazo[1,2-a]pyridin-6-yl]pyrimidin-2-yl]-3-(trifluoromethyl)azetidin-3-ol (enantiomer A mixture of Intermediate 1 (0.7 g, 2 mmol), Intermediate 3 (0.7 g, 2 mmol), 1,1'-bis(diphenylphosphino)ferrocene-palladium(II)dichloride dichloromethane complex (36 mg, 0.044 mmol) and 2 M sodium carbonate (2 mL) in dioxane (12 mL) was de-gassed and refluxed for 3 h. The cooled reaction mixture was diluted with EtOAc, washed twice with brine, the organic layer was dried (MgSO4) and concentrated in vacuo. The residue was columned flash column chromatography (SiO2, 0-90% EtOAc/heptane), yielding the title compound as a cream solid (500 mg, 50%). $^1$H NMR (300 MHz, DMSO-d$_6$): δ 8.51 (m, 3H), 7.95 (dd, J$_1$ 2.3 Hz, J$_2$ 6.7 Hz, 1H), 7.46 (m, 2H), 7.36 (m, 2H), 7.12 (m, 2H), 6.42 (d, J 4.4 Hz, 1H), 6.18 (d, J 4.4 Hz, 1H), 4.35 (m, 2H), 4.13 (d, J 10.2 Hz, 2H), 2.12 (s, 3H). LCMS (ES+) RT 1.34 min, 540.0 (M+H)$^+$. [α]+39.7°.

Example 2—Screens for Compounds that Bind to TNFα

The compounds of formulae (3) and (15) have been screened using the following assay.

384 well uncoated plates (standard binding) Meso Scale Discovery plates (MSD) were coated overnight with the extracellular domain of TNFR (TNFR-ECD) (10 μl, 1 ug/mL in PBS). To ensure even distribution plates were centrifuged at 1000 rpm for 2 minutes. The plates were then sealed and stored at +4° C. overnight.

The wells of the plates were then washed three times in 50 µl phosphate buffered saline pH 6.5 (PB) with 0.05% Tween 20 (wash buffer), and then blocked with 50 µl 2% BSA. The plates were then incubated at room temperature on a shaker (600 rpm) for 2 hours. After this incubation plates were washed (3×50 µl wash buffer per well).

Figure 2A:
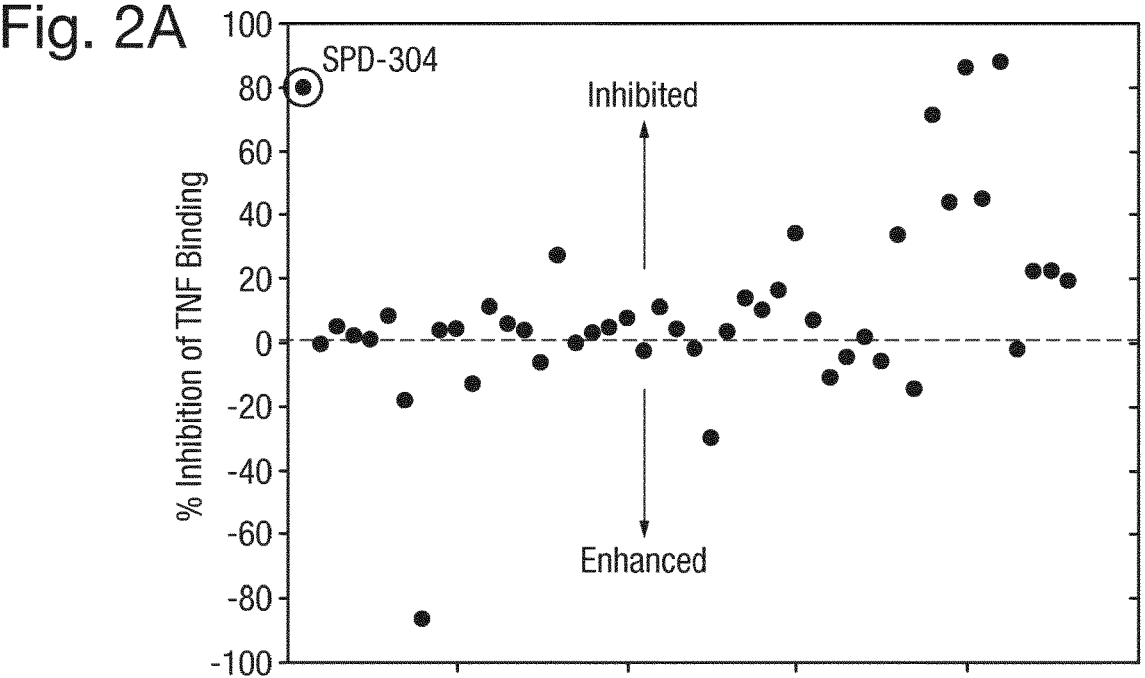
FIG. 2A shows the results of a screen (Mesoscale Discovery assay, MSD) of test compounds that affect the binding of TNFα to the TNF receptor. Multiple test compounds were investigated, and the level of % inhibition of TNFα binding to the TNF receptor calculated.

During the blocking incubation, compounds of formulae (3) and (15) were pre-incubated with TNF (R&D Systems) prior to addition to the pre-blocked and washed MSD plates. For a single point assay as shown in FIG. 2A the compounds were assayed at a final concentration of 100 µM (5% final v/v DMSO).

Figure 2B:
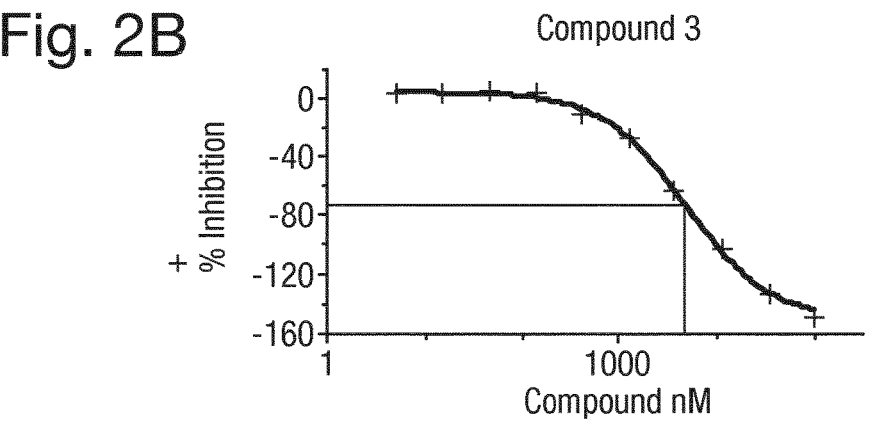
FIG. 2B shows a dose response curve for compound of formula (3) using this assay.
Figure 2C:
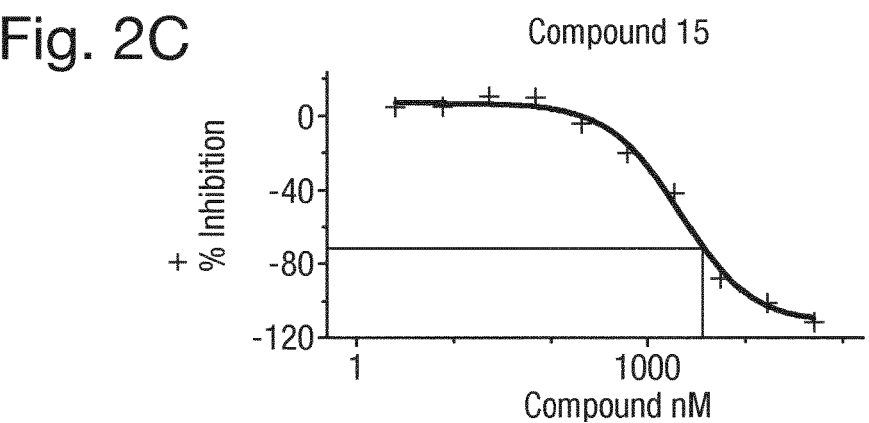
FIG. 2C shows the dose response curve for compound of formula (15).

For the determination of EC50 values (FIGS. 2B and 2C) compounds of formulae (3) and (15) were double or triple diluted in DMSO such that when added to the assay the highest concentration of the test compound was 50 or 100 µM (5% final v/v DMSO). Pre-diluted compounds of formulae (3) and (15) were added at a ratio of 1:1 to 4 ng/mL TNF (final concentration 2 ng/ml), and then incubated at room temperature on a shaker 600 rpm for 1 hour.

10 µl of pre-incubated mixtures of compound of formulae (3) or (15) with TNFα were added to the prepared MSD plate and incubated at room temperature on a shaker for 1 hour.

The plates were then washed with wash buffer (3×50 µl per well). Sulfo-tagged anti-TNF polyclonal antibody was then added to each well and the plates incubated for a further 1.5 hours at room temperature on a shaker.

The plates were then washed (3×50 µl wash buffer per well), followed by the addition of 50 µl MSD Read buffer T plus surfactant (diluted 1 in 2 in $H_2O$) and read on a SECTOR Imager 6000.

For single point assays percentage inhibition was calculated using a control sample without compound.

For EC50s determination results were calculated by standard means using a 4 parameter logistic model (sigmoidal dose response model).

As can be seen from FIG. 2A, the compound labelled "SPD-304", which is representative of TNFα antagonists known in the art, has a % inhibition value of +80%, indicating that this compound inhibits the binding of TNFα to its receptor. In contrast, several of the compounds tested, have negative % inhibition values, indicating that these compounds enhance the binding of TNFα to the TNF receptor.

Likewise, concentration responses for compounds of formula (3) (FIG. 2B) and formula (15) (FIG. 2C) produce negative inhibition curves. In other words the binding of TNFα to the immobilised ECD-TNFR appears to be enhanced as the concentrations of the compounds increase. For this reason an EC50 (concentration of compound giving 50% of total effect) must be calculated rather than an IC50. In this instance the EC50 for compound of formula (3) was 4.6 µM and the EC50 for compound of formula (15) was 3.7 µM.

BIA (Biomolecular Interaction Analysis) using surface plasmon resonance can also be used to measure compound induced enhanced binding of TNFα to TNF receptor. For this purpose a Biacore A100/4000 was used. In what is termed an in-solution competition/enhancement assay the extracellular domain of TNF receptor (ECD-TNFR) was immobilised at pH5 to a level of 1 KRU onto a CMS sensor in HBS-P buffer (10 mM HEPES pH 7.4, 0.15 M NaCl, 0.005% Surfactant P20, BIAcore, GE Healthcare).

Figure 3A:
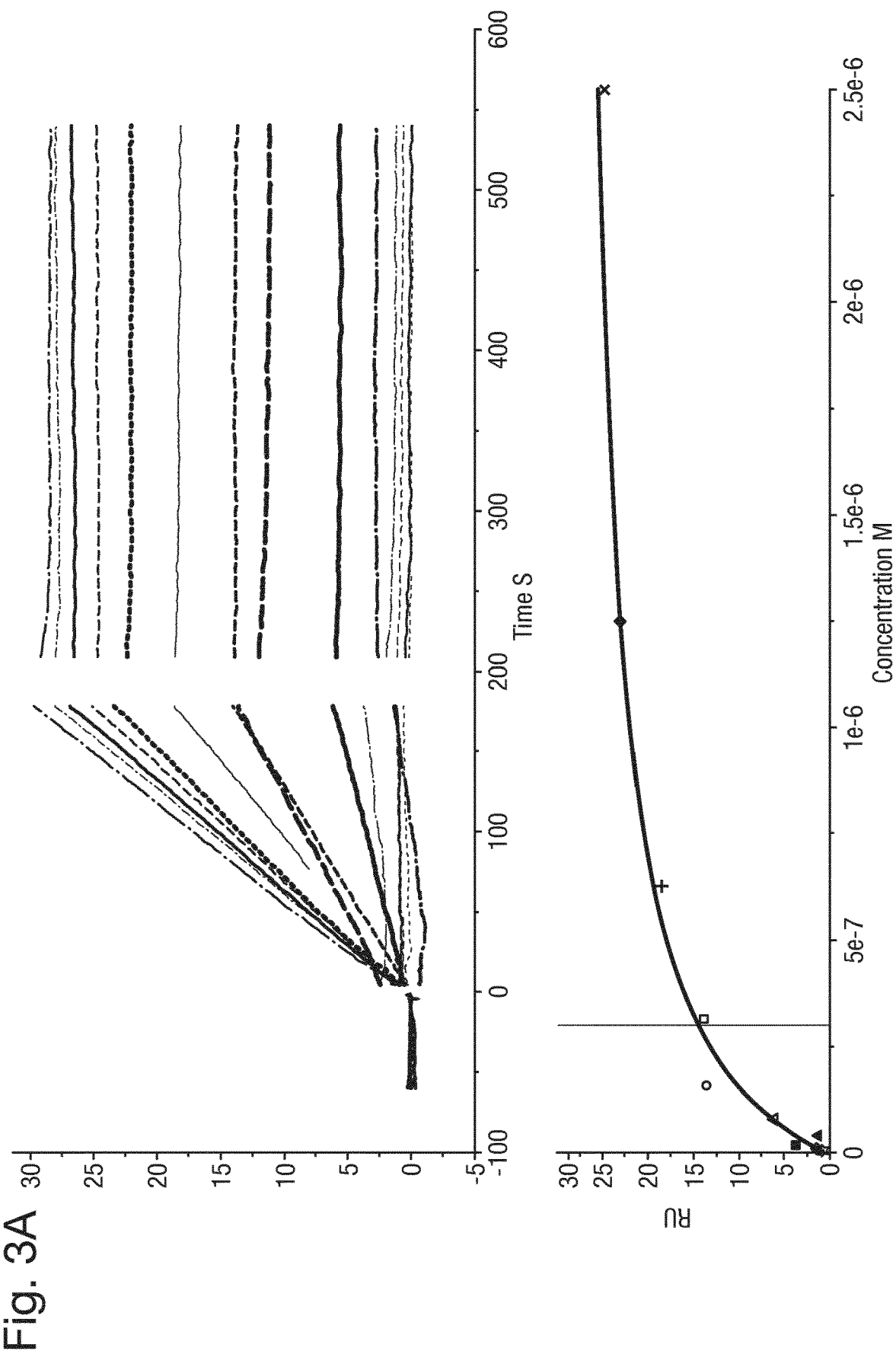
FIG. 3A shows a receptor-ligand binding assay demonstrating the enhanced binding of TNF to the extracellular domain (ECD) of TNFR1 in the presence of compound of formula (3).
Figure 3B:
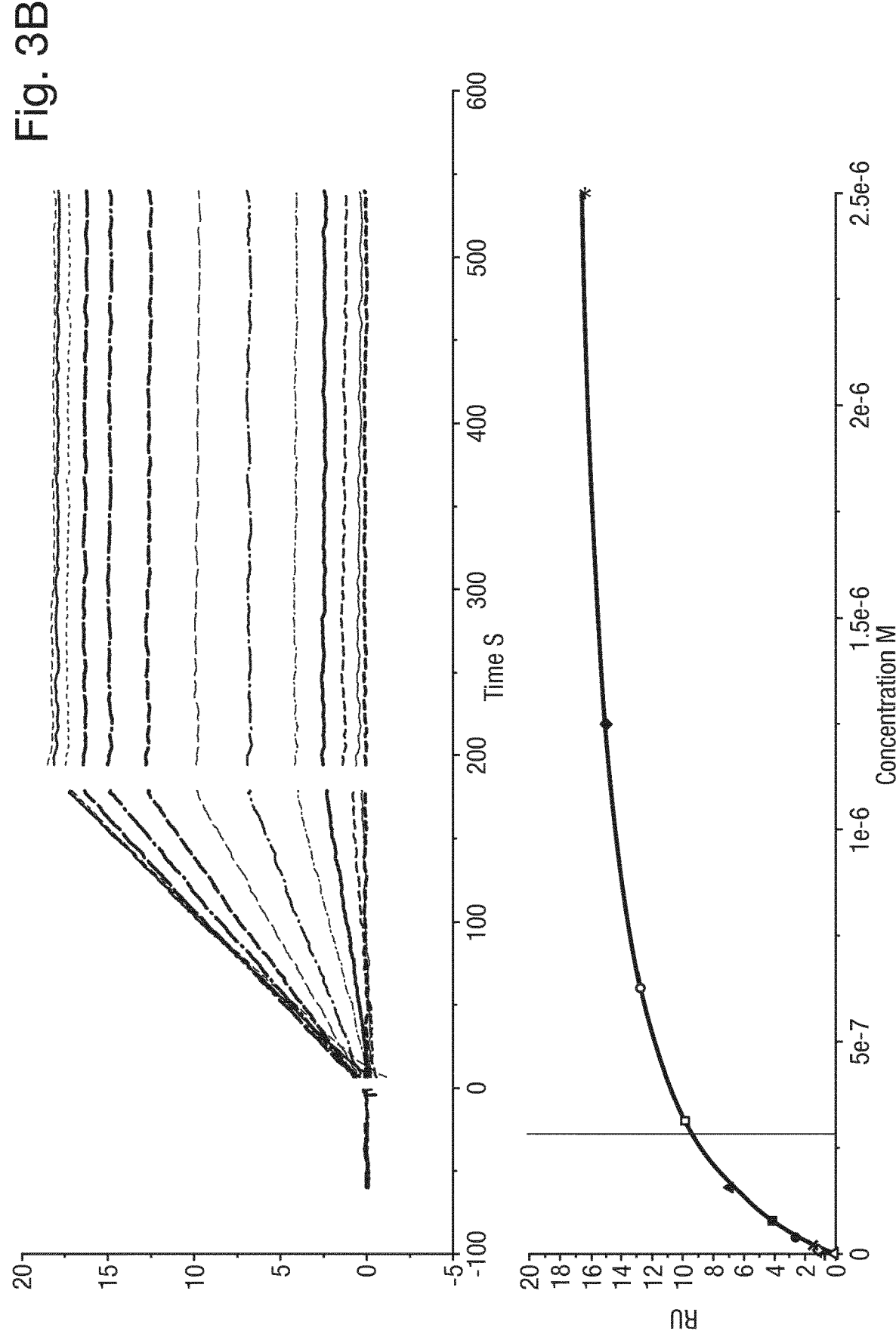
FIG. 3B shows enhanced binding induced by compound of formula (15) in the same assay.

Compounds were serially diluted two fold so that the highest concentration in the assay was 20 µM. For example a typical assay may use 20 µM, 10 µM, 5 µM, 2.5 µM, 1.25 µM, 0.625 µM, 0.312 µM, 0.156 µM, 0.078 µM, 0.039 µM solution of compound. The compounds were mixed with 0.5-1 nM TNFα and equilibrated for at least 5 hours. Control compounds were tested every 10-15 cycles. The TNFα/compound mix was flowed over immobilised TNFR for 3 minutes followed by surface regeneration after each cycle with one 30 ml injection of 10 mM HCL at a flow rate of 30 mL/min. Background subtraction binding curves were analysed using the BIAevaluation software following standard procedures. The EC50 data were determined using a four parameter logistic fit. FIG. 3A and FIG. 3B shows the progress curves for the compounds of formula (3) and formula (15), respectively. The RU (resonance unit) value for TNFα in the absence of compound was subtracted from the curves so these now show only the increase in binding induced by the compounds. The progress curves plateau at higher RU values as the concentration of compound increases. From this an EC50 value can be calculated by determining the concentration of compound that gives a 50% maximal effect using the 4 parameter logistic fit model. In these experiments the EC50 for the compound of formula (3) was calculated to be 298 nM and that for the compound of formula (15) to be 280 nM.

It may be noted that EC50s show inter-assay variability and the conditions for the Biacore assays and MSD assays are very different. As a result the measured EC50s are not expected to be identical for the two assay formats.

Example 3—Mass Spectrometric Analysis of Compound 3 Binding to TNFα

Mass spectrometry was typically performed using a Waters LCT-premier Time-of-Flight mass spectrometer or a Waters SynaptG2 Q-TOF mass spectrometer. Samples were introduced using an Advion Triversa Nanomate nanoflow infusion device which replaces the conventional spectrometer source, sample injection was via an "A" series chip with 5 µM nozzle size at a nominal flow rate of 100 nl/min. Further modifications to the Waters LCT-premier Time-of-Flight mass spectrometer include a customised source cooling device allowing precise control of the source temperature and a commercial pressure regulation device giving precise control over the vacuum conditions in the source region. Together these modifications help retain the TNFα trimer in a native, folded conformation and facilitate the detection of complexes formed with test compounds of weak affinities. Typical settings were Source temperature: 10° C., source pressure 3.74 $e^{-3}$ mbar, analyser pressure 1.54 $e^{-6}$ mbar.

Ions were generated using standard positive ion electrospray conditions resulting in multiple charging of TNFα.

Mass spectrometry is very sensitive to the buffer salts present in the protein sample. Typical buffer salts such as potassium or sodium phosphates have a severely detrimental affect on ionisation. Accordingly protein samples were pre-treated to remove these salts using a Zeba desalt spin column, the protein being exchanged into a mass spectrometry compatible buffer system, typically 50 mM Ammonium Acetate at pH 6.8.

Under soft ionisation conditions when 100% transmission of the trimeric species is observed, under native conditions in a 100% aqueous environment the trimeric form is observed as a charge state envelope comprising the +12, +13 and +14 ions, on addition of 5% v/v DMSO the charge state envelope shifts to lower a m/z (higher z) indicating that, as expected, the organic cosolvent causes partial unfolding in solution of the trimeric species, an increased level of the monomer is also detected. When 10% v/v DMSO is added only the charge state envelope associated with the monomeric form is observed indicating that this level of DMSO disrupts the trimer formation in solution. Typically the test compounds were presented as 10 mM DMSO stock solutions such that when they are incubated with TNFα in solution the final DMSO concentration is 5%. Under soft ionisation conditions the charge state envelope is observed to shift to higher m/z (lower z) compared not only with the 5% DMSO control spectrum but also with the spectrum acquired under 100% aqueous indicating that the test compounds are able to overcome the destabilising effect of the 5% DMSO and afford stabilisation over and above that observed under native conditions. This is evidenced by the changes in the number of charges acquired by the protein under the various conditions described.

The measured "on" rate is an arithmetic product of the rate constant $k_{on}$ and the concentration of the test compound, at high concentrations of the test compound the observed rate is larger than at low concentrations. Experimental measurement of the observed rate by mass spectrometry at different test compound concentrations allows the value of the rate constant ($k_{on}$) to be derived. In a typical experiment a mixture of the test compound and TNFα trimer is prepared at the desired concentration using an Advion Triversa Nanomate robot from stock solutions of TNFα and test compound. The sample is then infused into the mass spectrometer over several minutes during which time the ratio of the free TNFα and TNFα/test compound complex signals in the mass spectrum is recorded. This is repeated for several different test compound/TNFα ratios.

The data recorded for different test compound/TNFα ratios are then fitted to the theoretical one phase logarithmic association curve using Graphpad PRISM v.5 to derive the $k_{on}$ value. This confirmed the low $k_{on}$ value observed on the Biacore.

Test compounds were prepared as 10 mM solutions in dimethylsulphoxide (DMSO). Therefore, it was necessary to establish the effect of DMSO on the native TNFα trimer in the absence of a test compound. DMSO was added to an aqueous solution of TNFα trimer to give a final concentration of 5% v/v and the mass spectrum acquired.

In a 100% aqueous environment, i.e. in the absence of DMSO, a large proportion of TNFα exists in the trimeric form, with a significant proportion of the TNFα monomer. In a 100% aqueous environment, the trimeric form of TNFα is observed as a charge state envelope comprising the +12, +13 and +14 ions (FIG. 4, bottom trace).

Less trimeric TNFα was observed on addition of 5% v/v DMSO. The charge state envelope shifted to a lower mass/charge ratio (m/z) indicating that the DMSO caused partial unfolding of the trimeric species. An increased level of monomeric TNFα was also detected in the presence of 5% v/v DMSO.

Figure 4:
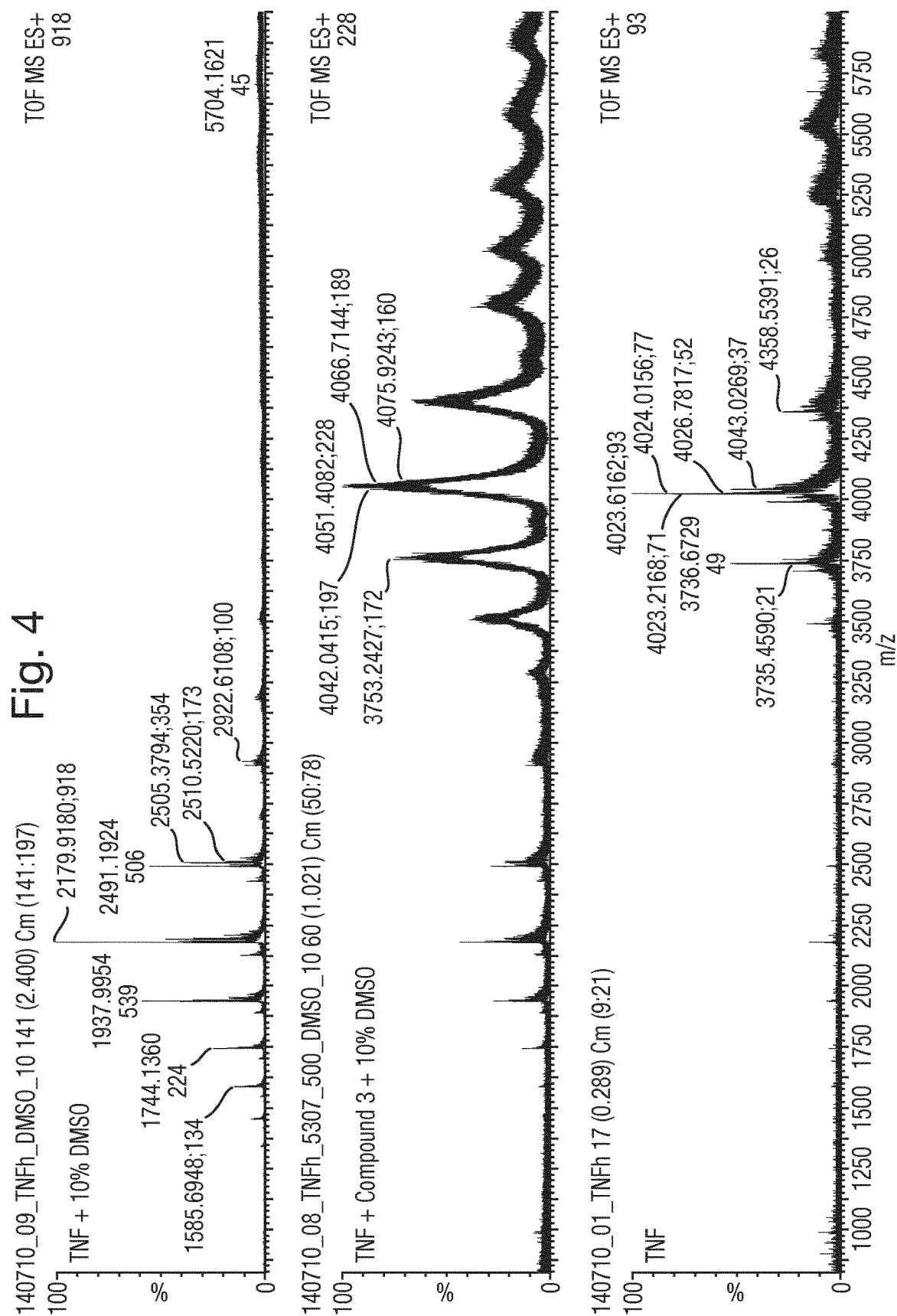
FIG. 4 (bottom trace) shows the deconvoluted mass spectrogram of TNFα in 100% aqueous solution.

When 10% v/v DMSO was added only the charge state envelope associated with the monomeric form is observed indicating that this level of DMSO disrupts trimer formation of TNFα (FIG. 4, top trace).

The compound of formula (3) was added to a solution containing TNFα and 5% v/v DMSO and the mass spectrum acquired. Trimeric TNFα was found to exist in the solution of 5% v/v DMSO in the presence of the compound of formula (3) (FIG. 4, middle trace). The charge state envelope observed for the compound of formula 3-bound TNFα shifts to higher m/z values (exclusively+12 and +11), revealing that the compound of formula (3) not only overcame the weak unfolding influence of the DMSO on TNFα, but also resulted in a stabilisation of the trimeric TNFα complex over and above that observed in the absence of DMSO.

To address the concern that it was necessary to have DMSO present in order to weaken the trimeric TNFα complex sufficiently before the test compounds could bind, the experiment was repeated with a water-soluble compound under 100% aqueous conditions. In the absence of DMSO compound bound to the trimeric complex causing the same shift to a higher m/z ratio that was observed when DMSO was present (data not shown). This confirmed that the test compounds do not need DMSO to be present to bind to the TNFα trimer and can exert their stabilizing affect regardless of the presence of a destabilising agent.

Further evidence for the stabilization of the trimeric form of TNFα by the test compounds was obtained from analyzing the samples under harsher ionization conditions that tend to favour breakdown of the native trimeric form into monomers. When TNFα was bound to the compound of formula (3) the quantity of TNFα monomer detected under these conditions was significantly reduced (data not shown). This suggests that the test compounds protect the TNFα trimer from mass spectrometric disruption.

Example 4—Stoichiometry of the TNFα—the Compound of Formula (3) Complex

Figure 5:
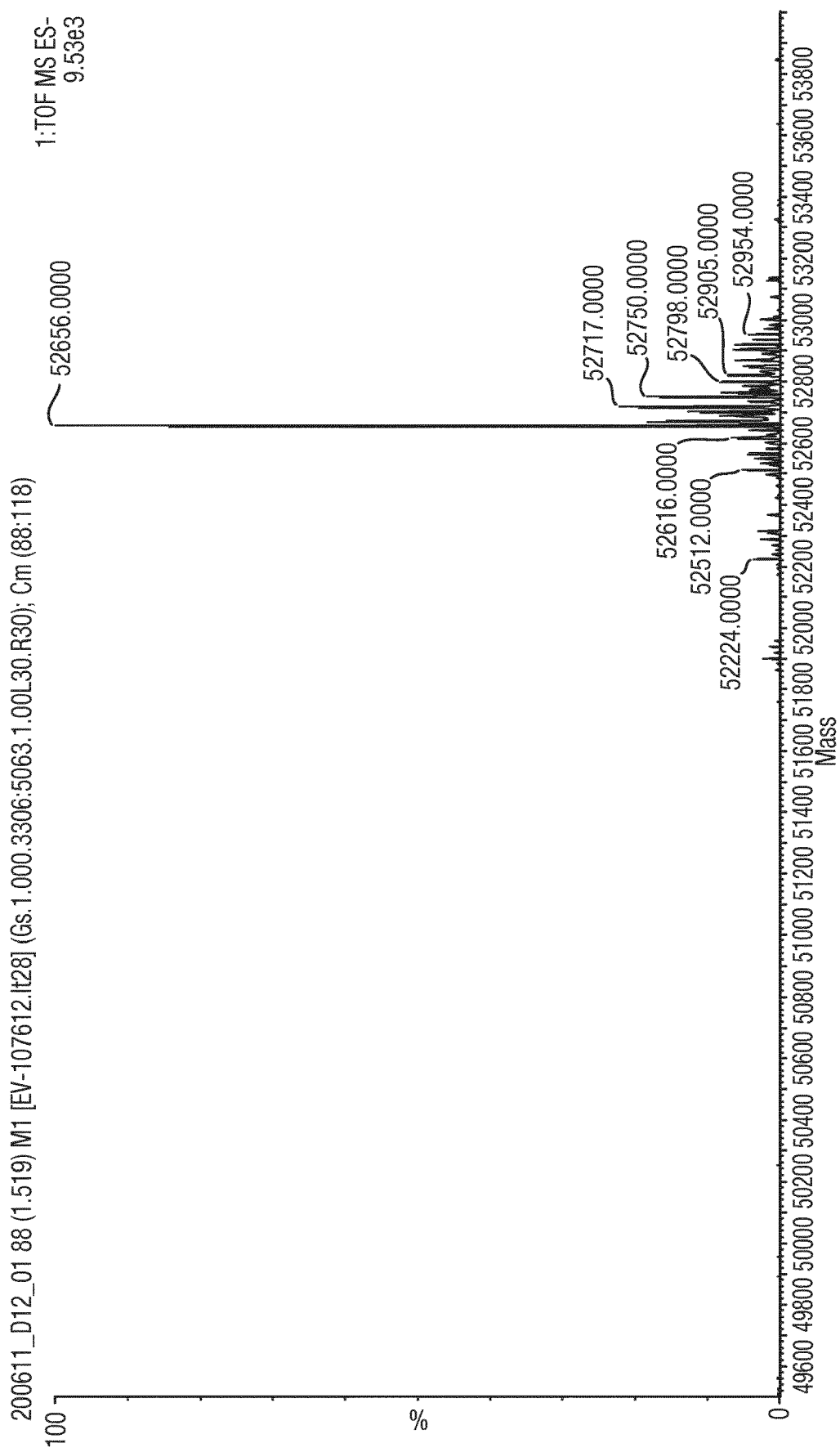
FIG. 5 shows the mass spectrogram of TNFα in a solution containing the compound of formula (3).

Incubation of a library of test compounds, including the compound of formula (3) with TNFα was monitored by mass spectrometry under soft ionization conditions. The data show the stoichiometry of binding as one molecule of the compound of formula (3) per TNFα trimer (FIG. 5). The compound of formula (3) was not observed to bind to the monomeric form of TNFα. There was no evidence for stabilization of the dimeric form of TNFα. This confirms that the test compounds, including the compound of formula (3), have a different mode of action to known compounds, which stabilize the dimeric form of TNFα.

Example 5—Monomer Exchange in TNFα Trimers

Human and mouse homotrimers of TNFα ($H_3$ and $M_3$ respectively) were incubated together and aliquots of the solution monitored by mass spectrometry appearance of the cross species heterotrimers. The mass spectrometric analysis confirmed that monomer exchange between native TNFα trimers was able to occur in solution. The exchange rate was slow and was monitored over a course of 4 hours before full equilibration was achieved (data not shown). The mechanism is unknown, although is it unlikely to involve formation of the dimeric forms as none of these were observed. Monomer exchange is likely to be occurring between pure human and mouse trimers, the mixing of mouse and human trimers simply makes this exchange visible by mass spectrometry.

In a second series of experiments an excess of the compound of formula (3) was incubated with Human TNFα, the excess compound of formula (3) was then removed. Mass Spectral analysis confirmed that a 1:1 complex had been formed between the compound of formula (3) and h-TNFα. Mouse TNFα was now added to this sample which was then subjected to mass spectral analysis over a number of hours. After 18 hours there was no observed change in the composition of the sample. Notably no monomer subunit exchange had occurred, formation of the mixed heterotrimeric species either free as $MH_2$ and $M_2H$ or ligated as $MH_2L$ and $M_2HL$ were not observed. In addition, there was no evidence of formation of the $M_3L$ species and no evidence of formation of the unligated $H_3$ species. This strongly suggests that once the compound of formula (3) is bound to h-TNFα there is no measurable off-rate. Thus, when preincubated with h-TNFα, the compound of formula (3) locked the human trimer, hence no cross species monomer subunit exchange was observed.

The experiment was then repeated in reverse. Excess compound of formula 3 was incubated with Mouse TNFα, the excess compound of formula (3) was then removed. Mass Spectral analysis confirmed that a 1:1 complex had been formed between the compound of formula (3) and m-TNFα. Human TNFα was now added to this sample which was then subjected to mass spectral analysis over a number of hours. The data show clearly that monomer subunit exchange can occur, formation of the mixed heterotrimeric species was observed in both the free ($MH_2$ and $M_2H$) and ligated ($MH_2L$ and $M_2HL$) state. In addition there was evidence of formation of the ligated human homotrimer ($H_3L$), the unligated mouse homotrimer ($M_3$) and for unbound compound of formula (3) (L). This suggests that although a 1:1 complex was formed between compound of formula (3) and the mouse TNFα homotrimer, there is a measurable off-rate. Once this complex ($M_3L$) has dissociated, monomer subunit exchange between the $H_3$ and $M_3$ species proceeds and the liberated ligand is then able to form complexes with all 4 trimer species present in solution. Thus, when preincubated with m-TNFα, the compound of formula (3) did not prevent monomer subunit exchange and the formation of the mixed heterotrimers was observed.

These two experiments were then repeated with the compound of formula (15) instead of the compound of formula (3). The results when the compound of formula (15) was pre-incubated with h-TNFα to give a 1:1 complex and then mixed with unligated m-TNFα were the same as with the compound of formula (3). No monomer subunit exchange was observed, after 18 hours only the $H_3L$ and $M_3$ species were observed in solution confirming that the compound of formula (15) has also no measurable off-rate when complexed with h-TNFα. Thus, when preincubated with h-TNFα, the compound of formula (15) locked the human trimer, hence no cross species monomer subunit exchange was observed.

However, in contrast to the compound of formula (3), when the compound of formula (15) was preincubated with m-TNFα to form a 1:1 complex and then mixed with unligated h-TNFα no monomer subunit exchange was observed, after 18 hours only the $M_3L$ and $H_3$ species were observed in solution. This suggests that the compound of formula (15) has also no measurable off-rate when complexed with m-TNFα. Thus, when preincubated with m-TNFα, the compound of formula (15) locked the mouse trimer, hence no cross species monomer subunit exchange was observed.

Together these data suggest that while the compound of formula (3) and the compound of formula (15) have similar affinities for the human TNFα, the compounds have different affinities for the mouse TNFα trimer, the compound of formula (15) binding more tightly than the compound of formula (3) to the latter.

Example 6—Mass Spectrometric Analysis of Fractions from Size Exclusion Experiments Using TNFα, TNF-R and the Compound of Formula (3)

Figure 6A:
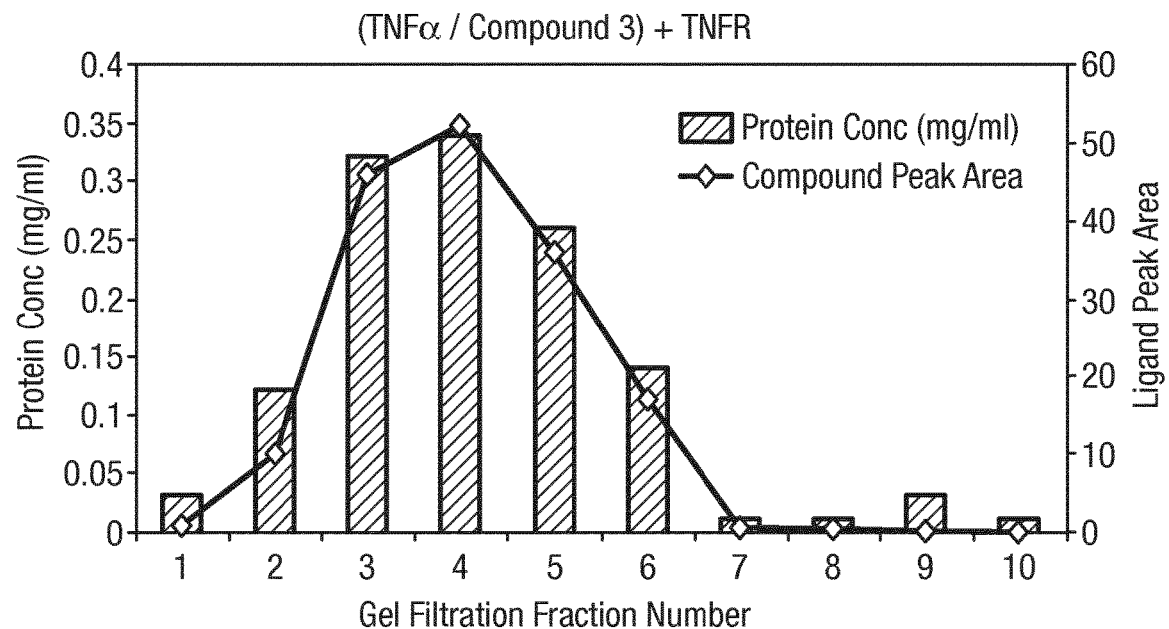
FIG. 6 shows an overlay of the elution profile of a size exclusion chromatography experiment and subsequent mass spectrometric analysis of (A) a sample of TNFα pre-incubated with the compound of formula (3) and then mixed with TNF-R and (B) a sample of TNFα pre-incubated with TNF-R and then mixed with the compound of formula (3).
Figure 6B:
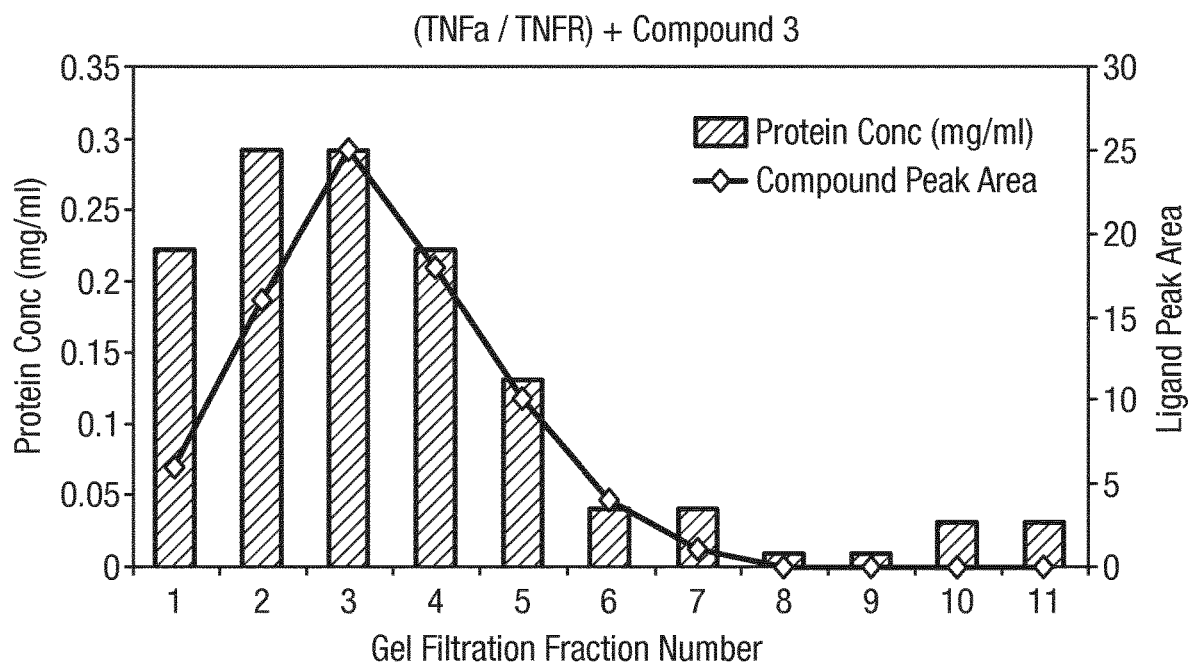

Fractions from size exclusion chromatographic separation of mixtures of TNFα, TNF-R and the compound of formula (3) were analysed by liquid chromatography-mass spectrometry (LC-MS). Two samples were prepared for size exclusion chromatography. In the first sample the compound of formula (3) was pre-incubated with TNFα before the addition of the compound-trimer complex to TNF-R. In the second sample the compound of formula (3) was added to a pre-formed complex of TNFα and TNF-R. The LC-MS analysis revealed that the compound of formula (3) was associated with those fractions that contain the two proteins (FIG. 6), suggesting that regardless of the order of addition the compound of formula (3) is still able to bind to TNFα, i.e. that the compound of formula (3) binds to TNFα even in the presence of TNF-R.

Example 7—Isothermal Calorimetric Analysis of TNFα and the Compound of Formula (15)—TNFα Trimer Complexes Binding to TNF-R TNFα (128 μM) in ITC buffer (50 mM HEPES, 150 mM NaCl, pH 7.4) was incubated for 60 minutes with a DMSO stock of compound 2 giving a final compound concentration of 300 mM in 5% DMSO (test sample). A control sample in which DMSO but not compound was added to the TNFα sample was also incubated for 60 minutes (control).

Following incubation the samples were gel filtered on a Nap 5 size exclusion column (GE Healthcare). The column was equilibrated with 15 ml of ITC buffer prior to the addition of 500 μl of sample which was run into the column and then eluted using 1ml of ITC buffer. This process separates the TNF and compound bound TNF from free compound and DMSO.

Absorbance readings at 280 nm were used to determine the concentration of TNFα in the test sample or the control following elution from the NAP 5 column and the samples were diluted to a TNFα concentration of 64 μM.

200 μl of the extracellular domain (ECD) of TNFR1 (10 mM) was loaded into the sample cell of an AutoITC200 (GE Healthcare) automatically (using the Plates Standard B protocol). In 2 experiments 40 μl of either the test sample or the control was loaded into the injection syringe automatically using the same protocol.

The ITC experiments were performed using the ITC injection protocol described on the Isotherm plots (FIGS. 7A and B) at 25 degrees centigrade stirring at 1000 rpm.

Data was collected and analysed using GE Healthcare ITC applications in Origin 4.0 Software and the results were calculated using a one-site binding algorithm.

Figure 7A:
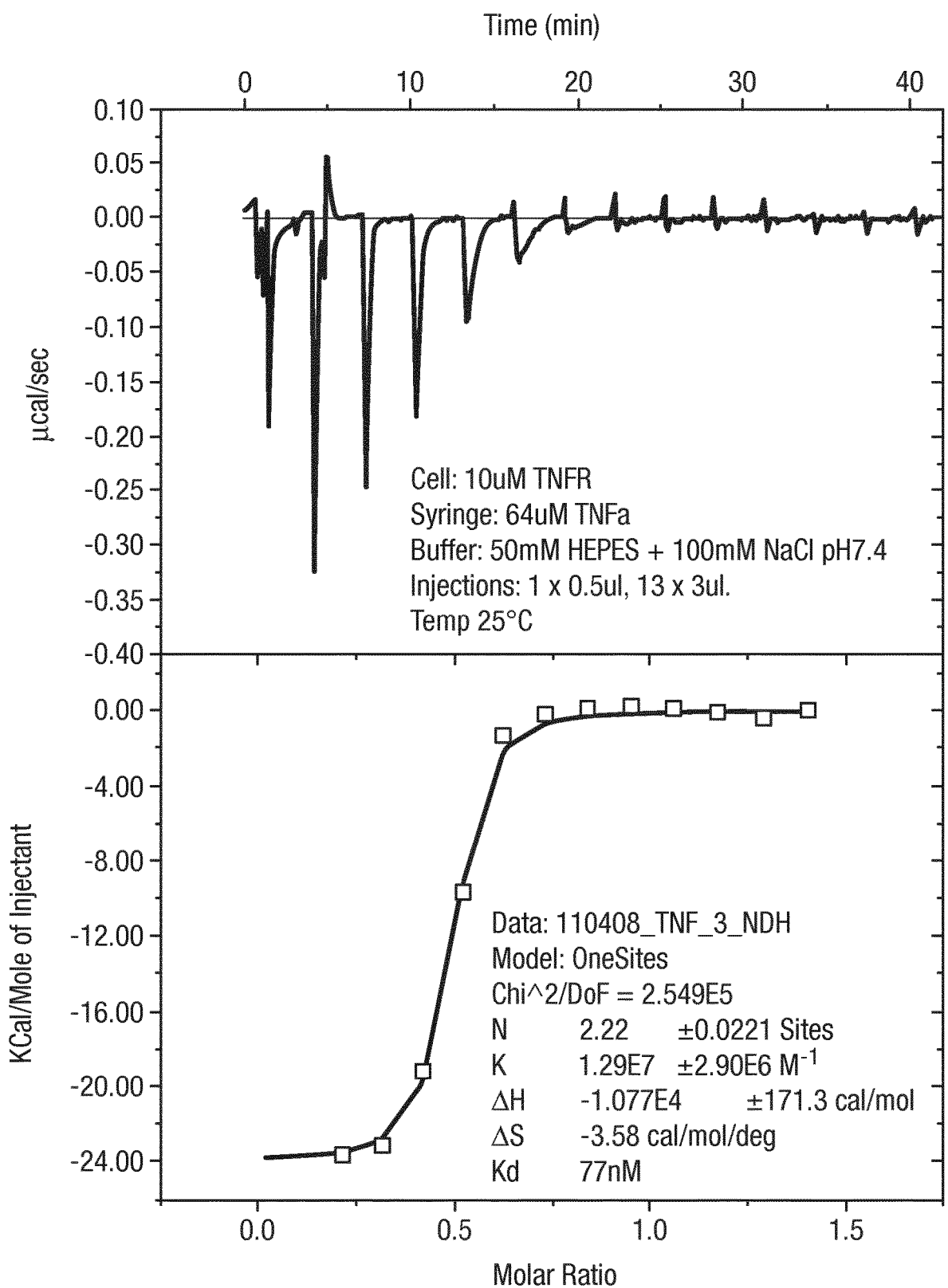
FIG. 7 shows (A) the results of isothermal calorimetric analysis of the binding of TNFα to TNF-R and (B) the results of isothermal calorimetric analysis of the binding of TNFα to TNF-R wherein the TNFα has been pre-incubated with the compound of formula (15).
Figure 7B:
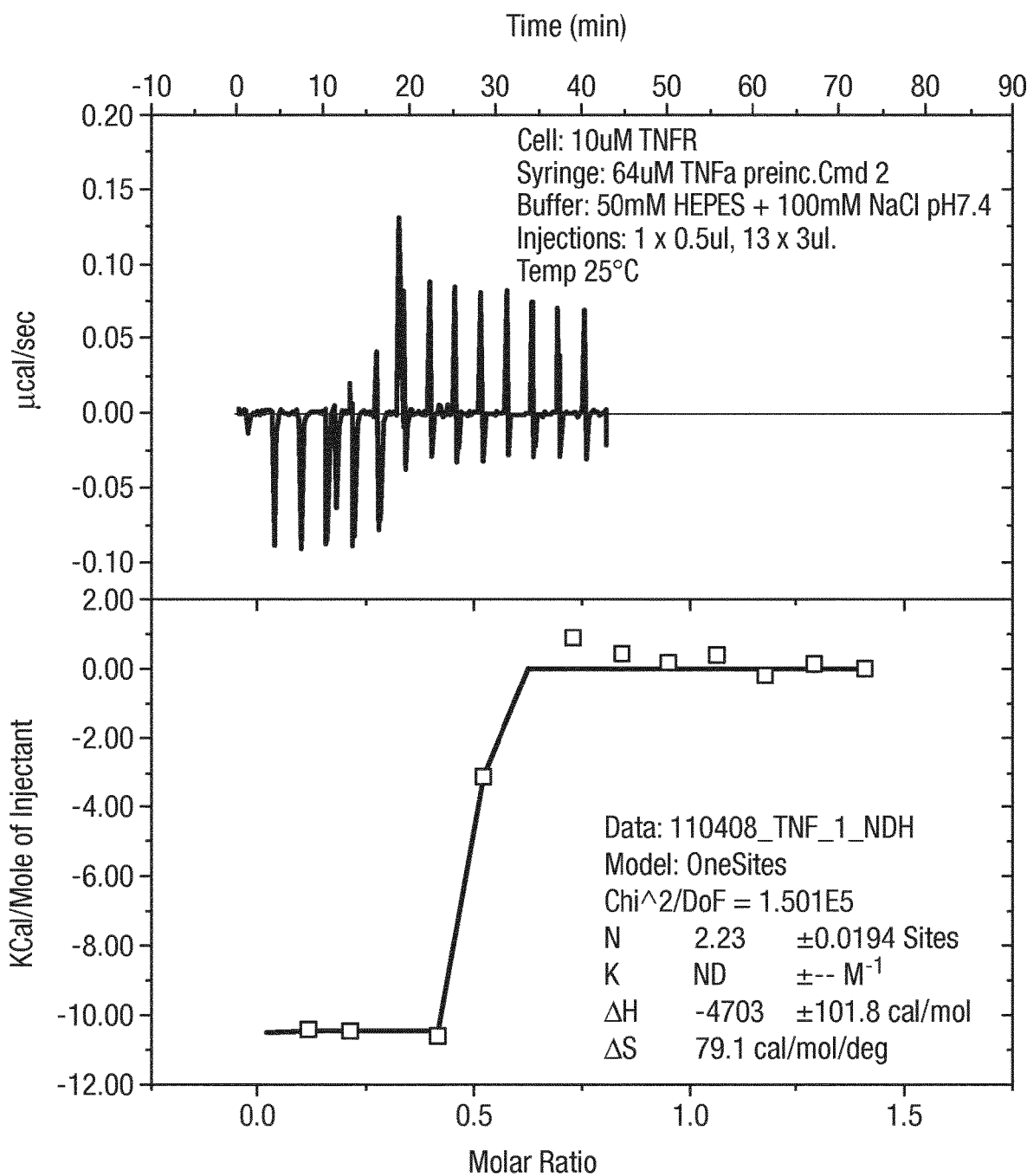

The $K_D$ of TNFα binding to TNF-R in the absence of any test compound was calculated to be 77 nM (FIG. 7A). The $K_D$ of TNFα binding to TNF-R in the presence of the compound of formula (15) was below the sensitivity range of the calorimeter and so could not be accurately calculated. However, the calorimeter has a lower sensitivity boundary of about 1 nM. Therefore, the $K_D$ of TNFα binding to TNF-R in the presence of the compound of formula (15) must be 1 nM or lower (see FIG. 7B).

Example 8—Neutralisation of TNFα by Compounds of the Invention

The L929 neutralisation assays were carried out using the protocol disclosed in Baarsch M J J et al (Immunol Methods 1991; 140: 15-22) and Galloway C J et al J (Immunol Methods 1991; 140: 37-43).

Briefly, L929 cells (ECACC, 85011425) were cultured in culture medium consisting of RPMI 1640 (Gibco) containing 10% FCS (PAA), 2 mM glutamine (Gibco), 50 U/ml penicillin (Gibco) and 50 µg/ml streptomycin (Gibco). When they were subcultured, the cells were washed three times with 10 mL Dulbecco's phosphate-buffered saline without calcium and magnesium (Gibco) and 3 ml of trypsin-EDTA (Gibco) was then added for 2 minutes to remove the cells from the flask. Culture medium was added to neutralise the trypsin and the cells pipetted up and down to remove any clumps.

The L929 cells were split ½ or ⅓ the day before use and cultured for a further 24 hours. The flasks were then trypsinised as above and 2×10⁴ cells in 100 µl were added per well of a 96 well flat-bottomed plate (Becton Dickinson). The plates were cultured for 24 hours before the assay was set up.

Serial dilutions were made from DMSO stocks of the compounds. Typically a 9 point titration curve would be generated by double diluting from a concentrated solution of compound to give a final assay concentration of 25, 12.5, 6.25, 3.125, 1.56, 0.78, 0.39, 0.2, 0.11.1M.

The assay medium was the same as culture medium but also contained 1 µg/ml actinomycin D (Sigma). The medium was flicked off the plates and the assay samples plus TNFα, standards and controls were added in 100 µl volumes in duplicate. Plates were incubated for a further 16 hours and then 10 µl per well of a 5 mg/ml methylthiazoletetrazolium (MTT; Sigma) solution in culture medium was added for a further 4 hours. The reaction was stopped by the addition of 100 µl of solubilisation buffer containing 20% sodium dodecyl sulphate (SDS, BDH) dissolved in 50% dimethyl formamide (DMF; BDH) and 50% deionised water.

After overnight incubation at 37° C. to allow the dye to dissolve, the plates were read on a Multiskan EX plate reader (Labsystem) at 570 nm with subtraction at 630 nm. Data were analysed using the Genesis software package.

Figure 9:
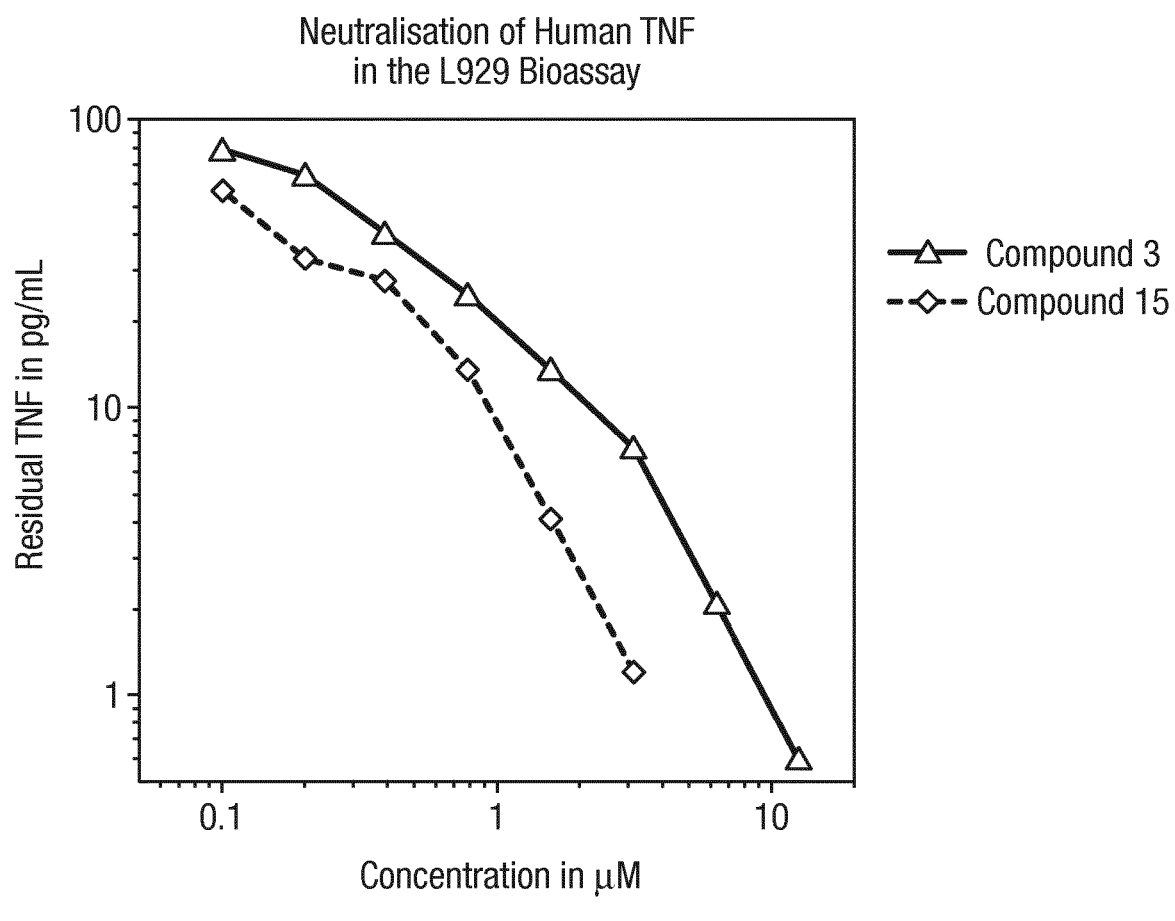
FIG. 9 shows a graph of the neutralisation of human TNFα by the compound of formula (3) and the compound of formula (15) as measured in terms of the concentration of the compound of formula (3) and the compound of formula (15) against residual human TNFα concentration (pg/ml) measured using an L929 murine fibrosarcoma cell-killing assay.

Both the compound of formula (3) and the compound of formula (15) inhibited the cell killing activity of human TNFα (FIG. 9), indicating that both the compound of formula (3) and the compound of formula (15) were able to inhibit human TNFα-induced signalling through TNF-R. In this instance the compound of formula (3) gave an $IC_{50}$ value of 306 nM and the compound of formula (15) gave an $IC_{50}$ value of 125 nM. The protocol was repeated using the compound of formula (39), which was also found to inhibit human TNFα-induced signalling through TNF-R. Thus, the compound of formula (39) gave an $IC_{50}$ value of 21 nM.

Example 9—Inhibition of TNFα-Induced IL-8 Production by the Compound of Formula (3)

Venous blood from healthy donors was collected by venupuncture into sodium/heparin containing tubes (BD Biosciences). Peripheral blood mononuclear cells (PBMC) were isolated by density gradient centrifugation with Ficoll Paque (Amersham Biosciences). Briefly, 10 mL of blood was diluted 1:1 (v/v) with RPMI 1640 (Gibco) and carefully layered onto 20 mL Ficoll Paque. Cells were spun down for 30 minutes (min) at 470 g, the PBMC collected, washed once in RPMI 1640 and any remaining contaminating erythrocytes lysed in erythrocyte lysis buffer (1 g/L $KHCO_3$, 8.3 g/L $NH_4Cl$, 0.0372 g/L EDTA). Isolation of monocytes from the PBMC was performed using CD14+ Magnetic MicroBeads (Miltenyi Biotec) according to the manufacturer's instructions. Briefly, PBMC were resuspended in Dulbecco's modified Eagle's medium containing 5% BSA (Sigma) and 2 mM EDTA (Sigma) at 1×10⁷ cells/ml. 25 µL of CD14 MicroBeads per 10⁷ total cells were incubated for 15 min at room temperature. The magnetic separation was performed using a LS column (Miltenyi Biotec). Prior to application of the cell/bead mixture to the column, the column was placed in the magnetic field and washed twice with 5 mL buffer. The cell suspension was then applied onto the column, in the magnetic field. Monocytes binding CD14⁺ MicroBeads were retained on the LS column while the remaining PBMC passed through the column. To isolate monocytes, the column (containing the retained cells) was then removed from the magnet and placed in a collection tube. 5 mL buffer were add to the column and the CD14⁺ cells collected from the column by applying a syringe plunger to the top of the column. The collected cells were washed once in RPMI 1640.

An 11 points 3-fold serial dilution (blank included) of the compounds (stock concentration 10 mM) was performed in DMSO in a 96 well round-bottomed plate. Purified monocytes were washed by centrifugation (300 g for 5 minutes) and resuspended in complete medium at a concentration of 1×10⁶ cells/mL. 160 of this cell population was incubated at 37° C. in a 96 well round-bottomed plate with 40 of the compounds and TNFα (final concentration (~1 ng/ml) in RPMI 1640 or relevant controls in triplicate.

After 18 hours the plate was spun down (300 g, 5 min) and the supernatants collected for cytokine measurement.

Figure 10:
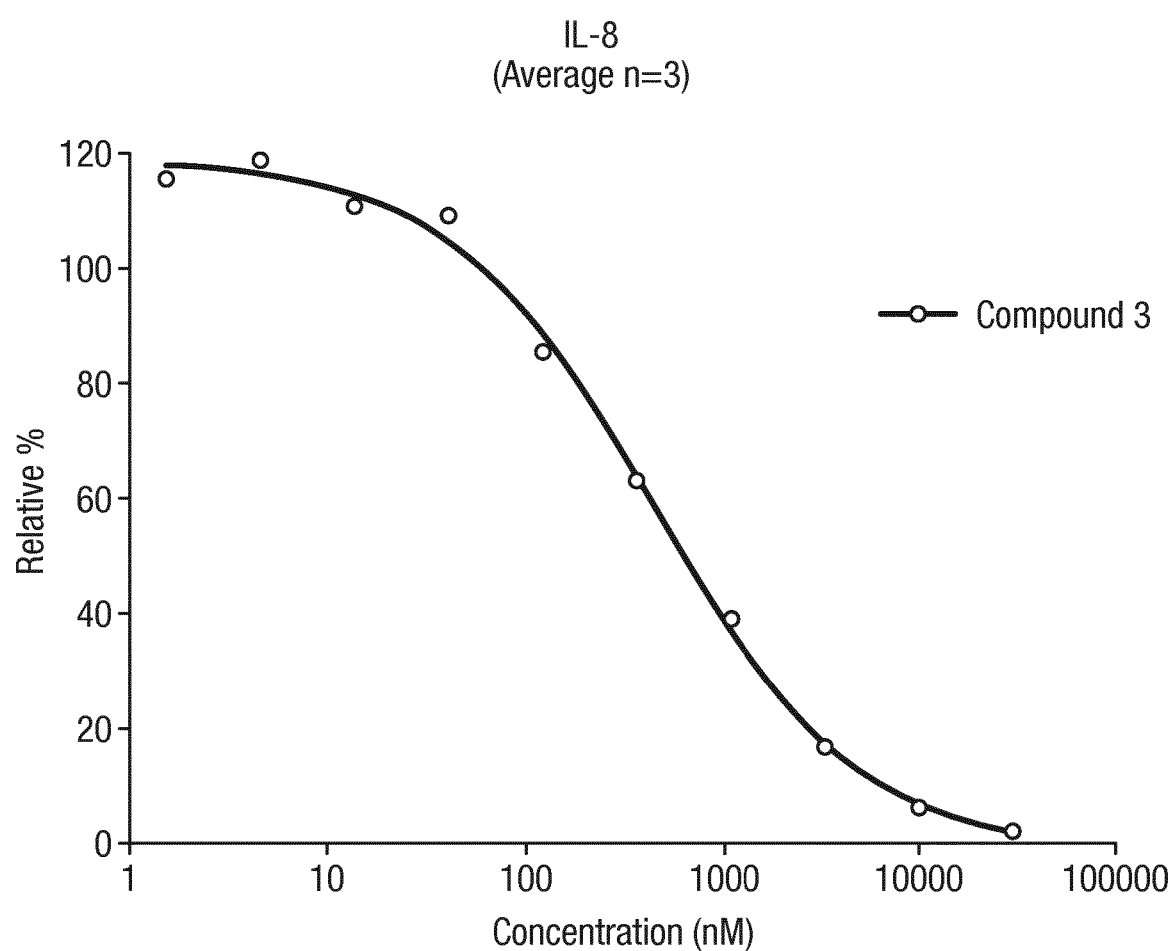
FIG. 10 shows a graph of the concentration of the compound of formula (3) (nM) against % relative IL-8 production in TNFα treated human monocytes.

Human IL-8 was measured in the cell culture supernatants using enzyme-linked immunosorbent assay (ELISA) kits from R&D Systems Ltd. according to the manufacturer's instructions. The substrate used for the ELISAs was TM Blue (Serologicals Corporation). Plates were read at a wavelength of 630 nm with correction at 470 nm. The compound of formula (3) inhibited the TNFα-induced production of IL-8 in a concentration dependent manner (FIG. 10), with an $IC_{50}$ value of 454.1 nM.

Example 10—Inhibition of TNFα-Induced NF-κB Activation by the Compounds of Formulae (1)-(64)—the Reporter Gene Assay Stimulation of HEK-293 cells by TNF-alpha leads to activation of the NF-kB pathway. The reporter cell line used to determine TNF alpha activity was purchased from Invivogen. HEK-Blue™ CD40L, is a stable transfectant expressing SEAP (secreted alkaline phosphatase) under the control of the IFN-beta minimal promoter fused to 5 NF-kB binding sites. Secretion of SEAP by these cells is stimulated in a concentration dependent manner by TNF-alpha (0.5 ng/ml), IL-1-beta (0.5 ng/ml) and an activating anti-human TNFR1 antibody (300 ng/ml).

Compounds were diluted from 10 mM DMSO stocks (final assay concentration 0.3%) to generate a 10 point 3 fold serial dilution curve (30,000 nM to 2 nM final concentration). They were mixed with stimulating ligand for 1 hour in a 384 well microtitre plate. Freshly thawed and washed cells were added to the compound/stimulus mixture and further incubated for 18 hours. SEAP activity was determined in the supernatant using the colorimetric substrate Quanti-blue™ (Invivogen).

Percentage inhibitions for compound dilutions were calculated between a DMSO control and maximum inhibition (by excess control compound) and an $IC_{50}$ calculated using xlfit (4 parameter logistic model) in Activity Base.

The specific activity of the compound of formula (15) against the TNF-alpha response was compared to that seen with the counterscreens (IL-1beta and anti-human TNFR1 antibody).

Figure 11A:
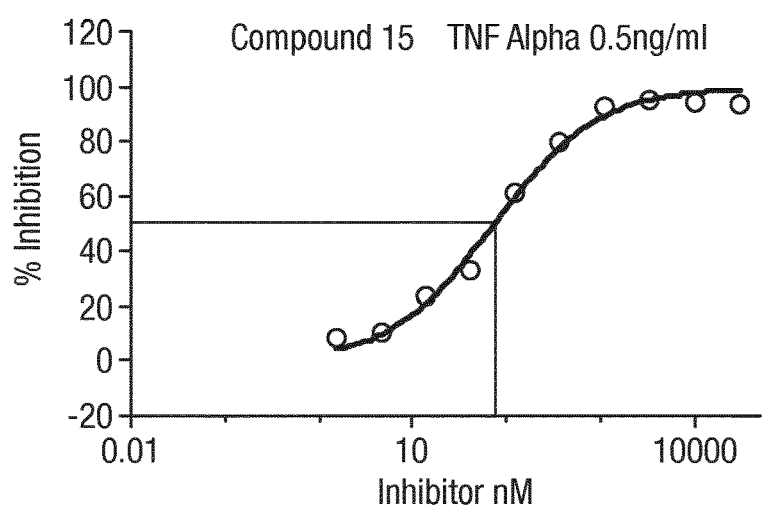
FIG. 11 shows a graph of the concentration of the compound of formula (15) (nM) against % inhibition of NF-κB activation in HEK293 cells in the presence of (A) TNFα (0.5 ng/mL), (B) IL-β (0.5 ng/mL) and (C) an activating TNF-R1 antibody (300 ng/mL).
Figure 11B:
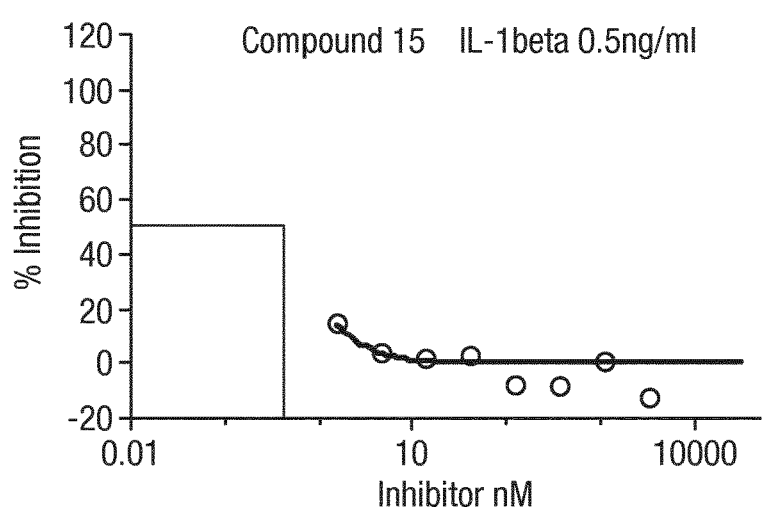
Figure 11C:
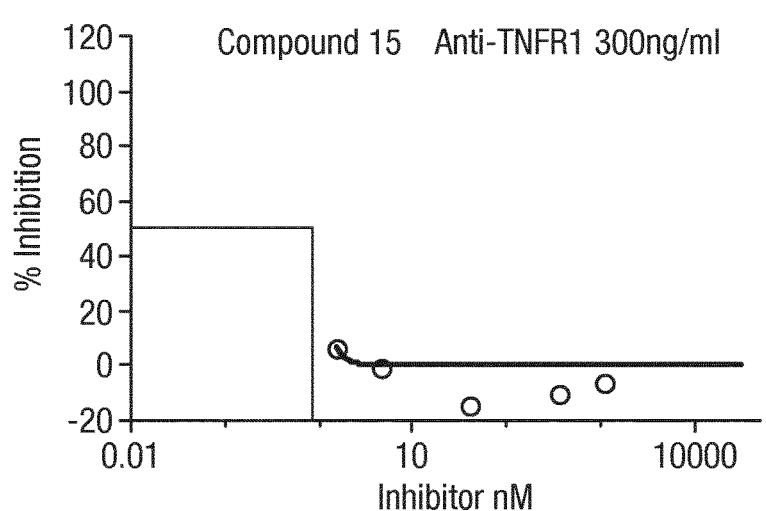

The compound of formula (15) inhibited the activation of NF-κB by TNFα in a concentration-dependent manner, with an $IC_{50}$ of 113 nM (FIG. 11A). In contrast, the compound of formula (15) did not inhibit the activation of NF-κB by IL-β (FIG. 11B) or the activating TNF-R1 antibody (FIG. 11C). Therefore, the compound of formula (15) specifically inhibits TNFα-induced signalling through the TNF-R1, but has no effect on NF-κB activation induced by other signalling pathways (such as by IL-1β), or when the initiation of signalling from the TNF-R1 by TNFα is bypassed (such as by using an activating TNF-R1 antibody).

Further, when tested in the reporter gene assay, compounds of formulae (1)-(64) were also found to inhibit the activation of NF-κB by TNFα in a concentration-dependent manner, exhibiting $IC_{50}$ values of 50 μM or less.

Example 11—Determining the Kinetics of Binding to TNFα

Figure 12A:
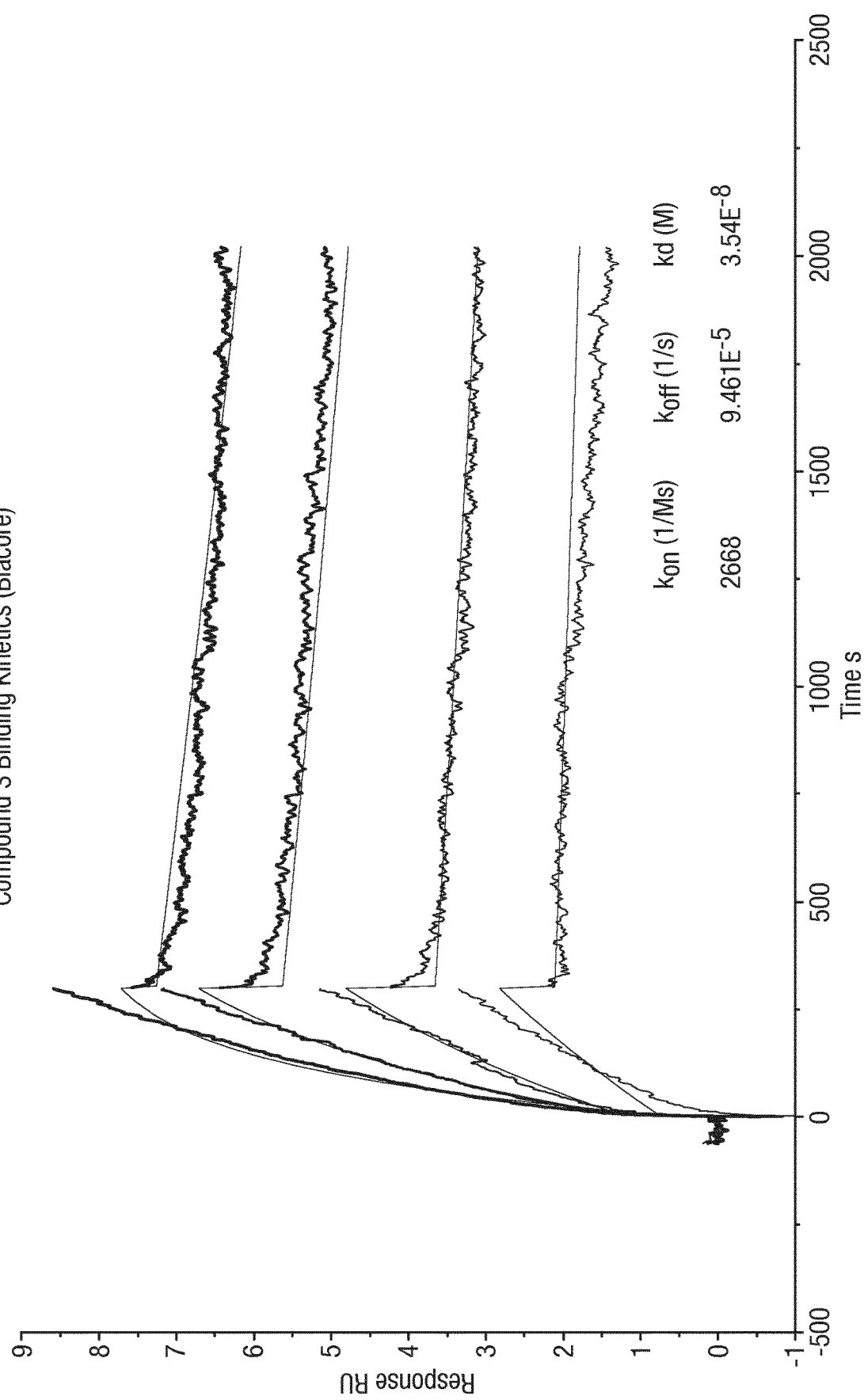
FIG. 12A shows the binding kinetics of the compound of formula (3) with TNFα over time as measured using surface plasmon resonance.

Surface plasmon resonance was used to measure the association rate, the dissociation rate and the affinity of the compounds of formulae (3) and (15) for TNFα (FIGS. 12A and B). For the purpose of this study a Biacore T100/T200 was used.

TNFα was immobilised at pH5 to a level of 5-8 KRU onto a CM5 sensor in HBS-P buffer (10 mM HEPES pH 7.4, 0.15 M NaCl, 0.005% Surfactant P20, BIAcore, GE Healthcare). The TNFα was then equilibrated in HBS-P with 5% DMSO for at least 5 hours. The samples were diluted from 10 mM stocks into DMSO matched buffer and left to solubilise for at least 5 hours. The flow rate was 30μl/min.

This assay was performed by adding 4 or 5 concentrations of compound starting from a highest concentration of 25 μM for compound of formula (3) and 1 μM for compound of formula (15) and then serially diluting this sample. Background subtraction binding curves were analysed using the BIAevaluation software following standard procedures. Binding, affinity and kinetic parameters were determined using Biacore software. The kinetic data were fitted using the levenberg marquardt algorithm.

Figure 12B:
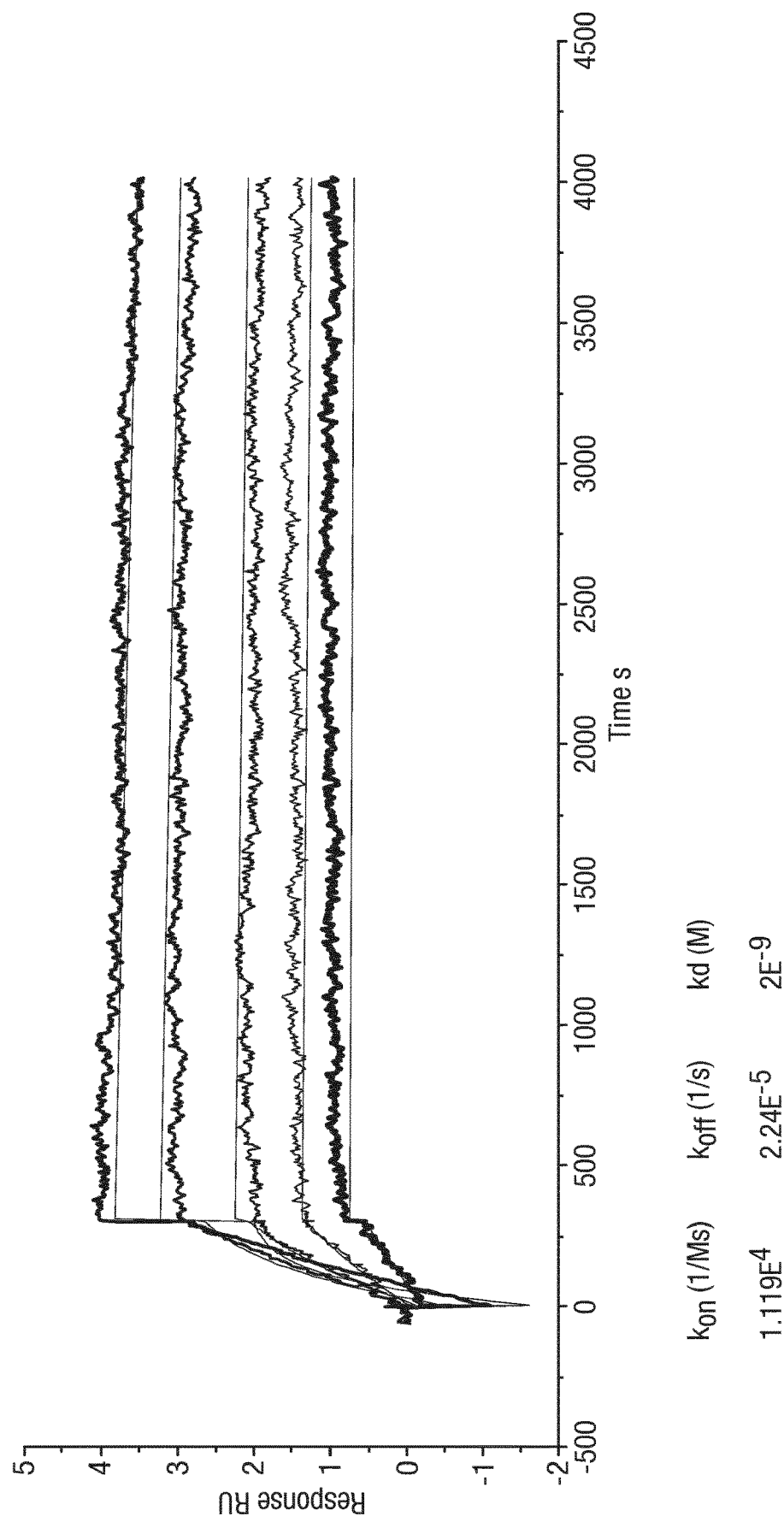
FIG. 12B shows the binding kinetics for the compound of formula (15) with TNFα.

The experiment showed that these compounds bind immobilised TNFα very slowly as evidenced by a $k_{on}$ of $2.668e^3$ $M^{-1}s^{-1}$ for compound of formula (3) (FIG. 12A) and $1.119e^3$ $M^{-1}s^{-1}$ for compound of formula (15) (FIG. 12B). They also have remarkably slow dissociation rates which appears to be a characteristic of compounds with this mode of action. The dissociation rate constant ($k_{off}$) for the compound of formula (3) is $9.46e^{-5}$ $s^{-1}$ and for compound of formula (15) is equal to $2.24e^{-5}$ $s^{-1}$. This equates to a dissociation half-life ($t_{1/2}$) of over 2 hours and 8 hours, respectively. The dissociation constant ($K_D$) can be calculated from the ratio of the two constants $k_{off}/k_{on}$. In this experiment the $K_D$ values for the compound of formula (3) and for the compound of formula (15) are 35 nM and 2 nM, respectively. This is significantly lower than the EC50s determined on the Biacore shown in Example 3 and is likely to reflect the differences in the format of the assays. Additionally the form of TNFα differs in that in the kinetic assay of Example 11 the TNFα is immobilised.

The experiment was repeated to measure the association rate, dissociation rate and affinity of the compound of formula (39) for TNFα (FIG. 12C). The compound of formula (39) was found to have a $k_{on}$ of 5470 $M^{-1}s^{-1}$, a dissociation rate constant of $4.067e^{-5}$ $s^{-1}$ and a $K_D$ of 7 nM.

Example 12—the Compound of Formula (3) and the Compound of Formula (15) Antagonise TNFα Activity In Vivo In separate studies, compounds of formula (3) and formula (15) were mixed with 20 μM solutions of TNFα dissolved in phosphate buffered saline (PBS) to a concentration of 2 μM, 20 μM and 200 μM. The ratio of each compound to TNFα was, therefore, 0.1:1 (sample 1), 1:1 (sample 2) and 10:1 (sample 3). The solutions were incubated at room temperature for 3 hours to allow the compounds to bind to TNFα, prior to gel filtration using a Zeba Spin desalting column (Thermo Scientific). This process separates protein bound compound and free compound. A control sample containing PBS only was processed in the same way to provide a vehicle control for the study. The concentration of eluted protein was determined using a Nanodrop (ND-1000). The TNFα: compound complexes were diluted in PBS to a concentration for injection of 0.03 μg/kg.

For the study, typically, each group contained 10 male Balb/c mice (Charles River) apart from an anti-human TNFα antibody positive control, which used a set of 5 mice. Antibody control mice were administered anti-hTNFα at 10 mg/kg (100μl) by intraperitoneal (i.p.) injection five minutes before (t=−5) being given an i.p. injection of either PBS or hTNFα at 0.1 μg/kg (t=0).

Test mice were injected i.p. at t=0 with 100μl of either gel filtered vehicle (PBS), hTNFα (0.03 μg/kg) or samples 1, 2 and 3 (compound bound to TNFα at a ratio of 0.1:1, 1:1 and 10:1, respectively).

Compound only mice were also included in the study to assess the effect of compound on neutrophil recruitment.

All mice were killed by cervical dislocation two hours post-injection of hTNFα (t=2 h) and the peritoneal cavity was lavaged with 3 mL of FACS buffer (500 mL PBS containing 2 g bovine serum albumin, 6 mL HEPES buffer and 500 mL EDTA). Lavage fluid was aspirated and neutrophil numbers were assessed by staining cells with anti-Gr1 PE and anti-CD45 FITC by FACS as detailed below.

100 μL of lavage fluid from each sample was aliquoted into FACS tubes. A FACS cocktail was made up using anti-GR-1 PE (BD cat #553128 Lot #75542) at 1 in 39 dilution and anti-CD45 FITC (BD cat #553080 Lot #80807) at 1 in 19 dilution in FACS buffer. Fc block (BD Cat #553142 Lot #87810) was prepared 1 in 10 with FACS buffer and 10 μL added to each sample 5 minutes before adding the antibody cocktail. 10 μl of antibody cocktail was added to each tube containing the 100μl of sample. Samples were then left for 20 mins on ice. 1 mL of FACS Lyse solution (BD Cat #349202 Lot #29076, diluted 1:10 in dH₂O) was added to each tube, mixed and left at room temperature for 5 minutes. 1 mL of FACS Buffer was then added to each tube and centrifuged at 400 g for 5 minutes. The FACS buffer was then carefully poured off and the tip of the tube dabbed on absorbent paper to leave the tube completely dry. Then 300μl of 1 in 10 Reference Bead solution (Sigma cat # P2477 Lot #116K1612) diluted in FACS buffer was added to each tube.

Samples were analysed using FACScalibur II and FloJo software.

Figure 13A:
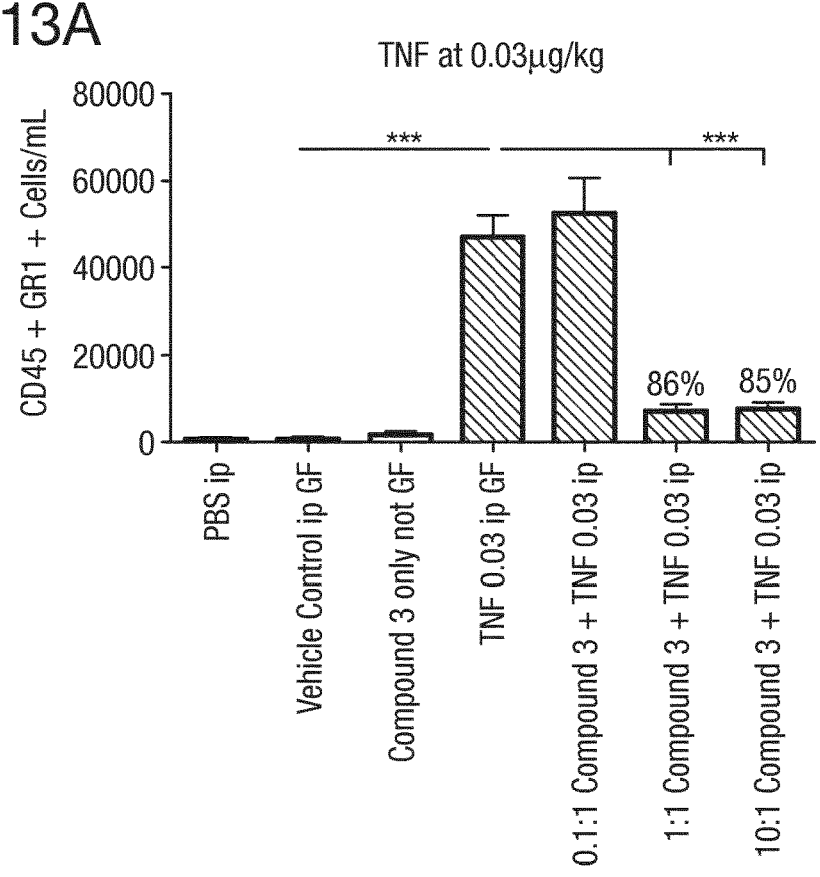
FIG. 13 shows the level of neutrophil recruitment in response to TNFα alone or TNFα that has been pre-incubated with increasing concentrations of (A) the compound of formula (3) or (B) the compound of formula (15) and administered by intraperitoneal injection (ip.).
Figure 13B:
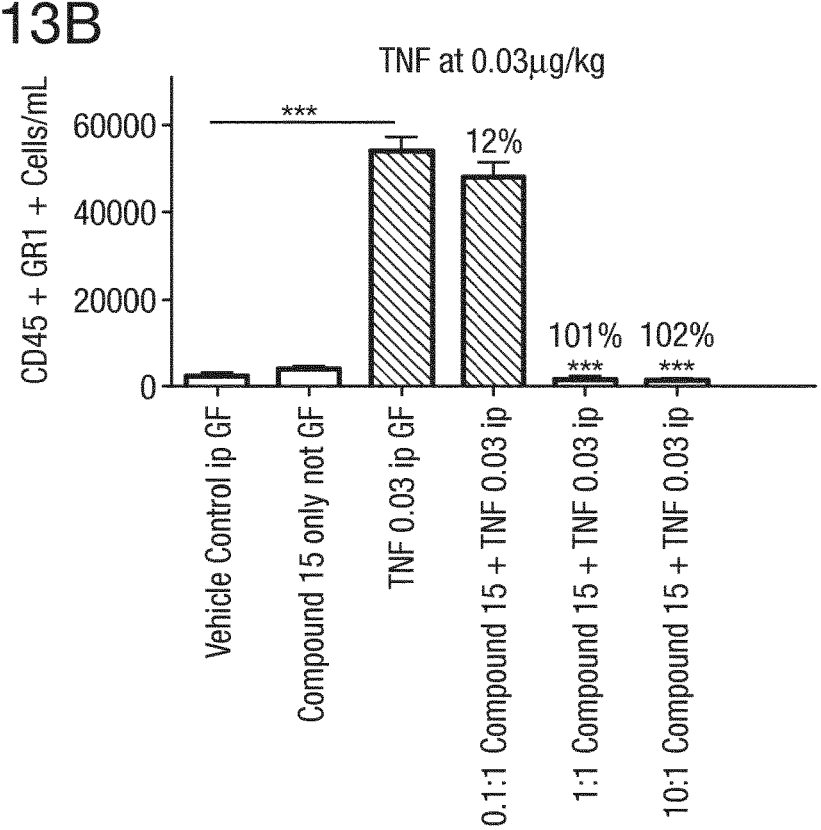

FIG. 13 shows the results for the compound of formula (3) (A) and the compound of formula (15) (B). Vehicle alone had a negligible effect on neutrophil recruitment as did compound alone (slightly higher in (B)). Sample 1 from each study (ratio compound:TNFα 0.1:1) was not significantly different from adding TNFα in the absence of the compound. Sample 2 (1:1) and sample 3 (10:1) showed significant inhibition of neutrophil recruitment, (86% and 85%, respectively). Similarly, sample 2 and sample 3 of the compound of formula (15) showed significant inhibition of neutrophil recruitment, (101% and 102%, respectively). The antibody control mice showed 100% inhibition of neutrophil recruitment (data not shown).

In a further experiment, mice were treated with hTNFα (0.3n/ml) and the compound of formula (3) was administered orally (p.o.).

The compound of formula (3) was made into a suspension in 1% methylcellulose vehicle using a covaris machine.

An anti-human TNFα monoclonal antibody (anti-hTNFα, UCB) was also utilised as a positive control in this study.

Ten male Balb/c mice were used per group except in the group that received anti-hTNFα for which 4 mice were used.

Mice received 100₄ of either vehicle (1% methylcellulose) or compound of formula (3) at 30 mg/kg or 100 mg/kg p.o. 30 minutes (t=−30) or anti-hTNFα at 10 mg/kg i.p. 5 minutes (t=−5) prior to being injected with human TNFα. At t=0 mice were injected with 100₄ i.p. of either PBS or hTNFα at 0.03 μg/kg.

All mice were killed by cervical dislocation two hours post-injection of hTNFα (t=2 h) and the peritoneal cavity was lavaged and neutrophil numbers measured as described above.

Figure 14:
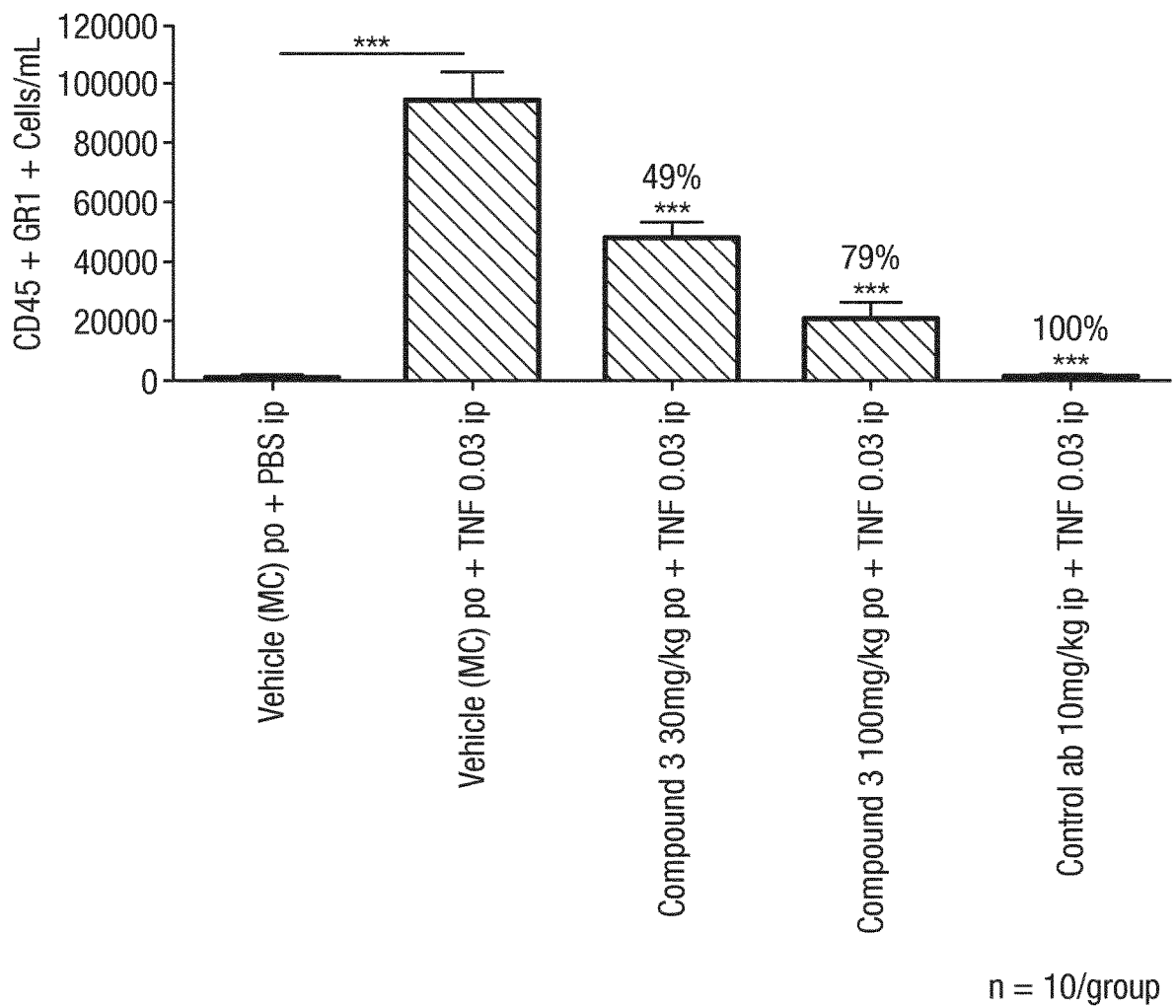
FIG. 14 shows the level of neutrophil recruitment in response to TNFα, alone or in the presence of increasing concentrations of the compound of formula (3) administered orally.

Oral administration of 30 mg/kg and 100 mg/kg of compound of formula (3) reduced TNFα stimulated neutrophil recruitment into the peritoneal cavity by 49% and 79%, respectively (FIG. 14). The positive control antibody (10 mg/kg) given by i.p. injection completely inhibited neutrophil recruitment.

Therefore, the compound of formula (3) can antagonise TNFα activity in vivo not only when premixed with the TNFα and administered by the i.p route but also when it is administered orally.

Example 13—Analysis of TNFα Trimer Stabilisation by the Compounds of Formulae (3) and (15)

A fluorescence probed thermal denaturation assay was performed to assess the effect of the compounds on the thermal stability of TNFα as a measure of compound binding. The reaction mix contained 5 μl of 30× SYPRO® Orange dye (Invitrogen) and 5 μl of TNFα (at 1.0 mg/ml), 37.5 μl PBS, pH 7.4 and 2.5 μl of compound (at 2 mM in DMSO). 10 μl of the mix was dispensed in quadruplicate into a 384 PCR optical well plate and was run on a 7900HT Fast Real-Time PCR System (Agilent Technologies). PCR System heating device was set at 20° C. to 99° C. with a ramp rate of 1.1° C./min; fluorescence changes in the wells were monitored by a Charge-coupled device (CCD). The fluorescence intensity increase was plotted as a function of temperature and the Tm calculated as the midpoint of this denaturation curve (determined as the point of inflection) (Table 1).

Stabilising TNFα is indicated by an increase in Tm. The compounds of formulae (3) and (15) both increase the Tm of TNFα (as shown in Table 1). Therefore, both the compounds of formulae (3) and (15) increase the stability of the TNFα trimer.

Table 1 shows the thermal transition midpoint (Tm) of TNFα in the presence of either compound (3) or (15).

| Sample | Tm (° C.) (mean ± sd) 82 | Tm difference (=(TNF + cpd) − (TNF + DMSO)) |
|---|---|---|
| TNFα + 5% DMSO | 61.4 ± 0.86 (n = 13) | — |
| TNFα + 5% DMSO + | 73.2 + 0.6 (n = 4) | 11.8 |

Example 14—Fluorescence Polarization Assay to Determine the Effect of Compounds of Formula (1)-(64) on the Binding of a Fluorescence Conjugate to TNFα

Preparation of Compound (A)

1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—was prepared by the procedure described in Example 499 of WO 2013/186229 (published 19 Dec. 2013).

Preparation of Fluorescence Conjugate

Compound (A) (27.02 mg, 0.0538 mmol) was dissolved in DMSO (2 mL). 5 (−6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H₂O for LC-MS analysis on the 1200RR-6140 LC-MS system. The chromatogram showed two closely eluting peaks at retention times of 1.42 and 1.50 minutes, both with mass $(M+H)^+$=860.8 amu, corresponding to the two products formed with the 5- and 6-substituted carboxyfluorescein group. A further peak at retention time 2.21 minutes had a mass of $(M+H)^+$=502.8 amu, corresponding to Compound (A). No peak was observed for unreacted 5(−6) carboxy-fluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An $IC_{50}$ value was calculated using XLfit™ (4 parameter logistic model) in ActivityBase.

When tested in the fluorescence polarisation assay, compounds of formulae (1)-(64) of the accompanying Examples were all found to exhibit $IC_{50}$ values of 50 μM or less.

In a further experiment, the compound of formula (3) was tested at 10 concentrations starting from 100 μM at a final concentration of 5% DMSO, by pre-incubation with TNFα for 60 minutes at ambient temperature in 20 mM Tris, 150 mM NaCl, 0.05% Tween 20, before addition of the fluorescence conjugate and a further incubation at ambient temperature overnight. The final concentrations of TNFα and the fluorescence conjugate were 50 nM and 10 nM respectively in a total assay volume of 25 μl. Plates were read on an Analyst HT reader. An IC50 was calculated using xlfit (4 parameter logistic model) in Activity Base.

Figure 15:
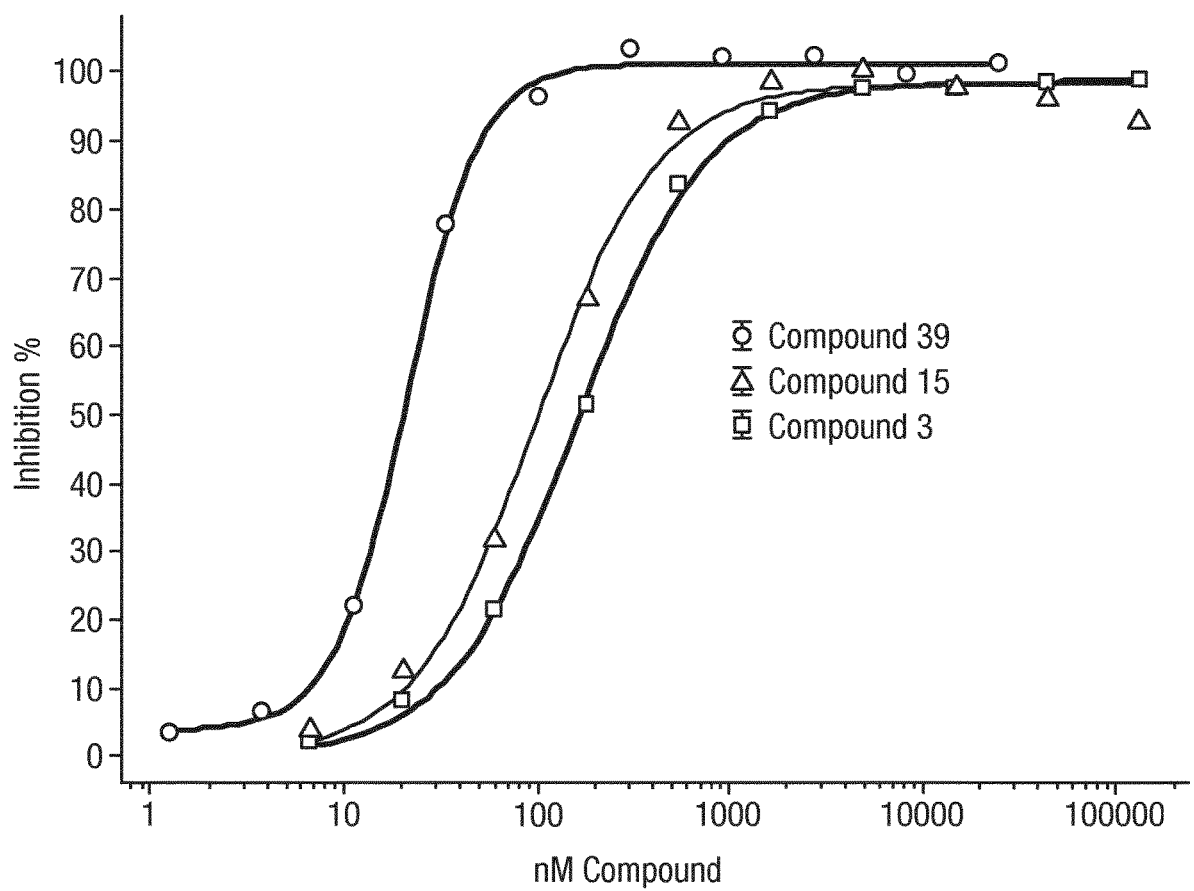
FIG. 15 is a graph of the results of a fluorescence polarization (FP) assay using test compounds of formula (3), (15) and (39). Concentrations of the test compound are plotted against the % inhibition of binding of the fluorescence conjugate to TNFα.

The results are illustrated graphically in FIG. 15. The compound of formula (3) was able to inhibit binding of the fluorescence conjugate to TNFα with an $IC_{50}$ value of 167 nM.

The experiment was repeated using the compounds of formula (15) and (39). The compound of formula (15) was able to inhibit binding of the fluorescence conjugate to TNFα with an $IC_{50}$ value of 102 nM. The compound of formula (39) was able to inhibit binding of the fluorescence conjugate to TNFα with an $IC_{50}$ value of 20 nM.

Example 15—Antibody Derivation

Following the immunisation of 5 Sprague Dawley rats with human TNFα in complex with the benzimidazole compound (15), immune B cells were cultured in 96-well plates to induce clonal expansion and antibody secretion (Tickle, S. et al., High throughput screening for high affinity antibodies Journal of Laboratory Automation 2009 14: 303-307). Culture supernatants were screened for IgG antibodies preferentially binding to human TNFα in complex with compound (15) (at a 50 fold molar excess), compared to apo human TNFα, in a homogeneous bead-based FMAT assay. Human TNFα (+/−compound (15)) was presented on bead surfaces (superavidin-coated Bangs Beads, catalogue number CP01N) by a capture system using a human TNF-Receptor I-Fc fusion protein (R&D Systems catalogue number 372-R1-050), bound with biotinylated anti-human Fc (Jackson catalogue number 109-066-098).

Antibodies which demonstrated preferential binding to the TNFα-compound (15) complex were termed 'conformation-selective' and were taken forward for cloning. The Fluorescent Foci method (U.S. Pat. No. 7,993,864/Europe EP1570267B1) was used to identify and isolate antigen-specific B cells from positive wells, and specific antibody variable region genes were recovered from single cells by reverse transcription (RT)-PCR.

The amino acid sequences of two representative antibodies, CA185_01974 and CA185_01979, which demonstrated conformation-selective binding to both human and mouse TNFα+compound are shown below:

```
CA185_01974.0 (VR0001837)
Light chain variable region (LCVR)
(CDRs underlined)
                                        SEQ ID NO: 7
DIQMTQSPASLPASPEEIVTITCQASQDIGNWLSWYQQKPGKSPQLLIY

GATSLADGVPSRFSASRSGTQYSLKISRLQVEDFGIFYCLQGQSTPYTF

GAGTKLELK

Heavy chain variable region (HCVR)
(CDRs underlined)
                                        SEQ ID NO: 8
DVQLVESGGGLVQPGRSLKLSCAASGFTFSAYYMAWVRQAPTKGLEWVA

SINYDGANTFYRDSVKGRFTVSRDNARSSLYLQMDSLRSEDTATYYCTT

EAYGYNSNWFGYWGQGTLVTVSS

CA185_01979.0 (VR0001842)
Light chain variable region (LCVR)
(CDRs underlined)
                                        SEQ ID NO: 22
DIQMTQSPASLSASLEEIVTITCQASQDIGNWLSWYQQKPGKSPHLLIY

GTTSLADGVPSRFSGSRSGTQYSLKISGLQVADIGIYVCLQAYSTPFTF

GSGTKLEIK

Heavy chain variable region (HCVR)
(CDRs underlined)
                                        SEQ ID NO: 23
EVHLVESGPGLVKPSQSLSLTCSVTGYSITNSYVVDWIRKFPGNKMEWM

GYINYSGSTGYNPSLKSRISISRDTSNNQFFLQLNSITTEDTATYYCAR

GTYGYNAYHFDYWGRGVMVTVSS
```

Example 16—High Performance Liquid Chromatography (HPLC) to Determine Antibody Characteristics Specific binding of mouse Fab fragments was demonstrated by complex formation between CA185_01974 and human TNFα complexed with compound (15) using size exclusion chromatography (data not shown). With a 0.5× molar excess of Fab the predominant peak corresponds to bound Fab and trimer-compound complex (although there is a small peak showing the presence of some trimer-compound complex not bound to Fab). At a 1.0× molar excess of Fab there is single higher molecular weight peak corresponding to Fab bound to trimer-compound complex. At 1.5× and 2× molar excesses of Fab, there is a growing lower molecular peak corresponding to unbound Fab.

The stoichiometry was therefore determined to be 1 Fab: 1 TNFα trimer, with excess Fab appearing at 1.5× and 2× molar excess.

Binding of CA185_01979 to human TNFα complexed with compound (15) was also investigated using size exclusion chromatography (data not shown). As for CA185_01974, the stoichiometry was determined to be 1 Fab: 1 TNFα trimer, with excess Fab appearing at 1.5× and 2× molar excess.

Example 17—BIAcore Assays to Determine Antibody Characteristics

Surface plasmon resonance was performed at 25° C. using a BIAcore T200 (GE Healthcare). Anti-Mouse Fc (Jackson 115-006-071) was immobilised on a CM5 Sensor Chip (GE Healthcare) via amine coupling chemistry to a capture level of ~6000 response units. HBS-EP buffer (10 mM HEPES pH 7.4, 0.15 M NaCl, 3 mM EDTA, 0.05% (v/v) surfactant P20—GE Healthcare)+1% DMSO was used as the running buffer. A 10 μl injection of each IgG at 1 μg/ml was used for capture by the immobilised anti-mouse Fc to create the TNFα-binding surface. Human or mouse TNFα (in-house) at 50 nM was pre-incubated with 2 μM compound in HBS-EP+(1% DMSO) for 5 hours.

A 3 minute injection of human or mouse TNFα+/−test compound was passed over each captured IgG at a flow rate of 30 μl/min. The surface was regenerated at a flow-rate of 10 μl/min by a 60 s injection of 40 mM HCl ×2 and a 30 s 5 mM NaOH. Double referenced background subtracted binding curves were analysed using the T200 Evaluation software (version 1.0) following standard procedures. Kinetic parameters were determined from the fitting algorithm.

The kinetic binding data for human and mouse TNFα in the presence and absence of test compounds from two chemical series are shown in Tables 2 and 3 below.

TABLE 2

BIAcore data with human TNFα

| Antibody | Human TNFα | ka (M$^{-1}$s$^{-1}$) | kd (s$^{-1}$) | KD (M) |
|---|---|---|---|---|
| CA185_01974 | + compound (39) | 4.2 × 10$^5$ | 3.9 × 10$^{-5}$ | 9.4 × 10$^{-11}$ |
| CA185_01974 | + compound 15 | 3.2 × 10$^5$ | 3.8 × 10$^{-5}$ | 1.2 × 10$^{-1}$ |
| CA185_01974 | apo | 6.6 × 10$^4$ | 1.3 × 10$^{-3}$ | 1.9 × 10$^{-8}$ |
| CA185_01979 | + compound (39) | 5.7 × 10$^5$ | 3.3 × 10$^{-5}$ | 5.8 × 10$^{-11}$ |
| CA185_01979 | + compound (15) | 4.7 × 10$^5$ | 1.6 × 10$^{-5}$ | 3.4 × 10$^{-11}$ |
| CA185_01979 | apo | 1.1 × 10$^5$ | 7.1 × 10$^{-4}$ | 6.7 × 10$^{-9}$ |

Both CA185_01974 and CA185_01979 demonstrated >2 log selective binding for compound-distorted human TNFα, with representative test compounds from two chemical series.

TABLE 3

BIAcore data with mouse TNFα

| Antibody | Mouse TNFα | ka (M$^{-1}$s$^{-1}$) | kd (s$^{-1}$) | KD (M) |
|---|---|---|---|---|
| CA185_01974 | + compound (39) | 6.7 × 10$^4$ | 4.8 × 10$^{-5}$ | 7.1 × 10$^{-1}$ |
| CA185_01974 | + compound (15) | 5.8 × 10$^4$ | 8.8 × 10$^{-5}$ | 1.5 × 10$^{-9}$ |
| CA185_01974 | apo | 4.2 × 10$^4$ | 4.9 × 10$^{-3}$ | 1.2 × 10$^{-7}$ |
| CA185_01979 | + compound (39) | 1.9 × 10$^5$ | 3.5 × 10$^{-5}$ | 1.9 × 10$^{-1}$ |
| CA185_01979 | + compound (15) | 1.6 × 10$^5$ | 6.3 × 10$^{-5}$ | 3.8 × 10$^{-1}$ |
| CA185_01979 | apo | 7.2 × 10$^4$ | 2.0 × 10$^{-3}$ | 2.7 × 10$^{-8}$ |

Both CA185_01974 and CA185_01979 demonstrated >1.5 and >2 log selective binding for compound-distorted mouse TNFα, with representative test compounds from two chemical series.

Conclusions

The antibodies CA185_01974 and CA185_01989 have been demonstrated specifically to bind to a compound-distorted state of TNFα, and will be useful target-engagement biomarkers for detecting the distorted trimeric structure of TNFα of the invention.

The antibodies have been shown to bind to a conformation of TNFα, which is specifically stabilised by compounds from different chemical series. It is envisaged that these antibodies will become standards in defining this, and closely related, biologically relevant conformations, of the TNFα trimer, which are stabilised by a wider range of chemical series than are described here. Based on the data shown, the human TNFα trimer could be considered to be stabilised in the defined, biologically relevant conformation described if either CA185_01974 or CA185_01989 antibody binds with a K$_D$ better than 1 nM in the BIAcore assay format described above.

Example 18—Crystal Structures of Trimeric TNFα Bound to the Compounds of Formulae (1)-(64)

The soluble form of human TNFα (VC 2043, UniProt P01375) was expressed as a fusion protein in *E. coli* and had the final sequence:

```
                                        (SEQ ID NO: 35)
SVRSSSRTPSDKPVAHVVANPQAEGQLQWLNRRANALLANGVELRDNQLV

VPSEGLYLIYSQVLFKGQGCPSTHVLLTHTISRIAVSYQTKVNLLSAIKS

PCQRETPEGAEAKPWYEPIYLGGVFQLEKGDRLSAEINRPDYLDFAESGQ

VYFGIIAL
```

The initial "S" of SEQ ID NO: 35 is a cloning artefact and not part of the native sequence of the TNF. The residue numbering of SEQ ID NO: 35 therefore starts from V i.e. V1, R2, S3 etc. SEQ ID NO: 36 represents SEQ ID NO: 35, but without this initial "S" residue i.e.

```
                                        (SEQ ID NO: 36)
VRSSSRTPSDKPVAHVVANPQAEGQLQWLNRRANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL
```

Cells were pre-cultured at 37° C. in rich media, induced with the addition of 0.1% arabinose and allowed to express overnight at 25° C. in vector pEMB54. This vector introduces a cleavable N-terminal His6Smt-tag. The cells were lysed and purified by Ni-NTA chelate chromatography. The fusion protein was eluted with buffer containing imidazole and cleaved by the addition of protease. The final cleaved TNFα protein was purified by a subtractive Ni chelate chromatography step to remove the fusion tag and further purified by size exclusion chromatography to remove the remaining impurities. The final TNFα product was typically concentrated to 20.0 mg/ml and flash frozen in liquid nitrogen.

Purified human TNF☐☐ (20.0 mg/ml, VC 2043) was diluted to 4-7 mg/ml in 10 mM HEPES pH 7.5, 150 mM NaCl buffer followed by overnight incubation at 4° C. with 0.3-0.5 mM compound (1-2 molar excess). The TNF☐☐ compound complexes were crystallized by sitting drop vapor diffusion by mixing 0.5 µl of complex with 0.5 µl of 21.44% PEG 3350, 100 mM Tris, pH 9.0 (UCB1474433); or 22.0% PEG 3350, 100 mM glycine, 100 mM Tris, pH 8.5 (UCB1480595); or 25.6% PEG 3350, 100 mM Tris, pH 8.3, 3% xylitol (UCB5143079) or other formulation with varying precipitant concentration or additives over 100 µl of the same crystallization solution. Other formulations for other compounds include a range of PEG 3350 of 8-28%. Other PEG-like additives include PEG 1000 (8-18%) or PEG 2000 (10-13%). Other additives include MPD (5-13%) or 200 mM NaCl. Other buffers include 100 mM Hepes (pH 7-8), 100 mM Tris or bis-Tris (pH 6.7-9.0). Other non-PEG 3350 crystallization solutions consist of PEG 2000 (14-19%), 100 mM Hepes, pH 8, 25 mM arginine; or 17% PEG 10000, 200 mM ammonium acetate, 100 mM bis-Tris, pH 5.5; or 30% PEG 2000 MME, 100 mM sodium acetate, 100 mM Mes, pH 6.5. More details of crystallization conditions and unit cells for each compound are listed in Table 4.

Crystals were briefly soaked in ethylene glycol and/or vitrified directly in liquid nitrogen for data collection.

X-ray diffraction data were collected from a synchrotron source at a wavelength, most frequently, of 0.976484 Å and recorded on CCD detector. Diffraction data were reduced with the XDS package (Kabsch, 2010a). The structure of the human TNF☐ (VC 2043) complexed with compound was solved by molecular replacement using Phaser with input model of ITNF. Data were integrated in XDS and scaled using XSCALE (Kabsch, 2010b). Iterative manual model building using Coot (Emsley and Cowtan, 2004) and Refmac (Murshudov et al., 1997) continued until R and R$_{free}$ converged. Model quality was validated using Coot and MolProbity (Chen et al., 2010). The resolution of the structures was most frequently around 2.15 Å.

Atomic coordinates for all 64 structures are given in the Supplementary Data of the present invention, each structure given the name "Compound X" or "CompoundX.pdb" with X being the formula number (X) of the Compound in FIG. 1 sitting at the centre of each trimer.

References:

Kabsch, W. 2010a. XDS. Acta Crystallogr. D Biol. Crystallogr. February; 66 (Pt 2): 1125-32. PMID: 20124692.

Kabsch W. 2010b. Integration, scaling, space-group assignment and post-refinement. Acta Crystallogr. D Biol. Crystallogr. February; 66 (Pt 2): 133-44. PMID: 20124693.

Emsley, P. and Cowtan, K. 2004. Coot: model-building tools for molecular graphics. Acta Crystallogr. D Biol. Crystallogr. December; 60 (Pt 12 Pt 1): 2126-32. PMID: 15572765.

Murshudov, G. N., Vagin, A. A., and Dodson, E. J. 1997. Refinement of macromolecular structures by the maximum-likelihood method. Acta Crystallogr. D Biol. Crystallogr. May 1; 53 (Pt 3): 240-55. PMID: 15299926.

Chen et al. 2010. MolProbity: all-atom structure validation for macromolecular crystallography. Acta Crystallogr. D Biol. Crystallogr. January; 66 (Pt 1): 12-21. PMID: 20057044.

TABLE 4

| Compound | Crystallization conditions | Unit cell dimensions | Space group |
|---|---|---|---|
| 1 | 13% MPD, 13% PEG 1000, 13% PEG 3350, 0.1M Hepes, pH 8.0, 298K | 54.530 81.600 92.260 90.00 90.00 90.00 | P 21 21 21 |
| 2 | 13% PEG 1000, 15% PEG 3350, 0.1M Hepes, pH 8.0, 298K | 53.380 81.610 92.230 90.00 90.00 90.00 | P 21 21 21 |
| 3 | 10% PEG 2000, 15% PEG 3350, 3% xylitol, 0.1M Hepes, pH 8.9, 298K | 53.520 81.170 93.350 90.00 90.00 90.00 | P 21 21 21 |
| 4 | 25% PEG 3350, 0.1M bis-Tris, pH 6.7, 298K | 54.680 81.760 92.280 90.00 90.00 90.00 | P 21 21 21 |
| 5 | 12% PEG 1000, 15% PEG 3350, 3% xylitol, 0.1M Hepes, pH 8.0, 298K | 53.820 81.570 93.080 90.00 90.00 90.00 | P 21 21 21 |
| 6 | 11% PEG 1000, 15% PEG 3350, 3% xylitol, 0.1M Hepes, pH 8.0, 298K | 54.370 81.720 92.710 90.00 90.00 90.00 | P 21 21 21 |
| 7 | 13% PEG 2000, 15% PEG 3350, 3% xylitol, 0.1M Hepes, pH 8.0, 298K | 53.800 81.320 92.230 90.00 90.00 90.00 | P 21 21 21 |
| 8 | 11% PEG 1000, 15% PEG 3350, 3% xylitol, 0.1M Hepes, pH 8.0, 298K | 53.540 81.160 93.100 90.00 90.00 90.00 | P 21 21 21 |
| 9 | 13% PEG 1000, 13% PEG 3350, 3% xylitol, 0.1M Hepes, pH 8.0, 298K | 54.250 82.150 93.800 90.00 90.00 90.00 | P 21 21 21 |
| 10 | 12% PEG 1000, 15% PEG 3350, 3% xylitol, 0.1M Hepes, pH 8.0, 298K | 53.750 81.280 94.100 90.00 90.00 90.00 | P 21 21 21 |
| 11 | 19% PEG 2000, 15% PEG 1000, 0.025M arginine, 0.1M Hepes, pH 8.0, 298K | 53.600 82.060 93.240 90.00 90.00 90.00 | P 21 21 21 |
| 12 | 11% PEG 2000, 15% PEG 3350, 3% xylitol, 0.1M Hepes, pH 8.0, 298K | 54.037 82.059 93.887 90.00 90.00 90.00 | P 21 21 21 |
| 13 | 11% PEG 1000, 15% PEG 3350, 3% xylitol, 0.1M Hepes, pH 8.0, 298K | 53.560 80.890 93.490 90.00 90.00 90.00 | P 21 21 21 |
| 14 | 13% PEG 1000, 8% PEG 3350, 5% MPD, 0.1M Hepes, pH 8.0, 298K | 53.870 81.090 94.600 90.00 90.00 90.00 | P 21 21 21 |
| 15 | 23.2% PEG 3350, 5% MPD, 100 mM Tris, pH 8.0, 298K | 54.170 81.990 94.170 90.00 90.00 90.00 | P 21 21 21 |
| 16 | 12% PEG 1000, 15% PEG 3350, 3% xylitol, 0.1M Hepes, pH 8.0, 298K | 53.600 80.450 92.760 90.00 90.00 90.00 | P 21 21 21 |
| 17 | 11% PEG 1000, 15% PEG 3350, 3% xylitol, 0.1M Hepes, pH 8.0, 298K | 53.780 80.570 93.590 90.00 90.00 90.00 | P 21 21 2 |
| 18 | 14% PEG 2000, 15% PEG 1000, 0.025M arginine, 0.1M Hepes, pH 8.0, 298K | 53.620 81.660 92.720 90.00 90.00 90.00 | P 21 21 21 |
| 19 | 19% PEG 2000, 15% PEG 1000, 0.025M arginine, 0.1M Hepes, pH 8.0, 298K | 53.650 81.340 93.720 90.00 90.00 90.00 | P 21 21 21 |
| 20 | 24.4% PEG 3350, 3% xylitol, 100 mM Tris, pH 8.5, 298K | 54.770 81.700 93.780 90.00 90.00 90.00 | P 21 21 21 |
| 21 | 10% PEG 1000, 15% PEG 3350, 0.1M Hepes, pH 8.0, 298K | 54.290 81.620 92.730 90.00 90.00 90.00 | P 21 21 21 |
| 22 | 26.8% PEG 3350, 100 mM Tris, pH 8.3, 298K | 54.650 81.680 92.720 90.00 90.00 90.00 | P 21 21 21 |
| 23 | 24.4% PEG 3350, 100 mM Tris, pH 7.7, 298K | 54.490 81.600 93.040 90.00 90.00 90.00 | P 21 21 21 |
| 24 | 17% PEG 10000, 200 mM ammonium acetate, 0.1M bis-Tris, pH 5.5, 298K | 54.350 81.270 92.600 90.00 90.00 90.00 | P 21 21 21 |
| 25 | 18.6% PEG 3350, 3% xylitol, 100 mM Tris, pH 7.5, 298K | 53.980 81.660 93.470 90.00 90.00 90.00 | P 21 21 21 |
| 26 | 13% PEG 3350, 18% PEG 1000, 5% MPD, 100 mM Hepes, pH 8.0, | 54.540 81.590 92.300 90.00 90.00 90.00 | P 21 21 21 |
| 27 | 28% PEG 3350, 100 mM glycine, 100 mM Tris, pH 8.3, 298K | 54.380 81.640 91.790 90.00 90.00 90.00 | P 21 21 21 |
| 28 | 21.4% PEG 3350, 100 mM Tris, pH 8.0, 298K | 54.160 81.470 93.420 90.00 90.00 90.00 | P 21 21 21 |
| 29 | 26.8% PEG 3350, 100 mM Tris, pH 9.0, 298K | 54.620 81.690 93.000 90.00 90.00 90.00 | P 21 21 21 |
| 30 | 25.0% PEG 3350, 200 mM NaCl, 100 mM Tris, pH 8.5, 298K | 54.320 81.640 92.280 90.00 90.00 90.00 | P 21 21 2 |
| 31 | 23.2% PEG 3350, 100 mM Tris, pH 7.5, 298K | 54.440 82.660 92.150 90.00 90.00 90.00 | P 21 21 21 |
| 32 | 21.44% PEG 3350, 100 mM Tris, pH 9.0, 298K | 54.520 81.960 93.240 90.00 90.00 90.00 | P 21 21 21 |
| 33 | 24.4% PEG 3350, 100 mM Tris, pH 8.3, 298K | 54.220 82.360 92.880 90.00 90.00 90.00 | P 21 21 21 |
| 34 | 22% PEG 3350, 100 mM Hepes, pH 7.5, 298K | 54.260 81.700 92.740 90.00 90.00 90.00 | P 21 21 21 |
| 35 | 23.2% PEG 3350, 100 mM Tris, pH 8.5, 298K | 54.620 81.990 92.090 90.00 90.00 90.00 | P 21 21 21 |
| 36 | 23.2% PEG 3350, 3% xylitol, 100 mM Tris, pH 8.0, 298K | 54.650 81.900 92.850 90.00 90.00 90.00 | P 21 21 21 |
| 37 | 25.6% PEG 3350, 3% xylitol, 100 mM Hepes, pH 7.5, 298K | 54.610 81.860 92.920 90.00 90.00 90.00 | P 21 21 21 |
| 38 | 26.8% PEG 3350, 100 mM Hepes, pH 7.5, 298K | 54.410 82.140 93.160 90.00 90.00 90.00 | P 21 21 21 |
| 39 | 24.4% PEG 3350, 100 mM Hepes, pH 7.0, 298K | 55.120 82.110 93.020 90.00 90.00 90.00 | P 21 21 21 |
| 40 | 23.2% PEG 3350, 100 mM Tris, pH 7.7, 298K | 54.650 81.750 92.060 90.00 90.00 90.00 | P 21 21 21 |

TABLE 4-continued

| Compound | Crystallization conditions | Unit cell dimensions | Space group |
|---|---|---|---|
| 41 | 26.8% PEG 3350, 100 mM glycine, 100 mM Tris, pH 8.0, 298K | 54.660 81.820 92.390 90.00 90.00 90.00 | P 21 21 21 |
| 42 | 26.8% PEG 3350, 3% xylitol, 100 mM Hepes, pH 7.5, 298K | 54.340 81.890 92.580 90.00 90.00 90.00 | P 21 21 21 |
| 43 | 22% PEG 3350, 100 mM glycine, 100 mM Tris, pH 8.5, 298K | 54.260 80.990 94.610 90.00 90.00 90.00 | P 21 21 21 |
| 44 | 22% PEG 3350, 5% MPD, 100 mM Tris, pH 8.0, 298K | 54.400 81.410 92.800 90.00 90.00 90.00 | P 21 21 21 |
| 45 | 23.2% PEG 3350, 100 mM Tris, pH 8.5, 298K | 54.760 81.400 93.250 90.00 90.00 90.00 | P 21 21 21 |
| 46 | 23.2% PEG 3350, 3% xylitol, 100 mM Tris, pH 9.0, 298K | 54.370 81.540 92.970 90.00 90.00 90.00 | P 21 21 21 |
| 47 | 25.6% PEG 3350, 3% xylitol, 100 mM Tris, pH 9.0, 298K | 54.640 82.120 93.830 90.00 90.00 90.00 | P 21 21 21 |
| 48 | 23.2% PEG 3350, 100 mM Hepes, pH 7.0, 298K | 54.290 81.510 92.320 90.00 90.00 90.00 | P 21 21 21 |
| 49 | 28% PEG 3350, 3% xylitol, 0.1M Hepes, pH 7.5, 298K | 54.450 81.380 92.670 90.00 90.00 90.00 | P 21 21 21 |
| 50 | 20.48% PEG 3350, 100 mM Tris, pH 7.5, 298K | 54.400 81.760 92.940 90.00 90.00 90.00 | P 21 21 21 |
| 51 | 25.6% PEG 3350, 3% xylitol, 100 mM Tris, pH 8.3, 298K | 54.530 81.350 93.120 90.00 90.00 90.00 | P 21 21 21 |
| 52 | 23.2% PEG 3350, 100 mM Tris, pH 8.5, 298K | 54.590 81.670 92.830 90.00 90.00 90.00 | P 21 21 21 |
| 53 | 10% PEG 3350, 8% PEG 1000, 5% MPD, 100 mM Hepes, pH 8.0, 298K | 54.470 81.860 93.400 90.00 90.00 90.00 | P 21 21 21 |
| 54 | 24.4% PEG 3350, 100 mM Tris, pH 8.5, 298K | 54.250 81.650 92.740 90.00 90.00 90.00 | P 21 21 21 |
| 55 | 18.56% PEG 3350, 100 mM glycine, 100 mM Tris, pH 7.5, 298K | 54.570 81.470 92.880 90.00 90.00 90.00 | P 21 21 21 |
| 56 | 26.8% PEG 3350, 100 mM Tris, pH 8.5, 298K | 54.250 81.820 93.390 90.00 90.00 90.00 | P 21 21 21 |
| 57 | 21.44% PEG 3350, 100 mM Tris, pH 7.5, 298K | 54.290 81.150 92.740 90.00 90.00 90.00 | P 21 21 21 |
| 58 | 24.4% PEG 3350, 5% MPD, 100 mM Tris, pH 9.0, 298K | 54.520 81.460 93.010 90.00 90.00 90.00 | P 21 21 21 |
| 59 | 23.2% PEG 3350, 100 mM Hepes, pH 7.0, 298K | 54.320 81.810 93.010 90.00 90.00 90.00 | P 21 21 21 |
| 60 | 23.2% PEG 3350, 100 mM Tris, pH 8.5, 298K | 47.700 95.780 100.740 90.00 99.12 90.00 | P 1 21 1 |
| 61 | 23.2% PEG 3350, 100 mM Tris, pH 8.5, 298K | 54.430 80.560 93.190 90.00 90.00 90.00 | P 21 21 21 |
| 62 | 30% PEG PEG 2000 MME, 100 mM sodium acetate, 100 mM Mes, pH 6.5, 298K | 54.400 81.700 92.500 90.00 90.00 90.00 | P 21 21 21 |
| 63 | 23.2% PEG 3350, 100 mM Tris, pH 8.5, 298K | 54.620 81.640 93.330 90.00 90.00 90.00 | P 21 21 21 |
| 64 | 25.6% PEG 3350, 100 mM Tris, 3% xylitol, pH 8.3, 298K | 54.090 82.090 93.230 90.00 90.00 90.00 | P 21 21 21 |

Figure 8:
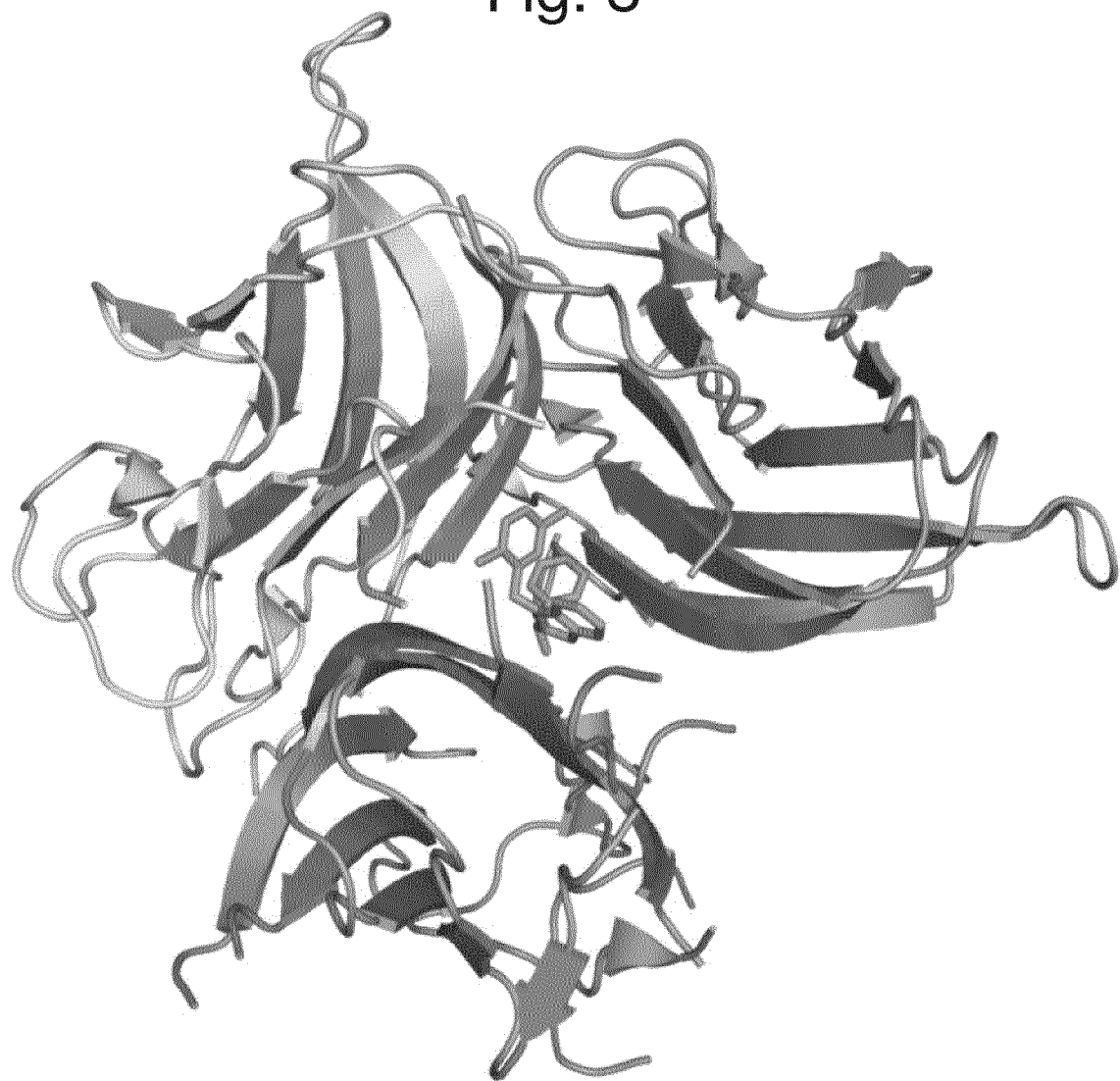
FIG. 8 shows the crystal structure of a compound of formula (3)-trimeric TNFα complex.

When the TNFα was pre-incubated with the compound of formula (3), the resulting compound-trimer complex crystallised, and the crystal structure of the compound-trimer TNFα complex determined using X-ray crystallography, the crystal structure of the complex (solved to a resolution of 2.2 Å) can be seen in FIG. 8. The compound can be seen in the middle of the trimer which is no longer symmetrical.

In more detail, when looking at a crystal structure of a TNFα trimer from the side it is approximately shaped like a pyramid/cone. When you look down the trimer axis with the N- and C-termini of the monomer ends pointing towards you then you are looking at the "fat" end of the trimer. In the distorted structure with compound, a cleft opens between A and C subunits in which, without being bound by theory, the CA185_01974 and CA185_01979 Abs bind.

Which chain is A, B or C may be ascertained by measuring three distances between three C-alpha atoms of three identical residues—e.g. P117 in each chain (G121 is also appropriate).

The three distances form a triangle which is equilateral in apo TNF but distorted when compound is bound. The shortest distance is between BC and the longest between AC (for instance AC=13.8 Å, AB=12.3 Å, BC=10.2 Å); thus looking down through the axis of the molecule with N/C termini pointing towards you the longest distance defines C then A chains going anti-clockwise, then B and C again continuing anti-clockwise.

It has been identified that binding of the compounds described herein to trimeric forms of TNF results in a conformational change in the TNF trimer. In particular, the TNF trimer takes on a deformed or distorted conformation when bound by a compound as disclosed herein.

For example, when compounds (1)-(64) are bound the soluble domain of human TNFα the TNF retains its trimeric structure but the A and C subunits move away from each other and A rotates to generate a cleft between these subunits. Without being bound by theory, it is believed that this distortion accounts for the trimer's ability to bind TNFR1 without the normal activation of the receptor.

This movement of the subunits also results in an enlargement of the cavity at centre of the trimer where the Compounds bind. Compounds (1)-(64) have between 20 and 41 non-hydrogen atoms. Typically the increase in surface area within the distorted TNFα trimer structures relative to apo TNFα structure 1A8M (using The PYMOL Molecular Graphics System, Version 1.7 Schrödinger, LLC; using the commands and settings: solvent radius=1.4 Å, dot_solvent=1, get_area) is between 500-1000 Å$^2$.

Example 19—Analysis of Crystal Structures of Trimeric TNFα Bound to the Compounds of Formulae (1)-(63), and Determination that the Distorted TNFα Trimer Structure "Compound 64.Pdb" is within the TNFα Trimer Structures of the Invention Root mean squared deviation (RMSD) calculations were carried out to ascertain the distance of each of the crystal structures of distorted TNFα trimer to a reference structure. RMSD calculations were done using the program PyMOL (www.pymol.org). In this example version 1.7. was used. The cmd.rms PyMOL command was used with defined pairs of atoms. The atoms used were the backbone Ca's of certain residues within the β-strands of TNFα. The residue numbers used are shown below:
12-18, 47-50, 54-64, 76-82, 91-97, 117-125, 129-137, 150-156

These residue numbers are those within the published structure of TNFα with PDB code 1A8M and within the distorted TNFα trimer structures of this invention. The residue numbers are also according to the sequence of SEQ ID NO:36. The residues in each of the three chains with the TNFα structures, (labelled A, B, and C according to our instructions) were used.

The command cmd.rms was used with the following arguments:

rms=cmd.rms("(moving)", "(target)", matchmaker=4, quiet=0, cycles=0)
where "(moving)" is the selection of atoms in a given TNFα structure and "(target)" is the selection of equivalent atoms within the reference structure.

The RMSD was calculated for each structure against all others. The "representative structure" or "Reference Structure" was chosen to be the one with the lowest sum RMSD to all others—the structure "Compound 34" or "Compound34.pdb".

Figure 16:
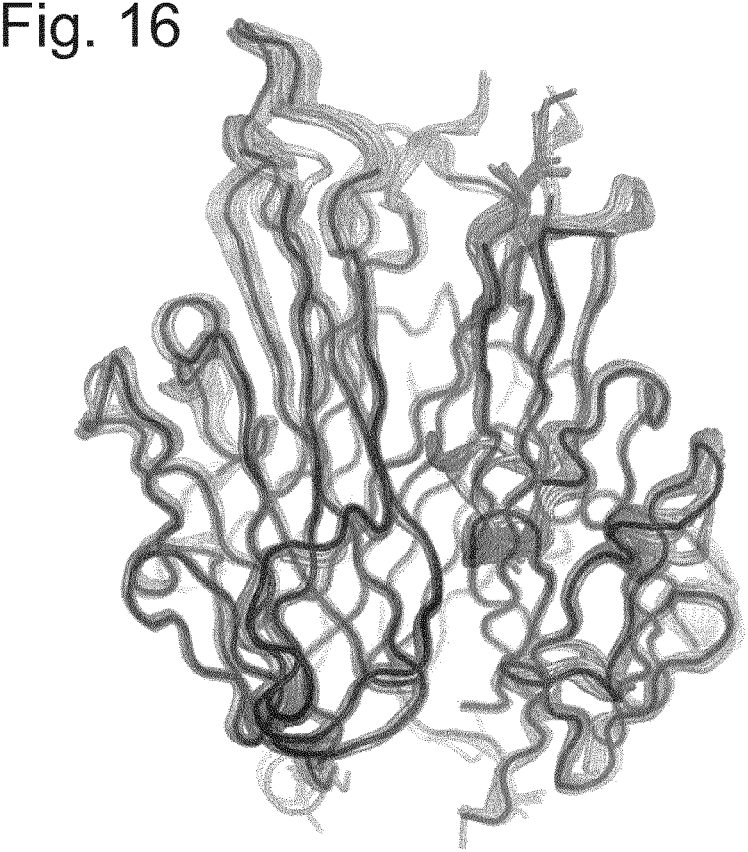
FIG. 16 shows an RMSD overlay of the Cα atoms of the β-sheets of the distorted TNFα trimer structures Compound 1-33,35-63 with the emboldened Reference Structure Compound 34.

The RMSD values, measured in Angstroms, for the remaining 63 structures with reference to the Compound 34 structure are shown below in Table 5. FIG. 16 shows an overlay of the structures with the Reference Structure emboldened; the structures cluster closely around the Reference Structure indicating the common distorted TNFα trimeric arrangement for all 64 structures.

TABLE 5

| Crystal structure | RMSD (Å) with Compound 34 |
| --- | --- |
| Compound 1 | 0.20 |
| Compound 2 | 0.24 |
| Compound 3 | 0.33 |
| Compound 4 | 0.21 |
| Compound 5 | 0.25 |
| Compound 6 | 0.21 |
| Compound 7 | 0.25 |
| Compound 8 | 0.30 |
| Compound 9 | 0.28 |
| Compound 10 | 0.25 |
| Compound 11 | 0.30 |
| Compound 12 | 0.27 |
| Compound 13 | 0.36 |
| Compound 14 | 0.30 |
| Compound 15 | 0.24 |
| Compound 16 | 0.47 |
| Compound 17 | 0.44 |
| Compound 18 | 0.31 |
| Compound 19 | 0.21 |
| Compound 20 | 0.22 |
| Compound 21 | 0.22 |
| Compound 22 | 0.23 |
| Compound 23 | 0.24 |
| Compound 24 | 0.28 |
| Compound 25 | 0.34 |
| Compound 26 | 0.38 |
| Compound 27 | 0.24 |
| Compound 28 | 0.29 |
| Compound 29 | 0.24 |
| Compound 30 | 0.23 |
| Compound 31 | 0.24 |
| Compound 32 | 0.24 |
| Compound 33 | 0.14 |
| Compound 35 | 0.16 |
| Compound 36 | 0.21 |
| Compound 37 | 0.22 |
| Compound 38 | 0.17 |
| Compound 39 | 0.22 |
| Compound 40 | 0.17 |
| Compound 41 | 0.20 |
| Compound 42 | 0.21 |
| Compound 43 | 0.36 |
| Compound 44 | 0.25 |
| Compound 45 | 0.24 |
| Compound 46 | 0.27 |
| Compound 47 | 0.26 |
| Compound 48 | 0.30 |
| Compound 49 | 0.28 |
| Compound 50 | 0.23 |
| Compound 51 | 0.34 |
| Compound 52 | 0.26 |
| Compound 53 | 0.24 |
| Compound 54 | 0.32 |
| Compound 55 | 0.26 |
| Compound 56 | 0.24 |
| Compound 57 | 0.30 |
| Compound 58 | 0.24 |
| Compound 59 | 0.25 |
| Compound 60 | 0.44 |
| Compound 61 | 0.28 |
| Compound 62 | 0.16 |
| Compound 63 | 0.36 |
| Compound 64 | 0.22 |

The RMSD to the Reference Structure of the apo form of the TNFα trimer published as PDB code 1A8M is 2.35 Å.

Figure 17:
FIG. 17 shows an RMSD overlay of the Cα atoms of the β-sheets of the distorted TNFα trimer structure Compound 64 with the emboldened Reference Structure Compound 34.

Example 19 b): Determination that the Distorted TNFα Trimer Structure "Compound 64" is within the TNFα Trimer Structures of the Invention Reference Structure (Compound 34) and Query Structure (Compound 64) were overlaid (see FIG. 17 with Reference Structure emboldened) by:
1. Reading pdb files for both crystal structures into PyMol
2. Creating selections for the identified residue c-alpha atoms for Compound 64 (Compound64.pdb) e.g. "(moving)" and Reference Structure (Compound34.pdb) e.g. "(target)" crystal structures. There should be 183 atoms selected in each structure.
3. Calculating the root mean squared deviation (RMSD) in Angstroms using the rms command.
4. The RMSD is less than 0.9 Å (0.22 Å) and so the distorted TNFα structure of Compound 64 falls within the scope of the present invention.

Record of the input and responses from PyMol:
PyMOL>load Compound34.pdb
CmdLoad: "Compound34.pdb" loaded as "Compound34".
PyMOL>load Compound64.pdb
CmdLoad: "Compound64.pdb" loaded as "Compound64".
PyMOL>select moving, Compound64 and name CA and (alt A or alt "\") and (resi 12-18 or resi 47-50 or resi 54-64 or resi 76-82 or resi 91-97 or resi 117-125 or resi 129-137 or resi 150-156) and (chain A or chain B or chain C)
Selector: selection "moving2" defined with 183 atoms.
PyMOL>select target, Compound34 and name CA and (alt A or alt "V") and (resi 12-18 or resi 47-50 or resi 54-64 or resi 76-82 or resi 91-97 or resi 117-125 or resi 129-137 or resi 150-156) and (chain A or chain B or chain C)
Selector: selection "target2" defined with 183 atoms.
PyMOL>from pymol import cmd
PyMOL>cmd.rms("(moving)", "(target)", matchmaker=4, quiet=0, cycles=0)
Executive: RMS=0.219 (183 to 183 atoms)

Example 19 c): Solving the Distorted TNFα Trimer Structure Complexed with Compound 65, and Determination that the Structure is within the TNFα Trimer Structures of the Invention Purified human TNFα (30.0 mg/ml, VC 2043) [produced as described above] was diluted to 4 mg/ml in 10 mM HEPES pH 7.5, 150 mM NaCl buffer followed by overnight incubation at 4° C. with 0.5 mM compound 65 (1-2 molar excess). The TNFα-compound 65 complex was crystallized by sitting drop vapor diffusion by mixing 0.5 μl of complex with 0.5 μl of 19% PEG 2000, 15% PEG 1000, 20 mM L-Arginine, 0.1M HEPES, pH 8.0 over 100 μl of the same crystallization solution. Crystals were harvested for data collection approximately 2 weeks after initial set up. They were briefly soaked in ethylene glycol and vitrified directly in liquid nitrogen for data collection. Structure determination was as described above. Statistics are shown in Table 5b below.

TABLE 5b

Data collection and refinement statistics

| Data collection | Dataset 1 |
|---|---|
| Beamline | CLSI 08ID-1 |
| Oscillation width (°) | 1.0 |
| Frames | 135 |
| Exposure (sec) | 3 |
| Distance (mm) | 250 |
| Wavelength (Å) | 0.97949 |
| Data processing | (outer shell) |
| Space Group | P212121 |
| Unit cell (Å, °) | a = 53.65, b = 81.34, c = 93.72 |
| Resolution (Å) | 50-2.55 (2.62-2.55) |
| I/σ | 21.1 (5.9) |
| Completeness (%) | 99.0 (99.7) |
| $R_{merge}$ (%) | 0.076 (0.439) |
| Reflections (unique) | 75,387 (13,765) |
| Multiplicity | 5.5 (5.5) |
| Refinement statistics | |
| $R_{work}/R_{free}$ overall | 0.171/0.237 |
| RMSD bonds (Å) | 0.015 |
| RMSD angles (°) | 1.508 |
| Ramachandran outliers (%) | 0.25 |
| Ramachandran favored (%) | 97.50 |
| Molprobity score | 1.67; 99$^{th}$ percentile* (N = 7646, 2.55Å ± 0.25Å) |

*100th percentile is the best among structures of comparable resolution; 0th percentile is the worst.

Reference Structure (Compound 34) and Query Structure (as determined above for Compound 65) were overlaid as described in Example 19 b). The RMSD was less than 0.9 Å (0.62 Å) and so the distorted TNFα structure of Compound 65 fell within the scope of the present invention. As for the structures described in Example 21, the pharmacophore of the invention within Compound 65 was within 4 Å of the same 7 TNFα residues.

Example 19 d)—Results from Further Structures

Further distorted TNFα trimer structures were generated with further compounds, and analysed as described above. All had an RMSD less than 0.9 Å compared to Reference Structure (the largest being 0.85 Å.

Example 20—Analysis of the Cavities within Crystal Structures of Distorted Trimeric TNFα

The analysis of a crystal structure of an Antibody/Antigen complex involves detailing important interactions at the paratope/epitope interface by looking for contacts within 4 Å. Similarly, the 64 distorted trimeric TNFα structures may be analysed for those important interactions that are consistently made between residues of TNFα and the compounds at the centre of the trimer.

Maestro from the Schrodinger program (Schrödinger Release 20144. Maestro, version 10.0, Schrödinger, LLC, New York, N.Y. 2014.) was used to analyse the 64 distorted TNFα trimer crystal structures. For each structure, a 4 Å radius around the ligand was selected and all residues from the TNFα trimer, situated within this 4 Å radius, were recorded.

Figure 18:
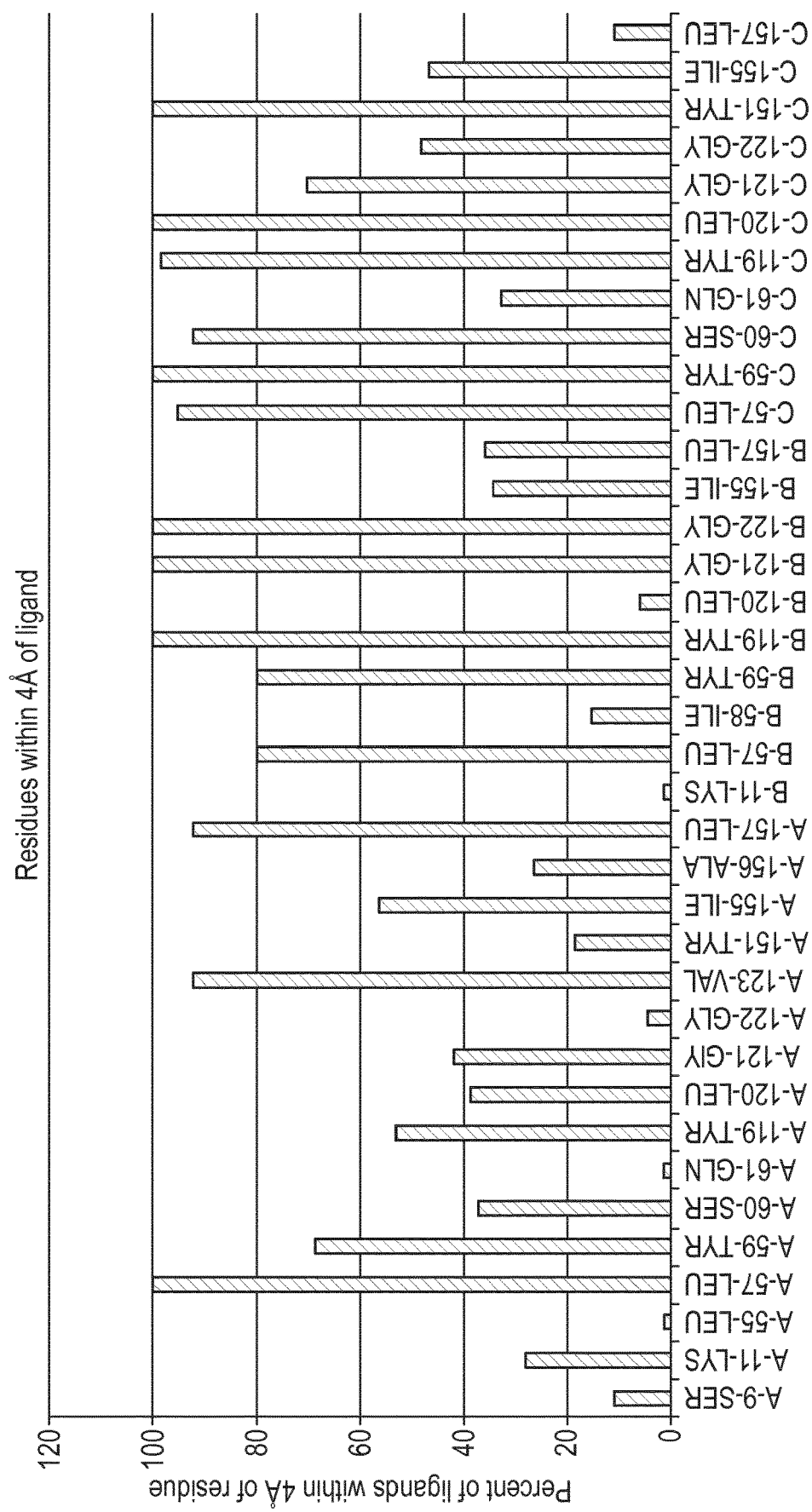
FIG. 18 shows a plot illustrating the percent of ligands from the 64 distorted TNFα trimer structures which are within 4 Å of a specific residue in the TNFα trimer.

FIG. 18 shows a plot illustrating the percent of ligands from the 64 distorted TNFα trimer structures which are within 4 Å of a specific residue (subunit specific) in the TNFα trimer. It was observed that 7 residues are always within 4 Å of the ligand: Leu57 from subunit A, Tyr119 from subunit B, Gly121 from subunit B, Gly122 from subunit B, Leu120 from subunit C and Tyr151 from subunit C. It should be noted that residues from all three subunits are always involved in the interaction; possibly a reason why the trimeric TNFα structure is stabilised.

Figure 19:
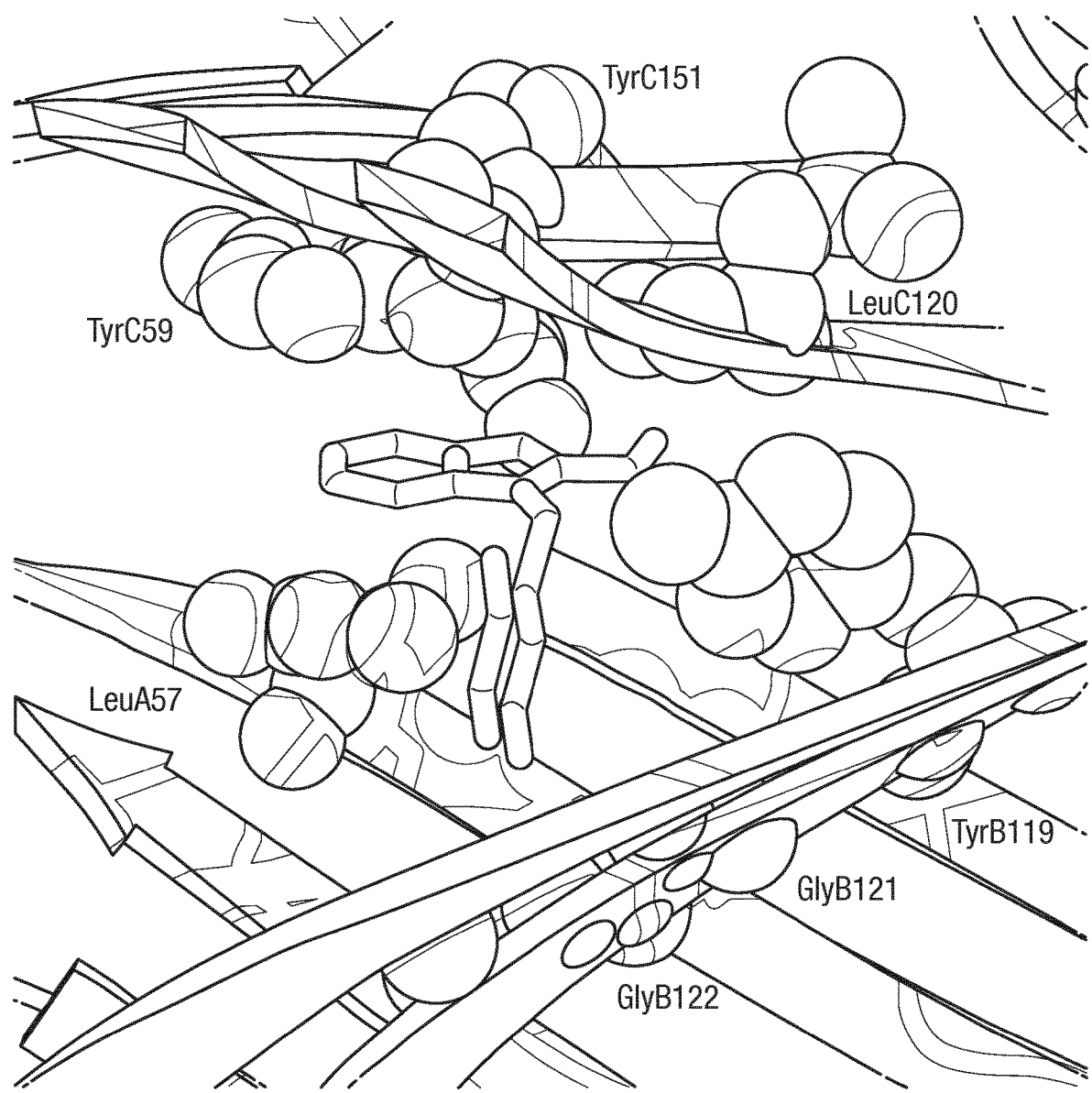
FIG. 19 shows a picture of the core of the Compound 1 distorted TNFα trimer structure highlighting all residues which are within 4 Å of the ligand in 100% of the 64 structures.

FIG. 19 shows a picture of the core of the Compound 1 distorted TNFα trimer structure highlighting all the above residues surrounding Compound 1.

Example 21—Analysis of the Pharmacophore Fitting at the Centre of the Distorted TNFα Trimer Structures of the Invention A pharmacophore can be described of a ligand which interacts with all 7 TNFα residues that are always within 4 Å of the ligand using the structures of Compounds (1)-(64) and the program Phase (Small-Molecule Drug Discovery Suite 2015-1: Phase, version 4.2, Schrödinger, LLC, New York, N.Y., 2015; Dixon, S. L.; Smondyrev, A. M.; Knoll, E. H.; Rao, S. N.; Shaw, D. E.; Friesner, R. A., "PHASE: A New Engine for Pharmacophore Perception, 3D QSAR Model Development, and 3D Database Screening. 1. Methodology and Preliminary Results," J. Comput. Aided Mol. Des., 2006, 20, 647-671; Dixon, S. L.; Smondyrev, A. M.; Rao, S. N., "PHASE: A Novel Approach to Pharmacophore Modeling and 3D Database Searching," Chem. Biol. Drug Des., 2006, 67, 370-372).

The features of the elucidated pharmacophore were as follows:

1) 2 fused 5- or 6-member rings (with centres at "R3" and "R2"), one ring (with centre at R2) with an H bond acceptor ("A1") [forming a hydrogen-bond with the sidechain of Tyr151 of subunit C] and which is also substituted through a linking non-hydrogen atom to a further 5- or 6-member ring (with centre at "R4");
2) Where the features may be arranged within the distorted TNFα trimer structure according to Table 6;
3) Where one or more of the rings may be aromatic;
4) Where one or more of the rings may be heteroaromatic;
5) Where the fused rings share 2 atoms;
6) Where the R3 ring may be 5 or 6 membered, the R2 ring may be 5 or 6 membered and the R4 ring may be 5 or 6 membered;
7) Where the linking non-hydrogen atom may be Carbon, Nitrogen, or Oxygen;
8) Where A1 may be through a nitrogen or oxygen atom in the R2 ring;
9) Where the pi system of the R2 ring may form a CH-pi interaction with the sidechain of Tyr59 on subunit C of the TNFα trimer;
10) Where the pi system of the R3 ring may form a pi stacking interaction with the sidechain of Tyr59 on subunit C of the TNFα trimer;
11) Where the pi system of the R3 ring may form a CH-pi interaction with the sidechain of Leu57 on subunit A of the TNFα trimer;
12) Where the pi system of the R4 ring may form a CH-pi interaction with the sidechain of Leu57 on subunit A of the TNFα trimer;
13) Where one or more of the distances between the R1, R2, R3 and A1 features may be according to those of Table 7 (about, exactly or within 10%);

14) Where one or more of the angles between the R1, R2, R3 and A1 features may be according to those of Table 8 (about, exactly or within 10%); the R3-R2-R4 angle defining a banana shape that may be involved in the desymmetrisation of the TNFα trimer;

15) Where the ligand comprising the pharmacophore may have 20-41 non-hydrogen atoms.

TABLE 6

| Distorted TNFα trimer amino acid | Pharmacophore Feature within 4Å of the TNFα trimer amino acid |
|---|---|
| TyrC151 | A1 Hydrogen-bond acceptor |
| TyrC59 | R2, R3 rings |
| LeuC120 | R2, R3 rings |
| LeuA57 | R3, R4 rings |
| TyrB119 | R4 ring |
| GlyB121 | R4 ring |
| GlyB122 | R4 ring |

TABLE 7

| Site 1 feature | Site 2 feature | Distance (Å) |
|---|---|---|
| A1 | R2 | 1.187 |
| A1 | R3 | 2.737 |
| A1 | R4 | 5.661 |
| R2 | R3 | 2.107 |
| R2 | R4 | 4.650 |
| R3 | R4 | 5.088 |

TABLE 8

| Site 1 feature | Site 2 feature | Site 3 feature | Angle (degrees) |
|---|---|---|---|
| R2 | A1 | R3 | 46.6 |
| R2 | A1 | R4 | 28.2 |
| R3 | A1 | R4 | 63.9 |
| A1 | R2 | R3 | 109.2 |
| A1 | R2 | R4 | 144.9 |
| R3 | R2 | R4 | 89.5 |
| A1 | R3 | R2 | 24.2 |
| A1 | R3 | R4 | 87.3 |
| R2 | R3 | R4 | 66.0 |
| A1 | R4 | R2 | 6.9 |
| A1 | R4 | R3 | 28.9 |
| R2 | R4 | R3 | 24.5 |

Figure 20:
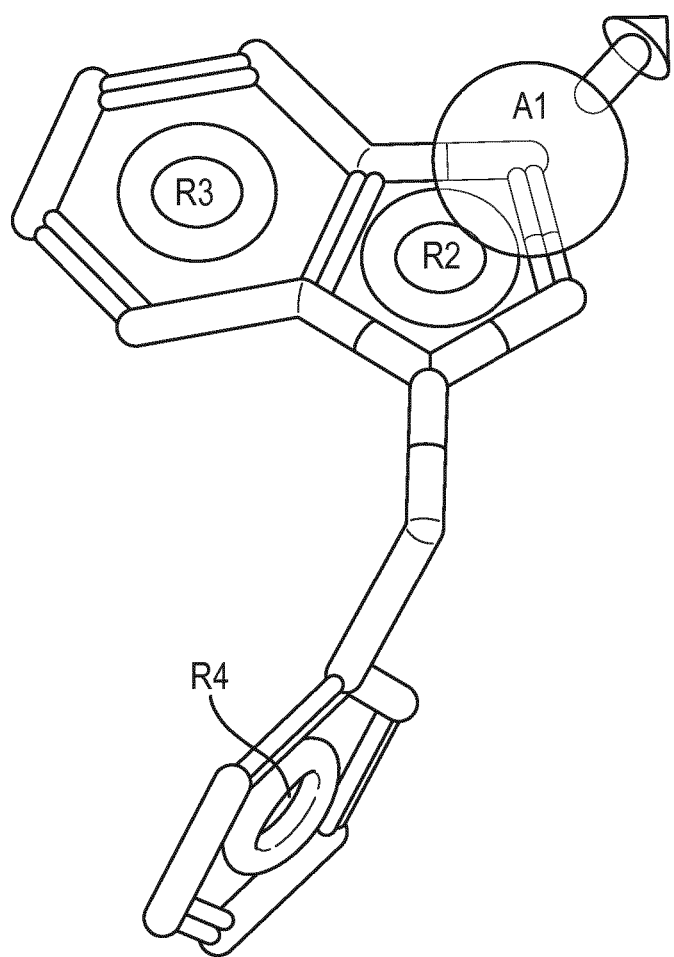
FIG. 20 shows an example of the pharmacophore that may fit within the distorted TNFα trimer structure of the invention showing the position of the R2, R3 and R4 centres of the three ring features, and the position of the Hydrogen Bond acceptor feature A1 within the R2 ring.

FIG. 20 shows an illustrative example of the pharmacophore that may fit within the distorted TNFα trimer structure of the invention showing the position of the R2, R3 and R4 centres of the three ring features, and the position of the Hydrogen Bond acceptor feature A1 within the R2 ring. In this example all the ring features are aromatic (with ring R2 being heteroaromatic), the linking atom between ring R2 and ring R4 is carbon, feature A1 within ring R2 is a nitrogen atom, ring R2 is a five-membered ring, rings R3 and R4 are six-membered, and with distances and angles between features according to Tables 7 and 8.

Example 22—Effects of TNF Small Molecules on Membrane TNF-TNFR2 Signalling

Existing inhibitors of TNFα bind and neutralise both soluble and membrane-bound TNFα (sTNFα and mTNFα, respectively) (Nesbitt et al. Inflamm Bowel Dis 2007 13:1323-1332).

It is known that sTNFα has specificity for the TNFR1 receptor, and mTNFα for the TNFR2 receptor (Grell et al. Cell 1995 83:793-802).

Existing inhibitors have black box warnings on their labels describing potential serious consequences of their use in the context of serious infection (particularly TB [tuberculosis], bacterial sepsis, and fungal infections) and malignancy (including lymphoma).

The immune response to TB (as well as *Listeria*) is known to be driven by mTNFα (Garcia et al. Chapter 20 p 187-201 "Roles of Soluble and Membrane TNF and Related Ligands in Mycobacterial Infections: Effects of Selective and Non-selective TNF Inhibitors During Infection" in D. Wallach et al. (eds.), *Advances in TNF Family Research*, Advances in Experimental Medicine and Biology 691, DOI 10.1007/978-1-4419-6612-4_20).

A TNFα inhibitor in development that selectively inhibits sTNFα but not mTNFα has the characteristics of attenuating experimental arthritis without suppressing innate immunity to infection (Zalevsky et al. J of Immunology 2007 179: 1872-1883).

The present example investigates how the mTNFα conformation upon binding Compounds described herein does not affect TNFR2 function; TNFR2 proximal and downstream signalling is not impaired.

A murine B cell line (NS0-mTNF) stably expressing non-cleavable human membrane TNF due to a mutation at the TACE cleavage site was used to trigger TNFR2 signalling in PHA-L and IL-2 expanded primary human T cells. T cells were expanded from PBMCs that were initially isolated from whole blood using Ficoll gradient centrifugation and showed increased levels of TNFR2 after activation and expansion with PHA-L and IL-2. TNFR1 was also present on these cells but was blocked using a UCB mouse anti-human-TNFR1 antibody 5R16.

NS0-mTNF cells were cultured with 10 μM NCEs for 1 hour to allow binding of Compounds to membrane TNF. T cells were then mixed with the NS0-mTNF cells and following a brief spin to allow cell-cell contact, cells were incubated for 5 min and then lysed in lysis buffer. The lysate was analysed for two proximal and downstream signalling events demonstrating TNFR2 signalling. First TRAF-2 recruitment to the TNFR2 receptor was measured in Co-immunoprecipitation experiments as a measure of membrane proximal signalling. After lysis of cells TNFR2 was isolated from the lysate using polyclonal goat anti-human TNFR2 antibodies followed by protein G sepharose bead purification. TNFR2 associated TRAF-2 was then measured in immunoblots after running the purified TNFR2 preparation on a SDS-PAGE. In addition, the whole cell lysate was also sampled for the presence of pNEκB using SDS-PAGE and pNEκB specific immunoblots.

NS0-wt cells were used as a control and showed very limited TRAF-2 recruitment to the TNFR2 receptor as well as low pNFκB signalling when mixed with expanded human primary T cells. In contrast, the presence of membrane TNF on NS0 cells lead to strong recruitment of TRAF-2 and potential ubiquitination due to the observed laddering effect, indicating TNFR2 specific membrane proximal signalling. In addition increased levels of pNFid3 was measured in the whole cell lysate, showing downstream TNFR2 signalling. The presence of Compounds did not alter the TNFR2 specific proximal and downstream signalling and led to similar recruitment of TRAF-2 to TNFR2 and similar levels of pNEκB in whole cell lysates. These results therefore show that binding of Compounds to membrane TNF over-expressed in NS0 cells does not impair TNFR2 specific membrane proximal (TRAF-2 recruitment to TNFR2) and downstream (pNEκB presence in whole cell lysates) signalling.

Detailed Method Part:

T-Cell Culture:
  PBMC from 3 three different donors were cultured in 6 well plates with 10×10^6 cells per well in 5 ml of RPMI1640 supplemented with 10% FCS, 1% human serum, HEPES GlutaMAX, 25 U/ml hIL-2 (Roche) and 2 µg/ml PHA-L (Sigma) to grow out T cells
  after 3 days cells were resuspended and cultured in 75 cm^2 flasks with the same media as above, but lacking the PHA-L
  growth of culture was monitored and media was changed every 3 days.

Culture of NS0-mTNF and NS0-Wt Cells
  NS0-wt: DMEM with 10% FCS, NEAA and GlutaMAX
  NS0-mTNF: DMEM with 10% FCS, NEAA (cells were cultured without GlutaMAX as membrane TNF was introduced into the cells on a vector expressing glutamine synthetase in order to produce both glutamine and the membrane TNF—using glutamine deficient media is keeping the cells selected for membrane TNF expressing cells.

Figure 21:
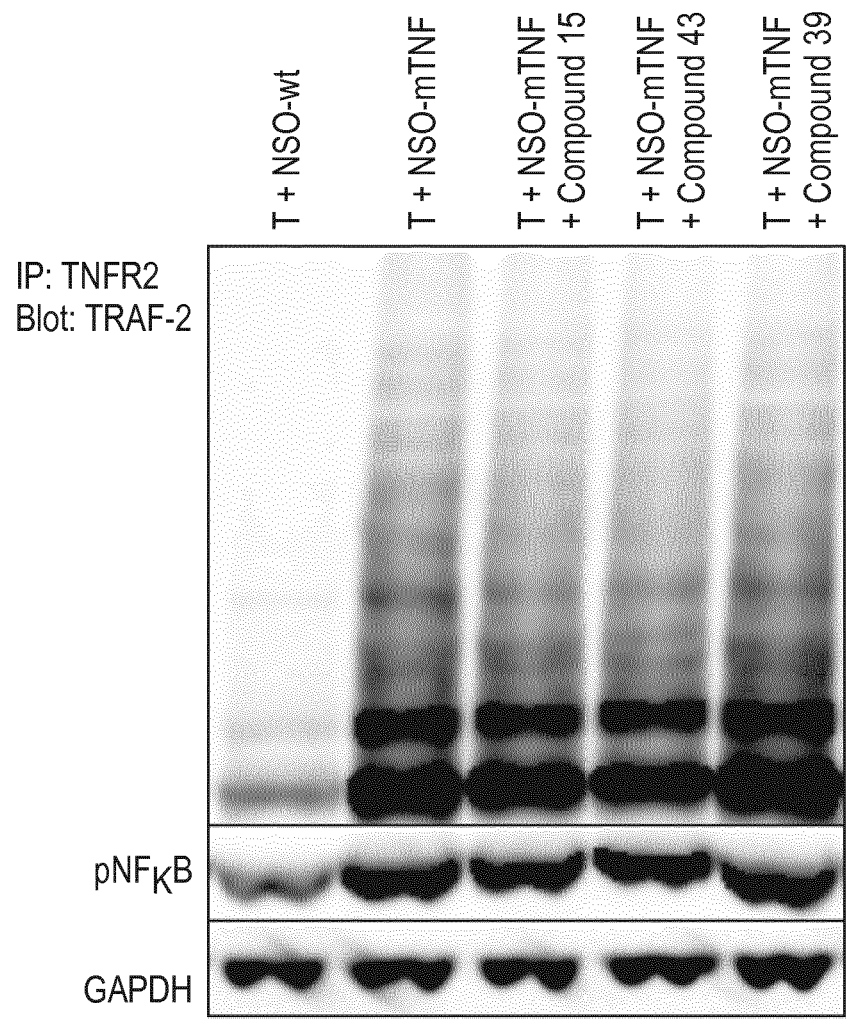
FIG. 21 is a gel showing the effect of Compounds described herein (that induce the distorted soluble TNFα trimer structure) on membrane TNFα-induced TNFR2 proximal and downstream signalling; binding of Compounds to membrane TNFα over-expressed in NS0 cells does not impair TNFR2 specific membrane proximal (TRAF-2 recruitment to TNFR2) and downstream (pNFκB presence in whole cell lysates) signalling.

IP and Blotting Procedure:
  prepare 500 µl media containing 10×10^6 NS0-mTMF cells in RPMI+10% FCS+HEPES+GlutMAX+−2004 (Compound 15, Compound 43 or Compound 39) or DMSO and incubate for 1 h at 37° C. to allow loading of compound into TNF. This is a 2× solution
  prepare 500 µl of 10×10^6 NS0-wt cells
  After 1 h add 500 µl human T cells (50×10^6 cells/test) in human media at 37° C. T cells were preincubated for 15 min @37° C. with 50 µg/ml 5R16 anti-TNFR1 Fab-PEG to block signalling via TNFR1 prior adding to the NS0 cells. Mix, spin briefly to get cells in contact and incubate for 5 min at 37° C., spin and immediately lyse by resuspending pellet with 1 ml ice cold lysis buffer and lyse for 1 h: 1% NP-40, 150 mM NaCl, 50 mM Tris pH8.0, 25 mM NaF 1 mM Vanadate->to 10 ml of this buffer 100 µl phosphatase inhibitor (Sigma P5726-5 ml) and 100 µl phosphatase inhibitor (Sigma P2850) was added as well as 20 µl of protease inhibitor cocktail (Sigma-P8430)
  spin 15 min at full speed in microcentrifuge and use supernatant. Save some of the supernatant to look for pNFkB in blots
  add 5 µg of polyclonal goat-anti-hTNFR2 (R&D) and incubate over night while rotating at 4° C., next morning add 20 µl of protG sepharose beads for another 1 h @4° C. while rotating
  spin, and wash beads 3× with lysis buffer, then spin and take off as much liquid as possible, add SDS-PAGE reducing sample buffer and boil for 10 min
  load 15 µl on a 4-12% Bis-Tris gel and run for 55 min @200V in MOPS buffer
  blot using iBlot 7 min protocol on nitrocellulose membrane and block in 5% milk in TBS/0.05% Tween for 2 h
  add primary antibody (anti-TRAF-2-1:250 sc-136999—Santa Cruz) in blocking buffer and incubate over night at 4° C. on roller in 5 ml
  wash 3× with TBS/0.05% Tween
  add secondary anti-mouse-HRP (1:2000) in blocking buffer for 2 h at RT while shaking
  wash 5× with TBS/0.05% Tween and develop Pnfkb Analysis:
  run 10 µl of sup on 4-12% Bis-Tris gel in MOPS buffer for 1 h @ 200V under reducing conditions and blot on nitrocellulose membrane using 7 min iBlot program.
  block for 2 h at RT while shaking with 5% milk in TBS/0.05% Tween
  add anti-pNFkB antibody 1:1000 (NEB-3033) and anti-GAPDH (1:4000 NEB) and incubate over night at 4° C. in 50 ml Falcon on roller
  wash 3× with TBS/0.05% Tween-add secondary anti-rabbit-HRP (1:2000) in blocking buffer for 2 h at RT while shaking
  wash 5× with TBS/0.05% Tween and develop FIG. 21 is a gel showing the effect of Compounds 15, 43 and 39 bound to membrane TNFα-induced TNFR2 proximal and downstream signalling; binding of Compounds to membrane TNFα over-expressed in NS0 cells does not impair TNFR2 specific membrane proximal (TRAF-2 recruitment to TNFR2) and downstream (pNFκB presence in whole cell lysates) signalling.

Example 23—Compounds and Complexes of Ma et al (2014) and Silvian et al (2011) have Different Characteristics to Those of the Present Invention As described on page 12458 of Ma et al. (2014) JBC 289:12457-12466, C87 was discovered through virtual screening by attempting to find molecules which fit the space occupied by a 7 amino-acid peptide from loop2/domain2 of TNFR1 in its interaction with the external surface of TNFβ. The C87 compound from Ma et al. and the BI08898 compound from Silvian et al. (2011) ACS Chemical Biology 6:636-647 were tested by the present inventors.

Summary of Findings
  The Biacore observations described in Ma et al. for C87 could not be repeated.
  No evidence of TNF specific inhibition in cells was observed.
  Additionally C87 was not observed to bind by mass spectrometry, which is sensitive to millimolar affinities.
  Extensive crystallography trials only produced apo-TNF (TNF without compound).
  In the fluorescence polarisation (FP) assay, C87 showed no significant inhibition above the interference level of the compound with the fluorescent read-out.
  Thermofluor, which measures stabilisation of the thermal melting temperature of TNFα, did show a small stabilisation for C87.
  In summary, no evidence was found that C87 binds in the centre of the trimer. The overwhelming majority of the data suggested no direct interaction with TNFα. BI08898 was also found not to bind to TNFα.

Cells—TNF Induced HEK NFKB Reporter Gene Assay
  C87 was preincubated with TNFα for 1 hour prior to the addition to HEK-293 cells stably transfected with SEAP under the control of NFκB. An appropriate counter-screen was also tested in order to detect non-TNF related (off target) activity. The assay was incubated overnight before inhibition was measured compared to 100% blocking by a control compound. The maximum C87 concentration was 10,000 nM, with a 3-fold serial dilution. No inhibitory effect could be detected that could not be attributed to off-target activity.

Biacore
  TNF was immobilised using an avi-tag linker and C87 was passed over the chip. In one experiment, a dose response of C87 from a highest concentration of 10 µM was performed. No binding was observed. In a second experiment, the flow rate of C87 passing over the chip was reduced. A small shift was observed but overall binding was negligible. The binding of C87 to TNF described in Ma et al was likely to be super-stoichiometric based on the RU value on the Y-axis. At standard TNF density on the chip this value was in the region of thirty times higher than expected for simple 1:1 binding.

In another experiment, BI08898 was tested against the immobilised soluble form of CD40L and the soluble form of TNFα by SPR on a Biacore 4000 machine. A geomean IC50 of 17 μM was determined for binding against CD40L whereas no binding was detected at a concentration of up to 100 μM for TNFα in this assay.

Mass Spectrometry

There was no evidence of C87 binding to human TNFα (20 μM) at a concentration of 400 μM. A species of lower molecular weight (~473 Da appears to bind at less than 5% occupancy). C87 has a molecular weight of 503 Da. Based on the occupancy at a concentration of 400 μM, an affinity of the low molecular weight species in excess of 1 mM is predicted.

Crystallography

Overall a large effort was put into crystallising C87 with TNFα, including testing conditions that routinely work with compounds described in the present application. This comprised setting up a large number of crystallization trials at different ligand concentrations, different protein concentrations, and different soaking times. A few crystals were observed that, on analysis, proved to be salt or TNF with no compound.

Fluorescent Polarization (FP)

C87 was preincubated with TNFα for 1 hour prior to assay against the fluorescent compound (probe). Competition with the fluorescent compound either directly (binding at the same site) or indirectly (disrupting TNF) is detected by a reduction in FP.

Extrapolation of the inhibition curve produced an IC50 of about 100 μM. Fluorescence quenching was, however, observed at the highest concentrations of inhibitor which, when subtracted, resulted in negligible inhibition of C87 in this assay.

Thermofluor

Thermofluor measures the change of melting temperature (Tm) of TNFα due to compound either stabilising or disrupting the protein. A stabilization effect of 3.8° C. was observed at a concentration of 500 μM C87, suggesting the possibility of weak binding, which may not be specific.

```
Sequence listing

SEQ ID NO: 1 (LCDR1 of 1974)
QASQDIGN

SEQ ID NO: 2 (LCDR2 of 1974)
GATSLAD

SEQ ID NO: 3 (LCDR3 of 1974)
LQGQSTPYT

SEQ ID NO: 4 (HCDR1 of 1974)
AYYMA

SEQ ID NO: 5 (HCDR2 of 1974)
ASINYDGANTFYRDSVKG

SEQ ID NO: 6 (HCDR3 of 1974)
EAYGYNSNWFGY

SEQ ID NO: 7 (LCVR of 1974)
DIQMTQSPASLPASPEEIVTITCQASQDIGNWLSWYQQKPGKSPQLLIYGATSLADGVPSRFSASRSGTQYSL
KISRLQVEDFGIFYCLQGQSTPYTFGAGTKLELK

SEQ ID NO: 8 (HCVR of 1974)
DVQLVESGGGLVQPGRSLKLSCAASGFTFSAYYMAWVRQAPTKGLEWVASINYDGANTFYRDSVKGRFTVSRD
NARSSLYLQMDSLRSEDTATYYCTTEAYGYNSNWFGYWGQGTLVTVSS

SEQ ID NO: 9 (LCVR DNA of 1974)
GACATCCAGATGACCCAGTCTCCTGCCTCCCTGCCTGCATCCCCGGAAGAAATTGTCACCATCACATGCCAGG
CAAGCCAGGACATTGGTAATTGGTTATCATGGTATCAGCAGAAACCAGGGAAATCGCCTCAGCTCCTGATCTA
TGGTGCAACCAGCTTGGCAGATGGGGTCCCATCAAGGTTCAGCGCCAGTAGATCTGGCACACAGTACTCTCTT
AAGATCAGCAGACTGCAGGTTGAAGATTTTGGAATCTTTTACTGTCTACAGGGTCAAAGTACTCCGTACACGT
TTGGAGCTGGGACCAAGCTGGAACTGAAA

SEQ ID NO: 10 (HCVR DNA of 1974)
GACGTGCAGCTGGTGGAATCTGGAGGAGGCTTAGTGCAGCCTGGAAGGTCCCTGAAACTCTCCTGTGCAGCCT
CAGGATTCACTTTCAGTGCCTATTACATGGCCTGGGTCCGCCAGGCTCCAACGAAGGGTCTGGAGTGGGTCGC
ATCCATTAATTATGATGGTGCTAACACTTTCTATCGCGACTCCGTGAAGGGCCGATTCACTGTCTCCAGAGAT
AATGCAAGAAGCAGCCTATACCTACAAATGGACAGTCTGAGGTCTGAGGACACGGCCACTTATTACTGTACAA
CAGAGGCTTACGGATATAACTCAAATTGGTTTGGTTACTGGGGCCAAGGCACTCTGGTCACTGTCTCGAGC

SEQ ID NO: 11 (1974 LC kappa full)
DIQMTQSPASLPASPEEIVTITCQASQDIGNWLSWYQQKPGKSPQLLIYGATSLADGVPSRFSASRSGTQYSL
KISRLQVEDFGIFYCLQGQSTPYTFGAGTKLELKRTDAAPTVSIFPPSSEQLTSGGASVVCFLNNFYPKDINV
KWKIDGSERQNGVLNSWTDQDSKDSTYSMSSTLTLTKDEYERHNSYTCEATHKTSTSPIVKSFNRNEC SEQ ID NO: 12 (1974 HC mIgG1 full)
DVQLVESGGGLVQPGRSLKLSCAASGFTFSAYYMAWVRQAPTKGLEWVASINYDGANTFYRDSVKGRFTVSRD
NARSSLYLQMDSLRSEDTATYYCTTEAYGYNSNWFGYWGQGTLVTVSSAKTTPPSVYPLAPGSAAQTNSMVTL
GCLVKGYFPEPVTVTWNSGSLSSGVHTFPAVLQSDLYTLSSSVTVPSSTWPSETVTCNVAHPASSTKVDKKIV
PRDCGCKPCICTVPEVSSVFIFPPKPKDVLTITLTPKVTCVVVDISKDDPEVQFSWFVDDVEVHTAQTQPREE
```

QFNSTFRSVSELPIMHQDWLNGKEFKCRVNSAAFPAPIEKTISKTKGRPKAPQVYTIPPPKEQMAKDKVSLTC
MITDFFPEDITVEWQWNGQPAENYKNTQPIMDTDGSYFVYSKLNVQKSNWEAGNTFTCSVLHEGLHNHHTEKS
LSHSPGK

SEQ ID NO: 13 (1974 HC mFabno hinge full)
DVQLVESGGGLVQPGRSLKLSCAASGFTFSAYYMAWVRQAPTKGLEWVASINYDGANTFYRDSVKGRFTVSRD
NARSSLYLQMDSLRSEDTATYYCTTEAYGYNSNWFGYWGQGTLVTVSSAKTTPPSVYPLAPGSAAQTNSMVTL
GCLVKGYFPEPVTVTWNSGSLSSGVHTFPAVLQSDLYTLSSSVTVPSSTWPSETVTCNVAHPASSTKVDKKIV
PRDC SEQ ID NO: 14 (1974 LC DNA kappa full)
GACATCCAGATGACCCAGTCTCCTGCCTCCCTGCCTGCATCCCCGGAAGAAATTGTCACCATCACATGCCAGG
CAAGCCAGGACATTGGTAATTGGTTATCATGGTATCAGCAGAAACCAGGGAAATCGCCTCAGCTCCTGATCTA
TGGTGCAACCAGCTTGGCAGATGGGGTCCCATCAAGGTTCAGCGCCAGTAGATCTGGCACACAGTACTCTCTT
AAGATCAGCAGACTGCAGGTTGAAGATTTTGGAATCTTTTACTGTCTACAGGGTCAAAGTACTCCGTACACGT
TTGGAGCTGGGACCAAGCTGGAACTGAAACGTACGGATGCTGCACCAACTGTATCCATCTTCCCACCATCCAG
TGAGCAGTTAACATCTGGAGGTGCCTCAGTCGTGTGCTTCTTGAACAACTTCTACCCCAAAGACATCAATGTC
AAGTGGAAGATTGATGGCAGTGAACGACAAAATGGCGTCCTGAACAGTTGGACTGATCAGGACAGCAAAGACA
GCACCTACAGCATGAGCAGCACCCTCACGTTGACCAAGGACGAGTATGAACGACATAACAGCTATACCTGTGA
GGCCACTCACAAGACATCAACTTCACCCATTGTCAAGAGCTTCAACAGGAATGAGTGT SEQ ID NO: 15 (1974 HC DNA mIgG1 full)
GACGTGCAGCTGGTGGAATCTGGAGGAGGCTTAGTGCAGCCTGGAAGGTCCCTGAAACTCTCCTGTGCAGCCT
CAGGGATTCACTTTCAGTGCCTATTACATGGCCTGGGTCCGCCAGGCTCCAACGAAGGGTCTGGAGTGGGTCGC
ATCCATTAATTATGATGGTGCTAACACTTTCTATCGCGACTCCGTGAAGGGCCGATTCACTGTCTCCAGAGAT
AATGCAAGAAGCAGCCTATACCTACAAATGGACAGTCTGAGGTCTGAGGACACGGCCACTTATTACTGTACAA
CAGAGGCTTACGGATATAACTCAAATTGGTTTGGTTACTGGGGCCAAGGCACTCTGGTCACTGTCTCGAGTGC
CAAAACGACACCCCCATCTGTCTATCCACTGGCCCCTGGATCTGCTGCCCAAACTAACTCCATGGTGACCCTG
GGATGCCTGGTCAAGGGCTATTTCCCTGAGCCAGTGACAGTGACCTGGAACTCTGGATCCCTGTCCAGCGGTG
TGCACACCTTCCCAGCTGTCCTGCAGTCTGACCTCTACACTCTGAGCAGCTCAGTGACTGTCCCCTCCAGCAC
CTGGCCCAGCGAGACCGTCACCTGCAACGTTGCCCACCCGGCCAGCAGCACCAAGGTGGACAAGAAAATTGTG
CCCAGGGATTGTGGTTGTAAGCCTTGCATATGTACAGTCCCAGAAGTATCATCTGTCTTCATCTTCCCCCCAA
AGCCCAAGGATGTGCTCACCATTACTCTGACTCCTAAGGTCACGTGTGTTGTGGTAGACATCAGCAAGGATGA
TCCCGAGGTCCAGTTCAGCTGGTTTGTAGATGATGTGGAGGTGCACACAGCTCAGACGCAACCCCGGGAGGAG
CAGTTCAACAGCACTTTCCGCTCAGTCAGTGAACTTCCCATCATGCACCAGGACTGGCTCAATGGCAAGGAGT
TCAAATGCAGGGTCAACAGTGCAGCTTTCCCTGCCCCCATCGAGAAAACCATCTCCAAAACCAAAGGCAGACC
GAAGGCTCCACAGGTGTACACCATTCCACCTCCCAAGGAGCAGATGGCCAAGGATAAAGTCAGTCTGACCTGC
ATGATAACAGACTTCTTCCCTGAAGACATTACTGTGGAGTGGCAGTGGAATGGGCAGCCAGCGGAGAACTACA
AGAACACTCAGCCCATCATGGACACAGATGGCTCTTACTTCGTCTACAGCAAGCTCAATGTGCAGAAGAGCAA
CTGGGAGGCAGGAAATACTTTCACCTGCTCTGTGTTACATGAGGGCCTGCACAACCACCATACTGAAGAGC
CTCTCCCACTCTCCTGGTAAA SEQ ID NO: 16 (1974 HC DNA mFabno hinge full)
GACGTGCAGCTGGTGGAATCTGGAGGAGGCTTAGTGCAGCCTGGAAGGTCCCTGAAACTCTCCTGTGCAGCCT
CAGGGATTCACTTTCAGTGCCTATTACATGGCCTGGGTCCGCCAGGCTCCAACGAAGGGTCTGGAGTGGGTCGC
ATCCATTAATTATGATGGTGCTAACACTTTCTATCGCGACTCCGTGAAGGGCCGATTCACTGTCTCCAGAGAT
AATGCAAGAAGCAGCCTATACCTACAAATGGACAGTCTGAGGTCTGAGGACACGGCCACTTATTACTGTACAA
CAGAGGCTTACGGATATAACTCAAATTGGTTTGGTTACTGGGGCCAAGGCACTCTGGTCACTGTCTCGAGTGC
CAAAACGACACCCCCATCTGTCTATCCACTGGCCCCTGGATCTGCTGCCCAAACTAACTCCATGGTGACCCTG
GGATGCCTGGTCAAGGGCTATTTCCCTGAGCCAGTGACAGTGACCTGGAACTCTGGATCCCTGTCCAGCGGTG
TGCACACCTTCCCGGCTGTCCTGCAATCTGACCTCTACACTCTGAGCAGCTCAGTGACTGTCCCCTCCAGCAC
CTGGCCCAGCGAGACCGTCACCTGCAACGTTGCCCACCCGGCCAGCAGCACCAAGGTGGACAAGAAAATTGTG
CCCAGGGATTGT SEQ ID NO: 17 (LCDR2 of 1979)
GTTSLAD SEQ ID NO: 18 (LCDR3 of 1979)
LQAYSTPFTF SEQ ID NO: 19 (HCDR1 of 1979)
NSYWD SEQ ID NO: 20 (HCDR2 of 1979)
YINYSGSTGYNPSLKS SEQ ID NO: 21 (HCDR3 of 1979)
GTYGYNAYHFDY SEQ ID NO: 22 (LCVR of 1979)
DIQMTQSPASLSASLEEIVTITCQASQDIGNWLSWYQQKPGKSPHLLIYGTTSLADGVPSRFSGSRSGTQYSL
KISGLQVADIGIYVCLQAYSTPFTFGSGTKLEIK SEQ ID NO: 23 (HCVR of 1979)
EVHLVESGPGLVKPSQSLSLTCSVTGYSITNSYWDWIRKFPGNKMEWMGYINYSGSTGYNPSLKSRISISRDT
SNNQFFLQLNSITTEDTATYYCARGTYGYNAYHFDYWGRGVMVTVSS -continued Sequence listing SEQ ID NO: 24 (LCVR DNA of 1979)
GACATCCAAATGACACAGTCTCCTGCCTCCCTGTCTGCATCTCTGGAAGAAATTGTCACCATTACATGCCAGG
CAAGCCAGGACATTGGTAATTGGTTATCATGGTATCAGCAGAAACCAGGAAATCTTCCTCACCTCCTGATCTA
TGGTACCACCAGCTTGGCAGATGGGGTCCCATCAAGGTTCAGCGGCAGTAGATCTGGTACACAGTATTCTCTT
AAGATCAGCGGACTACAGGTTGCAGATATTGGAATCTATGTCTGTCTACAGGCTTATAGTACTCCATTCACGT
TCGGCTCAGGGACAAAGCTGGAAATAAAA SEQ ID NO: 25 (HCVR DNA of 1979)
GAGGTGCACCTGGTGGAGTCTGGACCTGGCCTTGTGAAACCCTCACAGTCACTCTCCCTCACCTGTTCTGTCA
CTGGTTACTCCATCACTAATAGTTACTGGGACTGGATCCGGAAGTTCCCAGGAAATAAAATGGAGTGGATGGG
ATACATAAACTACAGTGGTAGCACTGGCTACAACCCATCTCTCAAAAGTCGAATCTCCATTAGTAGAGACACA
TCGAACAATCAGTTCTTCCTGCAGCTGAACTCTATAACTACTGAGGACACAGCCACATATTACTGTGCACGAG
GGACCTATGGGTATAACGCCTACCACTTTGATTACTGGGGCCGAGGAGTCATGGTCACAGTCTCGAGC SEQ ID NO: 26 (1979 LC Kappa full)
DIQMTQSPASLSASLEEIVTITCQASQDIGNWLSWYQQKPGKSPHLLIYGTTSLADGVPSRFSGSRSGTQYSL
KISGLQVADIGIYVCLQAYSTPFTFGSGTKLEIKRTDAAPTVSIFPPSSEQLTSGGASVVCFLNNFYPKDINV
KWKIDGSERQNGVLNSWTDQDSKDSTYSMSSTLTLTKDEYERHNSYTCEATHKTSTSPIVKSFNRNEC SEQ ID NO: 27 (1979 HC mIgG1 full)
EVHLVESGPGLVKPSQSLSLTCSVTGYSITNSYWDWIRKFPGNKMEWMGYINYSGSTGYNPSLKSRISISRDT
SNNQFFLQLNSITTEDTATYYCARGTYGYNAYHFDYWGRGVMVTVSSAKTTPPSVYPLAPGSAAQTNSMVTLG
CLVKGYFPEPVTVTWNSGSLSSGVHTFPAVLQSDLYTLSSSVTVPSSTWPSETVTCNVAHPASSTKVDKKIVP
RDCGCKPCICTVPEVSSVFIFPPKPKDVLTITLTPKVTCVVVDISKDDPEVQFSWFVDDVEVHTAQTQPREEQ
FNSTFRSVSELPIMHQDWLNGKEFKCRVNSAAFPAPIEKTISKTKGRPKAPQVYTIPPPKEQMAKDKVSLTCM
ITDFFPEDITVEWQWNGQPAENYKNTQPIMDTDGSYFVYSKLNVQKSNWEAGNTFTCSVLHEGLHNHHTEKSL
SHSPGK SEQ ID NO: 28 (1979 HC mFabno hinge full)
EVHLVESGPGLVKPSQSLSLTCSVTGYSITNSYWDWIRKFPGNKMEWMGYINYSGSTGYNPSLKSRISISRDT
SNNQFFLQLNSITTEDTATYYCARGTYGYNAYHFDYWGRGVMVTVSSAKTTPPSVYPLAPGSAAQTNSMVTLG
CLVKGYFPEPVTVTWNSGSLSSGVHTFPAVLQSDLYTLSSSVTVPSSTWPSETVTCNVAHPASSTKVDKKIVP
RDC SEQ ID NO: 29 (1979 LC DNA Kappa full)
GACATCCAAATGACACAGTCTCCTGCCTCCCTGTCTGCATCTCTGGAAGAAATTGTCACCATTACATGCCAGG
CAAGCCAGGACATTGGTAATTGGTTATCATGGTATCAGCAGAAACCAGGAAATCTTCCTCACCTCCTGATCTA
TGGTACCACCAGCTTGGCAGATGGGGTCCCATCAAGGTTCAGCGGCAGTAGATCTGGTACACAGTATTCTCTT
AAGATCAGCGGACTACAGGTTGCAGATATTGGAATCTATGTCTGTCTACAGGCTTATAGTACTCCATTCACGT
TCGGCTCAGGGACAAAGCTGGAAATAAAACGTACGGATGCTGCACCAACTGTATCCATCTTCCCACCATCCAG
TGAGCAGTTAACATCTGGAGGTGCCTCAGTCGTGTGCTTCTTGAACAACTTCTACCCCAAAGACATCAATGTC
AAGTGGAAGATTGATGGCAGTGAACGACAAAATGGCGTCCTGAACAGTTGGACTGATCAGGACAGCAAAGACA
GCACCTACAGCATGAGCAGCACCCTCACGTTGACCAAGGACGAGTATGAACGACATAACAGCTATACCTGTGA
GGCCACTCACAAGACATCAACTTCACCCATTGTCAAGAGCTTCAACAGGAATGAGTGT SEQ ID NO: 30 (1979 HC DNA mIgG1 full)
GAGGTGCACCTGGTGGAGTCTGGACCTGGCCTTGTGAAACCCTCACAGTCACTCTCCCTCACCTGTTCTGTCA
CTGGTTACTCCATCACTAATAGTTACTGGGACTGGATCCGGAAGTTCCCAGGAAATAAAATGGAGTGGATGGG
ATACATAAACTACAGTGGTAGCACTGGCTACAACCCATCTCTCAAAAGTCGAATCTCCATTAGTAGAGACACA
TCGAACAATCAGTTCTTCCTGCAGCTGAACTCTATAACTACTGAGGACACAGCCACATATTACTGTGCACGAG
GGACCTATGGGTATAACGCCTACCACTTTGATTACTGGGGCCGAGGAGTCATGGTCACAGTCTCGAGTGCCAA
AACGACACCCCCATCTGTCTATCCACTGGCCCCTGGATCTGCTGCCCAAACTAACTCCATGGTGACCCTGGGA
TGCCTGGTCAAGGGCTATTTCCCTGAGCCAGTGACAGTGACCTGGAACTCTGGATCCCTGTCCAGCGGTGTGC
ACACCTTCCCAGCTGTCCTGCAGTCTGACCTCTACACTCTGAGCAGCTCAGTGACTGTCCCCTCCAGCACCTG
GCCCAGCGAGACCGTCACCTGCAACGTTGCCCACCCGGCCAGCAGCACCAAGGTGGACAAGAAAATTGTGCCC
AGGGATTGTGGTTGTAAGCCTTGCATATGTACAGTCCCAGAAGTATCATCTGTCTTCATCTTCCCCCCAAAGC
CCAAGGATGTGCTCACCATTACTCTGACTCCTAAGGTCACGTGTGTTGTGGTAGACATCAGCAAGGATGATCC
CGAGGTCCAGTTCAGCTGGTTTGTAGATGATGTGGAGGTGCACACAGCTCAGACGCAACCCCGGGAGGAGCAG
TTCAACAGCACTTTCCGCTCAGTCAGTGAACTTCCCATCATGCACCAGGACTGGCTCAATGGCAAGGAGTTCA
AATGCAGGGTCAACAGTGCAGCTTTCCCTGCCCCCATCGAGAAAACCATCTCCAAAACCAAAGGCAGACCGAA
GGCTCCACAGGTGTACACCATTCCACCTCCCAAGGAGCAGATGGCCAAGGATAAAGTCAGTCTGACCTGCATG
ATAACAGACTTCTTCCCTGAAGACATTACTGTGGAGTGGCAGTGGAATGGGCAGCCAGCGGAGAACTACAAGA
ACACTCAGCCCATCATGGACACAGATGGCTCTTACTTCGTCTACAGCAAGCTCAATGTGCAGAAGAGCAACTG
GGAGGCAGGAAATACTTTCACCTGCTCTGTGTTACATGAGGGCCTGCACAACCACCATACTGAGAAGAGCCTC
TCCCACTCTCCTGGTAAA SEQ ID NO: 31 (1979 HC DNA mFabno hinge full)
GAGGTGCACCTGGTGGAGTCTGGACCTGGCCTTGTGAAACCCTCACAGTCACTCTCCCTCACCTGTTCTGTCA
CTGGTTACTCCATCACTAATAGTTACTGGGACTGGATCCGGAAGTTCCCAGGAAATAAAATGGAGTGGATGGG
ATACATAAACTACAGTGGTAGCACTGGCTACAACCCATCTCTCAAAAGTCGAATCTCCATTAGTAGAGACACA
TCGAACAATCAGTTCTTCCTGCAGCTGAACTCTATAACTACTGAGGACACAGCCACATATTACTGTGCACGAG
GGACCTATGGGTATAACGCCTACCACTTTGATTACTGGGGCCGAGGAGTCATGGTCACAGTCTCGAGTGCCAA
AACGACACCCCCATCTGTCTATCCACTGGCCCCTGGATCTGCTGCCCAAACTAACTCCATGGTGACCCTGGGA
TGCCTGGTCAAGGGCTATTTCCCTGAGCCAGTGACAGTGACCTGGAACTCTGGATCCCTGTCCAGCGGTGTGC -continued

```
Sequence listing

ACACCTTCCCGGCTGTCCTGCAATCTGACCTCTACACTCTGAGCAGCTCAGTGACTGTCCCCTCCAGCACCTG
GCCCAGCGAGACCGTCACCTGCAACGTTGCCCACCCGGCCAGCAGCACCAAGGTGGACAAGAAAATTGTGCCC
AGGGATTGT

SEQ ID NO: 32-RatTNFa
MSTESMIRDVELAEEALPKKMGGLQNSRRCLCLSLFSFLLVAGATTLFCLLNFGVIGPNKEEKFPNGLPLISS
MAQTLTLRSSSQNSSDKPVAHVVANHQAEEQLEWLSQRANALLANGMDLKDNQLVVPADGLYLIYSQVLFKGQ
GCPDYVLLTHTVSRFAISYQEKVSLLSAIKSPCPKDTPEGAELKPWYEPMYLGGVFQLEKGDLLSAEVNLPKY
LDITESGQVYFGVIAL

SEQ ID NO: 33-MouseTNFa
MSTESMIRDVELAEEALPQKMGGFQNSRRCLCLSLFSFLLVAGATTLFCLLNFGVIGPQRDEKFPNGLPLISS
MAQTLTLRSSSQNSSDKPVAHVVANHQVEEQLEWLSQRANALLANGMDLKDNQLVVPADGLYLVYSQVLFKGQ
GCPDYVLLTHTVSRFAISYQEKVNLLSAVKSPCPKDTPEGAELKPWYEPIYLGGVFQLEKGDQLSAEVNLPKY
LDFAESGQVYFGVIAL SEQ ID NO: 34-Human TNFa
MSTESMIRDVELAEEALPKKTGGPQGSRRCLFLSLFSFLIVAGATTLFCLLHFGVIGPQREEFPRDLSLISPL
AQAVRSSSRTPSDKPVAHVVANPQAEGQLQWLNRRANALLANGVELRDNQLVVPSEGLYLIYSQVLFKGQGCP
STHVLLTHTISRIAVSYQTKVNLLSAIKSPCQRETPEGAEAKPWYEPIYLGGVFQLEKGDRLSAEINRPDYLD
FAESGQVYFGIIAL SEQ ID NO: 35-Soluble form of human TNFa
SVRSSSRTPSDKPVAHVVANPQAEGQLQWLNRRANALLANGVELRDNQLVVPSEGLYLIYSQVLFKGQGCPST
HVLLTHTISRIAVSYQTKVNLLSAIKSPCQRETPEGAEAKPWYEPIYLGGVFQLEKGDRLSAEINRPDYLDFA
ESGQVYFGIIAL SEQ ID NO: 36-Soluble form of human TNFa, but lacking the "S" cloning
artefact of SEQ ID NO: 35
VRSSSRTPSDKPVAHVVANPQAEGQLQWLNRRANALLANGVELRDNQLVVPSEGLYLIYSQVLFKGQGCPSTH
VLLTHTISRIAVSYQTKVNLLSAIKSPCQRETPEGAEAKPWYEPIYLGGVFQLEKGDRLSAEINRPDYLDFAE
SGQVYFGIIAL
```

Lengthy table referenced here
US10775385-20200915-T00001
Please refer to the end of the specification for access instructions.

Lengthy table referenced here
US10775385-20200915-T00002
Please refer to the end of the specification for access instructions.

Lengthy table referenced here
US10775385-20200915-T00003
Please refer to the end of the specification for access instructions.

Lengthy table referenced here
US10775385-20200915-T00004
Please refer to the end of the specification for access instructions.

Lengthy table referenced here
US10775385-20200915-T00005
Please refer to the end of the specification for access instructions.

Lengthy table referenced here
US10775385-20200915-T00006
Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US10775385B2). An electronic copy of the table will also be available from the USPTO upon request and payment of the fee set forth in 37 CFR 1.19(b)(3).

The invention claimed is:

1. A method of treating one or more of autoimmune and inflammatory disorders, said method comprising administering to a patient in need thereof an asymmetrical TNFα trimer of a protein subunit comprising the amino-acid sequence of SEQ ID NO: 36, or corresponding sequence, wherein said TNFα trimer adopts a conformation when contacted with a compound that is capable of binding to the TNFα trimer to stabilize its asymmetric conformation, when determined by x-ray crystallography, with the Cα atoms of residues 12-18, 47-50, 54-64, 76-82, 91-97, 117-125, 129-137, and 150-156 of SEQ ID NO: 36, or corresponding sequence, for all subunits within 0.9 Å RMSD of the same atoms of the Reference Structure Compound34.pdb, said TNF-α trimer being able to bind TNFR1, but wherein signalling from said bound TNFR1 is attenuated or antagonised.

2. The method of claim 1, wherein:
   (a) the RMSD is within 0.85, 0.8, 0.7, 0.65, 0.6, 0.5, or 0.47 Å;
   (b) the protein subunit comprises or consists of the amino-acid sequence of SEQ ID NO: 36; or
   (c) the conformation is obtainable or obtained through the TNFα trimer forming a complex with any one of Compounds (1)-(64).

3. The method of claim 1, wherein:
   (a) the TNFα trimer antagonises the signalling of the TNFR1 receptor;
   (b) the TNFα trimer has increased stability compared to the stability of a symmetrical TNFα trimer; or
   (c) the TNFα trimer has increased stability compared to the stability of a symmetrical TNFα trimer and the increase in stability results in an increase in the thermal transition midpoint ($T_m$) of the TNFα trimer of at least 1° C., of at least 10° C., or is between 10° C. and 20° C.

4. The method of claim 1, wherein:
(a) the TNFα trimer has an increased binding affinity to the TNFR1 receptor compared to the binding affinity of a symmetrical TNFα trimer to the TNFR1 receptor;
(b) the TNFα trimer has an increased binding affinity to the TNFR1 receptor compared to the binding affinity of a symmetrical TNFα trimer to the TNFR1 receptor and the TNFα trimer has an increased binding affinity to the TNFR1 receptor by increasing the on rate ($k_{on\text{-}r}$) and/or decreasing the off rate ($k_{off\text{-}r}$) compared to the $k_{on\text{-}r}$ and $k_{off\text{-}r}$ values for binding of the symmetrical TNFα trimer to the TNFR1 receptor;
(c) the TNFα trimer has an increased binding affinity to the TNFR1 receptor compared to the binding affinity of a symmetrical TNFα trimer to the TNFR1 receptor and the TNFα trimer.

\* \* \* \* \*

SEQUENCE LISTING

<160> NUMBER OF SEQ ID NOS: 36

<210> SEQ ID NO 1
<211> LENGTH: 8
<212> TYPE: PRT
<213> ORGANISM: Artificial Sequence
<220> FEATURE:
<223> OTHER INFORMATION: LCDR1 of 1974/1979

<400> SEQUENCE: 1

Gln Ala Ser Gln Asp Ile Gly Asn
1               5

<210> SEQ ID NO 2
<211> LENGTH: 7
<212> TYPE: PRT
<213> ORGANISM: Artificial Sequence
<220> FEATURE:
<223> OTHER INFORMATION: LCDR2 of 1974

<400> SEQUENCE: 2

Gly Ala Thr Ser Leu Ala Asp
1               5

<210> SEQ ID NO 3
<211> LENGTH: 9
<212> TYPE: PRT
<213> ORGANISM: Artificial Sequence
<220> FEATURE:
<223> OTHER INFORMATION: LCDR3 of 1974

<400> SEQUENCE: 3

Leu Gln Gly Gln Ser Thr Pro Tyr Thr
1               5

<210> SEQ ID NO 4
<211> LENGTH: 5
<212> TYPE: PRT
<213> ORGANISM: Artificial Sequence
<220> FEATURE:
<223> OTHER INFORMATION: HCDR1 of 1974

<400> SEQUENCE: 4

Ala Tyr Tyr Met Ala
1               5

<210> SEQ ID NO 5
<211> LENGTH: 18
<212> TYPE: PRT
<213> ORGANISM: Artificial Sequence
<220> FEATURE:
<223> OTHER INFORMATION: HCDR2 of 1974

<400> SEQUENCE: 5

Ala Ser Ile Asn Tyr Asp Gly Ala Asn Thr Phe Tyr Arg Asp Ser Val
1               5                   10                  15

Lys Gly

<210> SEQ ID NO 6
<211> LENGTH: 12
<212> TYPE: PRT
<213> ORGANISM: Artificial Sequence
<220> FEATURE:
<223> OTHER INFORMATION: HCDR3 of 1974

<400> SEQUENCE: 6

Glu Ala Tyr Gly Tyr Asn Ser Asn Trp Phe Gly Tyr
1               5                   10

<210> SEQ ID NO 7
<211> LENGTH: 107
<212> TYPE: PRT
<213> ORGANISM: Artificial Sequence
<220> FEATURE:
<223> OTHER INFORMATION: LCVR of 1974

<400> SEQUENCE: 7

Asp Ile Gln Met Thr Gln Ser Pro Ala Ser Leu Pro Ala Ser Pro Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Ala
50                  55                  60

Ser Arg Ser Gly Thr Gln Tyr Ser Leu Lys Ile Ser Arg Leu Gln Val
65                  70                  75                  80

Glu Asp Phe Gly Ile Phe Tyr Cys Leu Gln Gly Gln Ser Thr Pro Tyr
                85                  90                  95

Thr Phe Gly Ala Gly Thr Lys Leu Glu Leu Lys
            100                 105

<210> SEQ ID NO 8
<211> LENGTH: 121
<212> TYPE: PRT
<213> ORGANISM: Artificial Sequence
<220> FEATURE:
<223> OTHER INFORMATION: HCVR of 1974

<400> SEQUENCE: 8

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45

Ala Ser Ile Asn Tyr Asp Gly Ala Asn Thr Phe Tyr Arg Asp Ser Val
50                  55                  60

Lys Gly Arg Phe Thr Val Ser Arg Asp Asn Ala Arg Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ser
        115                 120

<210> SEQ ID NO 9
<211> LENGTH: 321
<212> TYPE: DNA
<213> ORGANISM: Artificial Sequence
<220> FEATURE:
<223> OTHER INFORMATION: LCVR DNA of 1974

<400> SEQUENCE: 9
gacatccaga tgacccagtc tcctgcctcc ctgcctgcat ccccggaaga aattgtcacc    60

| | | |
|---|---|---|
| atcacatgcc aggcaagcca ggacattggt aattggttat catggtatca gcagaaacca | | 120 |
| gggaaatcgc ctcagctcct gatctatggt gcaaccagct tggcagatgg ggtcccatca | | 180 |
| aggttcagcg ccagtagatc tggcacacag tactctctta agatcagcag actgcaggtt | | 240 |
| gaagattttg gaatctttta ctgtctacag ggtcaaagta ctccgtacac gtttggagct | | 300 |
| gggaccaagc tggaactgaa a | | 321 |

<210> SEQ ID NO 10
<211> LENGTH: 363
<212> TYPE: DNA
<213> ORGANISM: Artificial Sequence
<220> FEATURE:
<223> OTHER INFORMATION: HCVR DNA of 1974

<400> SEQUENCE: 10

| | | |
|---|---|---|
| gacgtgcagc tggtggaatc tggaggaggc ttagtgcagc ctggaaggtc cctgaaactc | | 60 |
| tcctgtgcag cctcaggatt cactttcagt gcctattaca tggcctgggt ccgccaggct | | 120 |
| ccaacgaagg gtctggagtg ggtcgcatcc attaattatg atggtgctaa cactttctat | | 180 |
| cgcgactccg tgaagggccg attcactgtc tccagagata tgcaagaag cagcctatac | | 240 |
| ctacaaatgg acagtctgag gtctgaggac acggccactt attactgtac aacagaggct | | 300 |
| tacggatata actcaaattg gtttggttac tggggccaag gcactctggt cactgtctcg | | 360 |
| agc | | 363 |

<210> SEQ ID NO 11
<211> LENGTH: 214
<212> TYPE: PRT
<213> ORGANISM: Artificial Sequence
<220> FEATURE:
<223> OTHER INFORMATION: 1974 LC kappa full

<400> SEQUENCE: 11

Asp Ile Gln Met Thr Gln Ser Pro Ala Ser Leu Pro Ala Ser Pro Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Ala
    50                  55                  60

Ser Arg Ser Gly Thr Gln Tyr Ser Leu Lys Ile Ser Arg Leu Gln Val
65                  70                  75                  80

Glu Asp Phe Gly Ile Phe Tyr Cys Leu Gln Gly Gln Ser Thr Pro Tyr
                85                  90                  95

Thr Phe Gly Ala Gly Thr Lys Leu Glu Leu Lys Arg Thr Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr

```
                    180                 185                 190
Thr Cys Glu Ala Thr His Lys Thr Ser Thr Ser Pro Ile Val Lys Ser
            195                 200                 205

Phe Asn Arg Asn Glu Cys
        210

<210> SEQ ID NO 12
<211> LENGTH: 445
<212> TYPE: PRT
<213> ORGANISM: Artificial Sequence
<220> FEATURE:
<223> OTHER INFORMATION: 1974 HC mIgG1 full

<400> SEQUENCE: 12

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45

Ala Ser Ile Asn Tyr Asp Gly Ala Asn Thr Phe Tyr Arg Asp Ser Val
50                  55                  60

Lys Gly Arg Phe Thr Val Ser Arg Asp Asn Ala Arg Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
```

```
                    325                 330                 335
Thr Lys Gly Arg Pro Lys Ala Pro Gln Val Tyr Thr Ile Pro Pro Pro
                340                 345                 350

Lys Glu Gln Met Ala Lys Asp Lys Val Ser Leu Thr Cys Met Ile Thr
                355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
                420                 425                 430

His His Thr Glu Lys Ser Leu Ser His Ser Pro Gly Lys
                435                 440                 445

<210> SEQ ID NO 13
<211> LENGTH: 223
<212> TYPE: PRT
<213> ORGANISM: Artificial Sequence
<220> FEATURE:
<223> OTHER INFORMATION: 1974 HC mFabno hinge full

<400> SEQUENCE: 13

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
                20                  25                  30

Tyr Met Ala Trp Val Arg Gln Ala Pro Thr Lys Gly Leu Glu Trp Val
            35                  40                  45

Ala Ser Ile Asn Tyr Asp Gly Ala Asn Thr Phe Tyr Arg Asp Ser Val
        50                  55                  60

Lys Gly Arg Phe Thr Val Ser Arg Asp Asn Ala Arg Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys
    210                 215                 220

<210> SEQ ID NO 14
<211> LENGTH: 642
<212> TYPE: DNA
```

<213> ORGANISM: Artificial Sequence
<220> FEATURE:
<223> OTHER INFORMATION: 1974 LC DNA kappa full

<400> SEQUENCE: 14

```
gacatccaga tgacccagtc tcctgcctcc ctgcctgcat ccccggaaga aattgtcacc     60
atcacatgcc aggcaagcca ggacattggt aattggttat catggtatca gcagaaacca    120
gggaaatcgc ctcagctcct gatctatggt gcaaccagct ggcagatgg ggtcccatca    180
aggttcagcg ccagtagatc tggcacacag tactctctta agatcagcag actgcaggtt    240
gaagattttg gaatctttta ctgtctacag ggtcaaagta ctccgtacac gtttggagct    300
gggaccaagc tggaactgaa acgtacggat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag cacccctcacg   540
ttgaccaagg acgagtatga acgacataac agctatacct gtgaggccac tcacaagaca    600
tcaacttcac ccattgtcaa gagcttcaac aggaatgagt gt                       642
```

<210> SEQ ID NO 15
<211> LENGTH: 1335
<212> TYPE: DNA
<213> ORGANISM: Artificial Sequence
<220> FEATURE:
<223> OTHER INFORMATION: 1974 HC DNA mIgG1 full

<400> SEQUENCE: 15

```
gacgtgcagc tggtggaatc tggaggaggc ttagtgcagc ctggaaggtc cctgaaactc     60
tcctgtgcag cctcaggatt cactttcagt gcctattaca tggcctgggt ccgccaggct    120
ccaacgaagg gtctggagtg ggtcgcatcc attaattatg atggtgctaa cactttctat    180
cgcgactccg tgaagggccg attcactgtc tccagagata tgcaagaag cagcctatac    240
ctacaaatgg acagtctgag gtctgaggac acggccactt attactgtac aacagaggct    300
tacggatata actcaaattg gtttggttac tggggccaag gcactctggt cactgtctcg    360
agtgccaaaa cgacaccccc atctgtctat ccactggccc ctggatctgc tgcccaaact    420
aactccatgg tgaccctggg atgcctggtc aagggctatt ccctgagcc agtgacagtg    480
acctggaact ctggatccct gtccagcggt gtgcacacct cccagctgt cctgcagtct    540
gacctctaca ctctgagcag ctcagtgact gtccccctcca gcacctggcc cagcgagacc    600
gtcacctgca acgttgccca cccggccagc agcaccaagg tggacaagaa aattgtgccc    660
agggattgtg gttgtaagcc ttgcatatgt acagtcccag aagtatcatc tgtcttcatc    720
ttccccccaa gcccaagga tgtgctcacc attactctga ctcctaaggt cacgtgtgtt    780
gtggtagaca tcagcaagga tgatcccgag gtccagttca gctggtttgt agatgatgtg    840
gaggtgcaca cagctcagac gcaaccccgg gaggagcagt tcaacagcac tttccgctca    900
gtcagtgaac ttcccatcat gcaccaggac tggctcaatg gcaaggagtt caaatgcagg    960
gtcaacagtg cagctttccc tgcccccatc gagaaaacca tctccaaaac caaaggcaga   1020
ccgaaggctc acagggtgta caccattcca cctcccaagg agcagatggc caaggataaa   1080
gtcagtctga cctgcatgat aacagacttc ttccctgaag acattactgt ggagtggcag   1140
tggaatgggc agccagcgga gaactacaag aacactcagc ccatcatgga cacagatggc   1200
tcttacttcg tctacagcaa gctcaatgtg cagaagagca ctggggaggc aggaaatact   1260
```

```
ttcacctgct ctgtgttaca tgagggcctg cacaaccacc atactgagaa gagcctctcc    1320
cactctcctg gtaaa                                                    1335

<210> SEQ ID NO 16
<211> LENGTH: 669
<212> TYPE: DNA
<213> ORGANISM: Artificial Sequence
<220> FEATURE:
<223> OTHER INFORMATION: 1974 HC DNA mFabno hinge full

<400> SEQUENCE: 16
gacgtgcagc tggtggaatc tggaggaggc ttagtgcagc ctggaaggtc cctgaaactc     60
tcctgtgcag cctcaggatt cactttcagt gcctattaca tggcctgggt ccgccaggct    120
ccaacgaagg gtctggagtg ggtcgcatcc attaattatg atggtgctaa cactttctat    180
cgcgactccg tgaagggccg attcactgtc tccagagata tgcaagaag cagcctatac     240 ctacaaatgg acagtctgag gtctgaggac acggccactt attactgtac aacagaggct    300
tacggatata actcaaattg gtttggttac tggggccaag gcactctggt cactgtctcg    360
agtgccaaaa cgacaccccc atctgtctat ccactggccc ctggatctgc tgcccaaact    420
aactccatgg tgaccctggg atgcctggtc aagggctatt tccctgagcc agtgacagtg    480
acctggaact ctggatccct gtccagcggt gtgcacacct tcccggctgt cctgcaatct    540
gacctctaca ctctgagcag ctcagtgact gtcccctcca gcacctggcc cagcgagacc    600
gtcacctgca acgttgccca cccggccagc agcaccaagg tggacaagaa aattgtgccc    660
agggattgt                                                           669

<210> SEQ ID NO 17
<211> LENGTH: 7
<212> TYPE: PRT
<213> ORGANISM: Artificial Sequence
<220> FEATURE:
<223> OTHER INFORMATION: LCDR2 of 1979

<400> SEQUENCE: 17

Gly Thr Thr Ser Leu Ala Asp
1               5

<210> SEQ ID NO 18
<211> LENGTH: 10
<212> TYPE: PRT
<213> ORGANISM: Artificial Sequence
<220> FEATURE:
<223> OTHER INFORMATION: LCDR3 of 1979

<400> SEQUENCE: 18

Leu Gln Ala Tyr Ser Thr Pro Phe Thr Phe
1               5                   10

<210> SEQ ID NO 19
<211> LENGTH: 5
<212> TYPE: PRT
<213> ORGANISM: Artificial Sequence
<220> FEATURE:
<223> OTHER INFORMATION: HCDR1 of 1979

<400> SEQUENCE: 19

Asn Ser Tyr Trp Asp
1               5
```

```
<210> SEQ ID NO 20
<211> LENGTH: 16
<212> TYPE: PRT
<213> ORGANISM: Artificial Sequence
<220> FEATURE:
<223> OTHER INFORMATION: HCDR2 of 1979

<400> SEQUENCE: 20

Tyr Ile Asn Tyr Ser Gly Ser Thr Gly Tyr Asn Pro Ser Leu Lys Ser
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: HCDR3 of 1979

<400> SEQUENCE: 21

Gly Thr Tyr Gly Tyr Asn Ala Tyr His Phe Asp Tyr
1               5                   10

<210> SEQ ID NO 22
<211> LENGTH: 107
<212> TYPE: PRT
<213> ORGANISM: Artificial Sequence
<220> FEATURE:
<223> OTHER INFORMATION: LCVR 1979

<400> SEQUENCE: 22

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
                20                  25                  30

Leu Ser Trp Tyr Gln Gln Lys Pro Gly Lys Ser Pro His Leu Leu Ile
            35                  40                  45

Tyr Gly Thr Thr Ser Leu Ala Asp Gly Val Pro Ser Arg Phe Ser Gly
        50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys
            100                 105

<210> SEQ ID NO 23
<211> LENGTH: 120
<212> TYPE: PRT
<213> ORGANISM: Artificial Sequence
<220> FEATURE:
<223> OTHER INFORMATION: HCVR of 1979

<400> SEQUENCE: 23

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
                20                  25                  30

Tyr Trp Asp Trp Ile Arg Lys Phe Pro Gly Asn Lys Met Glu Trp Met
            35                  40                  45

Gly Tyr Ile Asn Tyr Ser Gly Ser Thr Gly Tyr Asn Pro Ser Leu Lys
        50                  55                  60

Ser Arg Ile Ser Ile Ser Arg Asp Thr Ser Asn Asn Gln Phe Phe Leu
```

```
            65                  70                  75                  80
Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser
        115                 120

<210> SEQ ID NO 24
<211> LENGTH: 321
<212> TYPE: DNA
<213> ORGANISM: Artificial Sequence
<220> FEATURE:
<223> OTHER INFORMATION: LCVR DNA of 1979

<400> SEQUENCE: 24
gacatccaaa tgacacagtc tcctgcctcc ctgtctgcat ctctggaaga aattgtcacc      60
attacatgcc aggcaagcca ggacattggt aattggttat catggtatca gcagaaacca     120
gggaaatctc ctcacctcct gatctatggt accaccagct ggcagatggg gtcccatca      180 aggttcagcg gcagtagatc tggtacacag tattctctta agatcagcgg actacaggtt     240
gcagatattg aatctatgt ctgtctacag gcttatagta ctccattcac gttcggctca      300
gggacaaagc tggaaataaa a                                               321

<210> SEQ ID NO 25
<211> LENGTH: 360
<212> TYPE: DNA
<213> ORGANISM: Artificial Sequence
<220> FEATURE:
<223> OTHER INFORMATION: HCVR DNA of 1979

<400> SEQUENCE: 25
gaggtgcacc tggtggagtc tggacctggc cttgtgaaac cctcacagtc actctccctc      60
acctgttctg tcactggtta ctccatcact aatagttact gggactggat ccggaagttc     120
ccaggaaata aaatggagtg gatgggatac ataaactaca gtggtagcac tgctacaac      180 ccatctctca aaagtcgaat ctccattagt agagacacat cgaacaatca gttcttcctg     240
cagctgaact ctataactac tgaggacaca gccacatatt actgtgcacg agggacctat     300
gggtataacg cctaccactt tgattactgg ggccgaggag tcatggtcac agtctcgagc     360

<210> SEQ ID NO 26
<211> LENGTH: 214
<212> TYPE: PRT
<213> ORGANISM: Artificial Sequence
<220> FEATURE:
<223> OTHER INFORMATION: 1979 LC Kappa full

<400> SEQUENCE: 26

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro His Leu Leu Ile
        35                  40                  45

Tyr Gly Thr Thr Ser Leu Ala Asp Gly Val Pro Ser Arg Phe Ser Gly
    50                  55                  60

Ser Arg Ser Gly Thr Gln Tyr Ser Leu Lys Ile Ser Gly Leu Gln Val
65                  70                  75                  80
```

```
Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys Arg Thr Asp Ala Ala
            100                 105                 110

Pro Thr Val Ser Ile Phe Pro Pro Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
        180                 185                 190

Thr Cys Glu Ala Thr His Lys Thr Ser Thr Ser Pro Ile Val Lys Ser
    195                 200                 205

Phe Asn Arg Asn Glu Cys
    210

<210> SEQ ID NO 27
<211> LENGTH: 444
<212> TYPE: PRT
<213> ORGANISM: Artificial Sequence
<220> FEATURE:
<223> OTHER INFORMATION: 1979 HC mIgG1 full

<400> SEQUENCE: 27

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Ser Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
            85                  90                  95

Arg Gly Thr Tyr Gly Tyr Asn Ala Tyr His Phe Asp Tyr Trp Gly Arg
        100                 105                 110

Gly Val Met Val Thr Val Ser Ser Ala Lys Thr Thr Pro Pro Ser Val
    115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Ser Val Thr Val Pro Ser
        180                 185                 190

Ser Thr Trp Pro Ser Glu Thr Val Thr Cys Asn Val Ala His Pro Ala
    195                 200                 205

Ser Ser Thr Lys Val Asp Lys Lys Ile Val Pro Arg Asp Cys Gly Cys
    210                 215                 220
```

-continued

```
Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
        260                 265                 270

Ser Trp Phe Val Asp Asp Val Glu Val His Thr Ala Gln Thr Gln Pro
    275                 280                 285

Arg Glu Glu Gln Phe Asn Ser Thr Phe Arg Ser Val Ser Glu Leu Pro
290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440
```

<210> SEQ ID NO 28
<211> LENGTH: 222
<212> TYPE: PRT
<213> ORGANISM: Artificial Sequence
<220> FEATURE:
<223> OTHER INFORMATION: 1979 HC mFabno hinge full

<400> SEQUENCE: 28

```
Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Ser Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140
```

```
Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Ser Val Thr Val Pro Ser
        180                 185                 190

Ser Thr Trp Pro Ser Glu Thr Val Thr Cys Asn Val Ala His Pro Ala
    195                 200                 205

Ser Ser Thr Lys Val Asp Lys Lys Ile Val Pro Arg Asp Cys
    210                 215                 220
```

<210> SEQ ID NO 29
<211> LENGTH: 642
<212> TYPE: DNA
<213> ORGANISM: Artificial Sequence
<220> FEATURE:
<223> OTHER INFORMATION: 1979 LC DNA Kappa full

<400> SEQUENCE: 29

```
gacatccaaa tgacacagtc tcctgcctcc ctgtctgcat ctctggaaga aattgtcacc      60
attacatgcc aggcaagcca ggacattggt aattggttat catggtatca gcagaaacca     120
gggaaatctc ctcacctcct gatctatggt accaccagct ggcagatggg gtcccatca     180
aggttcagcg gcagtagatc tggtacacag tattctctta agatcagcgg actacaggtt     240
gcagatattg gaatctatgt ctgtctacag gcttatagta ctccattcac gttcggctca     300
gggacaaagc tggaaataaa acgtacggat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gt                         642
```

<210> SEQ ID NO 30
<211> LENGTH: 1332
<212> TYPE: DNA
<213> ORGANISM: Artificial Sequence
<220> FEATURE:
<223> OTHER INFORMATION: 1979 HC DNA mIgG1 full

<400> SEQUENCE: 30

```
gaggtgcacc tggtggagtc tggacctggc cttgtgaaac cctcacagtc actctccctc      60
acctgttctg tcactggtta ctccatcact aatagttact gggactggat ccggaagttc     120
ccaggaaata aaatggagtg gatgggatac ataaactaca gtggtagcac tggctacaac     180
ccatctctca aaagtcgaat ctccattagt agagacacat cgaacaatca gttcttcctg     240
cagctgaact ctataactac tgaggacaca gccacatatt actgtgcacg agggacctat     300
gggtataacg cctaccactt tgattactgg ggccgaggag tcatggtcac agtctcgagt     360
gccaaaacga cacccccatc tgtctatcca ctggcccctg gatctgctgc ccaaactaac     420
tccatggtga ccctgggatg cctggtcaag ggctatttcc ctgagccagt gacagtgacc     480
tggaactctg gatccctgtc cagcggtgtg cacaccttcc cagctgtcct gcagtctgac     540
ctctacactc tgagcagctc agtgactgtc ccctccagca cctggcccag cgagaccgtc     600
acctgcaacg ttgcccaccc ggccagcagc accaaggtgg acaagaaaat tgtgcccagg     660
```

```
gattgtggtt gtaagccttg catatgtaca gtcccagaag tatcatctgt cttcatcttc      720
cccccaaagc ccaaggatgt gctcaccatt actctgactc ctaaggtcac gtgtgttgtg      780
gtagacatca gcaaggatga tcccgaggtc cagttcagct ggtttgtaga tgatgtggag      840
gtgcacacag ctcagacgca accccgggag gagcagttca acagcacttt ccgctcagtc      900
agtgaacttc ccatcatgca ccaggactgg ctcaatggca aggagttcaa atgcagggtc      960
aacagtgcag ctttccctgc ccccatcgag aaaaccatct ccaaaaccaa aggcagaccg     1020
aaggctccac aggtgtacac cattccacct cccaaggagc agatggccaa ggataaagtc     1080
agtctgacct gcatgataac agacttcttc cctgaagaca ttactgtgga gtggcagtgg     1140
aatgggcagc cagcggagaa ctacaagaac actcagccca tcatggacac agatggctct     1200
tacttcgtct acagcaagct caatgtgcag aagagcaact gggaggcagg aaatactttc     1260
acctgctctg tgttacatga gggcctgcac aaccaccata ctgagaagag cctctcccac     1320
tctcctggta aa                                                          1332

<210> SEQ ID NO 31
<211> LENGTH: 666
<212> TYPE: DNA
<213> ORGANISM: Artificial Sequence
<220> FEATURE:
<223> OTHER INFORMATION: 1979 HC DNA mFabno hinge full

<400> SEQUENCE: 31
gaggtgcacc tggtggagtc tggacctggc cttgtgaaac cctcacagtc actctccctc       60
acctgttctg tcactggtta ctccatcact aatagttact gggactggat ccggaagttc      120
ccaggaaata aaatggagtg gatgggatac ataaactaca gtggtagcac tggctacaac      180
ccatctctca aaagtcgaat ctccattagt agagacacat cgaacaatca gttcttcctg      240
cagctgaact ctataactac tgaggacaca gccacatatt actgtgcacg agggacctat      300
gggtataacg cctaccactt tgattactgg ggccgaggag tcatggtcac agtctcgagt      360
gccaaaacga caccccatc tgtctatcca ctggcccctg gatctgctgc ccaaactaac      420
tccatggtga ccctgggatg cctggtcaag ggctatttcc ctgagccagt gacagtgacc      480
tggaactctg gatccctgtc cagcggtgtg cacaccttcc cggctgtcct gcaatctgac      540
ctctacactc tgagcagctc agtgactgtc ccctccagca cctggcccag cgagaccgtc      600
acctgcaacg ttgcccaccc ggccagcagc accaaggtgg acaagaaaat tgtgcccagg      660
gattgt                                                                 666

<210> SEQ ID NO 32
<211> LENGTH: 235
<212> TYPE: PRT
<213> ORGANISM: Rattus norvegicus

<400> SEQUENCE: 32

Met Ser Thr Glu Ser Met Ile Arg Asp Val Glu Leu Ala Glu Glu Ala
1               5                   10                  15

Leu Pro Lys Lys Met Gly Gly Leu Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Asn Lys Glu Glu Lys Phe
    50                  55                  60
```

```
Pro Asn Gly Leu Pro Leu Ile Ser Ser Met Ala Gln Thr Leu Thr Leu
 65                  70                  75                  80

Arg Ser Ser Ser Gln Asn Ser Ser Asp Lys Pro Val Ala His Val Val
                 85                  90                  95

Ala Asn His Gln Ala Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Ile Tyr Ser Gln Val Leu Phe Lys
    130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Ser Leu Leu Ser Ala Ile Lys
                165                 170                 175

Ser Pro Cys Pro Lys Asp Thr Pro Glu Gly Ala Glu Leu Lys Pro Trp
            180                 185                 190

Tyr Glu Pro Met Tyr Leu Gly Gly Val Phe Gln Leu Glu Lys Gly Asp
        195                 200                 205

Leu Leu Ser Ala Glu Val Asn Leu Pro Lys Tyr Leu Asp Ile Thr Glu
    210                 215                 220

Ser Gly Gln Val Tyr Phe Gly Val Ile Ala Leu
225                 230                 235

<210> SEQ ID NO 33
<211> LENGTH: 235
<212> TYPE: PRT
<213> ORGANISM: Mus musculus

<400> SEQUENCE: 33

Met Ser Thr Glu Ser Met Ile Arg Asp Val Glu Leu Ala Glu Glu Ala
  1               5                  10                  15

Leu Pro Gln Lys Met Gly Gly Phe Gln Asn Ser Arg Arg Cys Leu Cys
                 20                  25                  30

Leu Ser Leu Phe Ser Phe Leu Leu Val Ala Gly Ala Thr Thr Leu Phe
             35                  40                  45

Cys Leu Leu Asn Phe Gly Val Ile Gly Pro Gln Arg Asp Glu Lys Phe
 50                  55                  60

Pro Asn Gly Leu Pro Leu Ile Ser Ser Met Ala Gln Thr Leu Thr Leu
 65                  70                  75                  80

Arg Ser Ser Ser Gln Asn Ser Ser Asp Lys Pro Val Ala His Val Val
                 85                  90                  95

Ala Asn His Gln Val Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Val Tyr Ser Gln Val Leu Phe Lys
    130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205
```

-continued

Gln Leu Ser Ala Glu Val Asn Leu Pro Lys Tyr Leu Asp Phe Ala Glu
    210                 215                 220

Ser Gly Gln Val Tyr Phe Gly Val Ile Ala Leu
225                 230                 235

<210> SEQ ID NO 34
<211> LENGTH: 233
<212> TYPE: PRT
<213> ORGANISM: Homo sapiens

<400> SEQUENCE: 34

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 35
<211> LENGTH: 158
<212> TYPE: PRT
<213> ORGANISM: Homo sapiens

<400> SEQUENCE: 35

Ser Val Arg Ser Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

```
Phe Lys Gly Gln Gly Cys Pro Ser Thr His Val Leu Leu Thr His Thr
 65              70                  75                  80

Ile Ser Arg Ile Ala Val Ser Tyr Gln Thr Lys Val Asn Leu Leu Ser
             85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
            115                 120                 125

Lys Gly Asp Arg Leu Ser Ala Glu Ile Asn Arg Pro Asp Tyr Leu Asp
            130                 135                 140

Phe Ala Glu Ser Gly Gln Val Tyr Phe Gly Ile Ile Ala Leu
145                 150                 155

<210> SEQ ID NO 36
<211> LENGTH: 157
<212> TYPE: PRT
<213> ORGANISM: Homo sapiens

<400> SEQUENCE: 36

Val Arg Ser Ser Ser Arg Thr Pro Ser Asp Lys Pro Val Ala His Val
 1               5                  10                  15

Val Ala Asn Pro Gln Ala Glu Gly Gln Leu Gln Trp Leu Asn Arg Arg
             20                  25                  30

Ala Asn Ala Leu Leu Ala Asn Gly Val Glu Leu Arg Asp Asn Gln Leu
             35                  40                  45

Val Val Pro Ser Glu Gly Leu Tyr Leu Ile Tyr Ser Gln Val Leu Phe
 50                  55                  60

Lys Gly Gln Gly Cys Pro Ser Thr His Val Leu Leu Thr His Thr Ile
 65              70                  75                  80

Ser Arg Ile Ala Val Ser Tyr Gln Thr Lys Val Asn Leu Leu Ser Ala
             85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
            130                 135                 140

Ala Glu Ser Gly Gln Val Tyr Phe Gly Ile Ile Ala Leu
145                 150                 155
```

UNITED STATES PATENT AND TRADEMARK OFFICE
CERTIFICATE OF CORRECTION

PATENT NO. : 10,775,385 B2  
APPLICATION NO. : 15/736614  
DATED : September 15, 2020  
INVENTOR(S) : James Philip O'Connell et al.

Page 1 of 1

It is certified that error appears in the above-identified patent and that said Letters Patent is hereby corrected as shown below:

In the Claims

Column 115, Line 19, (Claim 4): "the TNFα trimer" should be replaced with --the TNFα trimer has an increased binding affinity to the TNFR1 receptor by increasing the on rate ($k_{on-r}$) compared to the $k_{on-r}$ value for binding of the symmetrical TNFα trimer to the TNFR1 receptor;

(d) the TNFα trimer has an increased binding affinity to the TNFR1 receptor compared to the binding affinity of a symmetrical TNFα trimer to the TNFR1 receptor and the $K_{D-r}$ of the TNFα trimer to the TNFR1 receptor is decreased compared to the $K_{D-r}$ of the symmetrical TNFα trimer to the TNFR1 receptor, wherein:

(i) the $K_{D-r}$ of the TNFα trimer to the TNFR1 receptor is decreased by at least 10 times compared to the $K_{D-r}$ of the symmetrical TNFα trimer to the TNFR1 receptor;

(ii) the $K_{D-r}$ value of the TNFα trimer to the TNFR1 receptor is less than 10nM;

(e) the TNFα trimer has an increased binding affinity to the TNFR1 receptor compared to the binding affinity of a symmetrical TNFα trimer to the TNFR1 receptor and the $K_{D-r}$ of the TNFα trimer to the TNFR1 receptor is decreased compared to the $K_{D-r}$ of the symmetrical TNFα trimer to the TNFR1 receptor, wherein:

(i) the $K_{D-r}$ of the TNFα trimer to the TNFR1 receptor is decreased by at least 4 times compared to the $K_{D-r}$ of the symmetrical TNFα trimer to the TNFR1 receptor;

(ii) the $K_{D-r}$ value of the TNFα trimer to the TNFR1 receptor is less than 600pM, optionally less than 200pM;

(f) said TNFα trimer binds to either of the following antibodies with a $K_{D-ab}$ of 1 nM or less: CA185_1979 with a light chain of sequence SEQ ID NO: 26 and heavy chain of sequence SEQ ID NO:27; or CA185_1974 with a light chain of sequence SEQ ID NO: 11 and heavy chain of sequence SEQ ID NO:12; or (g) the TNFα trimer is soluble TNFα, membrane-bound TNFα, or both soluble TNFα and membrane-bound TNFα.--

Signed and Sealed this  
Second Day of February, 2021

Drew Hirshfeld  
*Performing the Functions and Duties of the